United States Patent
Feghali-Bostwick et al.

(10) Patent No.: US 10,844,392 B2
(45) Date of Patent: Nov. 24, 2020

(54) MATERIALS AND METHODS FOR PRODUCING ENDOSTATIN FUSION POLYPEPTIDES IN PLANT CELLS

(71) Applicants: iBio, Inc., New York, NY (US); Novici Biotech LLC, Vacaville, CA (US); MUSC Foundation for Research Development, Charleston, SC (US)

(72) Inventors: Carol Feghali-Bostwick, Mt Pleasant, SC (US); Terence E Ryan, Eagleville, PA (US); Hal S. Padgett, Vacaville, CA (US); Matthew McGee, Vacaville, CA (US)

(73) Assignees: iBio, Inc., New York, NY (US); MUSC FOUNDATION FOR RESEARCH DEVELOPMENT, Charleston, NC (US); NOVICI BIOTECH LLC, Vacaville, CA (US)

( * ) Notice: Subject to any disclaimer, the term of this patent is extended or adjusted under 35 U.S.C. 154(b) by 0 days.

(21) Appl. No.: 15/579,690

(22) PCT Filed: Jun. 3, 2016

(86) PCT No.: PCT/US2016/035858
§ 371 (c)(1),
(2) Date: Dec. 5, 2017

(87) PCT Pub. No.: WO2016/197018
PCT Pub. Date: Dec. 8, 2016

(65) Prior Publication Data
US 2018/0179263 A1  Jun. 28, 2018

Related U.S. Application Data

(60) Provisional application No. 62/257,607, filed on Nov. 19, 2015, provisional application No. 62/171,889, filed on Jun. 5, 2015.

(51) Int. Cl.
*C12N 15/82* (2006.01)

(52) U.S. Cl.
CPC .... *C12N 15/8257* (2013.01); *C07K 2319/036* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 750,375 A | 1/1904 | Kniphals | |
| 3,832,253 A | 8/1974 | Palma et al. | |
| 3,854,480 A | 12/1974 | Zaffaroni | |
| 4,452,775 A | 6/1984 | Kent | |
| 4,522,752 A | 6/1985 | Sisto et al. | |
| 4,667,014 A | 5/1987 | Nestor, Jr. et al. | |
| 4,683,195 A | 7/1987 | Mullis et al. | |
| 4,748,034 A | 5/1988 | de Rham | |
| 5,075,109 A | 12/1991 | Tice et al. | |
| 5,091,309 A | 2/1992 | Schlesinger et al. | |
| 5,093,258 A | 3/1992 | Cohen et al. | |
| 5,217,879 A | 6/1993 | Huang et al. | |
| 5,225,538 A | 7/1993 | Capon et al. | |
| 5,239,660 A | 8/1993 | Ooi | |
| 5,707,632 A | 1/1998 | Williams et al. | |
| 5,726,004 A | 3/1998 | Webber et al. | |
| 5,925,351 A | 7/1999 | Browning et al. | |
| 6,015,692 A | 1/2000 | Gyuris et al. | |
| 6,165,460 A | 12/2000 | Schlom et al. | |
| 6,218,371 B1 | 4/2001 | Krieg et al. | |
| 6,406,697 B1 | 6/2002 | Capon et al. | |
| 6,998,252 B1 | 2/2006 | Moss et al. | |
| 7,491,509 B2 | 2/2009 | Fedorkin et al. | |
| 8,507,441 B2 | 8/2013 | Feghali-Bostwick | |
| 8,716,232 B2 | 5/2014 | Feghali-Bostwick | |
| 9,365,616 B2 | 6/2016 | Feghali-Bostwick | |
| 9,556,252 B2 | 1/2017 | Feghali-Bostwick | |
| 10,172,923 B2 | 1/2019 | Feghali-Bostwick | |
| 2011/0070609 A1* | 3/2011 | Yusibov | A61K 36/31 435/69.1 |

FOREIGN PATENT DOCUMENTS

| | | |
|---|---|---|
| WO | WO 2000/01720 | 1/2000 |
| WO | WO 2000/46350 | 8/2000 |
| WO | WO 2011/050311 | 4/2011 |

OTHER PUBLICATIONS

Zheng, M. Endostatin derivative angiogenesis inhibitors. (2009) Chinese Medical Journal; vol. 122; pp. 1947-1951 (Year: 2009).*
Xu et al. NC1 domain of human type VIII collagen (alpha 1) inhibits bovine aortic endothelial cell proliferation and causes cell apoptosis. (2001) Biochemical and Biophysical Research Communications; vol. 289; pp. 264-268 (Year: 2001).*
Zhou et al. Contributions of disulfide bonds in a nested pattern to the structure, stability, and biological functions of endostatin. (2005) Journal of Biological Chemistry; vol. 280; pp. 11303-11312 (Year: 2005).*
Mekhaiel et al. Polymeric human Fc-fusion proteins with modified effector functions. (2011) Scientific Reports; vol. 1; pp. 1-11 (Year: 2011).*
Strand et al. Characterization of Fc-fusion protein aggregates derived from extracellular domain disulfide bond rearrangements. (2013) J. of Pharm. Sci.; vol. 102; pp. 441-453 (Year: 2013).*

(Continued)

*Primary Examiner* — Cathy Kingdon Worley
(74) *Attorney, Agent, or Firm* — Edwin S. Flores; Daniel J. Chalker; Chalker Flores, LLP

(57) ABSTRACT

This document provides materials and methods for producing endostatin fusion polypeptides having anti-fibrotic activity. For example, provided herein are fusion polypeptides having an IgG Fc domain and a portion of human endostatin that can form high molecular weight multimers, as well as methods for producing such fusion polypeptides in plant cells.

19 Claims, 42 Drawing Sheets
Specification includes a Sequence Listing.

(56) References Cited

OTHER PUBLICATIONS

Boesch et al. Highly parallel characterization of IgG Fc binding interactions. (2014) mABs; vol. 6; pp. 915-927 (Year: 2014).*
De Loose et al. Extensin precursor (Nicotiana plumbaginifolia). (2016) GenBank Accession AAA34073; pp. 1-2 (Year: 2016).*
Abdollahi et al., "Endostatin Antiangiogenic Signaling Network", Molecular Cell, vol. 13: 649-663, Mar. 12, 2004.
Altschul et al., "Basic Local Alignment Search Tool", J. Mol. Biol. 215: 403, 1990.
Altschul et al., "Issues in searching molecular sequence databases", Nature Genet. 6: 119, 1994.
Amalinei et al., "Biology of metalloproteinases", Romanian Journal of Morphology and Embryology, vol. 48:323-334, 2007.
Hsu et al., "Lung Tissues in Patients with Systemic Sclerosis have Gene Expression Patterns Unique to Pulmonary Fibrosis and Pulmonary Hypertension", Arthritis & Rheumatism, vol. 63:783-794, Mar. 2011.
Baca et al., "Chemical Ligation of Cysteine-Containing Peptides: Synthesis of a 22 kDa Tethered Dimer of HIV-1 Protease", J Am. Chem.Soc. 117: 1881-1887, 1995.
Bai et al., "Antiangiogenic Treatment Diminishes Renal Injury and Dysfunction via Regulation of Local AKT in Early Experimental Diabetes", Plos One. 9(4): 1-12, 2014.
Bergers et al., "Effects of Angiogenesis Inhibitors on Multistage Carcinogenesis in Mice", Science 284: 808-12, 1999.
Berkner, "Viral Expression Vectors", Cur. Top. Microbiol. Immunol., 158:39-6, 1992.
Berkner et al., "Development of Adenovirus Vectors for the Expression of Heterologous Genes", Bio Techniques, 6:616-629, 1988.
Bitter et al., "Expression and Secretion Vectors for Yeast", Meth Enzymol 153:516-544, 1987.
Bjoraker et al., "Progmotic Significance of Histopathologic Subsets in Idiopathic Pulmonary Fibrosis"Am. J. Respir. Crit. Care. Med 1998; 157: 199-203.
Bloch et al., "The angiogenesis inhibitor endostatin impairs blood vessel maturation during wound healing", The FASEB Journal, 2000; 14:2373-6.
Brandyopadhyay et al., "Expression of Completed Chicken Thymidine Kinase Gene Inserted in a Retrovirus Vector", Mol. Cell Biol., pp. 749-754, Apr. 1984.
Branton et al., "TGF-â and fibrosis", Microbes Infect., 1: 1349-65, 1999.
Breakefield et al., "Gene Transfer into the Nervous System", Mol. Neurobiol., 1: 337-371, 1987.
Buchschalcher et al., "Human Immunodeficiency Virus Vectors for Inducible Expression of Foreign Genes", Journal of Virology, vol. 66, pp. 2731-2739, May 1992.
Cattaneo et al., "Human endostatin-derived synthetic peptides possess potent antiangiogenic properties in vitro and in vivo", Exp Cell Res 283: 230-6, 2003.
Chaudhary et al., "A recombinant immunotoxin consisting of two antibody variable domains fused to Pseudomonas exotoxin", Nature 339: 394-397, 1989.
Chen et al., "Endostar, a novel human recombinant endostatin, attenuates liver fibrosis in CCl4-induced mice", Exp Biol Med. 239(8): 998-1006, 2014.
Choong et al., "Urokinase Plasminogen Activator System", Clin Orthop Relat Res., 415: S46-58, 2003.
Corpet et al., "Multiple sequence alignment with hierarchical clustering", Nuleic Acids Research, vol. 16, p. 10881, 1988.
Crystal, "The body as a manufacturer of endostatin", Nat Biotechnol 17: 336-7, 1999.
Cuttitta, "Peptide Amidation: Signature of Bioactivity", The Anatomical Record, 236: 87-93, 1993.
Dagan et al., "Ratios of Radical to Conservative Amino Acid Replacement are Affected by Mutational and Compositional Factors and May not be Indicative of Positive Darwinian Selection" Mol. Biol. Evol., 19(7), 1022-1025, 2002.
Dann et al., "Human renin: a new class of inhibitors.", Biochem Biophys Res Commun 124:141, 1986.
Dawson et al., "A Tobacco Mosaic Virus-Hybrid Expresses and Loses an Added Gene", Virology, 172: 285-292, 1989.
Dhanabal et al., "Cloning, Expression, and in Vitro Activity of Human Endostatin", Biochem Biophys Res Commun 358: 345-52, 1999.
Dhanabal et al., "Endostatin: Yeast Production, Mutants, and Antitumor Effect in Renal Cell Carcinoma", Cancer Res., 59: 189-197, 1999.
Ding et al., "Zinc-dependent dimers observed in crystals of human endostatin", Proc. Natl. Acad. Sci. USA,vol. 95: 10443-10448, Sep. 1998.
Duncan and Winter "The binding site for Clq and IgG", Nature 332: 738-740, 1988.
Dunsmore et al., "Mechanisms of Hepatocyte Growth Factor Stimulation of Keratinocyte Metalloproteinase Production", J. Biol. Chem., vol. 271: 24576-24582, Oct. 4, 1996.
Sato et al., "Synthesis and Antibiotic Activity of a Gramicidin S Analogue containing Bicyclic b-Turn Dipeptides", J Chem Soc Perkin Trans 1: 1231, 1986.
Feghali et al., "Identification of multiple, differentially expressed messenger RNAs in dermal fibroblasts from patients with systemic sclerosis", Arthritis & Rheum., vol. 42 :1451-7, 1999.
Felbor, "Secreted cathepsin L generatws endostatin from collagen XVII", The EMBO J., vol. 19: 1187-94, 2000.
Fink et al., "In vivo Expression of B-Galatosidase in Hippocampal Neurons by HSV-Mediated Gene Transfer", Hum. Gene. Ther., vol. 3:11-19, 1992.
Folkman and Kalluri, (2003) Cancer Medicine, 6th edition, pp. 161-194. Hamilton: B. C. Decker Inc.
Folkman, "Antiangiogenesis in cancer therapy—endostatin and its mechanisms of action", Exp Cell Res 312: 594-607, 2006.
Foronjy et al., "Transgenic Expression of Matrix Metalloproteinase-1 Inhibits Myocardial Fibrosis and Prevent the Transition to Heart Failure in a Pressure Overload Mouse Model", Hypertension Res., vol. 31:725-735, 2008.
French et al., "Bacterial Gene Inserted in an Engineered RNA Virus: Efficient Expression in Monocotyledonous Plant Cells", Science 231: 1294-1297, 1986.
Freese et al., "HSV-1 Vector mediated neuronal gene delivery", Biochem. Pharmacol. 40: 2189-2199, 1990.
Frolov et al., "Alphavirus-based expression vectors: Strategies nd applications", Proc. Natl. Acad. Sci. USA , vol. 93:11371-11377, Oct. 1996.
Garvey et al., "Peptides: Chemistry and Biology", G. R. Marshall ed., ESCOM Publisher: Leiden, Netherlands, p. 123, 1988.
George et al., "Transgenic expression of human matrix metalloproteinase-1 attenuates pulmonary arterial hypertension in mice", Clin Sci (Lond), 122: 83-92, 2012; publication retracted at, Retraction: Transgenic expression of human matrix metalloproteinase-1 attenuates pulmonary arterial hypertension in mice.
Gharaee-Kermani et al., "The role of urokinase in idiopathic pulmonary fibrosis and implication for therapy", Exp. Op. Invest. Drugs, 17: 905-916, 2008.
Gietz et al., "Transformation of Yeast by Lithium Acetate/Single-Stranded Carrier DNA/Polyethylene Glycol Method", Meth Enzymol 350: 87-96, 2002.
Gluzman et al., Current communications in Molecular Biology: Viral Vectors, Cold Spring Harbor Laboratory, NY, pp. 172-189, 1988.
Gordon et al., Design of Peptide Derived Amino Alcohols as Transition-State Analog Inhibitors of Angiotensin Converting Enzyme, Biochem Biophys Res Commun 126: 419, 1985.
Gorziglia et al., "Expression of the OSU Rotavirus Outer Capsid Protien VP4 by an Adenovirus Recombinant", J. Virol., vol. 66:4407-4412, Jul. 1992.
Grantham, "Amino Acid Difference Formula to Help Explain Protein Evolution", Science, 85: 862-864, 1974.
Grierson et al., "Plant Molecular Biology", Blackie, London, pp. 126-146, 1984.

(56) References Cited

OTHER PUBLICATIONS

Gunther et al., "Enhanced Tissue Factor Pathway Activity and Fibrin Turnover in the Alveolar Compartment of Patients with Interstitial Lung Disease",Thrombosis and Haemostasis, 83: 853-860, 2000.
Hajitou et al., "The antitumoral effect of endostatin and angistatin is associated with a down-regulation of vascular endothelial growth factor expression in tumor cells", The Faseb. J., vol. 16: 1802-1804, Sep. 19, 2002.
Hanai et al., "Endostatin Causes G1 Arrest of Endothelial Cells through Inhibition of Cyclin D1", J. Biol. Chem., vol. 277, pp. 16464-16469, May 10, 2002.
Hanai et al., "Endostatin is a potential inhibitor of Wnt signaling", J. Cell. Biol., vol. 158: 529-539, 2002.
Hellens et al., "pGreen: a versatile and flexible binary Ti vector for Agrobacterium-mediated plant transformation", Plant Mol Biol. 42(6): 819-832, 2000.
Herweijer et al., "A Plasmid-Based Self-Amplifying Sindbis Virus Vector", Human Gene Therapy 6: 1161-1167, 1995.
Higgins and Sharp, "Fast and sensitive multiple sequence alignments on a microcomputer", CABIOS 5: 151, 1989.
Higgins et al., "CLUSTAL: a package for performing multiple sequence alignment on a microcomputer", Gene 73: 237, 1988.
Hohenester et al., "Crystal structure of the angiogenesis inhibitor endonstatin at 1.5 A resolution", Embo. J., vol. 17: 1656-1664, 1998.
Hu et al., "Bioactivity, pharmacokinetics, and immunogenicity assays in a preclinical and clinical trials for recombinant human endostatin", Acta Pharmacol Sin, vol. 11 :1357-59, 2008.
Huet et al., "Inhibition of plasmin-mediated prostromelysin-1 activation by interaction of long chain unsaturated fatty acids with kringle 5", Biochem. Pharmacol. 67: 643-654, 2004.
Huffman et al., "Peptides:Chemistry and Biology", G. R. Marshall ed., ESCOM Publisher: Leiden, Netherlands, p. 105, 1988.
Idell, "The Matrix Unloaded", Am. J. Respir. Crit. Care Med., vol. 168:1268-1269, 2003.
Iimuro et al., "delivery of Matrix Metalloproteinase-1 Attenuates Established Liver Fibrosis in the Rat", Gastroenterology 2003; 124:445-458.
International Search Report and Written Opinion in international application No. PCT/US2016/035858, dated Jun. 3, 2016.
Jinnin et al., "Matrix metalloproteinase-1 up-regulation by hepatocyte growth factor in human dermal fibroblasts via ERK signaling pathway involves Ets1 and Fli1", Nucleic Acids Research, vol. 33:3540-3549, 2005.
Johnson et al., "Cytotoxicity of a Replication-Defective Mutant of Herpes Simplex Virus Type 1", J. Virol., vol. 66: 2952-2965, May 1992.
Kaar et al., "Matrix metalloproteinase-1 treatment of muscle fibrosis", Acta Biomaterialia 4: 1411-1420, 2008.
Kalluri et al., "Fibrosis and angiogenesis", Curr Opin Nephrol Hypertension, 9: 413-8, 2000.
Kanemura et al., "Hepatocyte growth factor gene transfer with naked plasmid DNA ameliorates dimethylnitrosamine-induced liver fibrosis in rats", Hepatology Res. 38: 930-939, 2008.
Karumanchi et al., "Cell Surface Glypicans are Low-Affinity Endostatin Receptors", Mol. Cell., vol. 7: 811-822, 2001.
Kim et al., "Peptides Constrained to Type VI B-Turns. 1. Evidence for an Exceptionally Stable Intramolecular Hydrogen Bond", J. Org. Chem. 62: 2847, 1997.
Kim et al., "Endostatin Inhibits Endothelial and Tumor Cellular Invasion by Blocking the Activation and Catalytic Activity of Matrix Metalloproteinase", Cancer Res., vol. 60: 5410-5413, 2000.
Kim et al., "Endostatin Blocks Vascular Endothelial Growth Factor-mediated Signaling via Direct Interaction with KDR/Flk-1", J. Biol. Chem., vol. 277: 27872-27879,2002.
Kisker et al., "Continuous Administration of Endostatin by Intraperitoneally Implanted Osmotic Pump Improves the Efficacy and Potency of Therapy in a Mouse Xenograft Tumor Model", Cancer Res., vol. 61:7669-7674, 2001.
Kuramoto et al., "Inhalation of urokinase-type plasminogen activator reduces airway remolding in a murine asthma model", Am. J. Physiol. Lung Cell. Mol. Physiol., 296:L337-346, 2009.
Lee et al., "Endostatin binds to the catalytic domain of matrix metalloproteinase", FEBS Letters, 519, pp. 147-152, 2002.
Liu et al., "Peptide segment ligation strategy without use of protecting groups", Natl. Acad. Sci. USA 91:6584-6588, 1994.
Liu and Tam, "Chemical Ligation Approach to Form a Peptide Bond between Unprotected Peptide Segments. Concept and Model Study", J. Am. Chem. Soc. 116: 4149-4153, 1994.
Liu et al., "Acyl Disulfide-Mediated Intramolecular Acylation for Orthogonal Coupling Between Unprotected Peptide Segments. Mechanism and Application", Tetrahedron Lett. 37: 933-936, 1996.
Loots et al., "Peptides: Chemistry and Biology", ESCOM Science Publishers, Leiden, p. 118, 1988.
Mackett et al., "Vaccinia virus: A selectable eukaryotic cloning and expression vector", Proc. Natl. Acad. Sci. USA 79:7415-7419, 1982.
Mackett et al., "Vaccinia Virus: A Selectable Eukaryotic Cloning and Expression Vector", Biotechnology, 24: 495-499, 1992.
Madzak et al., "Efficient in vivo encapsidation of a shuttle vector into pseudo-simian virus using a shuttle virus as helper", J. Gen. Virol., 73:1533-1536, 1992.
Muzyczka N., (eds) "Viral Expression Vectors", Current Topics in Microbiology and Immunology, vol. 158. Springer, Berlin, Heidelberg. pp. 67-95, 1992.
Monvoisin et al., "Involvement of matrix metalloproteinase type-3 hepatocyte growth factor-induced invasion of human hepatocellular carcinoma cells", Int. J. Cancer 97:157-162, 2002.
Morrison, "In Vitro Antibodies: Strategies for Production and Application", Annu. Rev. Immunol., 10, pp. 239-265, 1992.
Mullis et al., "Specific enzymatic amplification of DNA in vitro: the polymerase chain recation", Cold Spring Harbor Symp. Quant. Biol. 51: 263, 1987.
Nakagawa et al., "The Use of Polymer-Bound Oximes for the Synthesis of Large Peptides Usable in Segment Condensation: Synthesis of a 44 Amino Acid Amphiphilic Peptide Model of Apolipoprotein A-I", J. Am. Chem. Soc. 107: 7087-7092, 1985.
Naldini et al., "Biological activation of pro-HGF (Hepatocyte Growth Factor) by Urokinase is controlled by a stoichiometric reaction", J. Biol. Chemistry 270:603-611, 1995.
Needleman and Wunsch, "A general method applicable to the search for similarities in the amino acid sequence of two proteins", J. Mol. Biol. 48: 443, 1970.
Nyberg et al., "Endostatin inhibits human tongue carcinoma cell invasion and intravasation and blocks the activation of matrix metalloprotease", J. Biol. Chem., 278: 22404-22411, 2003.
Ohi et al., "Construction and replication of an adeno-associated virus expression vector that contains hman p-globin cDNA", Gene, 89: 279-282, 1990.
O'Reilly et al., "Endostatin: An endogenous inhibitor of angiogenesis and tumor growth", Cell, 88: 277-285, 1997.
Parks et al., "Matrix Metalloproteinases as Modulators of Inflammation and Innate Immunity", Nature Reviews Immunology 4: 6174-629, 2004.
Pearson et al., "Improved tools for biological sequence comparison", Proc. Natl. Acad. Sci. USA 85:2444, 1988.
Page et al., "Construction and use of a human immunodeficiency virus vector for analysis of virus infectivity", J. Virol. 64: 5270-5276, 1990.
Pilewski et al., "insulin-like growth factor binding proteins 3 and 5 are overexpressed in idiopathic pulmonary fibrosis and contribute to extracellular matrix deposition", Am. J. Pathol., 166:399-407, 2005.
Michael Cory, "Computer-Assisted Drug Design", Principles of Pharmacology, Munson (ed.) 1995, Ch. 102.
Quantin et al., "Adenovirus as an expression vector in muscle cells in vivo", Proc. Natl. Acad. Sci. USA, 89:2581-2584, 1992.
Ren et al., "Endostatin inhibits hypertrophic scarring in a rabbit ear model", J. Zhejiang Univ. Sci. B. 14(3)224-230, 2013.
Richter et al., "Soluble endostatin is a novel inhibitor of epithelial repair in idiopathic pulmonary fibrosis", Thorax 64:156-61, 2009.
Roark et al., "Peptides: Chemistry and Biology", G. R. Marshall ed., ESCOM Publisher: Leiden, Netherlands, p. 134, 1988.

(56) References Cited

OTHER PUBLICATIONS

"Rosenfeld et al., ""In Vivo Transfer of the Human Cystic Fibrosis Transmembrane Conductance Regulator Gene to the Airway Epithelium"", Cell, 68: 143-155, 1992."
Sasaki et al., "Structural basis and potential role of heparin/heparan sulfate binding to the angiogenesis inhibitor endostatin", Embo. J., 18: 6240-6248, 1999.
Schlesinger, "Alphaviruses—vectors for the expression of heterologous genes", Trends Biotechnol. 11: 18-22, 1993.
Schnolzer and Kent, "Constructing Proteins by Dovetailing Unprotected Synthetic Peptides: Backbone-Engineered HIV Protease", Science 256: 221-225, 1992.
Shichiri and Hirata "Antiangiogenesis signals by endostatin", Faseb J., 15: 1044-1053, 2001.
Shue et al., "Amide Bono Surrogates: A General Synthetic Route to Trans Carbon-Carbon Double Bond Isosteres.", Tetrahedron Letter 28: 3225, 1987.
Sisson et al., "Inducible lung-specific urokinase reduces fibrosis and mortality after lung injury in mice", Am. J. Physiol. Lung Cell. Mol. Physiol. 283:L1023-1032, 2002.
Sisson et al., "Treatment of Bleomycin-Induced Pulmonary Fibrosis by Transfer of Urokinase-Type Plasminogen Activator Genes", Human Gene Therapy, 10: 2315-2323, 1999.
Smith and Waterman, "Comparison of Biosequences", Adv. Appl. Math. 2: 482, 1981.
Soltero et al., "The oral delivery of protein and peptide drugs", Innovations in Pharmaceutical Technology, 1: 106-110, 2001.
Spitsin et al., "Expression of alfalfa mosaic virus coat protein in tobacco mosaic virus (TMV) deficient in the production of its native coat protein supports long-distance movement of a chimeric TMV", Proc. Natl. Acad. Sci. USA, 96(5): 2549-53, 1999.
Stratford-Perricaudet et al., "Evaluation of the Transfer and Expression in Mice of an Enzyme-Encoding Gene Using a Human Adenovirus Vector", Hum. Gene Ther., 1: 241-256, 1990.
Sudhakar et al., "Human tumstatin and human endostatin exhibit distinct antiangiogenic activities mediated by avB1 and a5B1 integrins", Proc. Natl. Acad. Sci. USA 100:4766-71, 2003.
Sumi et al., "Increased Serum Levels of Endostatin in Patients With Idiopathic Pulmonary Fibrosis", J. Clin. Lab. Anal. 19: 146-9, 2005.
Sun et al., "Results of phase III trial of rh-endostatin (YH-16) in advanced non-small cell lung cancer (NSCLC) patients", J Clin Oncol, (ASCO Annual meeting proceedings); 23: 7138, 2005, Abstract.
Takahashi et al., "Intraocular expression of endostatin reduces VEGF-induced retinal vascular permeability, neovascularization, and retinal detachment", Faseb J., 17: 896-898, 2003.
Takamatsu et al., "Expression of bacterial chloramphenicol acetyltransferase gene in tobacco plants mediated by TMV-RNA", EMBO J. 6:307-311, 1987.
Takamatsu et al., "Production of enkephalin in tobacco protoplasts using tobacco mosaic virus RNA vector", FEBS Lett. 269:73-76, 1990.
Tam et al., "Specificity and formation of unusual amino acids of an amide ligation strategy for unprotected peptides", Int. J. Peptide Protein Res. 45: 209-216, 1995.
Tan et al., "Classification Analysis of the Transcriptosome of Nonlesional Cultured Dermal Fibroblasts From Systemic Slerosis Patients With Early Disease", Arthritis Rheum. 52:865-76, 2005.
Tanabe et al., "Endostatin peptide, an inhibtor of angiogenesis, prevents the progression of peritoneal sclerosis in a mouse experimental model", Kidney Int 71:227-38, 2007.
Thomas et al., "Phase I Pharmacokinetic and Pharmacodynamic Study of Recombinant Human Endostatin in Patients With Advanced Solid Tumors", J Clin Oncol. 21(2): 223-231, 2003.
Tjin Than Sjin et al., "A 27-Amino-acid synthetic peptide corresponding to the NH2_Terminal zinc-binding domain of endostatin is responsible for its antitumor activity", Cancer Res 65:3656-63, 2005.
Toubi et al., "The association of serum matrix metalloproteinases and their tissue inhibitor levels with scleroderma disease severity", Clin. Exp. Rheumatol 20:221-4, 2002.
Varga et al., "Systemic sclerosis: a prototypic multisystem fibrotic disorder", J. Clin. Invest. 117:557-67, 2007.
Varga et al., "Transforming growth factor-B as a therapeutic target in systemic sclerosis", Nature Reviews Rheumatology 5:200-6, 2009.
Walters, "Computer-Assisted Modeling of Drugs" in Klegerman & Groves, eds., Pharmaceutical Biotechnology. Interpharm Press: Buffalo Grove, Ill., pp. 165-174, 1993.
Wan et al., "Endostatin, an angiogenesis inhibitor, ameliorates bleomycin-induced pulmonary fibrosis in rats", Respir. Res. 14(1):56, 2013.
Wen et al., "The generation of endostatin is mediated by elastase", Cancer Res 59:6052-6, 1999.
Wickstrom et al., "Endostatin associates with integrin a%B1 and caveolin-1, and activates src via a tyrosyl phosphatase-dependent pathway in human endothelial cells", Cancer Res, 62:5580-5589, 2002.
Wickstrom et al., "Endostatin associated with lipid rafts and induces reorganization of the actin cytoskeleton via down-regulation of RhoA activity", J Biol Chem, 278: 37895-37901, 2003.
Wilkinson et al., "Constitutive and enhanced expression from the CMV major IE promoter in a defective adenovirus vector", Nucl. Acids Res., 20:2233-2239, 1992.
Williams et al., "2-Substituted Piperazines as Constrained Amino Acids. Application to the Synthesis of Potent, Non Carboxylic Acid Inhibitors of Farnesyltransferase", J. Med. Chem. 39: 1345-1348, 1996.
Wynn, "Common and unique mechanisms regulate fibrosis in various fibroproliferative diseases", J. Clin. Invest. 117:524-29, 2007.
Xi et al., "Elevated Conformational Rigidity in Dipeptides Incorporating Piperazic Acid Derivatives", J. Am. Chem. Soc. 120: 80, 1998.
Xu et al., "Reside at position 331 in the IgG1 and IgG4 Ch2 domains contributes to their differential ability to bind and activate complement", J. biol. Chem. 269: 3469-3474, 1994.
Xu et al., "Research Advances of Endostatin and its Short Internal Fragments", Curr Protein Pept Sci. 9: 275-83, 2008.
Yamaguchi et al., "A peptide derived from endostatin ameliorates organ fibrosis", Science Translational Medicine, AAAS—American Association for the Advancement of Science, US, vol. 4, No. 136, May 30, 2012, p. 236.
Yamashiro and Li, "New segment synthesis of 2-inhibin-92 by the acyl disulfide method", Int. J. Peptide Protein Res. 31: 322-334, 1988.
Yang et al., "Gene expression profiling of familial and sporadic interstitial pneumonia", Am. J. Respir. Crit. Care. Med. 175:45-54, 2007.
Yasuoka et al., "Human skin culture as an ex vivo model for assessing the fibrotic effects of insulin-like growth factor binding proteins", The Open Rheumatol J. 2:17-22, 2008.
Yoon et al., "Mouse endostatin inhibits the formation of lung and liver metastases, Cancer Res, 59: 6251-6256, 1999.
Yusibov et al., "N-terminal basic amino acids of alfalfa mosaic virus coat protein involoved in the imitation of infection", Virology, 208(1): 405-7, 1995.
Zhang, "Rates of Conservative and Radical Nonsynonymous Nucleotide Substitutions in Mammalian Nuclear Genes", J. Mol. Evol., 50: 56-68, 2000.
Zhiyong et al., "Endostar Injection Inhibits Rabbit Ear Hypertrophic Scar Formation," Int. J. Low. Extrem. Wounds 11(4): 271-276, 2012.

\* cited by examiner

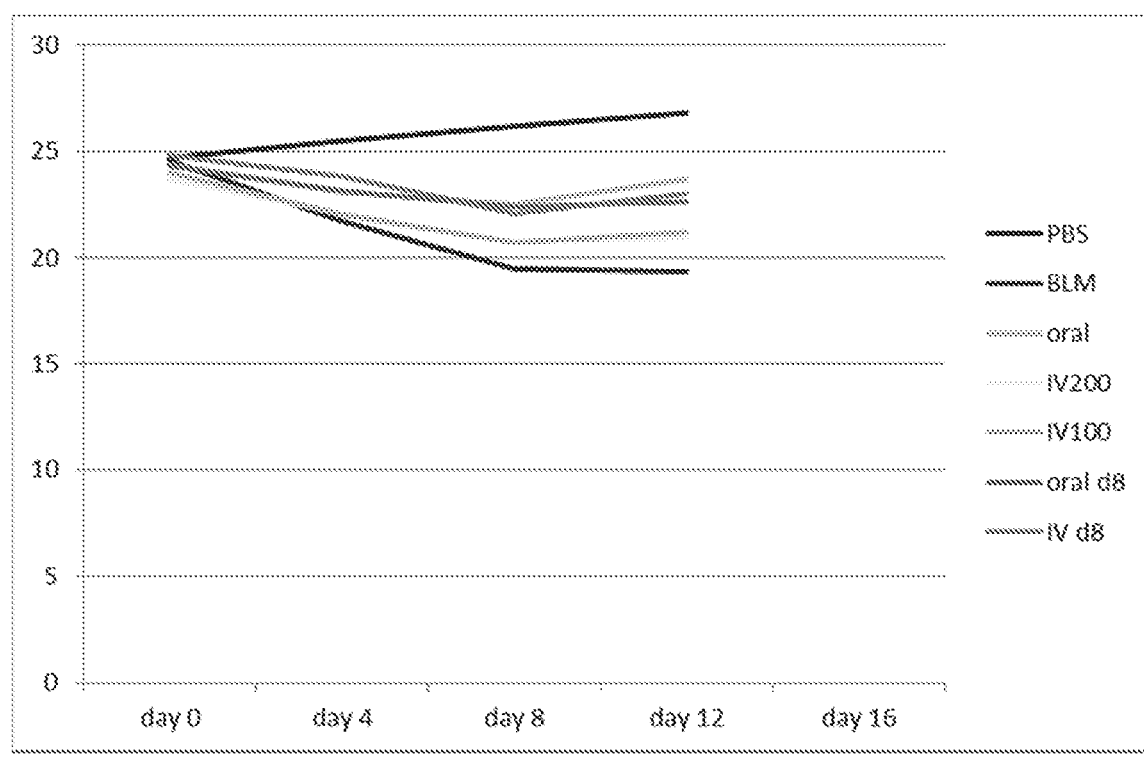
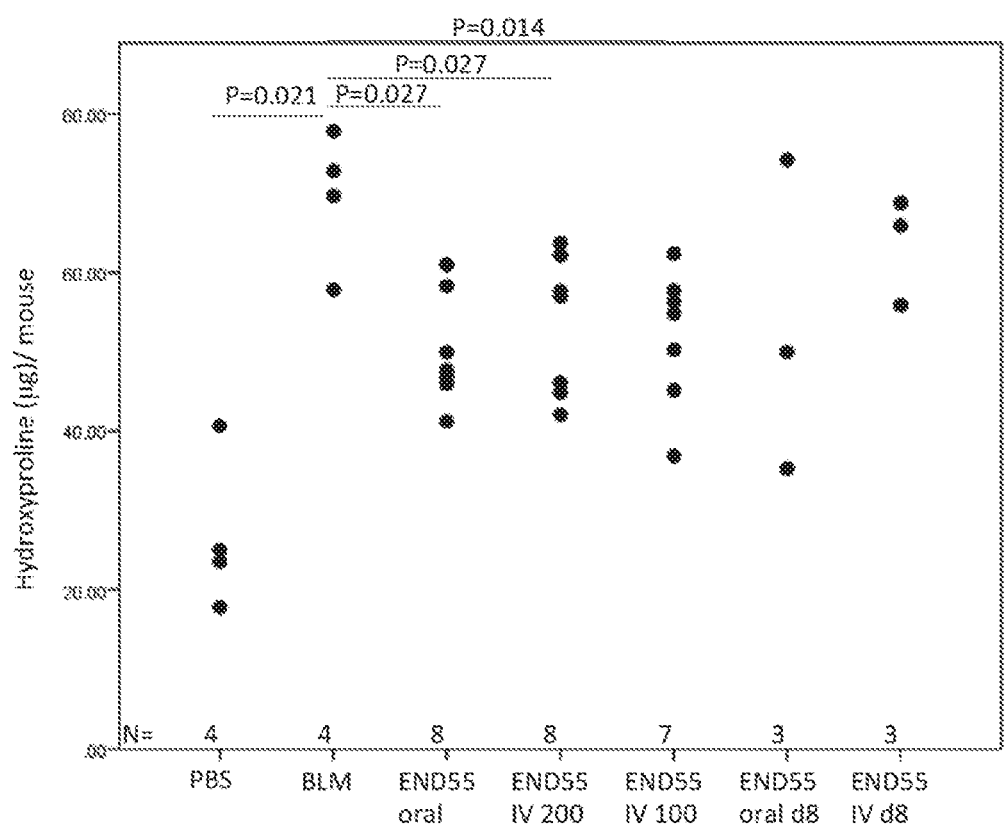
FIG. 21

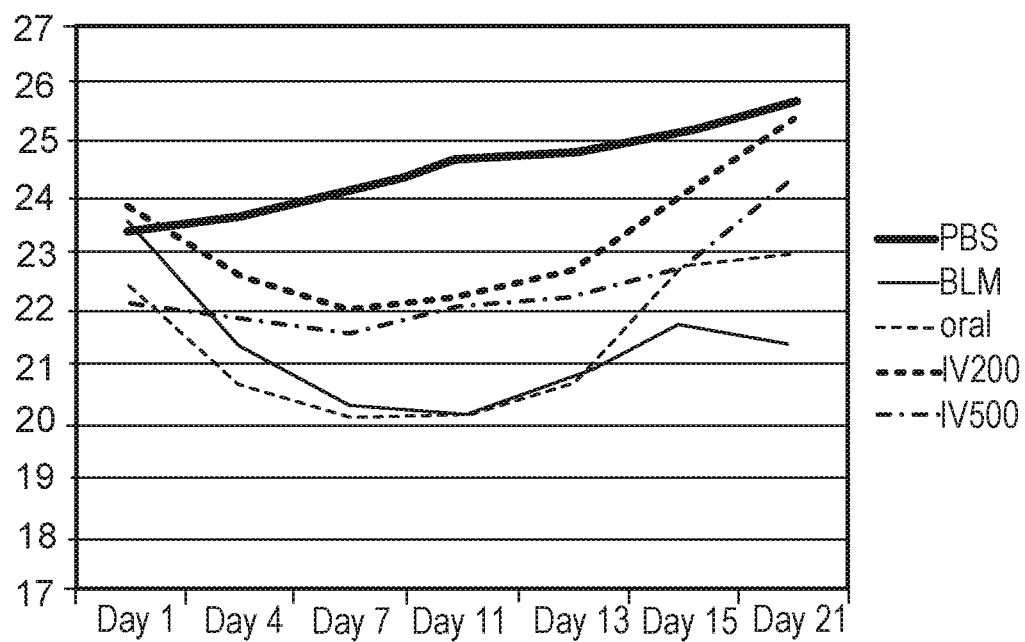
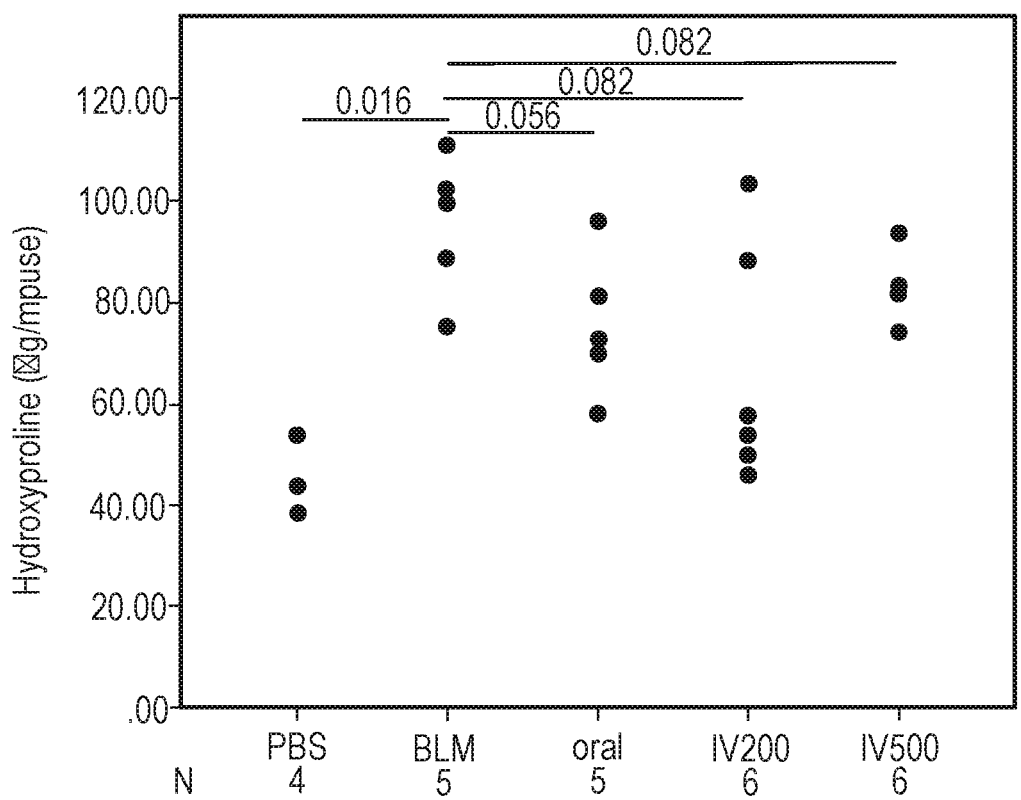
FIG. 22

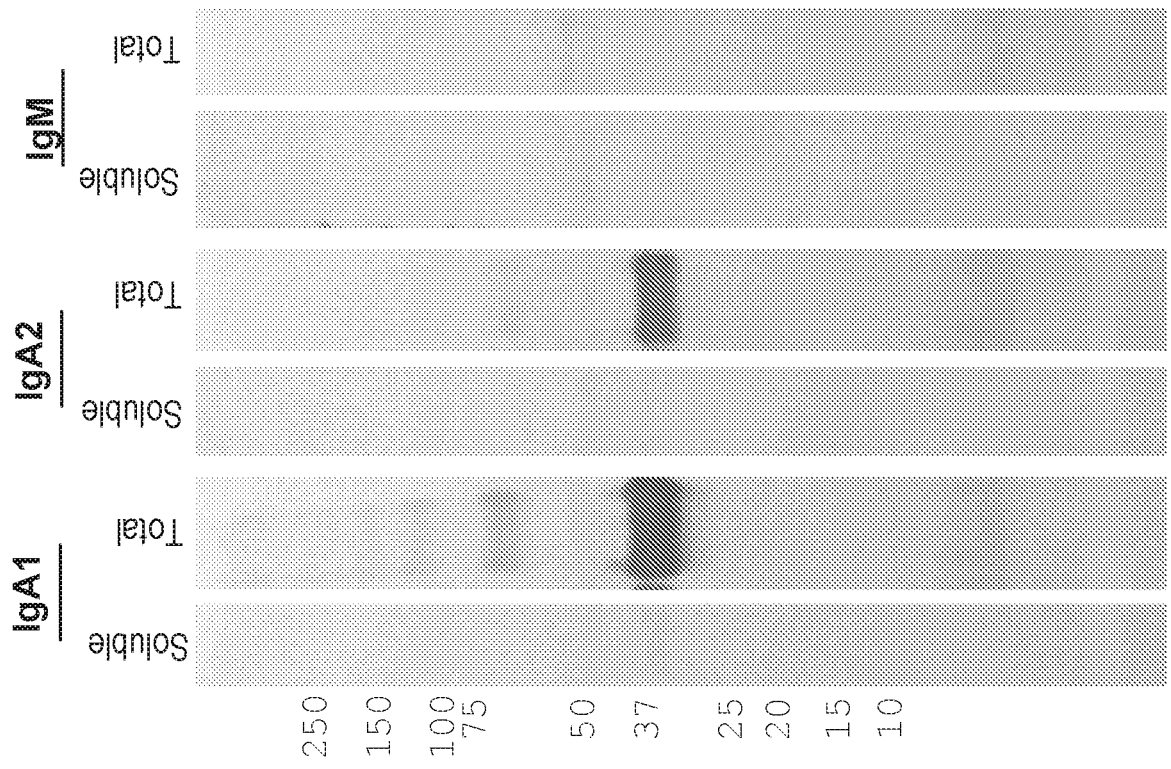
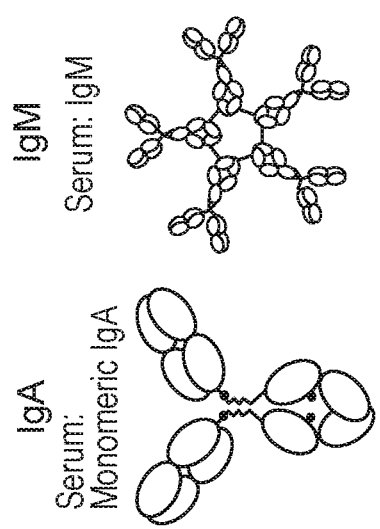
FIG. 25

E3-Fc Sequence:

MGKMASLFATFLVVLVSLSLASESSASYCETWRTEAPSATGQASSLL
GGRLLGQSAASCHHAYIVL<u>A</u>IENSFMT*EPKSCDKTHTCPPCPAPELLGG
PSVFLFPPKPKDTLMISRTPEVTCVVVDVSHEDPEVKFNWYVDGVEVHN
AKTKPREEQY<u>NST</u>YRVVSVLTVLHQDWLNGKEYKCKVSNKALPAPIEKTIS
KAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHY
TQKSLSLSPGK* (SEQ ID NO:16)

E3 Sequence:

SYCETWRTEAPSATGQASSLLGGRLLGQSAASCHHAYIVLCIENSFMT
(SEQ ID NO:20)

E4 Sequence:

SYCETWRTEAPSATGQASSLLGGRLLGQSAASCHHAYIVLCIENSFMT-
$R_nE(O)_xNR'_2$ (SEQ ID NO:21)

FIG. 26

| | | | | |
|---|---|---|---|---|
| SYCETWRTEA | PSATGQASSL | LGGRLLGQSA | ASCHHAYIVL | AIENSFMTEP |
| KSCDKTHTCP | PCPAPELLGG | PSVFLFPPKP | KDTLMISRTP | EVTCVVVDVS |
| HEDPEVKFNW | YVDGVEVHNA | KTKPREEQYN | STYRVVSVLT | VLHQDWLNGK |
| EYKCKVSNKA | LPAPIEKTIS | KAKGQPREPQ | VYTLPPSRDE | LTKNQVSLTC |
| LVKGFYPSDI | AVEWESNGQP | ENNYKTTPPV | LDSDGSFFLY | SKLTVDKSRW |
| QQGNVFSCSV | MHEALHNHYT | QKSLSLSPGK | | |

SEQUENCE LISTING

```
<160> NUMBER OF SEQ ID NOS: 29

<210> SEQ ID NO 1
<211> LENGTH: 555
<212> TYPE: DNA
<213> ORGANISM: Homo sapiens

<400> SEQUENCE: 1
atgcacagcc accgcgactt ccagccggtg ctccacctgg ttgcgctcaa cagcccctg      60 tcaggcggca tgcggggcat ccgcggggcc gacttccagt gcttccagca ggcgcgggcc    120
gtggggctgg cgggcacctt ccgcgccttc ctgtcctcgc gcctgcagga cctgtacagc    180
atcgtgcgcc gtgccgaccg cgcagccgtg cccatcgtca acctcaagga cgagctgctg    240
tttcccagct gggaggctct gttctcaggc tctgagggtc cgctgaagcc cggggcacgc    300
atcttctcct taacggcaa ggacgtcctg acccacccca cctggcccca gaagagcgtg     360
tggcatggct cggaccccaa cgggcgcagg ctgaccgaga gctactgtga gacgtggcgg    420
acggaggctc cctcggccac gggccaggcc tactcgctgc tggggggcag gctcctgggg    480
cagagtgccg cgagctgcca tcacgcctac atcgtgctat gcattgagaa cagcttcatg    540
actgcctcca agtag                                                     555

<210> SEQ ID NO 2
<211> LENGTH: 183
<212> TYPE: PRT
<213> ORGANISM: Homo sapiens

<400> SEQUENCE: 2

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
```

```
                    20                  25                  30

Cys Phe Gln Gln Ala Arg Ala Val Gly Leu Ala Gly Thr Phe Arg Ala
             35                  40                  45

Phe Leu Ser Ser Arg Leu Gln Asp Leu Tyr Ser Ile Val Arg Arg Ala
     50                  55                  60

Asp Arg Ala Ala Val Pro Ile Val Asn Leu Lys Asp Glu Leu Leu Phe
 65                  70                  75                  80

Pro Ser Trp Glu Ala Leu Phe Ser Gly Ser Glu Gly Pro Leu Lys Pro
                 85                  90                  95

Gly Ala Arg Ile Phe Ser Phe Asn Gly Lys Asp Val Leu Thr His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Tyr Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 3
<211> LENGTH: 552
<212> TYPE: DNA
<213> ORGANISM: Mus musculus

<400> SEQUENCE: 3
catactcatc aggactttca gccagtgctc cacctggtgg cactgaacac cccctgtct      60 ggaggcatgc gtggtatccg tggagcagat ttccagtgct ccagcaagc ccgagccgtg    120 gggctgtcgg gcaccttccg ggcttttcctg tcctctaggc tgcaggatct ctatagcatc    180
gtgcgccgtg ctgaccgggg gtctgtgccc atcgtcaacc tgaaggacga ggtgctatct    240
cccagctggg actccctgtt ttctggctcc cagggtcaac tgcaacccgg ggcccgcatc    300
ttttcttttg acggcagaga tgtcctgaga cacccagcct ggccgcagaa gagcgtatgg    360
cacggctcgg accccagtgg gcggaggctg atggagagtt actgtgagac atggcgaact    420
gaaactactg gggctacagg tcaggcctcc tccctgctgt caggcaggct cctggaacag    480
aaagctgcga gctgccacaa cagctacatc gtcctgtgca ttgagaatag cttcatgacc    540
tctttctcca aa                                                       552

<210> SEQ ID NO 4
<211> LENGTH: 184
<212> TYPE: PRT
<213> ORGANISM: Mus musculus

<400> SEQUENCE: 4

His Thr His Gln Asp Phe Gln Pro Val Leu His Leu Val Ala Leu Asn
  1               5                  10                  15

Thr Pro Leu Ser Gly Gly Met Arg Gly Ile Arg Gly Ala Asp Phe Gln
                 20                  25                  30

Cys Phe Gln Gln Ala Arg Ala Val Gly Leu Ser Gly Thr Phe Arg Ala
             35                  40                  45

Phe Leu Ser Ser Arg Leu Gln Asp Leu Tyr Ser Ile Val Arg Arg Ala
     50                  55                  60
```

Asp Arg Gly Ser Val Pro Ile Val Asn Leu Lys Asp Glu Val Leu Ser
65                  70                  75                  80

Pro Ser Trp Asp Ser Leu Phe Ser Gly Ser Gln Gly Gln Leu Gln Pro
            85                  90                  95

Gly Ala Arg Ile Phe Ser Phe Asp Gly Arg Asp Val Leu Arg His Pro
            100                 105                 110

Ala Trp Pro Gln Lys Ser Val Trp His Gly Ser Asp Pro Ser Gly Arg
        115                 120                 125

Arg Leu Met Glu Ser Tyr Cys Glu Thr Trp Arg Thr Glu Thr Thr Gly
        130                 135                 140

Ala Thr Gly Gln Ala Ser Ser Leu Leu Ser Gly Arg Leu Leu Glu Gln
145                 150                 155                 160

Lys Ala Ala Ser Cys His Asn Ser Tyr Ile Val Leu Cys Ile Glu Asn
                165                 170                 175

Ser Phe Met Thr Ser Phe Ser Lys
                180

<210> SEQ ID NO 5
<211> LENGTH: 699
<212> TYPE: DNA
<213> ORGANISM: Homo sapiens

<400> SEQUENCE: 5
gagcccaaat cttgtgacaa aactcacaca tgcccaccgt gcccagcacc tgaactcctg      60
gggggaccgt cagtcttcct cttccccca aaacccaagg acaccctcat gatctcccgg     120 accctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa gaccacgcct     540 cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga gagcctctc cctgtctccg ggtaaatga                             699

<210> SEQ ID NO 6
<211> LENGTH: 227
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Tyr
65                  70                  75                  80

-continued

```
Asn Ser Thr Tyr Arg Val Val Ser Val Leu Thr Val Leu His Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 7
<211> LENGTH: 48
<212> TYPE: DNA
<213> ORGANISM: artificial
<220> FEATURE:
<223> OTHER INFORMATION: nucleotide sequence encoding a thrombin
      cleavage site

<400> SEQUENCE: 7
tctagaggtg gtctagtgcc gcgcggcagc ggttcccccg ggttgcag                48

<210> SEQ ID NO 8
<211> LENGTH: 16
<212> TYPE: PRT
<213> ORGANISM: artificial
<220> FEATURE:
<223> OTHER INFORMATION: thrombin cleavage site

<400> SEQUENCE: 8

Ser Arg Gly Gly Leu Val Pro Arg Gly Ser Gly Ser Pro Gly Leu Gln
1               5                   10                  15

<210> SEQ ID NO 9
<211> LENGTH: 48
<212> TYPE: PRT
<213> ORGANISM: Rattus norvegicus

<400> SEQUENCE: 9

Ser Tyr Cys Glu Thr Trp Arg Thr Glu Ala Thr Gly Val Thr Gly Gln
1               5                   10                  15

Ala Ser Ser Leu Leu Ser Gly Arg Leu Leu Glu Gln Lys Ala Glu Ser
            20                  25                  30

Cys His Asn Ser Tyr Ile Val Leu Cys Ile Glu Asn Ser Phe Met Thr
        35                  40                  45

<210> SEQ ID NO 10
<211> LENGTH: 48
<212> TYPE: PRT
<213> ORGANISM: Bos taurus
```

<400> SEQUENCE: 10

Ser Tyr Cys Glu Thr Trp Arg Thr Asp Ser Arg Ala Ala Thr Gly Gln
1               5                   10                  15

Ala Ser Ser Leu Leu Ala Gly Arg Leu Leu Glu Gln Lys Ala Ala Gly
            20                  25                  30

Cys His Asn Ala Phe Ile Val Leu Cys Ile Glu Asn Ser Phe Met Thr
        35                  40                  45

<210> SEQ ID NO 11
<211> LENGTH: 48
<212> TYPE: PRT
<213> ORGANISM: Homo sapiens

<400> SEQUENCE: 11

Asn Tyr Cys Glu Ala Trp Arg Thr Ala Asp Thr Ala Val Thr Gly Leu
1               5                   10                  15

Ala Ser Pro Leu Ser Thr Gly Lys Ile Leu Asp Gln Lys Ala Tyr Ser
            20                  25                  30

Cys Ala Asn Arg Leu Ile Val Leu Cys Ile Glu Asn Ser Phe Met Thr
        35                  40                  45

<210> SEQ ID NO 12
<211> LENGTH: 552
<212> TYPE: DNA
<213> ORGANISM: Homo sapiens

<400> SEQUENCE: 12
cacagccacc gcgacttcca gccggtgctc cacctggttg cgctcaacag cccctgtca      60
ggcggcatgc ggggcatccg cggggccgac ttccagtgct ccagcaggc gcgggccgtg     120
gggctggcgg gcaccttccg cgccttcctg tcctcgcgcc tgcaggacct gtacagcatc    180
gtgcgccgtg ccgaccgcgc agccgtgccc atcgtcaacc tcaaggacga gctgctgttt    240
cccagctggg aggctctgtt ctcaggctct gagggtccgc tgaagcccgg gcacgcatc     300
ttctcctttg acggcaagga cgtcctgagg cacccccacct ggccccagaa gagcgtgtgg    360
catggctcgg accccaacgg cgcaggctg accgagagct actgtgagac gtggcggacg    420
gaggctccct cggccacggg ccaggcctcc tcgctgctgg ggggcaggct cctggggcag    480
agtgccgcga gctgccatca cgcctacatc gtgctctgca ttgagaacag cttcatgact    540
gcctccaagt ag                                                        552

<210> SEQ ID NO 13
<211> LENGTH: 183
<212> TYPE: PRT
<213> ORGANISM: Homo sapiens

<400> SEQUENCE: 13

His Ser His Arg Asp Phe Gln Pro Val Leu His Leu Val Ala Leu His
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

```
Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180
```

```
<210> SEQ ID NO 14
<211> LENGTH: 48
<212> TYPE: PRT
<213> ORGANISM: Homo sapiens

<400> SEQUENCE: 14

Ser Tyr Cys Glu Thr Trp Arg Thr Glu Ala Pro Ser Ala Thr Gly Gln
1               5                   10                  15

Ala Ser Ser Leu Leu Gly Gly Arg Leu Leu Gly Gln Ser Ala Ala Ser
            20                  25                  30

Cys His His Ala Tyr Ile Val Leu Ala Ile Glu Asn Ser Phe Met Thr
        35                  40                  45
```

```
<210> SEQ ID NO 15
<211> LENGTH: 84
<212> TYPE: PRT
<213> ORGANISM: artificial
<220> FEATURE:
<223> OTHER INFORMATION: amino acid sequence including a secretory
      sequence, a portion of human endostatin, and a peptide tag

<400> SEQUENCE: 15

Met Gly Lys Met Ala Ser Leu Phe Ala Thr Phe Leu Val Val Leu Val
1               5                   10                  15

Ser Leu Ser Leu Ala Ser Glu Ser Ala Ser Tyr Cys Glu Thr Trp
            20                  25                  30

Arg Thr Glu Ala Pro Ser Ala Thr Gly Gln Ala Ser Ser Leu Leu Gly
        35                  40                  45

Gly Arg Leu Leu Gly Gln Ser Ala Ala Ser Cys His His Ala Tyr Ile
    50                  55                  60

Val Leu Cys Ile Glu Asn Ser Phe Met Thr His His His His His His
65                  70                  75                  80

Lys Asp Glu Leu
```

```
<210> SEQ ID NO 16
<211> LENGTH: 306
<212> TYPE: PRT
<213> ORGANISM: artificial
<220> FEATURE:
<223> OTHER INFORMATION: E3-Fc amino acid sequence including a secretory
      sequence, a portion of human endostatin having a C67A mutation,
      and an IgG Fc domain

<400> SEQUENCE: 16
```

```
Met Gly Lys Met Ala Ser Leu Phe Ala Thr Phe Leu Val Leu Val
1               5                   10                  15

Ser Leu Ser Leu Ala Ser Glu Ser Ser Ala Ser Tyr Cys Glu Thr Trp
            20                  25                  30

Arg Thr Glu Ala Pro Ser Ala Thr Gly Gln Ala Ser Ser Leu Leu Gly
            35                  40                  45

Gly Arg Leu Leu Gly Gln Ser Ala Ala Ser Cys His His Ala Tyr Ile
50                  55                  60

Val Leu Ala Ile Glu Asn Ser Phe Met Thr Glu Pro Lys Ser Cys Asp
65                  70                  75                  80

Lys Thr His Thr Cys Pro Pro Cys Pro Ala Pro Glu Leu Leu Gly Gly
                85                  90                  95

Pro Ser Val Phe Leu Phe Pro Pro Lys Pro Lys Asp Thr Leu Met Ile
                100                 105                 110

Ser Arg Thr Pro Glu Val Thr Cys Val Val Val Asp Val Ser His Glu
            115                 120                 125

Asp Pro Glu Val Lys Phe Asn Trp Tyr Val Asp Gly Val Glu Val His
130                 135                 140

Asn Ala Lys Thr Lys Pro Arg Glu Glu Gln Tyr Asn Ser Thr Tyr Arg
145                 150                 155                 160

Val Val Ser Val Leu Thr Val Leu His Gln Asp Trp Leu Asn Gly Lys
                165                 170                 175

Glu Tyr Lys Cys Lys Val Ser Asn Lys Ala Leu Pro Ala Pro Ile Glu
                180                 185                 190

Lys Thr Ile Ser Lys Ala Lys Gly Gln Pro Arg Glu Pro Gln Val Tyr
                195                 200                 205

Thr Leu Pro Pro Ser Arg Asp Glu Leu Thr Lys Asn Gln Val Ser Leu
            210                 215                 220

Thr Cys Leu Val Lys Gly Phe Tyr Pro Ser Asp Ile Ala Val Glu Trp
225                 230                 235                 240

Glu Ser Asn Gly Gln Pro Glu Asn Asn Tyr Lys Thr Thr Pro Pro Val
                245                 250                 255

Leu Asp Ser Asp Gly Ser Phe Phe Leu Tyr Ser Lys Leu Thr Val Asp
                260                 265                 270

Lys Ser Arg Trp Gln Gln Gly Asn Val Phe Ser Cys Ser Val Met His
                275                 280                 285

Glu Ala Leu His Asn His Tyr Thr Gln Lys Ser Leu Ser Leu Ser Pro
                290                 295                 300

Gly Lys
305

<210> SEQ ID NO 17
<211> LENGTH: 104
<212> TYPE: PRT
<213> ORGANISM: artificial
<220> FEATURE:
<223> OTHER INFORMATION: amino acid sequence including a secretory
      sequence, a portion of collagen XVIII, a portion of human
      endostatin having a C67A mutation, and a peptide tag

<400> SEQUENCE: 17

Met Gly Lys Met Ala Ser Leu Phe Ala Thr Phe Leu Val Val Leu Val
1               5                   10                  15

Ser Leu Ser Leu Ala Ser Glu Ser Ser Ala Gln Lys Ser Val Trp His
            20                  25                  30

Gly Ser Asp Pro Asn Gly Arg Arg Leu Thr Glu Ser Tyr Cys Glu Thr
```

-continued

```
                 35                  40                  45
Trp Arg Thr Glu Ala Pro Ser Ala Thr Gly Gln Ala Tyr Ser Leu Leu
 50                  55                  60

Gly Gly Arg Leu Leu Gly Gln Ser Ala Ala Ser Cys His His Ala Tyr
 65                  70                  75                  80

Ile Val Leu Ala Ile Glu Asn Ser Phe Met Thr Ala Ser Lys His His
                 85                  90                  95

His His His His Lys Asp Glu Leu
                100

<210> SEQ ID NO 18
<211> LENGTH: 17
<212> TYPE: PRT
<213> ORGANISM: artificial
<220> FEATURE:
<223> OTHER INFORMATION: amino acid portion of collagen XVIII

<400> SEQUENCE: 18

Gln Lys Ser Val Trp His Gly Ser Asp Pro Asn Gly Arg Arg Leu Thr
 1               5                  10                  15

Glu

<210> SEQ ID NO 19
<211> LENGTH: 4
<212> TYPE: PRT
<213> ORGANISM: artificial
<220> FEATURE:
<223> OTHER INFORMATION: endoplasmic reticulum targeting sequence

<400> SEQUENCE: 19

Lys Asp Glu Leu
 1

<210> SEQ ID NO 20
<211> LENGTH: 48
<212> TYPE: PRT
<213> ORGANISM: artificial
<220> FEATURE:
<223> OTHER INFORMATION: E3 amino acid sequence

<400> SEQUENCE: 20

Ser Tyr Cys Glu Thr Trp Arg Thr Glu Ala Pro Ser Ala Thr Gly Gln
 1               5                  10                  15

Ala Ser Ser Leu Leu Gly Gly Arg Leu Leu Gly Gln Ser Ala Ala Ser
                20                  25                  30

Cys His His Ala Tyr Ile Val Leu Cys Ile Glu Asn Ser Phe Met Thr
                35                  40                  45

<210> SEQ ID NO 21
<211> LENGTH: 48
<212> TYPE: PRT
<213> ORGANISM: artificial
<220> FEATURE:
<223> OTHER INFORMATION: E4 amino acid sequence
<220> FEATURE:
<221> NAME/KEY: MISC_FEATURE
<222> LOCATION: (48)..(48)
<223> OTHER INFORMATION: carboxy-terminal amide

<400> SEQUENCE: 21

Ser Tyr Cys Glu Thr Trp Arg Thr Glu Ala Pro Ser Ala Thr Gly Gln
 1               5                  10                  15

Ala Ser Ser Leu Leu Gly Gly Arg Leu Leu Gly Gln Ser Ala Ala Ser
```

```
                    20                  25                  30
Cys His His Ala Tyr Ile Val Leu Cys Ile Glu Asn Ser Phe Met Thr
            35                  40                  45

<210> SEQ ID NO 22
<211> LENGTH: 302
<212> TYPE: PRT
<213> ORGANISM: artificial
<220> FEATURE:
<223> OTHER INFORMATION: E3_C67A-Fc_IgG2 fusion

<400> SEQUENCE: 22

Met Gly Lys Met Ala Ser Leu Phe Ala Thr Phe Leu Val Val Leu Val
1               5                   10                  15

Ser Leu Ser Leu Ala Ser Glu Ser Ser Ala Ser Tyr Cys Glu Thr Trp
            20                  25                  30

Arg Thr Glu Ala Pro Ser Ala Thr Gly Gln Ala Ser Ser Leu Leu Gly
            35                  40                  45

Gly Arg Leu Leu Gly Gln Ser Ala Ala Ser Cys His His Ala Tyr Ile
        50                  55                  60

Val Leu Ala Ile Glu Asn Ser Phe Met Thr Glu Arg Lys Cys Cys Val
65                  70                  75                  80

Glu Cys Pro Pro Cys Pro Ala Pro Pro Val Ala Gly Pro Ser Val Phe
                85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
        115                 120                 125

Gln Phe Asn Trp Tyr Val Asp Gly Val Glu Val His Asn Ala Lys Thr
    130                 135                 140

Lys Pro Arg Glu Glu Gln Phe Asn Ser Thr Phe Arg Val Val Ser Val
145                 150                 155                 160

Leu Thr Val Val His Gln Asp Trp Leu Asn Gly Lys Glu Tyr Lys Cys
                165                 170                 175

Lys Val Ser Asn Lys Gly Leu Pro Ala Pro Ile Glu Lys Thr Ile Ser
            180                 185                 190

Lys Thr Lys Gly Gln Pro Arg Glu Pro Gln Val Tyr Thr Leu Pro Pro
        195                 200                 205

Ser Arg Glu Glu Met Thr Lys Asn Gln Val Ser Leu Thr Cys Leu Val
    210                 215                 220

Lys Gly Phe Tyr Pro Ser Asp Ile Ser Val Glu Trp Glu Ser Asn Gly
225                 230                 235                 240

Gln Pro Glu Asn Asn Tyr Lys Thr Thr Pro Pro Met Leu Asp Ser Asp
                245                 250                 255

Gly Ser Phe Phe Leu Tyr Ser Lys Leu Thr Val Asp Lys Ser Arg Trp
            260                 265                 270

Gln Gln Gly Asn Val Phe Ser Cys Ser Val Met His Glu Ala Leu His
        275                 280                 285

Asn His Tyr Thr Gln Lys Ser Leu Ser Leu Ser Pro Gly Lys
    290                 295                 300

<210> SEQ ID NO 23
<211> LENGTH: 353
<212> TYPE: PRT
<213> ORGANISM: artificial
<220> FEATURE:
<223> OTHER INFORMATION: E3_C67A-Fc_IgG3 fusion
```

<400> SEQUENCE: 23

```
Met Gly Lys Met Ala Ser Leu Phe Ala Thr Phe Leu Val Val Leu Val
1               5                   10                  15

Ser Leu Ser Leu Ala Ser Glu Ser Ser Ala Ser Tyr Cys Glu Thr Trp
            20                  25                  30

Arg Thr Glu Ala Pro Ser Ala Thr Gly Gln Ala Ser Ser Leu Leu Gly
        35                  40                  45

Gly Arg Leu Leu Gly Gln Ser Ala Ala Ser Cys His His Ala Tyr Ile
    50                  55                  60

Val Leu Ala Ile Glu Asn Ser Phe Met Thr Glu Leu Lys Thr Pro Leu
65                  70                  75                  80

Gly Asp Thr Thr His Thr Cys Pro Arg Cys Pro Glu Pro Lys Ser Cys
                85                  90                  95

Asp Thr Pro Pro Pro Cys Pro Arg Cys Pro Glu Pro Lys Ser Cys Asp
            100                 105                 110

Thr Pro Pro Pro Cys Pro Arg Cys Pro Glu Pro Lys Ser Cys Asp Thr
        115                 120                 125

Pro Pro Pro Cys Pro Arg Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Gln Phe Lys Trp Tyr Val Asp Gly Val Glu Val His Asn
            180                 185                 190

Ala Lys Thr Lys Pro Arg Glu Glu Gln Tyr Asn Ser Thr Phe Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Thr Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Ser Gly Gln Pro Glu Asn Asn Tyr Asn Thr Thr Pro Pro Met Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Ile Phe Ser Cys Ser Val Met His Glu
                325                 330                 335

Ala Leu His Asn Arg Phe Thr Gln Lys Ser Leu Ser Leu Ser Pro Gly
            340                 345                 350

Lys
```

<210> SEQ ID NO 24
<211> LENGTH: 303
<212> TYPE: PRT
<213> ORGANISM: artificial
<220> FEATURE:
<223> OTHER INFORMATION: E3_C67A-Fc_IgG4 fusion

```
<400> SEQUENCE: 24

Met Gly Lys Met Ala Ser Leu Phe Ala Thr Phe Leu Val Val Leu Val
1               5                   10                  15

Ser Leu Ser Leu Ala Ser Glu Ser Ala Ser Tyr Cys Glu Thr Trp
            20                  25                  30

Arg Thr Glu Ala Pro Ser Ala Thr Gly Gln Ala Ser Ser Leu Leu Gly
            35                  40                  45

Gly Arg Leu Leu Gly Gln Ser Ala Ala Ser Cys His His Ala Tyr Ile
50                  55                  60

Val Leu Ala Ile Glu Asn Ser Phe Met Thr Glu Ser Lys Tyr Gly Pro
65                  70                  75                  80

Pro Cys Pro Ser Cys Pro Ala Pro Glu Phe Leu Gly Gly Pro Ser Val
                85                  90                  95

Phe Leu Phe Pro Pro Lys Pro Lys Asp Thr Leu Met Ile Ser Arg Thr
                100                 105                 110

Pro Glu Val Thr Cys Val Val Val Asp Val Ser Gln Glu Asp Pro Glu
                115                 120                 125

Val Gln Phe Asn Trp Tyr Val Asp Gly Val Glu Val His Asn Ala Lys
            130                 135                 140

Thr Lys Pro Arg Glu Glu Gln Phe Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Gly Leu Pro Ser Ser Ile Glu Lys Thr Ile
                180                 185                 190

Ser Lys Ala Lys Gly Gln Pro Arg Glu Pro Gln Val Tyr Thr Leu Pro
            195                 200                 205

Pro Ser Gln Glu Glu Met Thr Lys Asn Gln Val Ser Leu Thr Cys Leu
210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Arg Leu Thr Val Asp Lys Ser Arg
            260                 265                 270

Trp Gln Glu Gly Asn Val Phe Ser Cys Ser Val Met His Glu Ala Leu
            275                 280                 285

His Asn His Tyr Thr Gln Lys Ser Leu Ser Leu Ser Leu Gly Lys
            290                 295                 300

<210> SEQ ID NO 25
<211> LENGTH: 329
<212> TYPE: PRT
<213> ORGANISM: artificial
<220> FEATURE:
<223> OTHER INFORMATION: E3_C67A-Fc_IgA1 fusion

<400> SEQUENCE: 25

Met Gly Lys Met Ala Ser Leu Phe Ala Thr Phe Leu Val Val Leu Val
1               5                   10                  15

Ser Leu Ser Leu Ala Ser Glu Ser Ala Ser Tyr Cys Glu Thr Trp
            20                  25                  30

Arg Thr Glu Ala Pro Ser Ala Thr Gly Gln Ala Ser Ser Leu Leu Gly
            35                  40                  45

Gly Arg Leu Leu Gly Gln Ser Ala Ala Ser Cys His His Ala Tyr Ile
```

```
        50                  55                  60
Val Leu Ala Ile Glu Asn Ser Phe Met Thr Val Pro Cys Pro Val Pro
 65                  70                  75                  80

Ser Thr Pro Pro Thr Pro Ser Pro Ser Thr Pro Pro Thr Pro Ser Pro
                     85                  90                  95

Ser Cys Cys His Pro Arg Leu Ser Leu His Arg Pro Ala Leu Glu Asp
                    100                 105                 110

Leu Leu Leu Gly Ser Glu Ala Asn Leu Thr Cys Thr Leu Thr Gly Leu
                115                 120                 125

Arg Asp Ala Ser Gly Val Thr Phe Thr Trp Thr Pro Ser Ser Gly Lys
130                 135                 140

Ser Ala Val Gln Gly Pro Pro Glu Arg Asp Leu Cys Gly Cys Tyr Ser
145                 150                 155                 160

Val Ser Ser Val Leu Pro Gly Cys Ala Glu Pro Trp Asn His Gly Lys
                165                 170                 175

Thr Phe Thr Cys Thr Ala Ala Tyr Pro Glu Ser Lys Thr Pro Leu Thr
                180                 185                 190

Ala Thr Leu Ser Lys Ser Gly Asn Thr Phe Arg Pro Glu Val His Leu
            195                 200                 205

Leu Pro Pro Pro Ser Glu Glu Leu Ala Leu Asn Glu Leu Val Thr Leu
210                 215                 220

Thr Cys Leu Ala Arg Gly Phe Ser Pro Lys Asp Val Leu Val Arg Trp
225                 230                 235                 240

Leu Gln Gly Ser Gln Glu Leu Pro Arg Glu Lys Tyr Leu Thr Trp Ala
                245                 250                 255

Ser Arg Gln Glu Pro Ser Gln Gly Thr Thr Thr Phe Ala Val Thr Ser
            260                 265                 270

Ile Leu Arg Val Ala Ala Glu Asp Trp Lys Lys Gly Asp Thr Phe Ser
                275                 280                 285

Cys Met Val Gly His Glu Ala Leu Pro Leu Ala Phe Thr Gln Lys Thr
            290                 295                 300

Ile Asp Arg Leu Ala Gly Lys Pro Thr His Val Asn Val Ser Val Val
305                 310                 315                 320

Met Ala Glu Val Asp Gly Thr Cys Tyr
                325

<210> SEQ ID NO 26
<211> LENGTH: 316
<212> TYPE: PRT
<213> ORGANISM: artificial
<220> FEATURE:
<223> OTHER INFORMATION: E3_C67A-Fc_IgA2 fusion

<400> SEQUENCE: 26

Met Gly Lys Met Ala Ser Leu Phe Ala Thr Phe Leu Val Val Leu Val
 1               5                  10                  15

Ser Leu Ser Leu Ala Ser Glu Ser Ala Ser Tyr Cys Glu Thr Trp
                20                  25                  30

Arg Thr Glu Ala Pro Ser Ala Thr Gly Gln Ala Ser Ser Leu Leu Gly
            35                  40                  45

Gly Arg Leu Leu Gly Gln Ser Ala Ala Ser Cys His His Ala Tyr Ile
        50                  55                  60

Val Leu Ala Ile Glu Asn Ser Phe Met Thr Val Pro Cys Pro Val Pro
 65                  70                  75                  80

Pro Pro Pro Pro Cys Cys His Pro Arg Leu Ser Leu His Arg Pro Ala
```

```
              85                  90                  95
Leu Glu Asp Leu Leu Leu Gly Ser Glu Ala Asn Leu Thr Cys Thr Leu
            100                 105                 110

Thr Gly Leu Arg Asp Ala Ser Gly Ala Thr Phe Thr Trp Thr Pro Ser
            115                 120                 125

Ser Gly Lys Ser Ala Val Gln Gly Pro Pro Glu Arg Asp Leu Cys Gly
130                 135                 140

Cys Tyr Ser Val Ser Val Leu Pro Gly Cys Ala Gln Pro Trp Asn
145                 150                 155                 160

His Gly Glu Thr Phe Thr Cys Thr Ala Ala His Pro Glu Leu Lys Thr
                165                 170                 175

Pro Leu Thr Ala Asn Ile Thr Lys Ser Gly Asn Thr Phe Arg Pro Glu
                180                 185                 190

Val His Leu Leu Pro Pro Ser Glu Glu Leu Ala Leu Asn Glu Leu
            195                 200                 205

Val Thr Leu Thr Cys Leu Ala Arg Gly Phe Ser Pro Lys Asp Val Leu
            210                 215                 220

Val Arg Trp Leu Gln Gly Ser Gln Glu Leu Pro Arg Glu Lys Tyr Leu
225                 230                 235                 240

Thr Trp Ala Ser Arg Gln Glu Pro Ser Gln Gly Thr Thr Thr Phe Ala
                245                 250                 255

Val Thr Ser Ile Leu Arg Val Ala Ala Glu Asp Trp Lys Lys Gly Asp
                260                 265                 270

Thr Phe Ser Cys Met Val Gly His Glu Ala Leu Pro Leu Ala Phe Thr
                275                 280                 285

Gln Lys Thr Ile Asp Arg Met Ala Gly Lys Pro Thr His Val Asn Val
            290                 295                 300

Ser Val Val Met Ala Glu Val Asp Gly Thr Cys Tyr
305                 310                 315

<210> SEQ ID NO 27
<211> LENGTH: 422
<212> TYPE: PRT
<213> ORGANISM: artificial
<220> FEATURE:
<223> OTHER INFORMATION: E3_C67A-Fc_IgM fusion

<400> SEQUENCE: 27

Met Gly Lys Met Ala Ser Leu Phe Ala Thr Phe Leu Val Val Leu Val
1               5                   10                  15

Ser Leu Ser Leu Ala Ser Glu Ser Ala Ser Tyr Cys Glu Thr Trp
                20                  25                  30

Arg Thr Glu Ala Pro Ser Ala Thr Gly Gln Ala Ser Ser Leu Leu Gly
            35                  40                  45

Gly Arg Leu Leu Gly Gln Ser Ala Ala Ser Cys His His Ala Tyr Ile
50                  55                  60

Val Leu Ala Ile Glu Asn Ser Phe Met Thr Val Ile Ala Glu Leu Pro
65                  70                  75                  80

Pro Lys Val Ser Val Phe Val Pro Pro Arg Asp Gly Phe Phe Gly Asn
                85                  90                  95

Pro Arg Lys Ser Lys Leu Ile Cys Gln Ala Thr Gly Phe Ser Pro Arg
            100                 105                 110

Gln Ile Gln Val Ser Trp Leu Arg Glu Gly Lys Gln Val Gly Ser Gly
            115                 120                 125

Val Thr Thr Asp Gln Val Gln Ala Glu Ala Lys Glu Ser Gly Pro Thr
```

```
    130                 135                 140

Thr Tyr Lys Val Thr Ser Thr Leu Thr Ile Lys Glu Ser Asp Trp Leu
145                 150                 155                 160

Gly Gln Ser Met Phe Thr Cys Arg Val Asp His Arg Gly Leu Thr Phe
                165                 170                 175

Gln Gln Asn Ala Ser Ser Met Cys Val Pro Asp Gln Asp Thr Ala Ile
            180                 185                 190

Arg Val Phe Ala Ile Pro Pro Ser Phe Ala Ser Ile Phe Leu Thr Lys
        195                 200                 205

Ser Thr Lys Leu Thr Cys Leu Val Thr Asp Leu Thr Thr Tyr Asp Ser
    210                 215                 220

Val Thr Ile Ser Trp Thr Arg Gln Asn Gly Glu Ala Val Lys Thr His
225                 230                 235                 240

Thr Asn Ile Ser Glu Ser His Pro Asn Ala Thr Phe Ser Ala Val Gly
                245                 250                 255

Glu Ala Ser Ile Cys Glu Asp Asp Trp Asn Ser Gly Glu Arg Phe Thr
            260                 265                 270

Cys Thr Val Thr His Thr Asp Leu Pro Ser Pro Leu Lys Gln Thr Ile
        275                 280                 285

Ser Arg Pro Lys Gly Val Ala Leu His Arg Pro Asp Val Tyr Leu Leu
    290                 295                 300

Pro Pro Ala Arg Glu Gln Leu Asn Leu Arg Glu Ser Ala Thr Ile Thr
305                 310                 315                 320

Cys Leu Val Thr Gly Phe Ser Pro Ala Asp Val Phe Val Gln Trp Met
                325                 330                 335

Gln Arg Gly Gln Pro Leu Ser Pro Glu Lys Tyr Val Thr Ser Ala Pro
            340                 345                 350

Met Pro Glu Pro Gln Ala Pro Gly Arg Tyr Phe Ala His Ser Ile Leu
        355                 360                 365

Thr Val Ser Glu Glu Glu Trp Asn Thr Gly Glu Thr Tyr Thr Cys Val
    370                 375                 380

Ala His Glu Ala Leu Pro Asn Arg Val Thr Glu Arg Thr Val Asp Lys
385                 390                 395                 400

Ser Thr Gly Lys Pro Thr Leu Tyr Asn Val Ser Leu Val Met Ser Asp
                405                 410                 415

Thr Ala Gly Thr Cys Tyr
            420

<210> SEQ ID NO 28
<211> LENGTH: 163
<212> TYPE: PRT
<213> ORGANISM: artificial
<220> FEATURE:
<223> OTHER INFORMATION: J-Chain_PVX_sgp36

<400> SEQUENCE: 28

Met Gly Lys Met Ala Ser Leu Phe Ala Thr Phe Leu Val Val Leu Val
1               5                   10                  15

Ser Leu Ser Leu Ala Ser Glu Ser Ser Ala Gln Glu Asp Glu Arg Ile
            20                  25                  30

Val Leu Val Asp Asn Lys Cys Lys Cys Ala Arg Ile Thr Ser Arg Ile
        35                  40                  45

Ile Arg Ser Ser Glu Asp Pro Asn Glu Asp Ile Val Glu Arg Asn Ile
    50                  55                  60

Arg Ile Ile Val Pro Leu Asn Asn Arg Glu Asn Ile Ser Asp Pro Thr
```

```
                65                  70                  75                  80
Ser Pro Leu Arg Thr Arg Phe Val Tyr His Leu Ser Asp Leu Cys Lys
                    85                  90                  95

Lys Cys Asp Pro Thr Glu Val Glu Leu Asp Asn Gln Ile Val Thr Ala
                100                 105                 110

Thr Gln Ser Asn Ile Cys Asp Glu Asp Ser Ala Thr Glu Thr Cys Tyr
                115                 120                 125

Thr Tyr Asp Arg Asn Lys Cys Tyr Thr Ala Val Val Pro Leu Val Tyr
130                 135                 140

Gly Gly Glu Thr Lys Met Val Glu Thr Ala Leu Thr Pro Asp Ala Cys
145                 150                 155                 160

Tyr Pro Asp

<210> SEQ ID NO 29
<211> LENGTH: 306
<212> TYPE: PRT
<213> ORGANISM: artificial
<220> FEATURE:
<223> OTHER INFORMATION: IgG1_Fc-E3_C67A C-terminal fusion

<400> SEQUENCE: 29

Met Gly Lys Met Ala Ser Leu Phe Ala Thr Phe Leu Val Val Leu Val
1               5                   10                  15

Ser Leu Ser Leu Ala Ser Glu Ser Ala Glu Pro Lys Ser Cys Asp
                20                  25                  30

Lys Thr His Thr Cys Pro Pro Cys Pro Ala Pro Glu Leu Leu Gly Gly
                35                  40                  45

Pro Ser Val Phe Leu Phe Pro Pro Lys Pro Lys Asp Thr Leu Met Ile
50                  55                  60

Ser Arg Thr Pro Glu Val Thr Cys Val Val Val Asp Val Ser His Glu
65                  70                  75                  80

Asp Pro Glu Val Lys Phe Asn Trp Tyr Val Asp Gly Val Glu Val His
                85                  90                  95

Asn Ala Lys Thr Lys Pro Arg Glu Glu Gln Tyr Asn Ser Thr Tyr Arg
                100                 105                 110

Val Val Ser Val Leu Thr Val Leu His Gln Asp Trp Leu Asn Gly Lys
                115                 120                 125

Glu Tyr Lys Cys Lys Val Ser Asn Lys Ala Leu Pro Ala Pro Ile Glu
        130                 135                 140

Lys Thr Ile Ser Lys Ala Lys Gly Gln Pro Arg Glu Pro Gln Val Tyr
145                 150                 155                 160

Thr Leu Pro Pro Ser Arg Asp Glu Leu Thr Lys Asn Gln Val Ser Leu
                165                 170                 175

Thr Cys Leu Val Lys Gly Phe Tyr Pro Ser Asp Ile Ala Val Glu Trp
                180                 185                 190

Glu Ser Asn Gly Gln Pro Glu Asn Asn Tyr Lys Thr Thr Pro Pro Val
                195                 200                 205

Leu Asp Ser Asp Gly Ser Phe Phe Leu Tyr Ser Lys Leu Thr Val Asp
        210                 215                 220

Lys Ser Arg Trp Gln Gln Gly Asn Val Phe Ser Cys Ser Val Met His
225                 230                 235                 240

Glu Ala Leu His Asn His Tyr Thr Gln Lys Ser Leu Ser Leu Ser Pro
                245                 250                 255

Gly Lys Ser Tyr Cys Glu Thr Trp Arg Thr Glu Ala Pro Ser Ala Thr
                260                 265                 270
```

```
Gly Gln Ala Ser Ser Leu Leu Gly Gly Arg Leu Leu Gly Gln Ser Ala
            275                 280                 285

Ala Ser Cys His His Ala Tyr Ile Val Leu Ala Ile Glu Asn Ser Phe
        290                 295                 300

Met Thr
305
```

MATERIALS AND METHODS FOR PRODUCING ENDOSTATIN FUSION POLYPEPTIDES IN PLANT CELLS

CROSS-REFERENCE TO RELATED APPLICATIONS

This application is a 371 U.S. National Phase Application of PCT Application No. PCT/US2016/035858 filed on Jun. 3, 2016, which claims benefit of priority from U.S. Provisional Application No. 62/171,889, filed on Jun. 5, 2015, and U.S. Provisional Application No. 62/257,607, filed Nov. 19, 2015.

TECHNICAL FIELD

This document relates to materials and methods for treating fibrosis, and particularly to the use of polypeptides containing fragments and variants of endostatin for treating fibrosis.

BACKGROUND

Endostatin, a 183 amino acid proteolytic cleavage fragment corresponding to the C-terminus of collagen 18, has anti-tumor activity with no toxic side effects (O'Reilly et al. (1997) Cell, 88: 277-285; Kisker et al. (2001) Cancer Res, 61:7669-7674; Dhanabal et al. (1999) Cancer Res, 59: 189-197; Yoon et al. (1999) Cancer Res, 59: 6251-6256; Folkman and Kalluri, (2003) Cancer Medicine, 6th edition, pp. 161-194. Hamilton: B. C. Decker Inc.). A number of anti-angiogenic activities have been reported for this protein, such as inhibition of endothelial cell proliferation, migration, and tube formation. This activity has been localized to the N-terminal region of endostatin. Endostatin also suppresses vascular endothelial growth factor (VEGF)-induced vascular permeability (Takahashi et al. (2003) Faseb J, 17: 896-898). Endostatin inhibits endothelial cell migration by inhibiting phosphorylation of focal adhesion kinase via binding to α5β1 integrin (Wickstrom et al. (2002) Cancer Res, 62: 5580-5589). It also has been shown that cell surface glypicans are low-affinity endostatin receptors (Karumanchi et al. (2001) Mol Cell, 7: 811-822). Endostatin has been implicated in several signaling pathways, such as downregulation of c-myc (Shichiri and Hirata (2001) Faseb J, 15: 1044-1053), cyclin-D1 (Hanai et al. (2002) J Biol Chem, 277. 16464-16469) and RhoA activity (Wickstrom et al. (2003) J Biol Chem, 278: 37895-37901), blockage of VEGF signaling (Hajitou et al. (2002) Faseb J, 16: 1802-1804; Kim et al. (2002) J Biol Chem, 277: 27872-27879), and inhibition of the wnt-signaling pathway (Hanai et al. (2002) J Cell Biol, 158: 529-539). Further, endostatin has been shown to bind and inactivate metalloproteinases (Kim et al. (2000) Cancer Res, 60: 5410-5413; Nyberg et al. (2003) J Biol Chem, 278: 22404-22411; Lee et al. (2002) FEBS Lett, 519: 147-152) and to regulate a spectrum of genes which suppress angiogenesis (Abdollahi et al. (2004) Mol Cell, 13: 649-663).

The crystal structures of both murine and human endostatin have been resolved (Hohenester et al. (1998) Embo J, 17: 1656-1664; Ding et al. (1998) Proc Natl Acad Sci USA, 95: 10443-10448), and show a noncovalently held dimer at high concentration required for crystallization (Ding et al. (1998) Proc Natl Acad Sci USA, 95: 10443-10448). The presence of two disulfide bonds results in a highly folded structure. Endostatin binds one atom of zinc per monomer via three histidines in the N-terminus of the molecule (histidines 1, 3, and 11) and aspartic acid 76. The heparin binding property of endostatin is mediated by noncontiguous arginines clustered over the three dimensional globular surface of the molecule (Sasaki et al. (1999) Embo J, 18: 6240-6248).

Excessive deposition of extra cellular matrix (ECM) components such as fibronectin (FN) and type I collagen (Col1α1) by organ fibroblasts is defined as fibrosis. Organ fibrosis is the final common pathway for many diseases that result in end-stage organ failure. However, effective therapy for organ fibrosis is still unavailable (see, for example, Bjoraker et al., Am. J. Respir. Crit. Care. Med 2000; 157: 199-203). Uncontrollable wound-healing responses, including acute and chronic inflammation, angiogenesis, activation of resident cells, and ECM remodeling, are thought to be involved in the pathogenesis of fibrosis (Wynn, J Clin Invest 2007; 117:524-29; Kalluri et al., Curr Opin Nephrol Hypertension 2000; 9:413-8). TGF-β is the prototype fibrotic cytokine that is increased in fibrotic organs, and contributes to the development of fibrosis by stimulating the synthesis of ECM molecules, activating fibroblasts to α-smooth muscle actin (α-SMA)-expressing myofibroblasts, and downregulating matrix metalloproteinases (MMPs) (see, for example, Branton et al., Microbes Infect 1999; 1:1349-65). Despite high expectations, a clinical trial of a monoclonal anti-TGF-β antibody in patients with early systemic sclerosis (SSc) failed to show any efficacy (Varga et al., Nature Reviews Rheumatology 2009; 5:200-6). Thus, a need remains for other treatments of fibrosis.

SUMMARY

This document is based, at least in part, on the development of C-terminal endostatin fragments and variants thereof that have anti-fibrotic activity, as well as the development of methods for producing such fragments and variants in plants, and methods for using the fragments and variants to treat fibrosis in subjects in need thereof.

This document also is based, at least in part, on the discovery that an endostatin-based polypeptide containing the E3 region of endostatin (amino acids 133-180 of SEQ ID NO:2 and SEQ ID NO:13, for example) linked to an Ig-Fc polypeptide can form high molecular weight (HMW) multimers, unlike typical peptide-Fc fusion proteins. The HMW form can provide advantages in purification (e.g., by ultrafiltration or tangential flow filtration (TFF)), and may also be used in the treatment of fibrosis.

In one aspect, this document features an isolated polypeptide, wherein the polypeptide comprises SEQ ID NO:14 and has anti-fibrotic activity when administered to a subject in need thereof. The isolated polypeptide can further include a secretory sequence, a peptide tag (e.g., a 6His tag, a tag containing a KDEL (SEQ ID NO:19) polypeptide, or both), Ala-Ser-Lys sequence at the C-terminal end of SEQ ID NO:14, and/or an IgG Fc domain (e.g., an IgG1 Fc domain, such as a human IgG1 Fc domain), amino acids 27 to 43 of SEQ ID NO:17. The polypeptide can comprise SEQ ID NO:16 or SEQ ID NO:17. The polypeptide can be a high molecular weight multimer.

In another aspect, this document features an isolated polypeptide, wherein the polypeptide (a) comprises amino acids 133 to 180 of SEQ ID NO:2 and one or more of a secretory sequence, a peptide tag, a KDEL (SEQ ID NO:19) sequence, an Ala-Ser-Lys sequence at the C-terminal end of amino acids 133 to 180 of SEQ ID NO:2, an IgG Fc domain, and/or amino acids 27 to 43 of SEQ ID NO:17; and (b) has anti-fibrotic activity when administered to a subject in need thereof. The polypeptide can comprise SEQ ID NO:15.

In another aspect, this document features an isolated polypeptide, wherein the polypeptide (a) comprises amino acids 133 to 180 of SEQ ID NO:13 and one or more of a secretory sequence, a peptide tag, a KDEL (SEQ ID NO:19) sequence, an Ala-Ser-Lys sequence at the C-terminal end of amino acids 133 to 180 of SEQ ID NO:2, an IgG Fc domain, and/or amino acids 27 to 43 of SEQ ID NO:17; and (b) has anti-fibrotic activity when administered to a subject in need thereof.

In another aspect, this document features an isolated polynucleotide encoding a polypeptide as disclosed herein, where the polynucleotide is operably linked to a heterologous promoter. This document also features an expression vector containing the isolated polynucleotide. The expression vector can be a launch vector (e.g., a viral launch vector). In addition, this document features an *Agrobacterium tumefaciens* cell comprising the expression vector.

In another aspect, this document features a high molecular weight multimer comprising SEQ ID NO:14 and having anti-fibrotic activity when administered to a subject in need thereof.

In still another aspect, this document features a pharmaceutical composition containing (a) a polypeptide and/or multimers, as described herein, and (b) a pharmaceutically acceptable carrier.

This document also features a method for making a polypeptide having anti-fibrotic activity as disclosed herein. The method can include (a) introducing into a plant a plant viral vector that includes a polynucleotide encoding the polypeptide of claim 1, claim 12, claim 13, or claim 15 having antifibrotic activity; and (b) maintaining the plant under conditions and for a time sufficient that the polynucleotide is expressed in at least some plant cells. In some embodiments, the method can include (a) introducing into a plant (i) a carrier vector that includes a functional coat protein encoding component from a first plant virus, and (ii) a producer vector that includes a polynucleotide encoding the polypeptide having antifibrotic activity and at least one component from a second plant virus, but lacks a functional coat protein gene; or (i) a carrier vector that includes a functional movement protein encoding component from a first plant virus, and (ii) a producer vector that includes a polynucleotide encoding the polypeptide having antifibrotic activity and at least one component from a second plant virus but lacks a functional movement protein gene; or (i) a carrier vector that includes a functional coat protein encoding component from a first plant virus, and (ii) a producer vector that includes a polynucleotide encoding the polypeptide having antifibrotic activity and at least one component from a second plant virus but lacks one or more functional replication protein genes normally found in the second plant virus; (b) maintaining the plant under conditions and for a time sufficient to allow the carrier vector to complement the producer vector, so that the producer vector moves systemically in the plant; and (c) maintaining the plant under conditions and for a time sufficient that the polynucleotide is expressed in at least some plant cells.

The introducing step can include vacuum infiltration. The method can further include harvesting the plant, wherein the plant comprises the polypeptide having anti-fibrotic activity; extracting the polypeptide having anti-fibrotic activity from the plant; and/or purifying the polypeptide having anti-fibrotic activity.

In another aspect, this document features a method of treating a subject with fibrosis. The method can include selecting a subject with fibrosis, and administering to the subject a therapeutically effective amount of a polypeptide as described herein, thereby treating the subject with fibrosis. The subject can have a pulmonary fibrosis. The method can further include administering to the subject a therapeutically effective amount of another therapeutic agent (e.g., a therapeutic agent selected from the group consisting of corticosteroids, immunosuppressive agents, acetylcysteine, d-penicillamine, colchicine, Relaxin, steroids, cyclosporine, methotrexate, cyclophosphamide, azathioprine, mycophenolate, glitazones, endothelin receptor antagonists, and Fulvestrant). The corticosteroid can be prednisone. The immunosuppressive agent can be methotrexate or cyclosporine. The administering can include oral administration or intravenous administration.

In yet another aspect, this document features a composition comprising containing a pharmaceutically acceptable carrier and a polypeptide as described herein, wherein the composition is formulated for oral or intravenous administration to a subject. The polypeptide can include SEQ ID NO:15, SEQ ID NO:16, or SEQ ID NO:17.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A: FN and Col1α1 expression in human normal lung fibroblasts (NL) treated with vehicle (V), rE alone, or both with prior TGF-β stimulation. Proteins were detected with a Western blot. Glyceraldehyde e-phosphate dehydrogenase (GAPDH) was used as a loading control for lysates. FIG. 1B: FN and Col1α1 expression of endostatin polypeptide-treated lung fibroblasts following TGF stimulation in primary pulmonary fibroblasts from a healthy control, a patient with SSc, and a patient with IPF. FIG. 1C: Graphical summary of FN and Col1α1 expression in lung fibroblasts obtained using fibroblasts from 4 healthy controls (NL), 3 patients with SSc, and 3 patients with IPF. Intensity of bands was normalized to that of GAPDH and expressed as a ratio to Vehicle (V). Paired-t test was used for statistical analysis. *$P<0.04$, **$P<0.01$. FIG. 1D: Representative result of FN and Col1α1 levels in human skin fibroblasts obtained from a patient with morphea and a patient with SSc. FIG. 1E: Representative result of FN and Col1α1 expression in fibrotic fibroblasts obtained from a patients with IPF treated with V, 5 μg/ml of rE, or endostatin polypeptides alone (left). IPF fibroblasts were treated with different concentrations (5, 10, and 20 μg/ml) of E4. Dimethyl sulfoxide (DMSO) (V) was added in a volume equivalent to that in the lane corresponding to 20 μg/ml of E4 (right). FIG. 1F: α-SMA levels in normal lung fibroblasts treated with endostatin polypeptides following TGF-β stimulation.

FIG. 2A: Recombinant TGF-β or 1× phosphate buffered saline (PBS) (vehicle) was injected intradermally into human skin explants at a concentration of 1, 10, 50 ng/ml. Skin was harvested 1 week post-injection. Representative H&E (hematoxylin and eosin stain) images are shown in the upper row, and images of Masson trichrome-stained section are shown in the lower row. Magnification, 20×. FIG. 2B: Recombinant endostatin (rE) was injected into human skin at a concentration of 1, 5, 10 µg/ml. 1×PBS was used as a vehicle control (V). Representative H&E images are shown. Magnification, 20×. FIG. 2C: Endostatin polypeptides (E-1, E-2, E-3, and E-4; all at 10 µg/ml) were injected intradermally in human skin. DMSO was used as a vehicle control (V). Representative H&E images are shown. Magnification, 20×.

FIG. 3A: Representative H&E images of human skin injected with Vehicle, 10 ng/ml TGF-β alone, or rE (1, 5, and 10 µg/ml) in combination with TGF-β (10 ng/ml). Tissues were harvested one week post-injection. Magnification, 20×. FIG. 3B: Graphical presentation of dermal thickness. Data represent four independent experiments in triplicate using human skin explants from four different donors. Mann-Whitney U test was used for statistical analysis. *P<0.04.

FIG. 4A: Representative H&E images of human skin injected with Vehicle, 10 ng/ml TGF-β alone, or E-1, E-2, E-3, or E-4 (10 µg/ml) in combination with TGF-β (10 ng/ml). Magnification, 20×. FIG. 4B: Graphical presentation of dermal thickness data shown in FIG. 4A. Data represent two independent experiments using human skin explants from two donors, and each experiment was done in triplicate. Mann-Whitney U test was used for statistical analysis. *P<0.05, **P<0.02.

FIG. 5A: Representative H&E images of human skin injected with E-1 (upper row) or E-4 (lower row) at a concentration of 1, 5, 10, and 20 µg/ml in the presence of TGF-β (10 ng/ml). Magnification, 20×. FIG. 5B: Graphical analysis of dermal thickness data shown in FIG. 5A. DMSO was used as a vehicle control. Experiments were conducted in duplicate, and dermal thickness was measured in 6 fields from each section. Mann-Whitney U test was used for statistical analysis. *P<0.02, **P<0.01.

FIG. 6A: Mice were injected intradermally with vehicle, 10 ng/ml TGF-β alone, or E-1, E-2, E-3, and E-4 (10 µg/ml) in combination with TGF-β (10 ng/ml). Skin was harvested after 1 week post-injection. Sections were stained with H&E. Magnification, 20×. FIG. 6B: Graphical summary of dermal thickness data shown in FIG. 6A. Data represent four independent experiments, each done in duplicate. Mann-Whitney U test was used for statistical analysis. *P<0.04, **P<0.01.

FIG. 7A: Representative images of MATRIGEL® cultures of HUVECs treated with vehicle, rE (50 nM), or E4 (50 nM). An equivalent amount of DMSO was used as vehicle. Magnification 40×. FIG. 7B: Image quantification of the cord formation shown in FIG. 7A. Data shown summarize results of three independent experiments. *P<0.05, one-way ANOVA followed by Bonferroni's test.

FIG. 8A: Mice were injected subcutaneously with 1×PBS as vehicle (V) or Bleomycin (Bleo; 20 µg/mouse) daily. E-4 (10 µg/ml) was mixed with bleomycin on the first day, and daily bleomycin administration was continued without subsequent injections of E4 (Bleo+E-4). Skin was harvested after 10 days. Sections were stained with H&E. Magnification, 100×. FIG. 8B: Graphical summary of dermal thickness data shown in FIG. 8A. Data represent three independent experiments. Mann-Whitney U test was used for statistical analysis. *P<0.001, **P<0.00001. E4 administration caused a significant attenuation of bleomycin induced dermal fibrosis even with a single administration of E4.

FIG. 10A: Sixty µg of bleomycin was administrated intratracheally in combination with DMSO as a vehicle (Bleo) or E-4 (Bleo+E-4; 10 µg/ml). In some mice, E-4 (10 µg/ml) was administered intratracheally (IT) three days following bleomycin treatment (Bleo+E-4L). PBS was used as a vehicle for bleomycin (V). Lungs were harvested 10 days post-treatment. Representative images stained with H&E (left panel) and Masson trichrome (right panel) are representative of 3 independent experiments. Magnification, 100×. E4 administered concomitantly with bleomycin or three days following bleomycin caused a marked reduction in fibrosis and Masson Trichrome staining. FIG. 10B: Quantification of acid soluble collagen obtained from mouse lungs treated with V. Bleo, Bleo+E-4, and Bleo+E-4L. The levels of collagen are presented as µg/mg (lung) from three independent experiments. Unpaired-t test was used for statistical analysis. *P<0.05. E4 polypeptide given 3 days after bleomycin significantly reduced collagen levels in mouse lungs. FIG. 10C: Lower magnification (2×) of mouse lung shown in FIG. 9 (BLM+E4/E4L IT day 10). For Bleo+E4L, Bleo was administered first, then there was a lag of three days between Bleo and E4 administration).

FIG. 14A: E4 reduces fibrosis in vitro by inducing MMP-2 activity in primary human lung fibroblasts, thus resulting in increased degradation of collagen and other matrix proteins. Digital image of a gelatin zymography gel showing increased MMP-2 activity when primary human lung fibroblasts are treated with E-4 following TGF-β (lane 4). Lane 1: Vehicle (DMSO); Lane 2: E-4; Lane 3: TGF-β; Lane 4: TGF-β followed by E4. FIG. 14B: Digital image showing that both total and active MMP-2 levels are increased in cells treated with TGF-β and E-4. This suggests E-4 increases levels of MMP-2 pro-enzyme, but also increases levels of active matrix metalloproteinase (MMP-2, also called metalloprotease-2).

FIG. 17A: Vehicle (DMSO), E-1, or E-4 (10 mg/ml) was additionally injected to human skin 2 days post-administration of 10 ng/ml TGF-β (V, E-1L and E-4L, respectively). Representative H&E images of human skin were shown. Magnification, 20×. FIG. 17B: Graphical presentation of dermal thickness data shown in A. Data represent two independent experiments using human skin explants from two donors, and each experiment was done in duplicate. Mann-Whitney U test was used for statistical analysis. *P<0.01.

FIG. 21. Intravenous dosing of E3-Fc is comparable to oral administration.

FIG. 22. Intravenous E3-Fc has the potential to reverse lung fibrosis.

FIG. 25. Human IgA1, IgA2, and IgM Fc fusions to E3 are insoluble or poorly expressed.

FIG. 26. Amino acid sequences of E3-Fc (SEQ ID NO:16), E3 (SEQ ID NO:20), and E4 (SEQ ID NO:21).

SEQUENCE LISTING

Figure 1A:
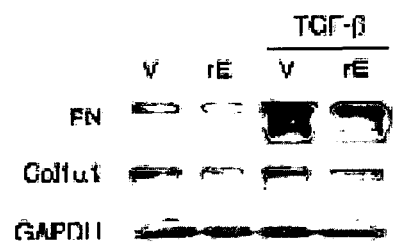
FIGS. 1A-1F. ECM production in recombinant endostatin (rE)- and endostatin-derived peptide-treated fibroblasts in combination with TGF-β stimulation.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-84102-03 Sequence Listing.txt, Apr. 4, 2012, 12.5 kilobytes], which is incorporated by reference herein. In the accompanying sequence listing:

SEQ ID NO:1 is an exemplary nucleic acid sequence encoding human endostatin.

SEQ ID NO:2 is the amino acid sequence of human endostatin.

SEQ ID NO:3 is an exemplary nucleic acid sequence encoding mouse endostatin.

SEQ ID NO:4 is the amino acid sequence of mouse endostatin.

SEQ ID NO:5 is an exemplary nucleic acid sequence encoding a human immunoglobulin (Ig)G1 protein.

SEQ ID NO:6 is the amino acid sequence of a human IgG1 protein.

SEQ ID NO:7 is an exemplary nucleic acid sequence encoding a linker.

SEQ ID NO:8 is an amino acid sequence of a linker.

SEQ ID NO:9 is a portion of the rat endostatin polypeptide.

SEQ ID NO:10 is a portion of the cow endostatin polypeptide.

SEQ ID NO:11 is a portion of the human collagen XV polypeptide.

SEQ ID NO:12 is an exemplary nucleic acid sequence encoding an endostatin.

SEQ ID NO:13 is an amino acid sequence of an exemplary endostatin polypeptide that differs from SEQ ID NO:2 by three amino acid substitutions.

SEQ ID NO:14 (SYCETWRTEAPSATGQASSLLG-GRLLGQSAASCHHAY IVLAIENSFMT) is a portion of human endostatin having a C→A mutation at the underlined position.

SEQ ID NO:15 is an exemplary amino acid sequence including a secretory sequence, a portion of human endostatin, and a peptide tag.

SEQ ID NO:16 is an exemplary amino acid sequence including a secretory sequence, a portion of human endostatin having a C67A mutation, and an IgG Fc domain.

SEQ ID NO:17 is an exemplary amino acid sequence including a secretory sequence, a portion of collagen XVIII, a portion of human endostatin having a C67A mutation, and a peptide tag.

SEQ ID NO:18 (QKSVWHGSDPNGRRLTE) is a 17 amino acid portion of collagen XVIII.

SEQ ID NO:19 is a four-amino acid endoplasmic reticulum targeting sequence.

SEQ ID NO:20 is the amino acid sequence of the E3 portion of human endostatin.

SEQ ID NO:21 is the amino acid sequence of the E4 portion of human endostatin.

SEQ ID NO:22 is the amino acid sequence of an E3_C67A-Fc_IgG2 fusion.

SEQ ID NO:23 is the amino acid sequence of an E3_C67A-Fc_IgG3 fusion.

SEQ ID NO:24 is the amino acid sequence of an E3_C67A-Fc_IgG4 fusion.

SEQ ID NO:25 is the amino acid sequence of an E3_C67A-Fc_IgA1 fusion.

SEQ ID NO:26 is the amino acid sequence of an E3_C67A-Fc_IgA2 fusion.

SEQ ID NO:27 is the amino acid sequence of an E3_C67A-Fc_IgM fusion.

SEQ ID NO:28 is the amino acid sequence of the J-Chain_ PVX_sgp36.

SEQ ID NO:29 is the amino acid sequence of an IgG1_Fc-E3_C67A C-terminal fusion.

DETAILED DESCRIPTION

C-terminal endostatin polypeptides are provided herein. In some embodiments, these polypeptides include, consist essentially of, or consist of (1) at least 40 consecutive amino acids of the amino acid sequence set forth as amino acids 133-180 of SEQ ID NO:13 or SEQ ID NO:2; (2) at least 40 consecutive amino acids of the amino acid sequence set forth as amino acids 133-180 of SEQ ID NO:13 or SEQ ID NO:2, with at most 5 amino acid substitutions, (3) the amino acid sequence set forth as amino acids 133-180 of SEQ ID NO:13 or SEQ ID NO:2; (4) the amino acid sequence set forth as amino acids 133-180 of SEQ ID NO:13 or SEQ ID NO:2 with at most 5 amino acid substitutions; or (5) the amino acid sequence set forth as SEQ ID NO:14; wherein the polypeptide has anti-fibrotic activity and wherein the polypeptide does not include amino acids 1-92 of SEQ ID NO:13 or SEQ ID NO:2. In some embodiments, the polypeptide is amidated at the C-terminus. Methods of making these polypeptides also are provided. In some embodiments, the polypeptides can be produced in plants. In addition, polynucleotides encoding the polypeptides, host cells transformed with the polynucleotides, and methods of using the polypeptides and polynucleotides are provided. The methods can include the treatment of fibrosis in a subject. For example, methods are provided for treating fibrotic conditions of the lung and the skin, as well as other organs (e.g., liver cirrhosis, corneal fibrosis, and kidney fibrosis). In some embodiments, the anti-fibrotic C-terminal endostatin polypeptides disclosed herein can selectively inhibit fibrosis. In some examples, fibrosis is inhibited without inhibiting angiogenesis. Thus, the C-terminal endostatin polypeptides can be used to more specifically and selectively target unwanted fibrosis, without interfering with angiogenesis, to achieve a desired therapeutic outcome.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Amidation or amide derivative: A post-translational modification to form an amide that can enhance the biological activity of the polypeptide. In amidation, the C-terminal amino acid (polypeptide-COOH) is modified to form an amide (polypeptide-$CONH_2$). The amide may be formed by post-translational C-terminal amidation. The amino acid to be modified can be followed by a glycine, which provides the amide group. The process of post-translational amidation of a polypeptide derived from a precursor proprotein is well characterized and involves three enzymatic steps (Cuttitta, *The Anatomical Record*, 236:87-93, 1993). Step one involves endoproteolytic cleavage at a pair of basic amino acids near the carboxy terminus of the protein. Step two involves carboxypeptidase-mediated removal of basic residues. Step three is the amidation reaction, which involves oxidation of a terminal glycine to form the amide of the neighboring carboxy terminal amino acid. Glycine is the only known amino acid to function as an amide donor for its neighboring amino acid. Although the free acid and amidated forms of a polypeptide are difficult to distinguish structurally, the amide can be 100-1000 times more biologically active than the free acid form of the polypeptide (Cuttitta, *The Anatomical Record*, 236:87-93, 1993). C-terminal amidation is essential to the biological activity of many polypeptides.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Collagen: Proteins that are found in the form of elongated fibrils in mammals that are mostly found in fibrous tissues such as tendon, ligament and skin, and is also abundant in cornea, cartilage, bone, blood vessels, the gut, and intervertebral disc. The tropocollagen or "collagen molecule" is a subunit of larger collagen aggregates such as fibrils. It is approximately 300 nm long and 1.5 nm in diameter, made up of three polypeptide strands (called alpha chains), each possessing the conformation of a left-handed helix. In type I collagen, each triple-helix associates into a right-handed super-super-coil that is referred to as the collagen microfibril. Endostatin is the first 183 amino acids of collagen.

Conservative variants: "Conservative" amino acid substitutions are those substitutions that do not substantially affect or decrease an activity of a C-terminal endostatin polypeptide, such as the ability of the polypeptide to inhibit fibrosis. Specific, non-limiting examples of conservative substitutions include the following:

| Original Residue | Conservative Substitution(s) |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity, such as the ability of a protein to inhibit fibrosis.

Consists Essentially Of/Consists Of: With regard to a polypeptide, a polypeptide that consists essentially of a specified amino acid sequence does not include any additional amino acid residues. However, the polypeptide can include additional non-peptide components, such as labels (for example, fluorescent, radioactive, or solid particle labels), sugars or lipids, that do not materially affect the basic and novel characteristics of the polypeptide. A polypeptide that consists of a specified amino acid sequence does not include any additional amino acid residues, nor does it include additional biological components, such as nucleic acids lipids, sugars, nor does it include labels. A polypeptide that consists or consists essential of a specified amino acid sequence can be glycosylated or have an amide modification. With regard to a polynucleotide, a polynucleotide that consists essentially of a specified nucleic acid sequence does not include any additional nucleic acid residues. However, the polynucleotide can include additional non-nucleic acid components, such as labels (for example, fluorescent, radioactive, or solid particle labels) or polypeptides, that do not materially affect the basic and novel characteristic(s)" of the polynucleotides. A polynucleotide that consists of a specified nucleic acid sequence does not include any additional nucleic acid residues, nor does it include additional biological components or labels.

Degenerate variant: A polynucleotide encoding a C-terminal endostatin polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the C-terminal endostatin polypeptide encoded by the nucleotide sequence is unchanged.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Meth Enzymol* 153:516-544, 1987). For example, when cloning in bacterial systems, inducible promoters such as pL of bacteriophage lambda, plac, ptrp, ptac (ptrp-lac hybrid promoter) and the like can be used. In some embodiments, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Endostatin: A 183 amino acid proteolytic cleavage fragment corresponding to the C-terminus of collagen XVIII. C-terminal polypeptides of endostatin include consecutive amino acids from the C-terminal region, which is from amino acid 93 to amino acid 183. Exemplary human endostatin polypeptides are set forth in SEQ ID NO:2 and SEQ ID NO:13.

Fibrosis: The formation or development of excess fibrous connective tissue in an organ or tissue as a reparative or reactive process, as opposed to a formation of fibrous tissue as a normal constituent of an organ or tissue. Skin and lungs are susceptible to fibrosis. Exemplary fibrotic conditions are scleroderma idiopathic pulmonary fibrosis, morphea, fibrosis as a result of Graft-Versus-Host Disease (GVHD), keloid and hypertrophic scar, and subepithelial fibrosis, endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and multifocal fibrosclerosis.

Heterologous: Originating from separate genetic sources or species. A polypeptide that is heterologous to endostatin originates from a nucleic acid that does not encode endostatin. In specific, non-limiting examples, a polypeptide containing a C-terminal endostatin polypeptide and a heterologous amino acid sequence includes an Ig (such as IgG1) β-galactosidase, a maltose binding protein, and albumin, hepatitis B surface antigen, or an immunoglobulin amino acid sequence. Generally, an antibody that specifically binds to a protein of interest such as endostatin will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Idiopathic Pulmonary Fibrosis: A condition also known as cryptogenic fibrosing alveolitis (CFA) that is a chronic, progressive form of lung disease characterized by fibrosis of the supporting framework (interstitium) of the lungs. By definition, the term is used only when the cause of the pulmonary fibrosis is unknown ("idiopathic"). When lung tissue from patients with IPF is examined under a microscope by a pathologist, it shows a characteristic set of histologic/pathologic features known as usual interstitial pneumonia (UIP). UIP is characterized by progressive scarring of both lung that involves the supporting framework (interstitium) of the lung.

Inhibiting or treating a disease: Inhibiting a disease, such as fibrosis, refers to inhibiting the full development of a disease. In several examples, inhibiting a disease refers to lessening symptoms of a fibrosis, such as the formation of scar tissue or an increase in range of motion or a decrease in pain. "Treatment" refers to a therapeutic intervention that ameliorates a sign or symptom of a disease or pathological condition related to the disease, such as the fibrosis.

Isolated: An "isolated" biological component (such as a nucleic acid or protein or organelle) has been substantially separated or purified away from other biological components in the cell of the organism in which the component naturally occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Keloid or keloidal scar: A type of scar, which depending on its maturity, is composed of mainly either type III (early) or type I (late) collagen. It is a result of an overgrowth of granulation tissue (collagen type 3) at the site of a healed skin injury which is then slowly replaced by collagen type 1. Keloids are firm, rubbery lesions or shiny, fibrous nodules, and can vary from pink to flesh-colored or red to dark brown in color. A keloid scar is benign, non-contagious, and usually accompanied by severe itchiness, sharp pains, and changes in texture. In severe cases, it can affect movement of skin. Keloids are different than hypertrophic scars, which are raised scars that do not grow beyond the boundaries of the original wound.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker sequence: A linker sequence is an amino acid sequence that covalently links two polypeptide domains. Linker sequences can be included in the between the C-terminal endostatin polypeptides disclosed herein to provide rotational freedom to the linked polypeptide domains and thereby to promote proper domain folding and presentation to the MHC. By way of example, in a recombinant polypeptide containing two C-terminal endostatin polypeptides, linker sequences can be provided between them, such as a poly peptide containing C-terminal endostatin polypeptide-linker-C-terminal endostatin polypeptide. Linker sequences, which are generally between 2 and 25 amino acids in length, are well known in the art and include, but are not limited to, the glycine(4)-serine spacer (×3) described by Chaudhary et al., *Nature* 339:394-397, 1989.

Lysyl oxidase (LOX): Lysyl oxidase is an extracellular copper enzyme that catalyzes formation of aldehydes from lysine residues in collagen and elastin precursors. These aldehydes are highly reactive, and undergo spontaneous chemical reactions with other lysyl oxidase-derived aldehyde residues, or with unmodified lysine residues. This results in cross-linking collagen and elastin, which is essential for stabilization of collagen fibrils and for the integrity and elasticity of mature elastin.

Mammal: This term includes both human and non-human mammals. Similarly, the term "subject" includes both human and veterinary subjects.

Matrix metalloproteinase-2: A 72 kDa type IV collagenase also known as gelatinase A. Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis. Most MMP's are secreted as inactive proproteins which are activated when cleaved by extracellular proteinases. MMP-2 degrades type IV collagen, the major structural component of basement membranes. MMP-2 also degrades additional substrates such as native and denatured collagen I and fibronectin (see the clip.ubc.ca/archive/mmp_timp_folder/mmp_substrates.shtm website).

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a polypeptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence, such as a sequence that encodes a C-terminal endostatin polypeptide. Generally, operably linked DNA sequences are contiguous and, where necessary to join two protein-coding regions, in the same reading frame.

Peptide Modifications: C-terminal endostatin polypeptides include synthetic embodiments of polypeptides described herein. In addition, analogs (non-peptide organic molecules), derivatives (chemically functionalized polypeptide molecules obtained starting with the disclosed polypeptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified polypeptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the polypeptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the polypeptide side chains may be converted to $C_1$-$C_{16}$ alkoxy or to a $C_1$-$C_{16}$ ester using well-recognized techniques. Phenyl and phenolic rings of the polypeptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the polypeptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the polypeptide backbone and component amino acid side chains, resulting in such peptido- and organomimetics of C-terminal endostatin polypeptide having measurable or enhanced ability to treat fibrosis. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition to achieve a desired effect in a subject being treated. For instance, this can be the amount necessary to induce an immune response, inhibit fibrosis, reduce scar volume, or measurably alter outward symptoms of the fibrotic condition. When administered to a subject, a dosage will generally be used that will achieve target tissue concentrations (for example, in skin cells or lung tissue) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Peptide or Polypeptide: Any chain of amino acids, regardless of length or post-translational modification (e.g., glycosylation or phosphorylation). In some embodiments, the polypeptide is a C-terminal endostatin polypeptide. A polypeptide can be between 5 and 60 amino acids in length. In some embodiments, a polypeptide is from about 10 to about 55 amino acids in length. In yet another embodiment, a polypeptide is from about 20 to about 50 amino acids in length. In yet another embodiment, polypeptide is about 50 amino acids in length. With regard to polypeptides, the word "about" indicates integer amounts. Thus, in one example, a polypeptide "about" 50 amino acids in length is from 49 to 51 amino acids in length. In some embodiments, a polypeptide can be in multimeric form. For example, a polypeptide can be a high molecular weight multimer that includes a plurality of endostatin fragments and/or fusions as described herein. A high molecular weight multimer can have a molecular weight greater than 500 kDa, for example, (e.g., 500 to 750 kDa, 750 kDa to 1 mega-Dalton (MDa), 1 to 1.5 MDa, 1.5 to 2 MDa, 2 to 2.5 MDa, or 2.5 to 3 MDa).

Post-translational modification: The modification of a newly formed protein; may involve deletion of amino acids, chemical modification of certain amino acids (for example, amidation, acetylation, phosphorylation, glycosylation, formation of pyroglutamate, oxidation/reduction of sulfa group on a methionine, or addition of similar small molecules) to certain amino acids.

Probes and primers: A probe includes an isolated nucleic acid attached to a detectable label or reporter molecule. Primers are short nucleic acids, preferably DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by polymerase chain reaction (PCR) or other nucleic-acid amplification methods known in the art. One of skill in the art will appreciate that the specificity of a particular probe or primer increases with its length. Thus, for example, a primer containing 20 consecutive nucleotides will anneal to a target with a higher specificity than a corresponding primer of only 15 nucleotides. Thus, in order to obtain greater specificity, probes and primers can be selected that contain about 20, 25, 30, 35, 40, 50 or more consecutive nucleotides.

Purified: The C-terminal endostatin polypeptides disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982). Substantial purification denotes purification from other proteins or cellular components. A substantially purified protein is at least about 60%, 70%, 80%, 90%, 95%, 98% or 99% pure. Thus, in one specific, non-limiting example, a substantially purified protein is 90% free of other proteins or cellular components.

Thus, the term purified does not require absolute purity; rather, it is intended as a relative term. For example, a purified nucleic acid is one in which the nucleic acid is more enriched than the nucleic acid in its natural environment within a cell. In additional embodiments, a nucleic acid or cell preparation is purified such that the nucleic acid or cell represents at least about 60% (such as, but not limited to, 70%, 80%, 90%, 95%, 98% or 99%) of the total nucleic acid or cell content of the preparation, respectively.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids. e.g., by genetic engineering techniques.

Scleroderma: A chronic autoimmune disease characterized by fibrosis (or hardening), vascular alterations, and autoantibodies. There are two major forms, one is a systemic form that includes limited cutaneous scleroderma mainly affects the hands, arms and face, although pulmonary hypertension is frequent. Diffuse cutaneous scleroderma (or systemic sclerosis) is rapidly progressing and affects a large area of the skin and one or more internal organs, frequently the kidneys, esophagus, heart and lungs. Systemic scleroderma in both of its forms can be fatal. The other form of scleroderma is a localized form that has two subtypes: morphea and linear scleroderma. The disclosed endostatin peptides can be used to treat any form of scleroderma.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a C-terminal endostatin polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a C-terminal endostatin polypeptide are typically characterized by possession of at least 75%, for example at least 80%, sequence identity counted over the full length alignment with the amino acid sequence of endostatin using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the interne. One of skill in the art will appreciate that these sequence identity ranges are provided for guidance only; it is entirely possible that strongly significant homologs could be obtained that fall outside of the ranges provided.

Therapeutically effective amount: A quantity of compound, such as the C-terminal endostatin polypeptide sufficient to achieve a desired effect in a subject being treated. For instance, this can be the amount necessary to treat or ameliorate fibrosis, such as skin or lung fibrosis, in a subject. In some embodiments, it is the amount necessary to treat a subject by a measurable amount over a period of time, or to measurably inhibit progression of disease, in a subject. In other embodiments, a therapeutically effective amount is the amount necessary to prophylactically inhibit a disease.

An effective amount of a C-terminal endostatin polypeptide may be administered in a single dose, or in several doses, for example daily, during a course of treatment. However, the effective amount will be dependent on the compound applied, the subject being treated, the severity and type of the affliction, and the manner of administration of the compound.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells and insect cells.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or peptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

C-Terminal Endostatin Polypeptide

C-terminal endostatin polypeptides and variants thereof are disclosed herein. The polypeptides can inhibit fibrosis present in fibrotic conditions such as, without limitation, scleroderma. The polypeptides contain a C-terminal amino acid sequence of an endostatin protein, but do not include full length endostatin. The endostatin protein can be a mammalian protein, such as from a human, a non-human primate, a canine, a feline, an equine, a bovine, an ovine, a sheep, or a rodent (e.g., mouse or rat). An exemplary nucleotide sequence encoding human endostatin (the amino acid sequence set forth as SEQ ID NO:2) is:

```
                                         (SEQ ID NO: 1)
ATGCACAGCC ACCGCGACTT CCAGCCGGTG CTCCACCTGG

TTGCGCTCAA CAGCCCCCTG TCAGGCGGCA TGCGGGGCAT

CCGCGGGGCC GACTTCCAGT GCTTCCAGCA GGCGCGGGCC

GTGGGGCTGG CGGGCACCTT CCGCGCCTTC CTGTCCTCGC

GCCTGCAGGA CCTGTACAGC ATCGTGCGCC GTGCCGACCG

CGCAGCCGTG CCCATCGTCA ACCTCAAGGA CGAGCTGCTG

TTTCCCAGCT GGGAGGCTCT GTTCTCAGGC TCTGAGGGTC

CGCTGAAGCC CGGGGCACGC ATCTTCTCCT TTAACGGCAA

GGACGTCCTG ACCCACCCCA CCTGGCCCCA GAAGAGCGTG

TGGCATGGCT CGGACCCCAA CGGGCGCAGG CTGACCGAGA

GCTACTGTGA GACGTGGCGG ACGGAGGCTC CCTCGGCCAC

GGGCCAGGCC TACTCGCTGC TGGGGGGCAG GCTCCTGGGG

CAGAGTGCCG CGAGCTGCCA TCACGCCTAC ATCGTGCTAT

GCATTGAGAA CAGCTTCATG ACTGCCTCCA AGTAG
```

See also GENBANK® Accession Nos. NM030582.3; NM130444.2; NM130445.2, all of which are incorporated herein by reference.

Another exemplary nucleotide sequence encoding a human endostatin (the amino acid sequence set forth as SEQ ID NO:13) is:

```
                                         (SEQ ID NO: 12)
CACAGCCACCGC GACTTCCAGC CGGTGCTCCACCTGGTTGCG

CTCAACAGCC CCCTGTCAGG CGGCATGCGG GGCATCCGCG

GGGCCGACTTCCAGTGCTTC CAGCAGGCGC GGGCCGTGGG

GCTGGCGGGC ACCTTCCGCG CCTTCCTGTC CTCGCGCCTG

CAGGACCTGT ACAGCATCGT GCGCCGTGCC GACCGCGCAG

CCGTGCCCATCGTCAACCTC AAGGACGAGC TGCTGTTTCC
```

-continued
```
CAGCTGGGAG GCTCTGTTCT CAGGCTCTGA GGGTCCGCTG

AAGCCCGGGG CACGCATCTT CTCCTTTGAC GGCAAGGACG

TCCTGAGGCA CCCCACCTGG CCCCAGAAGA GCGTGTGGCA

TGGCTCGGAC CCCAACGGGC GCAGGCTGAC CGAGAGCTAC

TGTGAGACGT GGCGGACGGA GGCTCCCTCG GCCACGGGCC

AGGCCTCCTC GCTGCTGGGG GGCAGGCTCC TGGGGCAGAG

TGCCGCGAGC TGCCATCACG CCTACATCGT GCTCTGCATT

GAGAACAGCT TCATGACTGC CTCCAAGTAG
```

The exemplary human endostatin polypeptide sequence encoded by SEQ ID NO:1 is:

```
                                            (SEQ ID NO: 2)
HSHRDFQPVL HLVALNSPLS GGMRGIRGAD FQCFQQARAV

GLAGTFRAFL SSRLQDLYSI VRRADRAAVP IVNLKDELLF

PSWEALFSGS EGPLKPGARI FSFNGKDVLT HPTWPQKSVW

HGSDPNGRRL TESYCETWRT EAPSATGQAY SLLGGRLLGQ

SAASCHHAYI VLCIENSFMTASK
```

This protein is 183 amino acids in length, and is identical to GENBANK® Accession number AAF01310 except that it is lacking the initiator methionine of AAF01310).

The exemplary human endostatin polypeptide sequence encoded by SEQ ID NO:12 is:

```
                                            (SEQ ID NO: 13)
HSHRDFQPVL HLVALHSPLS GGMRGIRGAD FQCFQQARAV

GLAGTFRAFL SSRLQDLYSI VRRADRAAVP IVNLKDELLF

PSWEALFSGS EGPLKPGARI FSFDGKDVLR HPTWPQKSVW

HGSDPNGRRL TESYCETWRT EAPSATGQAS SLLGGRLLGQ

SAASCHHAYI VLCIENSFMTASK
```

See also GENBANK® Accession No, CAB90482, which is incorporated herein by reference.

SEQ ID NO:2 is identical to SEQ ID NO:13, with the exception of three amino acid substitutions, indicated by underlining in SEQ ID NOS:2 and 13 above.

An exemplary nucleotide sequence encoding mouse endostatin is:

```
                                            (SEQ ID NO: 3)
CATACTCATC AGGACTTTCA GCCAGTGCTC CACCTGGTGG

CACTGAACAC CCCCCTGTCT GGAGGCATGC GTGGTATCCG

TGGAGCAGAT TTCCAGTGCT TCCAGCAAGC CCGAGCCGTG

GGGCTGTCGG GCACCTTCCG GGCTTTCCTG TCCTCTAGGC

TGCAGGATCT CTATAGCATC GTGCGCCGTG CTGACCGGGG

GTCTGTGCCC ATCGTCAACC TGAAGGACGA GGTGCTATCT

CCCAGCTGGG ACTCCCTGTT TTCTGGCTCC CAGGGTCAAC

TGCAACCCGG GGCCCGCATC TTTTCTTTTG ACGGCAGAGA

TGTCCTGAGA CACCCAGCCT GGCCGCAGAA GAGCGTATGG

CACGGCTCGG ACCCCAGTGG GCGGAGGCTG ATGGAGAGTT

ACTGTGAGAC ATGGCGAACT GAAACTACTG GGGCTACAGG

TCAGGCCTCC TCCCTGCTGT CAGGCAGGCT CCTGGAACAG

AAAGCTGCGA GCTGCCACAA CAGCTACATC GTCCTGTGCA

TTGAGAATAG CTTCATGACC TCTTTCTCCA AA
```

The exemplary mouse endostatin polypeptide sequence encoded by SEQ ID NO:3 is:

```
                                            (SEQ ID NO: 4)
HTHQDFQPVL HLVALNTPLS GGMRGIRGAD FQCFQQARAV

GLSGTFRAFL SSRLQDLYSI VRRADRGSVP IVNLKDEVLS

PSWDSLFSGS QGQLQPGARI FSFDGRDVLR HPAWPQKSVW

HGSDPSGRRL MESYCETWRT ETTGATGQAS SLLSGRLLEQ

KAASCHNSYI VLCIENSFMT SFSK
```

This protein is identical to GENBANK® Accession number AAF69009. Endostatin nucleotide and amino acid sequences from other species also are publicly available.

In some embodiments, the C-terminal endostatin polypeptide contains about 10 to about 60 consecutive amino acids of the C-terminal region of an endostatin protein, but does not include a full length endostatin protein, or the N-terminal region of an endostatin protein. The peptide can include from about 10 to about 55 consecutive amino acids or from about 20 to about 54 consecutive amino acids of the C-terminal region of an endostatin protein, such as about 53 consecutive amino acids of the C-terminal region of an endostatin protein (such as SEQ ID NO:2). For example, the peptide may include about 40, about 45, about, 46, about 47, about 48, about 49, about 50, about 51, about 52 or about 53 consecutive amino acids of the C-terminal region of an endostatin protein, such as amino acids 93 to 183 of an endostatin sequence such as SEQ ID NO:2, SEQ ID NO:13, or SEQ ID NO:4. In the context of an amino acid or nucleic acid sequence, "about" means within one residue (one more or one less than the specified number).

The endostatin peptide can include 40, 45, 46, 47, 48, 49, 50, 51, 52, 53, 40-45, 45-50, or 50-55 consecutive amino acids of the C-terminal region of an endostatin protein. In some examples the peptide consists of 40, 45, 46, 47, 48, 49, 50, 51, 52, 53 consecutive amino acids of the C-terminal region of an endostatin polypeptide such as, without limitation, SEQ ID NO:2, SEQ ID NO:4, or SEQ ID NO:13. In some embodiments, the peptide includes or consists of at least 30 amino acids of amino acids 133 to 180 of endostatin, or a variant thereof that has anti-fibrotic activity.

The endostatin peptide may include, consist of, or consist essentially of about amino acid 120, 125, 130, 131, 132, 133, 134, or 135 to about amino acid 175, 180, 181, 182 or 183 of an endostatin protein, such as SEQ ID NO:2, SEQ ID NO:4, or SEQ ID NO:13. In some examples, the peptide includes, consists of, or consists essentially of amino acid 120 to 183, 125 to 183, 130 to 183, 131 to 183, 132 to 183, 134 to 183, 135 to 183, 120 to 180, 125 to 180, 130 to 180, 131 to 180, 132 to 180, 133 to 180, 134 to 180, or 135 to 180 of SEQ ID NO:2, SEQ ID NO:4, or SEQ ID NO:13. In specific examples, the peptide includes, consists of, or consists essentially of amino acids 133-180 of SEQ ID NO:2, amino acids 133-180 of SEQ ID NO:4, amino acids 133-180 of SEQ ID NO:13. In this context, "consists essentially of" means that a peptide does not include additional amino acid residues but can include additional components, such as a label.

Other endostatin peptide variants disclosed herein may comprise, consist of or consist essentially of an amino acid sequence that has at least about 70%, 80%, 90%, 95%, 98% or 99% identity or homology with a C-terminal endostatin polypeptide. C-terminal endostatin polypeptides do not include a full length endostatin protein or the N-terminal region of an endostatin protein (such as amino acids 1-92 of SEQ ID NO:2).

In some non-limiting examples, C-terminal endostatin polypeptides can include substitutions, such as conservative amino acid substitutions, in a naturally occurring C-terminal endostatin polypeptide (see SEQ ID NO:2, 4, or 13) in at most about 1, 2, 3, 4, 5 substitutions would be expected to retain anti-fibrotic activity. The C-terminal endostatin polypeptide can include at most 1, at most 2, at most 3 or at most 4 amino acid substitutions, such as conservative amino acid substitutions.

Polypeptides that are similar to the sequences described above may contain substitutions, deletions or additions. The differences can be, for example, in regions of the polypeptide that are not significantly conserved among different species. Such regions can be identified by aligning the amino acid sequences of endostatin proteins from various animal species. Thus, the endostatin peptide can include, consist essentially of, or consist of at least 40, at least 45, at least 46, at least 47, at least 48, at least 50, at least 51, at least 52, or all of the amino acids set forth as amino acids 133-180 of SEQ ID NO:2, SEQ ID NO:4, or SEQ ID NO:13. Alternatively, the endostatin peptide can include at most 1, 2, 3, 4, or 5 amino acid substitutions in one of these sequences, provided the peptide has anti-fibrotic activity. The peptide can be 40, 45, 46, 47, 48, 49, 50, 51, 52, 53, 40-45, 45-50, or 50-55 amino acids in length. The peptide does not include the entire sequence of endostatin, or the N-terminal region, such as of SEQ ID NO:2, SEQ ID NO:4, or SEQ ID NO:13. In additional embodiments, the peptide is at most 40, 45, 46, 47, 48, 49, 50, 51, 52, or 53 amino acids in length, such as peptide that is 40, 45, 46, 47, 48, 49, 50, 51, 52, or 53 amino acids in length.

In some embodiments, the peptide is modified, such as to include a C-terminal amide. Any of the C-terminal endostatin polypeptides disclosed herein can include a C-terminal amide.

C-terminal endostatin polypeptides include three cysteine residues in the amino acid 133-180 of endostatin. Without being bound by theory, it is believed that two of the three cysteine residues participate in forming an intramolecular disulfide bridge which is important to the tertiary structure of the peptide. The third cysteine residue may participate in intermolecular interactions. In some embodiments, C-terminal endostatin polypeptides can include a cysteine modification. The cysteine modification may be substituted with any amino acid. In some embodiments, the cysteine modification can be a cysteine to alanine substitution. Without being bound by theory, it is believed that substitution of a cysteine with an alanine (e.g., C67A) can enhance solubility of a C-terminal endostatin polypeptide as described herein. An exemplary C-terminal endostatin polypeptide having a cysteine to alanine substitution is set forth in SEQ ID NO:14.

The following is an alignment of the human (amino acids 133-180), mouse, rat, and cow collagen XVIII endostatin amino acid sequences, and human collagen XV:

| SEQ ID: | |
|---|---|
| Human | SYCETWRTE*EAPS*ATGQASSLL*G*GRLL*GQ*S*AAS*CH*HA*YIVLCIENSFMT<br>SYCETWRTE   ATGQASSLL GRLL Q AASCH +YIVLCIENSFMT |
| Mouse | SYCETWRTE*TTG*ATGQASSLL*S*GRLL*EQ*K*AASCH*NS*YIVLCIENSFMT |
| Rat | SYCETWRTE*ATGV*TGQASSLL*S*GRLL*EQ*KA*E*SCH*NS*YIVLCIENSFMT |
| Cow | SYCETWRT*DSRA*ATGQASSLL*A*GRLL*EQ*KAA*G*CH*NR*F*TVLCIENSFMT |
| HumXV | N<u>YC</u>EAWRTADTAVTGLASPLSTGKILDQKAYSCANRL<u>IVLCIENSFMT</u> |

Amino acids 133-141, 145-153, 155-158, 162-166, and 169-180 are conserved between the endostatin sequences (second line above). For the full human endostatin sequence, see SEQ ID NO:2; for the full mouse endostatin sequence, see SEQ ID NO:4; for the full rat endostatin sequence, see SEQ ID NO:9; and for the full cow endostatin sequence, see SEQ ID NO:10. The full human collagen XV is provided as SEQ ID NO:11.

In some embodiments, the amino acids in the second line of the above alignment show regions of SEQ ID NO:2, SEQ ID NO:4, or SEQ ID NO:13 that can be conserved to preserve anti-fibrotic activity of the polypeptide. In further embodiments, the underlined amino acids should be retained in order to preserve anti-fibrotic activity of the polypeptide. Thus, in some embodiments, the C-terminal endostatin polypeptide includes amino acids 133-141, 145-153, 155-158, 162-166 and 169-180 of SEQ ID NO:2, SEQ ID NO:4 or SEQ ID NO:13. In some embodiments, the A at position 145 is conserved.

The polypeptide referred to herein as E4 is amino acids 133-180 of human endostatin (see amino acids 133-180 of SEQ ID NO:2) with a C-terminal amide. In some embodiments, a region that can be retained in the peptide to retain anti-fibrotic activity includes one or both potential phosphorylation sites in the first seven amino acids of E4 that are conserved: SYCE and TWR (amino acids 1-4 and 5-7 of E4, respectively, see also amino acids 133-136 and 137-139 of SEQ ID NO:2 or SEQ ID NO:13). In some embodiments, regions that can be retained in the peptide to retain anti-fibrotic activity include one or both potential myristoylation sites: GQaySL and GQsaAS (amino acids 15-20 and 27-32 of E4, respectively, see amino acids 147-152 and amino acids 159-164 of SEQ ID NO:2 or SEQ ID NO:13). Thus, in some embodiments, the C-terminal endostatin polypeptide includes zero, or at most 1, at most 2, at most 3, at most 4, or at most 5 substitutions in amino acids 133-180 of SEQ ID NO:2, SEQ ID NO:4, or SEQ ID NO:13, wherein the substitutions are not within amino acids 133-141, 145-153, 155-158, 162-166, and 169-180 of SEQ ID NO:2, SEQ ID NO:4, or SEQ ID NO:13, and includes a C-terminal amide.

In other embodiments, amino acids can be substituted that differ between the human and mouse sequences without affecting anti-fibrotic activity. In other embodiments, the bolded and italicized amino acids shown above in the human sequence are those amino acids that can be substituted while preserving anti-fibrotic activity. For example, amino acids 142-144, 154, 159-161, and 181-183 of the amino acid sequence can be altered in the C-terminal endostatin polypeptide. These amino acids can be substituted, for example, with those found in another species, as shown above (SEQ ID NOs: 9-10). For example, the C-terminal endostatin polypeptide can include amino acids 133-180 of SEQ ID NO:2 or SEQ ID NO:13, wherein amino acids 142-144, 154, and amino acids 159-161 are substituted. This polypeptide can include a C-terminal amide.

Other amino acids that can be substituted, inserted or deleted at these or other locations can be identified by mutagenesis studies coupled with biological assays. The above alignment is provided only as a guideline.

Also encompassed herein are multimers of polypeptides containing C-terminal endostatin polypeptides (e.g., E3), including fusion polypeptides as described below. In some embodiments, a multimer can be a dimer, trimer, or tetramer, each comprising a C-terminal endostatin fragment.

Also encompassed herein are C-terminal endostatin polypeptides that are fused to a heterologous peptide, such as a peptide that can be used for detecting, purifying, stabilizing, or solubilizing the endostatin polypeptide. These polypeptides do not include a full length endostatin protein or an N-terminal region of an endostatin protein. In some embodiments, a C-terminal polypeptide can be linked to an immunoglobulin (Ig) constant heavy or light chain domain or portion thereof at its N-terminus. For example, a polypeptide such as, without limitation, amino acids 133-180 of SEQ ID NO:2, SEQ ID NO:4, SEQ ID NO:13 (e.g., E4), or SEQ ID NO:14 may be linked to a CH1, CH2 and/or CH3 domain of a heavy chain. If the constant region is from a light chain, it can be from a kappa or lambda light chain. If the constant region is from a heavy chain, it can be from an antibody of any one of the following classes of antibodies: IgG, IgA, IgE, IgD, and IgM. IgG can be an IgG1, IgG2, IgG3 or IgG4. The constant domain may be an Fc fragment. The constant domain can be from a mammalian antibody, such as a human antibody. Soluble receptor-IgG fusion proteins are common immunological reagents and methods for their construction are known in the art (see, for example, U.S. Pat. Nos. 5,225,538, 5,726,044; 5,707,632; 750,375, 5,925,351, 6,406,697 and Bergers et al. Science 1999 284: 808-12). In one example, the immunoglobulin is the constant part of the heavy chain of human IgG, particularly IgG1, where dimerization between two heavy chains takes place at the hinge region. It is recognized that inclusion of the CH2 and CH3 domains of the Fc region as part of the fusion polypeptide increases the in vivo circulation half-life of the polypeptide comprising the Fc region, and that of the oligomer or dimer comprising the polypeptide.

An Fc portion of human IgG1 which includes the hinge region, and domains CH2 and CH3 has the nucleotide sequence:

(SEQ ID NO: 5)
GAG CCC AAA TCT TGT GAC AAA ACT CAC ACA TGC CCA

CCG TGC CCA GCA CCT GAA CTC CTG GGG GGA CCG TCA

GTC TTC CTC TTC CCC CCA AAA CCC AAG GAC ACC CTC

ATG ATC TCC CGG ACC CCT GAG GTC ACA TGC GTG GTG

GTG GAC GTG AGC CAC GAA GAC CCT GAG GTC AAG TTC

AAC TGG TAC GTG GAC GGC GTG GAG GTG CAT AAT GCC

AAG ACA AAG CCG CGG GAG GAG CAG TAC AAC AGC ACG

TAC CGT GTG GTC AGC GTC CTC ACC GTC CTG CAC CAG

GAC TGG CTG AAT GGC AAG GAG TAC AAG TGC AAG GTC

TCC AAC AAA GCC CTC CCA GCC CCC ATC GAG AAA ACC

ATC TCC AAA GCC AAA GGG CAG CCC CGA GAA CCA CAG

GTG TAC ACC CTG CCC CCA TCC CGG GAT GAG CTG ACC

AAG AAC CAG GTC AGC CTG ACC TGC CTG GTC AAA GGC

TTC TAT CCC AGC GAC ATC GCC GTG GAG TGG GAG AGC

AAT GGG CAG CCG GAG AAC AAC TAC AAG ACC ACG CCT

CCC GTG CTG GAC TCC GAC GGC TCC TTC TTC CTC TAC

AGC AAG CTC ACC GTG GAC AAG AGC AGG TGG CAG CAG

GGG AAC GTC TTC TCA TGC TCC GTG ATG CAT GAG GCT

CTG CAC AAC CAC TAC ACG CAG AAG AGC CTC TCC CTG

TCT CCG GGT AAA TGA, which encodes a polypeptide having the amino acid sequence:

(SEQ ID NO: 6)
Glu Pro Lys Ser Cys Asp Lys Thr His Thr Cys Pro

Pro Cys Pro Ala Pro Glu Leu Leu Gly Gly Pro Ser

Val Phe Leu Phe Pro Pro Lys Pro Lys Asp Thr Leu

Met Ile Ser Arg Thr Pro Glu Val Thr Cys Val Val

Val Asp Val Ser His Glu Asp Pro Glu Val Lys Phe

Asn Trp Tyr Val Asp Gly Val Glu Val His Asn Ala

Lys Thr Lys Pro Arg Glu Glu Gln Tyr Asn Ser Thr

Tyr Arg Val Val Ser Val Leu Thr Val Leu His Gln

Asp Trp Leu Asn Gly Lys Glu Tyr Lys Cys Lys Val

Ser Asn Lys Ala Leu Pro Ala Pro Ile Glu Lys Thr

Ile Ser Lys Ala Lys Gly Gln Pro Arg Glu Pro Gln

Val Tyr Thr Leu Pro Pro Ser Arg Asp Glu Leu Thr

Lys Asn Gln Val Ser Leu Thr Cys Leu Val Lys Gly

Phe Tyr Pro Ser Asp Ile Ala Val Glu Trp Glu Ser

Asn Gly Gln Pro Glu Asn Asn Tyr Lys Thr Thr Pro

Pro Val Leu Asp Ser Asp Gly Ser Phe Phe Leu Tyr

Ser Lys Leu Thr Val Asp Lys Ser Arg Trp Gln Gln

Gly Asn Val Phe Ser Cys Ser Val Met His Glu Ala

Leu His Asn His Tyr Thr Gln Lys Ser Leu Ser Leu

Ser Pro Gly Lys

Constant Ig domains can also contain one or more mutations that reduce or eliminate one or more effector function, e.g., binding to Fc receptors and complement activation (see, for example, Morrison, *Annu. Rev. Immunol.,* 10, pp. 239-65 (1992); Duncan and Winter (1988) *Nature* 332: 738-740; and Xu et al. (1994) *J Biol. Chem.* 269: 3469-3474). For example, mutations of amino acids corresponding to Leu 235 and Pro 331 of human IgG1 to Glu and Ser respectively, are provided. Such constructs are further described in U.S. Pat. No. 6,656,728.

The C-terminal endostatin polypeptide can also be linked to a linker sequence with a thrombin cleavage site, such as between the C-terminal endostatin polypeptide and a heterologous polypeptide. An exemplary nucleotide sequence encoding such a site has the following nucleotide sequence: 5' TCT AGA GGT GGT CTA GTG CCG CGC GGC AGC GGT TCC CCC GGG TTG CAG 3' (SEQ ID NO:7), which encodes a polypeptide having the amino acid sequence: Ser Arg Gly Gly Leu Val Pro Arg Gly Ser Gly Ser Pro Gly Leu Gln (SEQ ID NO:8). A C-terminal endostatin polypeptide can also be fused to a signal sequence. For example, when prepared recombinantly, a nucleic acid encoding the peptide can be linked at its 5' end to a signal sequence, such that the peptide is secreted from the cell.

Peptides can be used as a substantially pure preparation, such as wherein at least about 90% of the peptides in the preparation are the desired peptide. Compositions comprising at least about 50%, 60%, 70%, or 80% of the desired peptide may also be used. Peptides can be denatured or non-denatured and may be aggregated or non-aggregated as a result thereof.

Other C-terminal endostatin polypeptides that are encompassed herein are those that include modified amino acids. Exemplary peptides are derivative peptides that may be one modified by glycosylation, pegylation, phosphorylation or any similar process that retains at least one biological function of the peptide from which it was derived. Peptides may also comprise one or more non-naturally occurring amino acids. For example, nonclassical amino acids or chemical amino acid analogs can be introduced as a substitution or addition into peptides. Non-classical amino acids include, but are not limited to, the D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, fluoro-amino acids, designer amino acids such as beta-methyl amino acids, Calpha-methyl amino acids, Nalpha-methyl amino acids, and amino acid analogs in general. In some embodiments, substitution with selenomethionine can be useful (e.g., for X-ray diffraction analysis). Further, the amino acid can be D (dextrorotary) or L (levorotary). In other specific embodiments, branched versions of the peptides listed herein are provided, such as by substituting one or more amino acids within the sequence with an amino acid or amino acid analog with a free side chain capable of forming a peptide bond with one or more amino acids (and thus capable of forming a "branch"). Cyclical peptides are also contemplated.

Also included are peptide derivatives which are differentially modified during or after synthesis, such as by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus.

In one example, the peptide includes a carboxy terminal amide. One specific non-limiting example of this type of C-terminal endostatin polypeptide is E4 (see, for example, amino acids 133-180 of SEQ ID NO:13), which is described in detail in the examples section below. This peptide, or any of the C-terminal endostatin polypeptides disclosed herein can be amidated at the C-terminus.

Also provided are derivatives of C-terminal endostatin polypeptides, such as chemically modified peptides and peptidomimetics. Peptidomimetics are compounds based on, or derived from, peptides and proteins. Peptidomimetics can be obtained by structural modification of known peptide sequences using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptides.

Mimetopes of the C-terminal endostatin polypeptides are included in the present disclosure. Such peptidomimetics can have such attributes as being non-hydrolyzable (e.g., increased stability against proteases or other physiological conditions which degrade the corresponding peptide), increased specificity and/or potency for stimulating cell differentiation. For illustrative purposes, peptide analogs can be generated using, for example, benzodiazepines (e.g., see Freidinger et al. in *Peptides: Chemistry and Biology,* G. R. Marshall ed., ESCOM Publisher: Leiden, Netherlands, 1988), substituted gamma lactam rings (Garvey et al. in *Peptides: Chemistry and Biology,* G. R. Marshall ed., ESCOM Publisher: Leiden, Netherlands, 1988, p 123), C-7 mimics (Huffman et al. in *Peptides: Chemistry and Biology,* G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1: 1231), β-aminoalcohols (Gordon et al. (1985) *Biochem Biophys Res Commun* 126:419; and Dann et al. (1986) *Biochem Biophys Res Commun* 134:71), diaminoketones (Nataraj an et al. (1984) *Biochem Biophys Res Commun* 124:141), and methyleneamino-modified (Roark et al. in *Peptides: Chemistry and Biology,* G. R. Marshall ed., ESCOM Publisher: Leiden, Netherlands, 1988, p 134). Also, see generally, Session III: Analytic and synthetic methods, in *Peptides: Chemistry and Biology,* G. R. Marshall ed., ESCOM Publisher: Leiden, Netherlands, 1988).

In addition to a variety of side-chain replacements which can be carried out to generate peptidomimetics, the present disclosure specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides. Additionally, peptidomimetics based on more substantial modifications of the backbone of a peptide can be used. Peptidomimetics which fall in this category include (i) retro-inverso analogs, and (ii) N-alkyl glycine analogs (so-called peptoids). Furthermore, the methods of combinatorial chemistry can be used to produce peptidomimetics. For example, some embodiments of a so-called "peptide morphing" strategy focus on the random generation of a library of peptide analogs that comprise a wide range of peptide bond substitutes. In an exemplary embodiment, the peptidomimetic can be derived as a retro-inverso analog of the peptide. Such retro-inverso analogs can be made according to the methods known in the art, such as that described by the Sisto et al. U.S. Pat. No. 4,522,752. A retro-inverso analog can be generated as described, for example in PCT Publication No. WO 00/01720. A mixed peptide, such as one including some normal peptide linkages, can be generated. As a general guide, sites which are most susceptible to proteolysis are typically altered, with less susceptible amide linkages being optional for mimetic switching. The final product, or intermediates thereof, can be purified by HPLC.

In some embodiments, peptides can include at least one amino acid or every amino acid that is a D stereoisomer. Other peptides can include at least one amino acid that is reversed. The amino acid that is reversed may be a D stereoisomer. Every amino acid of a peptide may be reversed and/or every amino acid can be a D stereoisomer. In another illustrative embodiment, a peptidomimetic can be derived as a retro-enantio analog of a peptide. Retro-enantio analogs such as this can be synthesized with commercially available D-amino acids (or analogs thereof) and standard solid- or solution-phase peptide-synthesis techniques, as described, for example in PCT Publication No. WO 00/01720. The final product can be purified by HPLC to yield the pure retro-enantio analog. In still another illustrative embodiment, trans-olefin derivatives can be made for the subject peptide. Trans-olefin analogs can be synthesized according to the method of Shue et al. (1987) *Tetrahedron Letters* 28:3225 and as described in PCT Publication WO 00/01720. It is further possible to couple pseudodipeptides synthesized by the above method to other pseudodipeptides, to make peptide analogs with several olefinic functionalities in place of amide functionalities. Still another class of peptidomimetic derivatives include the phosphonate derivatives. The synthesis of such phosphonate derivatives can be adapted from known synthesis schemes (see, for example, Loots et al. in *Peptides: Chemistry and Biology*, (Escom Science Publishers, Leiden, 1988, p. 118)); Petrillo et al. in *Peptides: Structure and Function* (Proceedings of the 9th American Peptide Symposium, Pierce Chemical Co. Rockland, Ill., 1985).

Many other peptidomimetic structures are known in the art and can be readily adapted for use in the subject peptidomimetics. For example, a peptidomimetic may incorporate the 1-azabicyclo[4.3.0]nonane surrogate (see Kim et al. (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analogue (see Williams et al. (1996) *J. Med. Chem.* 39:1345-1348). In still other embodiments, certain amino acid residues can be replaced with aryl and bi-aryl moieties, such as monocyclic or bicyclic aromatic or heteroaromatic nucleus, or a biaromatic, aromatic-heteroaromatic, or biheteroaromatic nucleus. The subject peptidomimetics can be optimized such as by combinatorial synthesis techniques combined with high throughput screening. Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of inhibiting fibrosis. A mimetope can also be obtained, for example, from libraries of natural and synthetic compounds, in particular, chemical or combinatorial libraries (e.g., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (for example, plants, animals, bacteria and fungi).

All of the C-terminal endostatin polypeptides of use in the disclosed methods have anti-fibrotic activity. For example, they can reduce or inhibit fibrosis by a factor of at least about 50%, 60%, 70% 80%, 90%, or 2 fold, 5 fold, 10 fold, 30 fold or 100 fold, as compared to a control, such as in an assay described herein.

The C-terminal endostatin polypeptides (including amidated forms of the peptides) can be readily synthesized by automated solid phase procedures well known in the art. Techniques and procedures for solid phase synthesis are described in *Solid Phase Peptide Synthesis: A Practical Approach*, by E. Atherton and R. C. Sheppard, published by IRL, Oxford University Press, 1989. Alternatively, these peptides may be prepared by way of segment condensation, as described, for example, in Liu et al., Tetrahedron Lett. 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116:4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). Other methods useful for synthesizing peptides of the present disclosure are described in Nakagawa et al., *J. Am. Chem. Soc.* 107:7087-7092, 1985. Peptides of the disclosure can also be readily purchased from commercial suppliers of synthetic peptides. Such suppliers include, for example, Advanced ChemTech (Louisville, Ky.), Applied Biosystems (Foster City, Calif.), Anaspec (San Jose, Calif.), and Cell Essentials (Boston, Mass.).

Polynucleotides Encoding the C-Terminal Endostatin Polypeptides and Host Cells

Polynucleotides encoding the C-terminal endostatin polypeptides disclosed herein are also provided. These polynucleotides include DNA, cDNA and RNA sequences which encode the peptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, *Biochemistry*, 3.sup.rd Edition, W. H. 5 Freeman and Co., NY).

A nucleic acid encoding a C-terminal endostatin polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., Cold Spring Harbor Symp. Quant. Biol. 51:263, 1987; and Erlich, ed., PCR Technology, (Stockton Press, NY, 1989). Polynucleotides also can be isolated by screening genomic or cDNA libraries with probes selected from the sequences of the desired polynucleotide under stringent hybridization conditions.

The polynucleotides encoding a C-terminal endostatin polypeptide include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

In some embodiments, vectors are used for expression in yeast such as S. cerevisiae or Kluyveromyces lactis. Several promoters are known to be of use in yeast expression systems such as the constitutive promoters plasma membrane H+-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on K. lactis are known, such as pKLAC1. Thus, in one example, after amplification in bacteria, plasmids can be introduced into the corresponding yeast auxotrophs by methods similar to bacterial transformation. The polynucleotides can also be designed to express in insect cells.

The C-terminal endostatin polypeptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the C-terminal endostatin polypeptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Natl. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol. 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol. 40:2189-2199), Sindbis viruses (Herweijer et al., 1995, Human Gene Therapy 6:1161-1167; U.S. Pat. Nos. 5,091,309 and 5,217, 879), alphaviruses (Schlesinger, 1993, Trends Biotechnol. 11:18-22; Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in some embodiments, the polynucleotide encoding a C-terminal endostatin polypeptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which in nature are not contiguous with the flanking vaccinia regulatory DNA sequences that encode a C-terminal endostatin polypeptide. The recombinant virus containing such a chimeric gene is effective at expressing the C-terminal endostatin polypeptide. In one example, the vaccine viral vector comprises (A) a segment comprised of (i) a first DNA sequence encoding a C-terminal endostatin polypeptide and (ii) a poxvirus promoter, wherein the poxvirus promoter is adjacent to and exerts transcriptional control over the DNA sequence encoding a C-terminal endostatin polypeptide; and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

Poxviral vectors that encode a C-terminal endostatin polypeptide include at least one expression control element operationally linked to the nucleic acid sequence encoding the C-terminal endostatin polypeptide. The expression control elements are inserted in the poxviral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the C-terminal endostatin polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in *Current Protocols in Molecular Biology*, John Wiley and Sons, New York, N.Y.) and are commercially available.

Basic techniques for preparing recombinant DNA viruses containing a heterologous DNA sequence encoding the C-terminal endostatin polypeptide, are known in the art. Such techniques involve, for example, homologous recombination between the viral DNA sequences flanking the DNA sequence in a donor plasmid and homologous sequences present in the parental virus (Mackett et al., 1982, *Proc. Natl. Acad. Sci. USA* 79:7415-7419). In particular, recombinant viral vectors such as a poxviral vector can be used in delivering the gene. The vector can be constructed for example by steps known in the art, such as steps analogous to the methods for creating synthetic recombinants of the fowlpox virus described in U.S. Pat. No. 5,093,258, incorporated herein by reference. Other techniques include using a unique restriction endonuclease site that is naturally present or artificially inserted in the parental viral vector to insert the heterologous DNA.

DNA sequences encoding a C-terminal endostatin polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding a C-terminal endostatin polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts cells can include microbial, yeast, insect and mammalian host cells.

Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, *Cell Culture. Methods in Enzymology*, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods, *Meth Enzymol* 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a C-terminal endostatin polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

The endostatin fragments and variants also can be produced in plants. For example, polypeptides can be expressed in plants using the IBIOLAUNCH™ gene expression platform (iBio, Inc., Newark, Del.) as described in, for example, U.S. Pat. No. 7,491,509 (which is incorporated herein by reference in its entirety). The IBIOLAUNCH™ platform can be used to produce high levels of target proteins in non-transgenic plants. This platform can have benefits over methods utilizing animal cells, or microbes, and over systems that require transgenic plants.

To use this system, a desired gene is cloned into an IBIOLAUNCH™ vector, which is introduced into the leaves of plants (e.g., by automated vacuum infiltration). The vector is allowed to spread to cells in the stems and leaves, where the desired protein is expressed at extremely high levels over the next 4-7 days. The green plant material is then harvested and the protein product purified. The entire IBIOLAUNCH™ gene expression process can be repeated for a different protein with a new plant crop in the same facility, making this technology the most flexible and fastest way to produce protein drugs and vaccines.

A plant expression vector system can include one or more viral vector components. A wide variety of viruses are known that infect various plant species, and can be employed for polynucleotide expression. Families of viruses that infect plants include, without limitation, Tobamoviridae, Caulimoviridae (dsDNA), Geminiviridae (ssDNA), Reoviridae and Partitiviridae (dsRNA), and Rhabdoviridae, Bunyaviridae, Bromoviridae, and Comoviridae (ssRNA). Additional information can be found, for example, in "The Classification and Nomenclature of Viruses, Sixth Report of the International Committee on Taxonomy of Viruses" (Ed. Murphy et al.), Springer Verlag: New York, 1995, the entire contents of which are incorporated herein by reference (see also, Grierson et al., *Plant Molecular Biology*, Blackie, London, pp. 126-146, 1984; Gluzman et al., *Communications in Molecular Biology: Viral Vectors*, Cold Spring Harbor Laboratory, NY, pp. 172-189, 1988; and Mathew, *Plant Viruses Online.*

In order to successfully establish either a local (intraleaf) or systemic infection a virus must be able to replicate. Many viruses contain genes encoding one or more proteins that participate in the replication process (referred to herein as replication proteins or replicase proteins). For example, many RNA plant viruses encode an RNA polymerase. Additional proteins also may be required, such as helicase or methyltransferase protein(s). The viral genome may contain various sequence components in addition to functional genes encoding replication proteins, which are also required for or facilitate replication.

Any virus that infects plants can be used to prepare a viral vector or vector system in accordance with the methods described herein. ssRNA viruses can be particularly useful, especially those with a (+)-stranded genome. Techniques and reagents for manipulating the genetic material present in such viruses include those that are well known in the art. Typically, for example, a DNA copy of the viral genome is prepared and cloned into a microbial vector (e.g., a bacterial vector). Certain ssDNA viruses, including geminiviruses, are particularly useful. It will be appreciated that in general the vectors and viral genomes may exist in RNA or DNA form. In addition, where reference is made to a feature such as a genome or portion thereof of an RNA virus, which is present within a DNA vector, it is to be understood that the feature is present as the DNA copy of the RNA form.

Viruses of a number of different types may be used. Suitable viruses include, for example, members of the Bromoviridae (e.g., bromoviruses, alfamoviruses, ilarviruses) and Tobamoviridae. Useful virus species include, for example, Alfalfa Mosaic Virus (AlMV), Apple Chlorotic Leaf Spot Virus, Apple Stem Grooving Virus, Barley Stripe Mosaic Virus, Barley Yellow Dwarf Virus, Beet Yellow Virus, Broad Bean Mottle Virus, Broad Bean Wilt Virus, Brome Mosaic Virus (BMV), Carnation Latent Virus, Carnation Mottle Virus, Carnation Ringspot Virus, Carrot Mottle Virus, Cassava Latent Virus (CLV), Cowpea Chlorotic Mottle Virus, Cowpea Mosaic Virus (CPMV), Cucumber Green Mottle Mosaic Virus, Cucumber Mosaic Virus, Lettuce Infectious Yellow Virus, Maize Chlorotic Mottle Virus, Maize Rayado Fino Virus, Maize Streak Virus (MSV), Parsnip Yellow Fleck Virus, Pea Enation Mosaic Virus, Potato Virus X, Potato Virus Y, Raspberry Bushy Dwarf Virus, Rice Necrosis Virus (RNV), Rice Stripe Virus, Rice Tungro Spherical Virus, Ryegrass Mosaic Virus, Soilborne Wheat Mosaic Virus, Southern Bean Mosaic Virus, Tobacco Etch Virus (TEV), Tobacco Mosaic Virus (TMV), Tobacco Necrosis Virus, Tobacco Rattle Virus, Tobacco Ring Spot Virus, Tomato Bushy Stunt Virus, Tomato Golden Mosaic Virus (TGMV), and Turnip Yellow Mosaic Virus (TYMV).

Elements of these plant viruses are genetically engineered according to known techniques (see, for example, (see, for example, Sambrook et al., *Molecular Cloning*, $2^{nd}$ Edition, Cold Spring Harbor Press, NY, 1989; Clover et al., *Molecular Cloning*, IRL Press, Oxford, 1985; Dason et al., *Virology*, 172:285-292, 1989; Takamatsu et al., *EMBO J.* 6:307-311, 1987; French et al., *Science* 231: 1294-1297, 1986; Takamatsu et al., *FEBS Lett.* 269:73-76, 1990; Yusibov and Loesch-Fries, *Virology*, 208(1): 405-7, 1995; and Spitsin et al., *Proc. Natl. Acad. Sci. USA*, 96(5): 2549-53, 1999) to generate viral vectors for use in plant production of polypeptides of interest, including the endostatin polypeptides provided herein. At least two vectors are employed, one or both of which are incapable of systemic infection, but which together provide all functions needed to support systemic infection of at least one of the vectors and allow expression of a polynucleotide of interest throughout the plant. Thus, the viral components can complement each other in trans to provide systemic infection capability.

In particular, a producer vector is prepared. This vector includes a polynucleotide of interest (e.g., a polynucleotide encoding an endostatin polypeptide) under control of regulatory sequences that direct expression in the relevant plant host. In some embodiments, the polynucleotide is placed under control of a viral promoter, for example the CP promoter. For instance, it can be desirable to replace the natural viral CP gene with the polynucleotide of interest. The producer vector lacks one or more components required for systemic movement. For example, the producer vector may not contain sequences sufficient for expression of functional CP (e.g., a CP gene), but may include a gene encoding a cell-to-cell movement protein. The producer vector may contain one or more sequence elements (e.g., an origin of assembly) that may be required in cis to facilitate spread of the virus when present in cis. For example, the producer vector may contain an origin of assembly that is needed for or facilitates activity of a CP, either from the same type of virus as the producer virus or from another virus. Such sequence elements may comprise a recognition site for a CP. In other embodiments, the producer vector may lack sequences sufficient for expression of functional MP and/or replicase proteins. In these embodiments, the producer vector may or may not lack sequences sufficient for expression of functional CP.

A carrier vector also is prepared. This vector complements the producer vector, such that it provides components needed for systemic infection that are missing in the producer vector. For example, certain carrier vectors include a functional coat protein encoding component. These carrier vectors are suitable for complementing a producer vector that lacks a functional coat protein encoding component.

The carrier vector may lack at least one viral component (e.g., a gene encoding a replicase or movement protein) required for successful systemic infection of a plant, provided that such component is not also absent in the producer vector. The carrier vector may include a polynucleotide of interest (which may be the same as or different from the polynucleotide of interest in the producer vector). In such cases it may be desirable to use a carrier vector that is defective for systemic infection, e.g., because it lacks one or more necessary cis-acting sequences, in order to minimize spread of the recombinant carrier vector to non-target plants.

The carrier vector may (but need not) include a cell-to-cell movement component (e.g., a gene encoding a cell-to-cell movement protein or a noncoding component that is needed for cell-to-cell movement) and/or may lack one or more replicase protein encoding components. In embodiments in which the carrier vector does not include a cell-to-cell movement component (e.g., a functional MP encoding portion), such a component should be included in the producer vector.

A complete vector set includes all components necessary for successful systemic viral infection and expression of a polynucleotide of interest. The term "component" is intended to include both protein coding sequences and non-coding sequences such as cis-acting sequences (e.g., promoters, origin of assembly, portions corresponding to untranslated regions in mRNA). Different vectors, or vector elements, may be derived from different plant viruses. In fact, it may be desirable to prepare vectors from elements of different viruses in order to take advantage of different viral characteristics (e.g., host range, promoter activity level, virion dimensions, etc.).

In some embodiments, a producer vector is provided that includes a polynucleotide of interest, a replicase gene, and a movement protein gene, but lacks a functional coat protein encoding component, and a carrier vector is provided that expresses a coat protein gene. For example, a producer vector may include a TMV-based vector in which the TMV CP coding sequence has been replaced by a polynucleotide of interest, under control of the TMV CP promoter. This producer vector is unable to move systemically. A wild type AlMV vector can serve as the carrier vector. The AlMV vector contains a functional coat protein encoding component. Co-infection with both producer and carrier vectors allows the CP produced from the AlMV vector CP coding sequence to complement the TMV-based vector, resulting in systemic movement of the TMV-based vector and expression of the polynucleotide in leaves that were not initially infected. Alternately, an AlMV-based vector in which one or more viral components other than those required for expression of AlMV CP has been removed can be used (e.g., an AlMV-based vector lacking functional MP or replication protein coding components), provided that functional CP coding sequences and an operably linked promoter are present. The CP can be from AlMV or from another virus.

In some embodiments, the CP allows for systemic movement of the carrier vector, while in other embodiments a CP is selected that does not allow for systemic movement of the carrier vector but does allow for systemic movement of the producer vector. In those embodiments in which the carrier vector lacks one or more of the viral components other than those required for expression of AlMV CP, the producer vector may complement the carrier vector. For example, the producer vector may supply a component such as a functional MP or replicase protein coding sequence that allows for cell-to-cell movement or replication, respectively, of the carrier vector (and, in some cases, also the producer vector).

It will be appreciated that where either the producer or the carrier is lacking a replication protein encoding component (e.g., a functional RNA polymerase coding component) and the other vector (carrier or producer, respectively) supplies the missing component, it will often be desirable to insert a promoter (e.g., a genomic promoter) from the vector that supplies the functional replication component into the vector lacking the functional replication protein coding component in order to achieve effective trans-complementation of replication function.

Another example of a useful viral vector system includes a producer vector in which a polynucleotide of interest is inserted into an AlMV vector, replacing the native AlMV CP encoding component. The polynucleotide of interest is placed under control of the AlMV CP promoter. This producer vector is incapable of systemic infection since it lacks CP but is able to replicate and move cell-to-cell within an infected leaf. The system also includes a cauliflower mosaic virus (CMV)-based carrier vector in which an AlMV CP encoding portion, with or without the AlMV CP 3' UTR is inserted into a CMV vector, replacing the CMV CP encoding component found in the genome of naturally occurring CMV. The AlMV CP encoding component is placed under control of the CMV CP promoter. This vector expresses AlMV CP. Co-infection with the producer and carrier vectors allows CP expressed from the carrier vector to trans-complement the producer vector's lack of functional CP encoding components, allowing systemic movement of the producer vector. The AlMV CP also allows systemic movement of the carrier vector.

In some embodiments, it can be desirable to insert a portion of coding or noncoding sequence from the carrier vector into the producer vector, or vice versa. For example, certain sequences may enhance replication or facilitate cell-to-cell or long distance movement. In particular, certain sequences may serve as recognition sites for formation of a complex between a viral transcript and a CP (e.g., an origin of assembly). In such a case, if systemic movement of a first viral vector is to be achieved using CP provided in trans from a second viral vector, it may be desirable to insert such sequences from the second viral vector that facilitate activity of the CP into the first viral vector. Such sequences may include, for example, part or all of a viral transcript 3' UTR. In some cases, part or all of the RNA3 3' UTR of AlMV is inserted into a different viral vector, e.g., a TMV-based vector. Including this component in the TMV-based vector facilitates the ability to AlMV CP to trans-complement a TMV-based vector that lacks a functional TMV CP encoding portion. It will be appreciated that this general principle may be applied to any viral vector system comprising trans-complementing vectors, e.g., trans-complementing producer and carrier vector systems.

As will be appreciated by those of ordinary skill in the art, so long as a vector set includes a producer vector that is incapable of systemic viral infection (e.g., lacking one or more functional replication protein, movement protein, or coat protein encoding components) and a carrier vector that provides the function(s) lacking in the producer vector, that set is appropriate for use in accordance with the methods described herein. In some embodiments, no individual vector is capable of systemic viral infection but, as a set, one or both of the vectors is/are competent for such infection and expression of the polynucleotide of interest. Such a system can offer a number of advantages. For example, it will be appreciated that if the producer vector infects a plant in the absence of the carrier vector, no systemic infection will result. This diminishes the risk that the polynucleotide of interest will be expressed in unintended (non-target) plants, even of the same species as the target plant. In particular, if the carrier vector is not competent for replication or cell-to-cell movement (because it lacks a component required for replication or cell-to-cell movement) or if it is incompetent for systemic infection (e.g., because it lacks a cis-acting sequence such as an origin of assembly that is required for long distance movement), the likelihood that both producer and carrier vectors will co-infect an unintended plant host are greatly reduced.

Generally, in order to preserve viral function and also simply for ease of genetic manipulation, vectors are prepared by altering an existing plant virus genome (e.g., by removing particular genes and/or by disrupting or substituting particular sequences so as to inactivate or replace them). In such circumstances, the vectors will show very high sequence identity with natural viral genomes. Of course, completely novel vectors may also be prepared, for example, by separately isolating individual desired genetic elements and linking them together, optionally with the inclusion of additional elements. Also, it should be noted that where a particular vector is said to lack a given gene, protein, or activity (e.g., the producer vector lacks a coat protein gene), it is sufficient if no such protein or activity is expressed from the vector under conditions of infection, even though the vector may still carry the relevant coding sequence. In general, however, it is typically desirable to remove the relevant coding sequences from the vector.

Analogously, when a vector is said to affirmatively express a particular protein or activity, it is not necessary that the relevant gene be identical to the corresponding gene found in nature. For instance, it has been found that the coat protein can sometimes tolerate small deletions (see, for example, WO 00/46350, which is incorporated herein by reference in its entirety). So long as the protein is functional, it may be used in accordance with the methods described herein. Very high sequence identity with the natural protein, however, is generally considered to be most useful. For instance, large deletions (e.g., greater than about 25 amino acids) generally should be avoided. Typically, viral proteins will show at least 50% (e.g., 60%, 70%, 80%, 85%, 90%, 91%, 92%, 93%, 94%, 95%, 96%, 97%, 98%, or 99%) sequence identity with the corresponding natural viral protein. More particularly, the viral protein typically should have 100% identity with critical functional portions (typically of at least several amino acids, often of at least 10, 20, 30, 40, 50 or more amino acids) of the relevant natural viral protein.

It is noted that in the case of many proteins, a number of amino acid changes can be made without significantly affecting the functional activity and/or various other properties of the protein such as stability, etc. In particular, many proteins tolerate conservative amino acid changes—the substitution of an amino acid with a different amino acid having similar properties, without significant reduction in activity. Conservative amino acid substitution is well known in the art and represents one approach to obtaining a polypeptide having similar or substantially similar properties to those of a given polypeptide while altering the amino acid sequence. In general, amino acids have been classified and divided into groups according to (1) charge (positive, negative, or uncharged); (2) volume and polarity; (3) Grantham's physico-chemical distance; and combinations of these. See, e.g., Zhang, *J. Mol. Evol.,* 50:56-68, 2000; Grantham, *Science,* 85:862-864, 1974; Dagan et al., *Mol. Biol. Evol.,* 19(7), 1022-1025, 2002; *Biochemistry,* 4th Ed., Stryer et al., W. Freeman and Co., 1995; and U.S. Pat. No. 6,015,692. For example, amino acids may be divided into the following categories based on volume and polarity: special (C); neutral and small (A, G, P, S, T); polar and relatively small (N, D, Q, E); polar and relatively large (R, H, K), nonpolar and relatively small (I, L, M, V), and nonpolar and relatively large (F, W, Y). A conservative amino acid substitution may be defined as one that replaces one amino acid with an amino acid in the same group. Thus a variety of functionally equivalent proteins can be derived by making one or more conservative amino acid substitutions in a given viral protein.

Any plant susceptible to viral infection may be utilized in accordance with the methods described herein. In general, it will often be desirable to utilize plants that are amenable to growth under defined conditions, for example in a greenhouse and/or in aqueous systems. It also may be desirable to select plants that are not typically consumed by human beings or domesticated animals and/or are not typically part of the human food chain, so that they may be grown outside without concern that the expressed polynucleotide may be undesirably ingested. In other embodiments, however, it will be desirable to employ edible plants.

Often, certain desirable plant characteristics will be determined by the particular polynucleotide to be expressed. To give but a few examples, when the polynucleotide encodes a protein to be produced in high yield (as will often be the case, for example, when therapeutic proteins are to be expressed), it will often be desirable to select plants with relatively high biomass (e.g., tobacco, which has the additional advantages that it is highly susceptible to viral infection, has a short growth period, and is not in the human food chain). Where the polynucleotide encodes a protein whose full activity requires (or is inhibited by) a particular post-translational modification, the ability (or inability) of certain plant species to accomplish the relevant modification (e.g., a particular glycosylation) may direct selection.

In some embodiments, crop plants, or crop-related plants, are utilized. In some embodiments, edible plants are utilized.

Plants suitable for use in accordance with the methods described herein include, without limitation, Angiosperms, Bryophytes (e.g., Hepaticae, Musci, etc.), Pteridophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). In some embodiments, members of the family Leguminosae (Fabaceae; e.g., pea, alfalfa, soybean); Gramineae (Poaceae; e.g., corn, wheat, rice); Solanaceae, particularly of the genus *Lycopersicon* (e.g., tomato), *Solanum* (e.g., potato, eggplant), *Capsium* (e.g., pepper), or *Nicotiana* (e.g., tobacco); Umbelliferae, particularly of the genus *Daucus* (e.g., carrot), Apium (e.g., celery), or Rutaceae (e.g., oranges); Compositae, particularly of the genus *Lactuca* (e.g., lettuce); and Brassicaceae (Cruciferae), particularly of the genus *Brassica* or *Sinapis*, can be particularly useful. For example, useful Brassicaceae family members include *Brassica campestris, B. carinata, B. juncea, B. napus, B. nigra, B. oleraceae, B. tournifortii, Sinapis alba,* and *Raphanus sativus.*

The expression system may be employed to infect, and/or to express a polynucleotide in plants at any stage of development including, for example, mature plants, seedlings, sprouts, and seeds. The system may be employed to infect any part of a plant (e.g., roots, leaves, stems, etc.). In some embodiments, the system is used to infect sprouts. Generally, a plant is considered to be a sprout when it is a seedling that does not require external nutrients or energy in the form of light or heat beyond what is required to achieve normal germination temperatures. Often, a seedling that is less than two weeks old, and typically less than 10 days old, is considered to be a sprout.

In general, viral vectors may be delivered to plants according to known techniques. For example, the vectors themselves may be directly applied to plants (e.g., via abrasive inoculations, mechanized spray inoculations, vacuum infiltration, particle bombardment, or electroporation). Alternatively, virions may be prepared (e.g., from already infected plants), and may be applied to other plants according to known techniques.

As noted above, in some embodiments, viral vectors are applied to sprouts (e.g., through infiltration or mechanical inoculation [spray]).

Where infection is to be accomplished by direct application of a viral genome to a plant, any available technique may be used to prepare the genome. For example, many viruses that are usefully employed in accordance with the methods described herein have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that ssRNA vectors will often be prepared by in vitro transcription, particularly with T7 or SP6 polymerase.

In some embodiments, it will be desirable to isolate polynucleotide expression products from the plant tissues that express them. It also may be desirable to formulate such isolated products for their intended use (e.g., as a pharmaceutical or diagnostic agents, as reagents, etc.). In other embodiments, it will be desirable to formulate the products together with some or all of the plant tissues that express them.

To isolate the expression product from some or all of the plant tissue that expresses it, any available purification techniques may be employed. Those of ordinary skill in the art are familiar with a wide range of fractionation and separation procedures (see, for example, Scopes et al., *Protein Purification: Principles and Practice*, 3$^{rd}$ Ed., Janson et al., "Protein Purification: Principles, High Resolution Methods, and Applications," Wiley-VCH, 1998; Springer-Verlag, NY, 1993; and Roe, *Protein Purification Techniques*, Oxford University Press, 2001, each of which is incorporated herein by reference in its entirety). Often, it will be desirable to render the product more than about 50%, preferably more than about 60%, 70%, 80%, 85%, 90%, 91%, 92%, 93%, 94%, 95%, 96%, 97%, 98%, or 99% pure.

To formulate the product together with the plant material, it will often be desirable to have utilized a plant that is not toxic to the relevant recipient (e.g., a human or other animal). Relevant plant tissue (e.g., leaves) may simply be harvested and processed according to techniques known in the art, with due consideration to maintaining activity of the expressed product. In some embodiments, the polynucleotide can be expressed in an edible plant (and, specifically in edible portions of the plant) so that the material can subsequently be eaten. For example, where the polynucleotide encodes a nutritionally relevant protein or a therapeutic protein that is active after oral delivery (when properly formulated), it may be useful to produce the protein in an edible plant portion, and to formulate the expressed polynucleotide for oral delivery together with some or all of the plant material with which the polynucleotide was expressed.

Where the polynucleotide encodes or produces a therapeutic agent, it may be formulated according to known techniques. For example, an effective amount of a pharmaceutically active product can be formulated together with one or more organic or inorganic, liquid or solid, pharmaceutically suitable carrier materials. A pharmaceutically active product may be employed in dosage forms such as tablets, capsules, troches, dispersions, suspensions, solutions, capsules, creams, ointments, aerosols, powder packets, liquid solutions, solvents, diluents, surface active agents, isotonic agents, thickening or emulsifying agents, preservatives, and solid bindings, as long as the biological activity of the protein is not destroyed by such dosage form.

Materials that can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening agents, flavoring agents, and perfuming agents, preservatives, and antioxidants can also be present in the composition, according to the judgment of the formulator (see also *Remington's Pharmaceutical Sciences*, Fifteenth Edition, E. W. Martin, Mack Publishing Co., Easton Pa., 1975). For example, a polynucleotide expression product may be provided as a pharmaceutical composition by means of conventional mixing granulating dragee-making, dissolving, lyophilizing, or similar processes.

In some embodiments, it may be useful to prolong the effect of a pharmaceutical preparation by slowing the absorption of the pharmaceutically active product (e.g., protein) that is subcutaneously or intramuscularly injected. This may be accomplished by the use of a liquid suspension of crystalline or amorphous material with poor water solubility. The rate of absorption of the product then depends upon its rate of dissolution, which in turn, may depend upon size and form. Alternatively, delayed absorption of a parenterally administered product is accomplished by dissolving or suspending the product in an oil vehicle. Injectable depot forms are made by forming microencapsule matrices of the protein in biodegradable polymers such as polylactide-polyglycolide. Depending upon the ratio of product to polymer and the nature of the particular polymer employed, the rate of release can be controlled. Examples of other biodegradable polymers include poly(orthoesters) and poly (anhydrides). Depot injectable formulations may be prepared by entrapping the product in liposomes or microemulsions, which are compatible with body tissues.

Enterically administered preparations of pharmaceutically active products may be introduced in solid, semi-solid, suspension or emulsion form and may be compounded with any pharmaceutically acceptable carriers, such as water, suspending agents, and emulsifying agents. The expression products may also be administered by means of pumps or sustained-release forms, especially when administered as a preventive measure, so as to prevent the development of disease in a subject or to ameliorate or delay an already established disease.

Pharmaceutically active products, optionally together with plant tissue, can be particularly well suited for oral administration as pharmaceutical compositions. Harvested plant material may be processed in any of a variety of ways (e.g., air drying, freeze drying, extraction etc.), depending on the properties of the desired therapeutic product and its desired form. In preferred embodiments, such compositions as described above are ingested orally alone or ingested together with food or feed or a beverage. Compositions for oral administration include infected plants; extractions of the infected plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any infected plant biomass that has been dried, for example, freeze dried, air dried, or spray dried. For example, the plants may be air dried by placing them in a commercial air dryer at about 120 degrees Fahrenheit until the biomass contains less than 5% moisture by weight. The dried plants may be stored for further processing as bulk solids or further processed by grinding to a desired mesh sized powder. Alternatively, freeze-drying may be used for products that are sensitive to air-drying. Products may be freeze dried by placing them into a vacuum drier and dried frozen under a vacuum until the biomass contains less than about 5% moisture by weight. The dried material can be further processed.

Infected plants may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, liquid dosage, etc. Those skilled in the art will appreciate the various formulations and modalities of delivery of herbal preparations that may be applied.

Those skilled in the art will also appreciate that a particularly useful method of obtaining the desired pharmaceutically active products is by extraction. Infected plants may be extracted to remove the desired products from the residual biomass, thereby increasing the concentration and purity of the product. Plants also may be extracted in a buffered solution. For example, the fresh harvested plants may be transferred into an amount of ice-cold water at a ratio of one to one by weight that has been buffered with, e.g., phosphate buffer. Protease inhibitors can also be added as required. The plants can be disrupted by vigorous blending or grinding while suspended in the buffer solution and the extracted biomass removed by filtration or centrifugation. The transgene product carried in solution can be further purified by additional steps or converted to a dry powder by freeze-drying or precipitation. Extraction can also be carried out by pressing. Live plants can also be extracted by pressing in a press or by being crushed as they are passed through closely spaced rollers. The fluids expressed from the crushed plants are collected and processed according to methods well known in the art. Extraction by pressing allows the release of the products in a more concentrated form. However, the overall yield of the product may be lower than if the product were extracted in solution.

Infected plants, extractions, powders, dried preparations and purified protein products, etc., can also be in encapsulated form with or without one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active product may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In some embodiments, an infected plant expressing a pharmaceutically active product, or biomass of an infected plant, is administered orally as medicinal food. Such edible compositions are consumed by eating raw, if in a solid form, or by drinking, if in liquid form. In some embodiments, the transgenic plant material is directly ingested without a prior processing step or after minimal culinary preparation. For example, the pharmaceutically active protein is expressed in a sprout that can be eaten directly (e.g., an alfalfa sprout, mung bean sprout, or a spinach or lettuce leaf sprout). In some embodiments, the plant biomass is processed and the material recovered after the processing step is ingested.

Therapeutic Methods and Pharmaceutical Compositions

The C-terminal endostatin polypeptides disclosed herein, or nucleic acids encoding the C-terminal endostatin polypeptides, can be used to treat fibrosis. In several examples, the C-terminal endostatin polypeptides, or nucleic acid encoding these polypeptides are of use to decrease fibrosis, such as in a subject. Thus, in several embodiments, the methods include administering to a subject a therapeutically effective amount of one or more of the C-terminal endostatin polypeptides disclosed herein, or polynucleotides encoding these polypeptides, in order to decrease fibrosis. In some examples, the C-terminal endostatin polypeptide comprises or consists of amino acids 133-180 of SEQ ID NO:2, SEQ ID NO:4, SEQ ID NO:13, or SEQ ID NO:14. However, any of the C-terminal endostatin polypeptides disclosed herein can be used to decrease fibrosis. In some embodiments, the peptides can be administered as a unit dose. In some embodiments, the polypeptides are administered as multimers.

Suitable subjects include those with a fibrosis of the skin or lungs, but fibrosis of any tissue can be treated using the methods disclosed herein. In one example, the subject has scleroderma. In other examples, the subject has idiopathic pulmonary fibrosis, morphea, fibrosis as a result of Graft-Versus-Host Disease (GVHD), a keloid or hypertrophic scar, subepithelial fibrosis, endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and multifocal fibrosclerosis.

In further examples, the methods are used to treat the systemic form of scleroderma, such as limited cutaneous scleroderma or diffuse cutaneous scleroderma (or systemic sclerosis). The methods can be used to treat the localized form of scleroderma, including morphea and linear scleroderma.

The methods can include selecting a subject in need of treatment, such as a subject with a fibrotic disease, such as scleroderma, idiopathic pulmonary fibrosis, morphea, a keloid scar, a hypertrophic scar, or subepithelial fibrosis. In exemplary applications, compositions are administered to a subject having a fibrotic disease, such as scleroderma, idiopathic pulmonary fibrosis, morphea, a keloid scar, a hypertrophic scar, or subepithelial fibrosis, or any of the disorders listed above, in an amount sufficient to reduce the fibrosis. Amounts effective for this use will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer.

A method is provided herein for decreasing skin thickness. The method includes administering a therapeutically effective amount of a C-terminal endostatin polypeptide, thereby decreasing skin thickness. In another embodiment, a method is provided for decreasing lung fibrosis. The method includes administering a therapeutically effective amount of a C-terminal endostatin polypeptide, thereby decreasing skin thickness. Any of the C-terminal endostatin polypeptides disclosed herein can be used in these methods. In some embodiments, the C-terminal endostatin polypeptide comprises, or consists of, amino acids 133-180 of SEQ ID NO:2, SEQ ID NO:4, SEQ ID NO:13, or SEQ ID NO:14.

Methods are provided herein for decreasing lysyl oxidase (LOX), such as transforming growth factor (TGF)-β induced LOX. The method includes contacting a cell with an effective amount of a C-terminal endostatin polypeptide, thereby decreasing LOX. The methods can be practiced in vivo or in vitro. In some embodiments, the methods include comparing the amount of LOX produced by a cell contacted with a C-terminal endostatin polypeptide to a control. The control can be a standard value, or the amount of LOX produced by a cell not contacted with the C-terminal endostatin polypeptide, such as a cell contacted with a carrier.

Methods are provided herein for increasing matrix metalloproteinase-2 (MMP-2). The method includes contacting a cell with an effective amount of a C-terminal endostatin polypeptide, thereby increasing MMP-2 production. The methods can be practiced in vivo or in vitro. In some embodiments, the methods include comparing the amount of MMP-2 produced by a cell contacted with a C-terminal endostatin polypeptide to a control The control can be a standard value, or the amount of MMP-2 produced by a cell not contacted with the C-terminal endostatin polypeptide, such as a cell contacted with a carrier.

A C-terminal endostatin polypeptide can be administered by any means known to one of skill in the art (see Banga, "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intradermal, intrathecal, intramuscular, subcutaneous, intraperitoneal or intravenous injection, but even oral, nasal, transdermal or anal administration is contemplated. In some embodiments, administration is by subcutaneous, intradermal, or intramuscular injection. In another embodiment, administration is by intraperitoneal or intrathecal administration. To extend the time during which the peptide or protein is available to stimulate a response, the peptide or protein can be provided as an implant, an oily injection, or as a particulate system. The particulate system can be a microparticle, a microcapsule, a microsphere, a nanoparticle, a nanocapsule, or similar particle. (see, e.g., Banga, supra).

For treatment of the skin, a therapeutically effective amount of at least one C-terminal endostatin polypeptide, or a nucleic acid encoding the peptide, can be locally administered to the affected area of the skin, such as in the form of an ointment. In some embodiments, the ointment is an entirely homogenous semi-solid external agent with a firmness appropriate for easy application to the skin. Such an ointment can include fats, fatty oils, lanoline, VASELINE®, paraffin, wax, hard ointments, resins, plastics, glycols, higher alcohols, glycerol, water or emulsifier and a suspending agent. Using these ingredients as a base, a decoy compound can be evenly mixed. Depending on the base, the mixture can be in the form of an oleaginous ointment, an emulsified ointment, or a water-soluble ointment oleaginous ointments use bases such as plant and animal oils and fats, wax, VASELINE® and liquid paraffin. Emulsified ointments are comprised of an oleaginous substance and water, emulsified with an emulsifier. They can take either an oil-in-water form (O/W) or a water-in-oil-form (W/O). The oil-in-water form (O/W) can be a hydrophilic ointment. The water-in-oil form (W/O) initially lacks an aqueous phase and can include hydrophilic VASELINE® and purified lanoline, or it can contain a water-absorption ointment (including an aqueous phase) and hydrated lanoline. A water-soluble ointment can contain a completely water-soluble Macrogol base as its main ingredient.

Pharmaceutically acceptable carriers include a petroleum jelly, such as VASELINE®, wherein the petroleum jelly contains 5% stearyl alcohol, or petroleum jelly alone, or petroleum jelly containing liquid paraffin. Such carriers enable pharmaceutical compositions to be prescribed in forms appropriate for consumption, such as tablets, pills, sugar-coated agents, capsules, liquid preparations, gels, ointments, syrups, slurries, and suspensions. When locally administered into cells in an affected area or a tissue of interest, the at least one C-terminal endostatin polypeptide, or polynucleotide encoding the peptide can be administered in a composition that contains a synthetic or natural hydrophilic polymer as the carrier. Examples of such polymers include hydroxypropyl cellulose and polyethylene glycol. One or more C-terminal endostatin polypeptides, or polynucleotide encoding the polypeptides, can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used. A therapeutically effective amount of one or more C-terminal endostatin polypeptide, or polynucleotide encoding the peptide can also be incorporated into bandages and dressings.

For administration by inhalation, the C-terminal endostatin polypeptide, or polynucleotide encoding the peptide can be conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

In some embodiments, the C-terminal endostatin polypeptide, such as, but not limited to E4, can be administered by inhalation. For example, the C-terminal endostatin polypeptide can be administered in an aerosolized form, such as using a nebulizer or a metered dose inhaler. Technologies of use include micropump nebulizers (such as the AEROGEN GO® system), jet nebulizers designed to produce large fine particle fractions (such as the PARI LC STAR®), jet nebulizers developing less shear during atomization (such as the HUDSON MICROMIST®), and ultrasonic nebulizers (such as the DeVilbiss ULTRA-NEB®).

The endostatin polypeptide can be dissolved in a carrier, such as saline, and atomized using the devices above. The associated aerosols can be collected using a NEXT GENERATION IMPACTOR® (NGI) (MSP Corp., Shoreview, Minn.), which uses a series of aerodynamic stages to separate and collect the aerosol into separate fractions based on droplet size. Since droplet size is the primary determinant of deposition location in the lungs, this device allows us to specifically isolate the portion of the liquid aerosol that will deposit in the small airways and alveoli.

Aerosol particle size is often expressed in terms of mass median aerodynamic diameter (MMAD), a parameter that is based on particle size, shape, and density. For a spherical particle, MMAD is equal to MMD ($p^{1/2}$), in which MMD is mass median diameter and r is the bulk density. For a non-spherical particle, MMAD is equal to MMD $(p/x)^{1/2}$, in which X is the shape factor. Thus, particles with larger than unit density will have actual diameters smaller than their MMAD.

The site of particle deposition within the respiratory tract is demarcated based on particle size. In one example, particles of about 1 to about 500 microns are utilized, such as particles of about 25 to about 250 microns, or about 10 to about 25 microns are utilized. In other embodiments, particles of about 1 to 50 microns are utilized. For use in a metered dose inhaler, for administration to lungs particles of less than about 10 microns, such as particles of about 2 to about 8 microns, such as about 1 to about 5 microns, such as particles of 2 to 3 microns, can be utilized.

A therapeutically effect amount of a C-terminal endostatin polypeptide, or polynucleotide encoding the peptide can be administered in the pharmaceutically acceptable carrier. Pharmacologically acceptable carriers (e.g., physiologically or pharmaceutically acceptable carriers) are well known in the art, and include, but are not limited to buffered solutions as a physiological pH (e.g. from a pH of about 7.0 to about 8.0, or at a pH of about 7.4). One specific, non-limiting example of a physiologically compatible buffered solution is phosphate buffered saline. Other pharmacologically acceptable carriers include penetrants, which are particularly suitable for pharmaceutical formulations that are intended to be topically applied (for example in the application of surgical wounds to promote healing).

The pharmacological compositions disclosed herein facilitate the use of at least one C-terminal endostatin polypeptide, or polynucleotide encoding the peptide, either in vivo or ex vivo, to decrease fibrosis. Such a composition can be suitable for delivery of the active ingredient to any suitable subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically. Proper formulation is dependent upon the route of administration chosen. Thus, for injection, the active ingredient can be formulated in aqueous solutions. For transmucosal administration, penetrants appropriate to the barrier to be permeated are used in the formulation. Such penetrants are generally known in the art.

For oral administration, a therapeutically effective amount of at least one C-terminal endostatin polypeptide, or a nucleic acid encoding the peptide, can be combined with carriers suitable for incorporation into tablets, pills, capsules, liquids, gels, syrups, slurries, suspensions and the like.

Protein drugs are subject to protease-mediated degradation in the digestive tract through the action of enzymes such as trypsin, chymotrypsin, and brush border peptidases, such that oral administration of large protein molecules often does not result in the intended therapeutic effect (Soltero and Ekwruibe, 2001 Innovations in Pharmaceutical Technology, 1:106-110). Surprisingly, the C-terminal endostatin polypeptide described herein can maintain its activity and therapeutic effects even when administered via an oral route. Without being bound by theory, it is believed that the C-terminal endostatin polypeptide described herein includes additional properties that allow it to escape protease activity and become adsorbed in the small intestine and enter circulation to provide therapeutic benefit.

In some embodiments, for parenteral administration, a therapeutically effective amount of at least one C-terminal endostatin polypeptide, or a nucleic acid encoding the peptide, can be administered by injection, such as by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

Optionally, the at least one C-terminal endostatin polypeptide, or polynucleotide encoding the peptide can be contained within or conjugated with a heterologous protein, hydrocarbon or lipid, whether for in vitro or in vivo administration. Co-administration can be such that the at least one C-terminal endostatin polypeptide, or polynucleotide encoding the peptide is administered before, at substantially the same time as, or after the protein, hydrocarbon, or lipid. In some embodiments, the at least one C-terminal endostatin polypeptide, or polynucleotide encoding the peptide is administered at substantially the same time, as the protein, hydrocarbon, or lipid.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the at least one C-terminal endostatin polypeptide, or polynucleotide encoding the peptide is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as scleroderma. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. These systems have been described for use with oligodeoxynucleotides (see U.S. Pat. No. 6,218,371). For use in vivo, nucleic acids and peptides are preferably relatively resistant to degradation (such as via endo- and exo-nucleases). Thus, modifications, such as the inclusion of a C-terminal amide, can be used.

The therapeutically effective amount of C-terminal endostatin polypeptide, or polynucleotide encoding the peptide will be dependent on the C-terminal endostatin polypeptide, or polynucleotide encoding the peptide that is utilized, the subject being treated, the severity and type of the affliction, and the manner of administration. For example, a therapeutically effective amount of a polynucleotide encoding the peptide can vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound the age, weight, sex and physiological condition of the subject.

With regard to the administration of nucleic acids, one approach to administration of nucleic acids is direct treatment with plasmid DNA, such as with a mammalian expression plasmid. As described above, the nucleotide sequence encoding a N-terminal endostatin peptide can be placed under the control of a promoter to increase expression of the molecule.

When a viral vector is utilized for administration in vivo, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal either prior to any evidence of a cancer, or to mediate regression of the disease in a mammal afflicted with the cancer. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier. Generally, the quantity of recombinant viral vector, carrying the nucleic acid sequence of one or more C-terminal endostatin polypeptides to be administered is based on the titer of virus particles. An exemplary range of the immunogen to be administered is $10^5$ to $10^{10}$ virus particles per mammal, such as a human.

In one specific, non-limiting example, a pharmaceutical composition for intravenous administration would include about 0.1 µg to 10 mg of C-terminal endostatin polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Sciences*, $19^{th}$ Ed., Mack Publishing Company, Easton, Pa., 1995.

Single or multiple administrations of the compositions are administered depending on the dosage and frequency as required and tolerated by the subject. In some embodiments, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In a further method, an additional agent is administered. In one example, this administration is sequential. In other examples, the additional agent is administered simultaneously with the C-terminal endostatin polypeptide.

For the treatment of scleroderma, examples of additional agents that can be used with a C-terminal endostatin polypeptides include nifedipine, amlodipine, diltiazem, felodipine, or nicardipine. An investigational drug GLEEVEC®, is also used for the treatment of scleroderma. GLEEVEC® or other tyrosine kinase inhibitors can be used with the C-terminal endostatin polypeptides disclosed herein. Patients with lung involvement of scleroderma benefit from oxygen therapy; the C-terminal endostatin polypeptides disclosed herein can be administered with this therapy.

For the treatment of fibrosis of the skin and scleroderma, additional agents of use are d-penicillamine, colchicine, Relaxin, steroids, and cyclosporine. C-terminal endostatin polypeptides also can be used in combination with immunosuppressive agents. Additionally, the C-terminal endostatin polypeptides can be used with methotrexate, cyclophosphamide, azathioprine, mycophenolate, glitazones, endothelin receptor antagonists, or Fulvestrant (ICI-182, 780).

The invention will be further described in the following examples, which do not limit the scope of the invention described in the claims.

EXAMPLES

Excessive deposition of extra cellular matrix (ECM) components such as fibronectin (FN) and type I collagen (Col1α1) by organ fibroblasts is defined as fibrosis. Organ fibrosis is the final common pathway for many diseases that result in end-stage organ failure. However, effective therapy for organ fibrosis is still unavailable (see, for example, Bjoraker et al., *Am. J. Respir. Crit. Care. Med.* 2000; 157:199-20; Varga and Abraham, *J Clin Invest* 2007; 117: 557-67; Wynn, *J Clin Invest* 2007; 117:524-29). Uncontrollable wound-healing responses, including acute and chronic inflammation, angiogenesis, activation of resident cells, and ECM remodeling, are thought to be involved in the pathogenesis of fibrosis (Wynn, *J Clin Invest* 2007; 117:524-29;

Kalluri and Sukhatme. *Curr Opin Nephrol Hypertens* 2000; 9:413-8). TGF-β is the prototype fibrotic cytokine that is increased in fibrotic organs and contributes to the development of fibrosis by stimulating the synthesis of ECM molecules, activating fibroblasts to α-smooth muscle actin (α-SMA)-expressing myofibroblasts, and downregulating matrix metalloproteinases (MMPs) (Branton, *Microbes Infect* 1999; 1:1349-65; Varga and Pasche *Nature Reviews Rheumatology* 2009; 5:200-6). Despite high expectations, a clinical trial of a monoclonal anti-TGF-β antibody in patients with early SSc failed to show any efficacy (Varga and Pasche, *Nature Reviews Rheumatology* 2009; 5:200-6).

Endostatin is a 20-kDa internal fragment of the carboxy terminus of collagen XVIII. It was originally identified in the supernatant of a cultured murine hemangioendothelioma cell line with potent antiangiogenic activity (O'Reilly et al., *Cell* 1997; 88:277-85). Endostatin inhibits endothelial proliferation and tube formation in vitro, and tumor growth in vivo (Dhanabal et al., *Biochem Biophys Res Commun* 1999; 258:345-52). Studies have been conducted to assess endostatin's anti-tumor properties, including clinical trials (Folkman, *Exp Cell Res* 2006; 312:594-607). The $NH_2$-terminal domain of endostatin has been reported as the functional domain responsible for inhibiting angiogenesis (Tjin Than Sjin et al., *Cancer Res* 2005; 65:3656-63). Although the exact molecular mechanism of its effect remains unclear, integrins, glypicans, flk-1, and nucleolin have been reported as endostatin receptors (Sudhakar et al., *Proc Natl Acad Sci USA* 2003; 100:4766-71; Karumanchi et al., *Mol Cell* 2001; 7:811-22). Recent studies have shown that endostatin is increased in serum and/or BALF obtained from IPF and SSc patients with pulmonary fibrosis (for example, Sumi, *J Clin Lab Anal* 2005; 19:146-9).

In the studies discussed herein, the effects of endostatin on fibrosis were evaluated. The effect of endostatin and endostatin-derived peptides on fibrosis in vitro was assessed using primary human fibroblasts, ex vivo using human skin, and in vivo in mice skin treated with TGF-β. Surprisingly, the findings demonstrate that a carboxy-terminal peptide of endostatin has anti-fibrotic activity and provide a novel therapy for fibrotic disorders.

Example 1

Materials and Methods

Reagents and Antibodies. The full-length recombinant human endostatin (rE) was purchased from Sigma-Aldrich (St. Louis, Mo.). Recombinant human TGF-β was from R&D Systems Inc. (Minneapolis, Minn.). Mouse monoclonal anti-human fibronectin (FN) antibody, goat polyclonal anti-human type I Collagen αI chain (Col1α1) antibody, and mouse monoclonal anti-human GAPDH antibody were from Santa Cruz Biotechnology (Santa Cruz, Calif.). Mouse monoclonal anti-human α-smooth muscle actin (α-SMA) antibody was from Sigma-Aldrich.

Synthesis of Human Endostatin Peptides. Peptides were synthesized by the solid-phase on Liberty Microwave Synthesizer (CEM Corporation, Mathews, N.C.) using FMOC synthesis protocol. Briefly, synthesis was performed by stepwise addition of activated amino acids to the solid support (Wang resin and PEG-PS) starting from the carboxy terminus to the amino terminus. Activation of amino acids was performed by DIPEA/HOBT/TBTU chemistry. At the end of the synthesis, peptides were cleaved off the resin with reagent R (90% TFA, 5% Thioanisole, 3% Ethanedithiol, and 2% Anisole) and subjected to multiple ether extractions. The crude peptides were analyzed, characterized, and purified by Gel filtration (G-25 column), Reversed-Phase High Performance Liquid Chromatography (RP-HPLC, 486 and 600E by Waters Corporation). The correct mass was confirmed by MALDI-TOF Mass Spectroscopy (The Voyager-DE STR Biospectrometry Workstation). Sequences of the peptides are shown in TABLE 1 and correspond to amino acids 1-45 (E1); 71-115 (E2); 133-180 (E3), 133-180A (E4) which differs from E3 by the presence of a carboxy-terminal amide. The purity of all peptides was >98%. All peptides were dissolved in DMSO at a concentration 5 mg/ml, and diluted in 1×PBS to 1-20 µg/ml.

Primary Fibroblast Culture. Human primary lung and skin fibroblasts were cultured. The explanted lungs of normal organ donors, patients with SSc or IPF, and clinically involved skin of SSc patients, a morphea patient and healthy donors were used for primary fibroblast culture. Approximately 2-cm pieces of peripheral lung and skin were minced and fibroblasts were cultured in Dulbecco's modified Eagle's medium (DMEM; Mediatech, Herndon, Va.) supplemented with 10% FBS, penicillin, streptomycin, and antimycotic agent, as previously described (Feghali et al., *Arthritis Rheum* 1999; 42:1451-7). All the cells were used between passages 3-6.

Western Blot Analysis. Cellular lysates were obtained from cultured fibroblasts as previously described (Pilewski et al., *Am J Pathol* 2005; 166:399-407). Briefly, $2.0 \times 10^5$ primary fibroblasts were cultured in 35-mm wells in 0.5% FBS-containing medium supplemented with 10 ng/ml of human recombinant TGF-β or PBS as vehicle control for 24 h, following which 5 µg/ml of human rE, endostatin peptides (E1-E4), or DMSO (vehicle) was added for 48 h. In some experiments, endostatin peptides were used without TGF-β stimulation. Cellular lysates were analyzed by Western blot. Signals were detected following incubation with horseradish peroxidase-conjugated secondary antibody and chemiluminescence (Perkin Elmer Life Sciences, Inc., Boston, Mass.). The intensity of individual bands with expected molecular sizes was semi-quantitatively analyzed using the image/J® software available at on the internet (/rsb.info.nih.gov/ij/index.html), and normalized to individual GAPDH intensity.

Ex vivo human skin assays. Human abdominal skin was obtained from corrective plastic surgery. As previously described (Yasuoka et al., *The Open Rheumatol J* 2008; 2:17-22), subcutaneous fat tissue was removed uniformly and skin tissue was cut into 1.5 cm×1.5 cm sections. The following were injected intradermally in a total volume of 100 µl 1×PBS: rE alone (1-10 µg/ml), endostatin peptides alone (10 µg/ml), rE or endostatin peptides (1-20 µg/ml) in combination with TGF-β (10 ng/ml), and TGF-β alone (10 ng/ml). In some experiments, human skin was first injected with TGF-β for 48 h followed by recombinant endostatin (rE) administration in the same injection site as TGF-β. Independent experiments were conducted in duplicate or triplicate as indicated in the figure legends. Explants containing complete epidermal and dermal layers were cultured in an air liquid interface with the epidermal and keratin layers side up and exposed to air. The culture medium was replaced every other day. After 1 or 2 weeks, skin tissue corresponding to an area with 8-mm diameter centered around the injection site was harvested using disposable 8-mm ACUPUNCH® (Acuderm, Inc., Lauderdale, Fla.). Skin tissue was fixed in 10% formalin prior to embedding in paraffin.

In Vivo Mouse Experiments. CB57BL6/J male mice were purchased from The Jackson Laboratory (Bar Harbor, Me.). Human rE (10 µg/ml) or Endostatin peptides (10 µg/ml) in combination with TGF-β (10 ng/ml), or TGF-β alone were injected intradermally on the back of mice in a total volume of 100 μl 1×PBS. Mice were injected in two different skin sites and sacrificed one week post-injection. Skin surrounding the injection site was harvested and fixed in 10% formalin prior to embedding in paraffin.

Measurement of Skin Dermal Thickness. Six μm sections of paraffin-embedded human and mouse skin tissues were stained with hematoxylin and eosin (H&E). In some experiments, sections were stained with Masson trichrome which identifies collagens. Images were taken on a Nikon Eclipse 800 microscope. The thickness of the dermis was measured in 6 random fields of each section using the image/J® software. Data are shown in arbitrary units.

Tubular formation assay. The ability of endostatin peptide to inhibit angiogenesis was examined in tubular formation assay using MATRIGEL® culture. Human umbilical vein endothelial cells (HUVECs) were maintained in endothelial cell basal medium-2 (EBM-2; Clonetics, San Diego, Calif.) supplemented with EBM-2 MV SINGLEQUOTS®. HUVECs ($5 \times 10^4$) were cultured in duplicate on 24-well MATRIGEL® plates (BD Biosciences, San Diego, Calif.) alone, or in the presence of rE or E4 peptide (50 nM) in EBM-2 at 37° C. DMSO was used as vehicle control. After 24 hours, images were captured using a converted microscope. The degree of cord formation was quantified by measuring the area occupied by tubes in 6 random fields per well. Three independent experiments were performed.

Statistical Analysis. All continuous variables were expressed as the mean±standard deviation. Comparisons between 2 groups were tested for statistical significance using the paired t-test or Mann-Whitney U test as appropriate. Comparison among 3 groups was performed using ANOVA followed by Bonferroni's test.

Example 2

Human Endostatin Inhibits FN and Col1α1 Production in TGF-β-Treated Human Primary Lung and Skin Fibroblasts In Vitro To evaluate whether endostatin modulates production of ECM components in fibroblasts, FN and Col1α1 expression was examined in normal human lung fibroblasts by Western blot analysis. Cells were treated with 5 μg/ml rE for 48 h with or without pre-stimulation with human TGF-β for 24 h. As shown FIG. 1A, rE dramatically reduced FN and Col1α1 levels in TGF-β pre-treated fibroblasts. To define the functional domain of endostatin that mediates its inhibitory effect, four different peptides were synthesized corresponding to different regions of endostatin (TABLE 1).

Figure 1B:
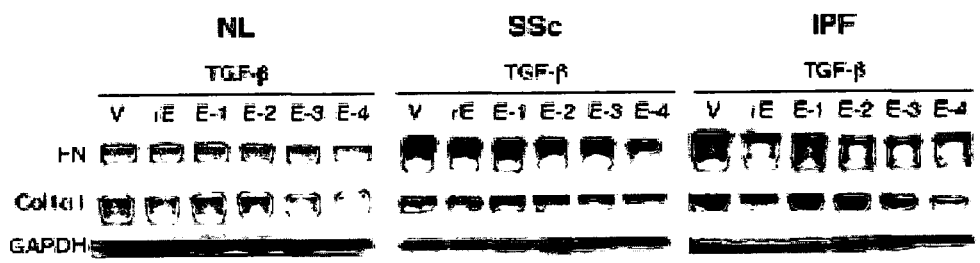
Figure 1C:
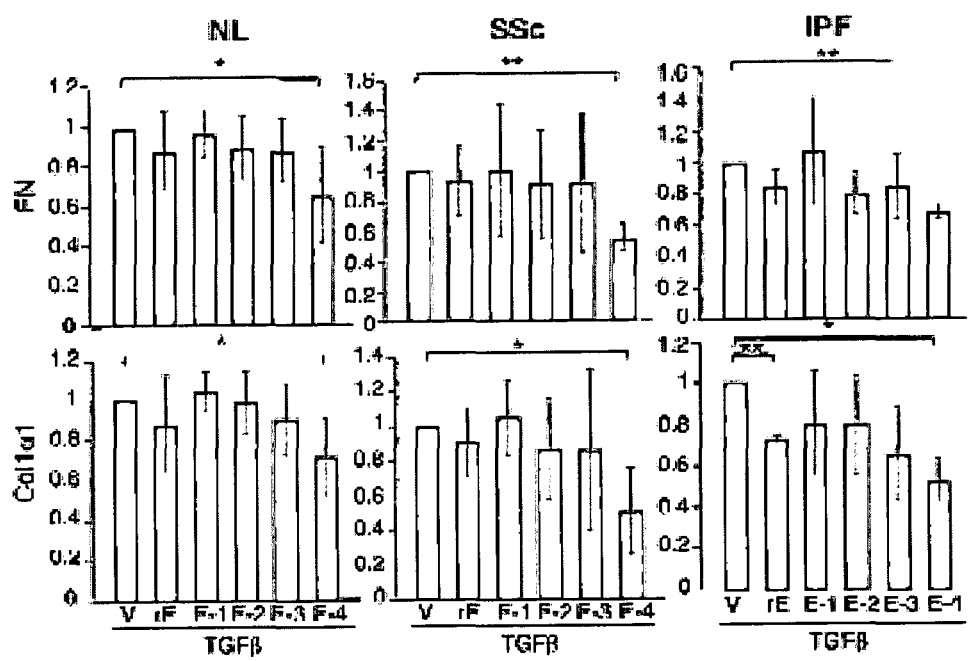
Figure 1D:
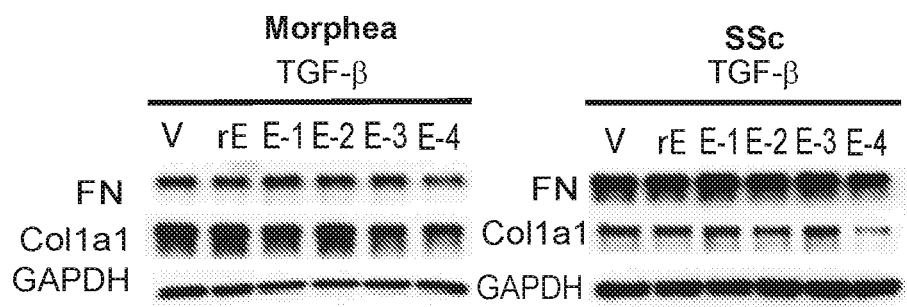

As shown in FIGS. 1B and 1C, a fragment from the carboxy terminus of endostatin (E4) significantly suppressed FN and Col1α1 production in TGF-β treated cells compared with normal lung fibroblasts treated with TGF-β alone (P=0.03, in both comparisons). On the other hand, E1 peptide, located in the amino terminal region of endostatin, had no effect. In addition to healthy fibroblasts, lung fibroblasts obtained from SSc and IPF patients, who had clinical lung fibrosis, were used in parallel assays with similar results (FIGS. 1B and 1C). Having demonstrated anti-fibrotic effects of rE and E4 in lung fibroblasts, the effects of these peptides was examined on skin fibroblasts since skin is a major organ affected by fibrosis in SSc. Primary fibroblasts obtained from the skin of healthy controls, patients with systemic sclerosis (SSc) or localized scleroderma (morphea) were treated with rE or E4. Similarly to lung fibroblasts, rE and E4 reduced TGF-β-induced ECM production in dermal fibroblasts. Representative results are shown in FIG. 1D.

Example 3

Figure 1E:
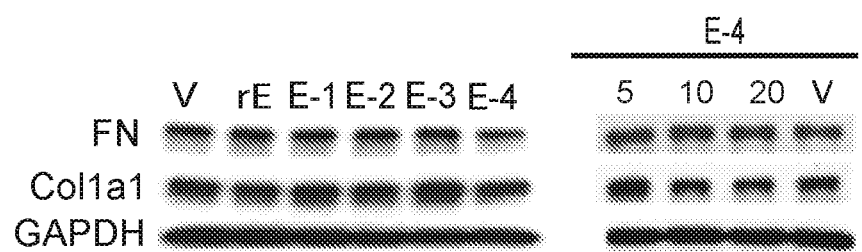

Endostatin Peptides Reverse the Fibrotic Phenotype of Primary Lung Fibroblasts from Patients with SSc and IPF Since it has been shown that TGF-β is upregulated in fibrotic tissue, it was examined if matrix production in fibrotic lung fibroblasts was altered by treatment with endostatin peptide in the absence of TGF-β stimulation. As shown in FIG. 1E left panel, both FN and Col1α1 levels decreased in E4-treated fibroblasts. In addition, the same fibroblasts were treated with different concentrations of E4 to identify the optimal anti-fibrotic dose. E4 dose-dependently reduced Col1α1 levels when compared to vehicle control (FIG. 1E, right panel), but had a modest effect on FN levels. The reduction in ECM was more modest than that observed following TGF-β stimulation. Taken together, the results indicate that E4 can reduce baseline production of ECM components in fibroblasts from a fibrotic milieu and thus reverse the fibrotic phenotype.

Figure 1F:
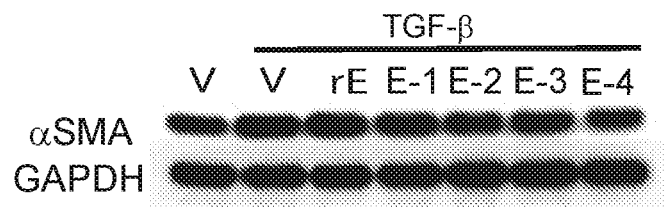

Myofibroblasts, activated fibroblasts which express α-SMA, are induced by TGF-β stimulation and play a central role in fibrosis. Therefore, the effects of endostatin peptides on α-SMA expression in normal lung fibroblasts was examined. As shown in FIG. 1F, TGF-β stimulation greatly increased α-SMA expression. Interestingly, E4, and to a lesser extent E3, decreased TGF-β-induced α-SMA levels suggesting that the carboxy-terminal region of endostatin can prevent the activation of fibroblasts and their transition to a myofibroblastic phenotype.

TABLE 1

Amino acid sequence of human endostatin fragments.

E1 (amino acids 1-45 of SEQ ID NO: 2)
H-$^{1}$HSHRDFQPVLHLVALNSPLSGGMRGIRGADFQCFQQARAVGLAGT$^{45}$-OH E2 (amino acids 71-115 of SEQ ID NO: 2)
H-$^{71}$IVNLKDELLFPSWEALFSGSEGPLKPGARIFSFDGKDVLRHPTWP$^{115}$-OH E3 (SEQ ID NO: 20; amino acids 133-180 of SEQ ID NO: 2)
H-$^{133}$SYCETWRTEAPSATGQASSLLGGRLLGQSAASCHHAYIVLCIENSFMT$^{180}$-OH E4 (SEQ ID NO: 21; amino acids 133-180A of SEQ ID NO: 2)
H-$^{133}$SYCETWRTEAPSATGQASSLLGGRLLGQSAASCHHAYIVLCIENSFMT$^{180}$-CONH$_2$

Example 4

Figure 2A:
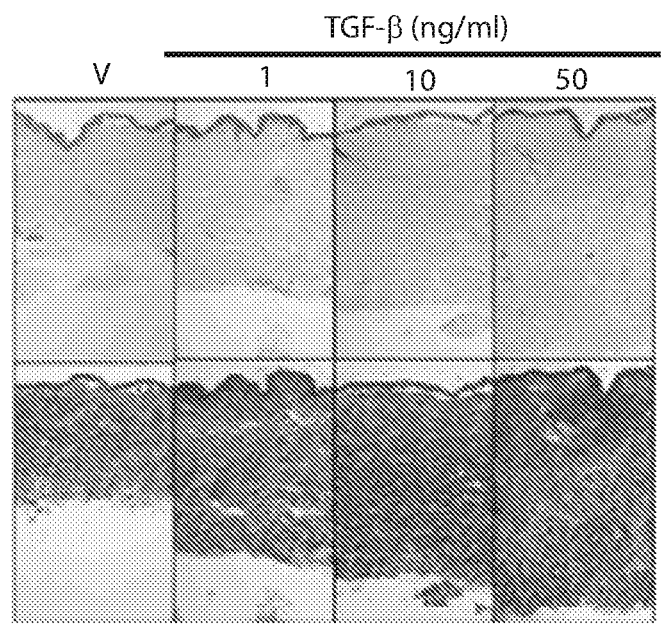
FIGS. 2A-2C. Ex vivo human skin fibrosis organ culture model.
Figure 2B:
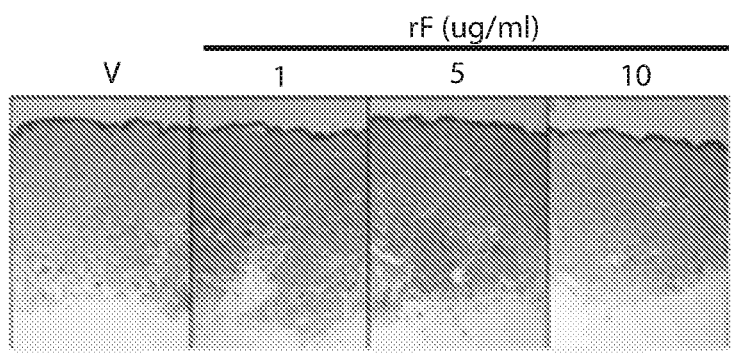
Figure 2C:
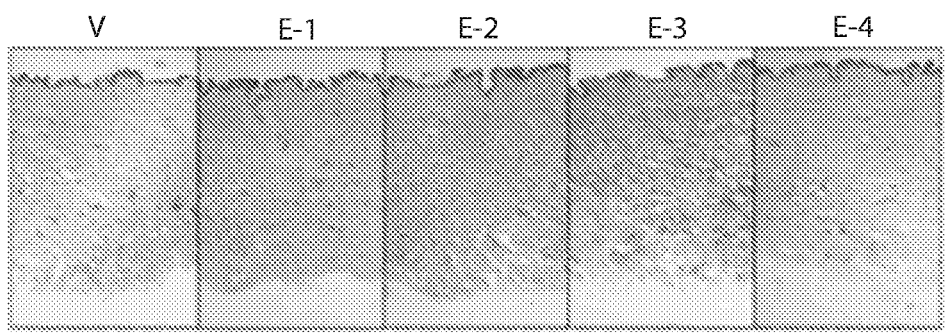
Figure 3A:
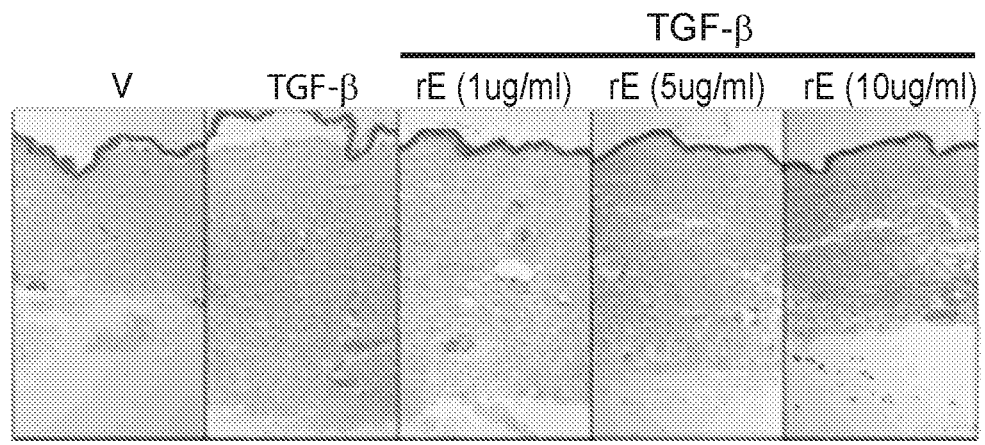
FIGS. 3A-3B. The effect of recombinant endostatin on TGF-β-induced fibrosis and dermal thickness in human skin.
Figure 3B:
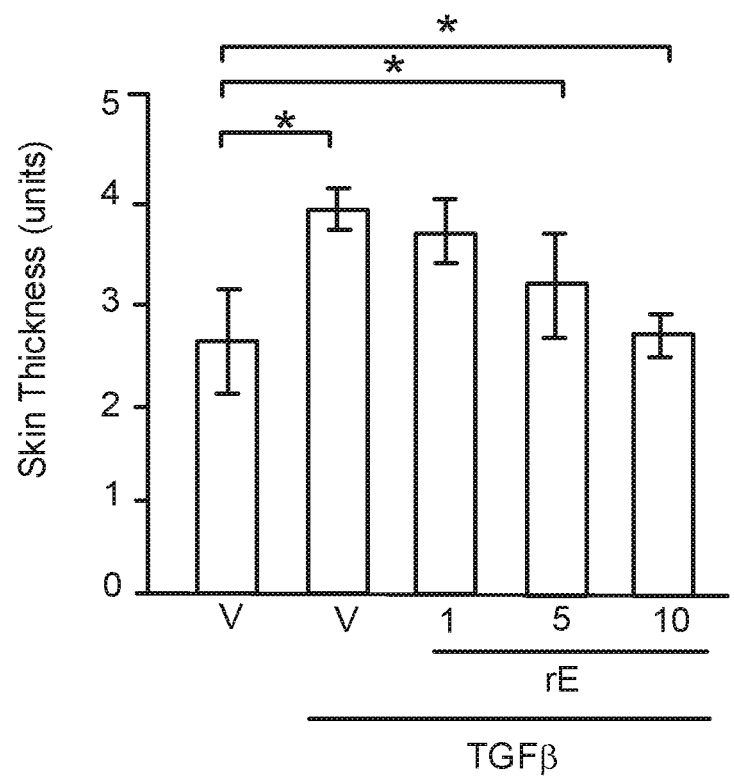

Endostatin Reduces Dermal Thickness and Prevents TGF-β-Induced Fibrosis in Human Skin Cultured human skin explants can be used as an organ model to assess the effects of fibrogenic factors and for evaluating the efficacy of inhibitors/therapies to halt the progression of fibrosis and potentially reverse it (Yasuoka, The Open Rheumatol J 2008; 2:17-22). To evaluate the efficacy of endostatin as a potential therapeutic agent for fibrosis, this ex vivo human skin model was used. Since TGF-β is a well-known pro-fibrotic factor that plays a central role in fibrosis, human recombinant TGF-β was first injected intradermally to assess the level of fibrosis. As shown in FIG. 2A, TGF-β injection dramatically increased dermal thickness in a dose-dependent manner one week post-injection. The fibrotic effect of TGF-β (10 ng/ml) resolved by two weeks. The baseline effects of rE (1, 5, and 10 μg/ml) or endostatin peptides (10 μg/ml) were also examined individually. Although rE and E1-4 did not significantly alter dermal thickness, rE, E3, and E4 showed a tendency towards reduction in human dermal thickness (FIGS. 2B and 2C). It was determined if rE could inhibit fibrosis in TGF-β-treated human skin. TGF-β and rE were injected simultaneously. One week post-administration, rE in combination with TGF-β significantly reduced dermal thickness in a dose-dependent manner (FIG. 3). To assess the effects of rE on reversing fibrosis, the peptide was injected 2 days after TGF-β administration. Similarly to co-treatment, delayed rE also significantly ameliorated TGF-β-induced dermal fibrosis. The findings indicate that human endostatin can prevent the development and progression of fibrosis and also reverse TGF-β-induced fibrosis in human skin.

Example 5

Figure 4A:
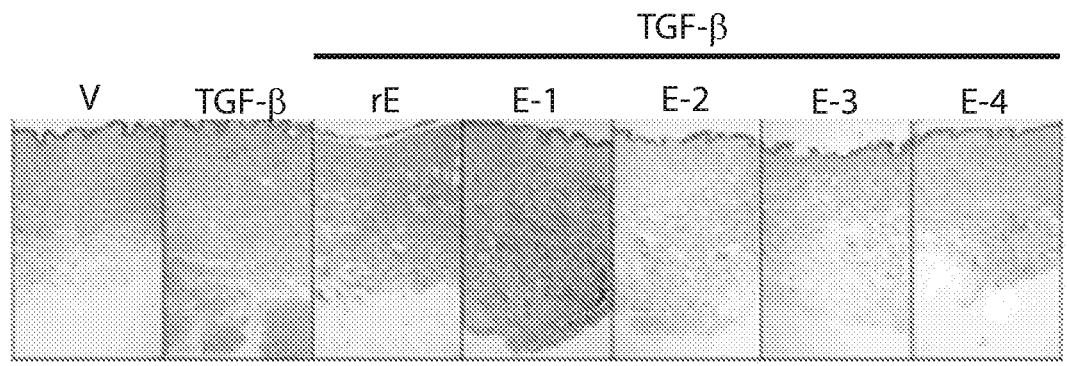
FIGS. 4A-4B. The effect of endostatin polypeptides TGF-β-induced fibrosis and dermal thickness in human skin.
Figure 4B:
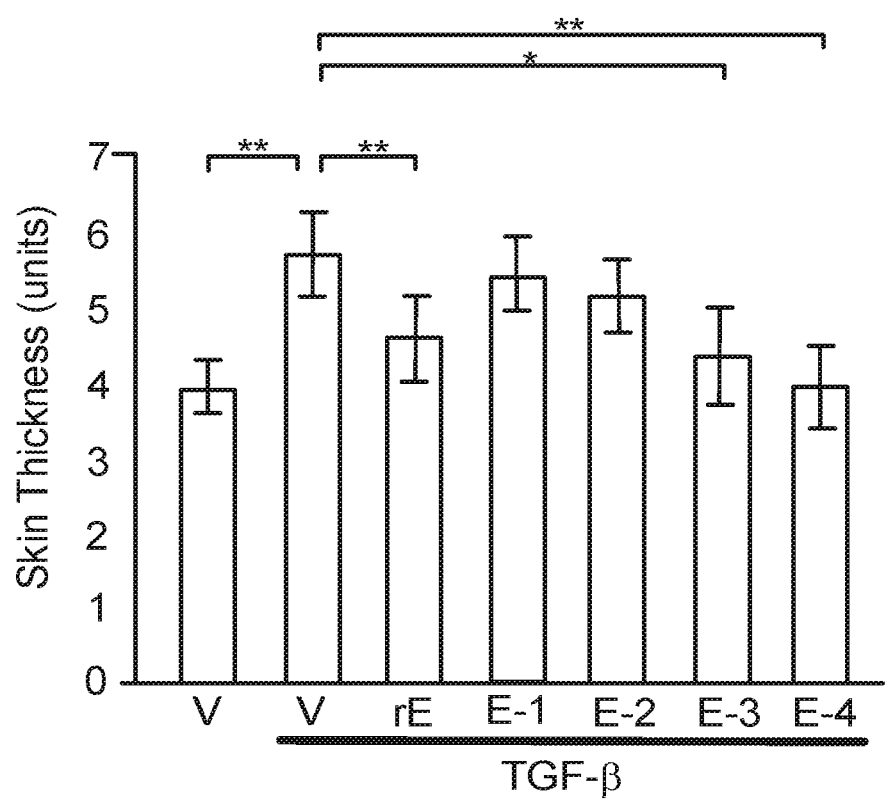
Figure 5A:
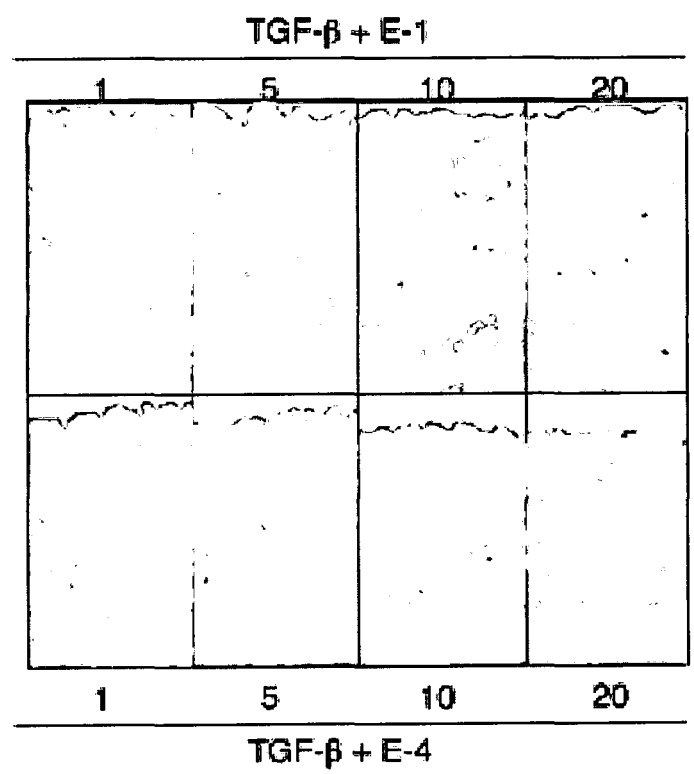
FIGS. 5A-5B. Dose response of E-1 and E-4 in TGF-β-induced fibrosis.
Figure 5B:
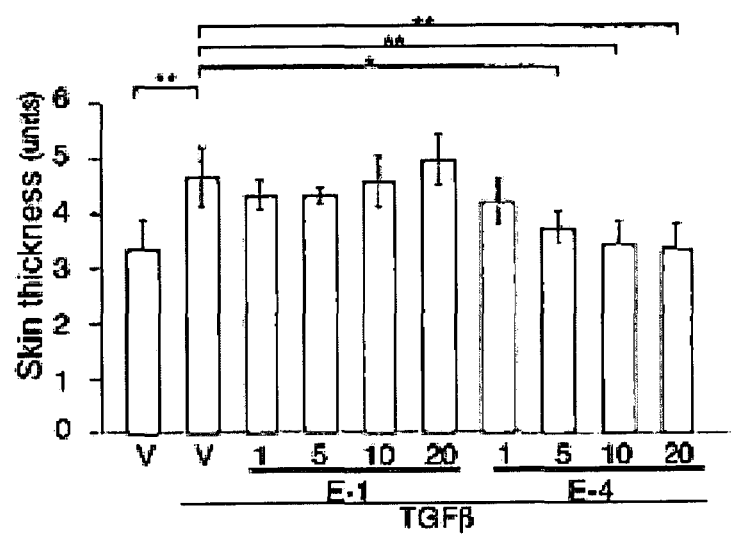
Figure 17A:
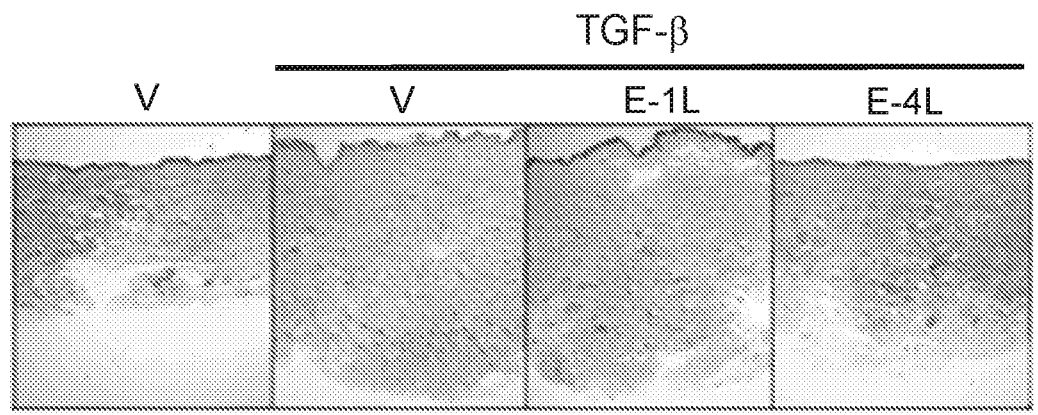
FIG. 17A-17B. The effect of endostatin peptides on established fibrosis triggered by TGF-β in human skin.
Figure 17B:
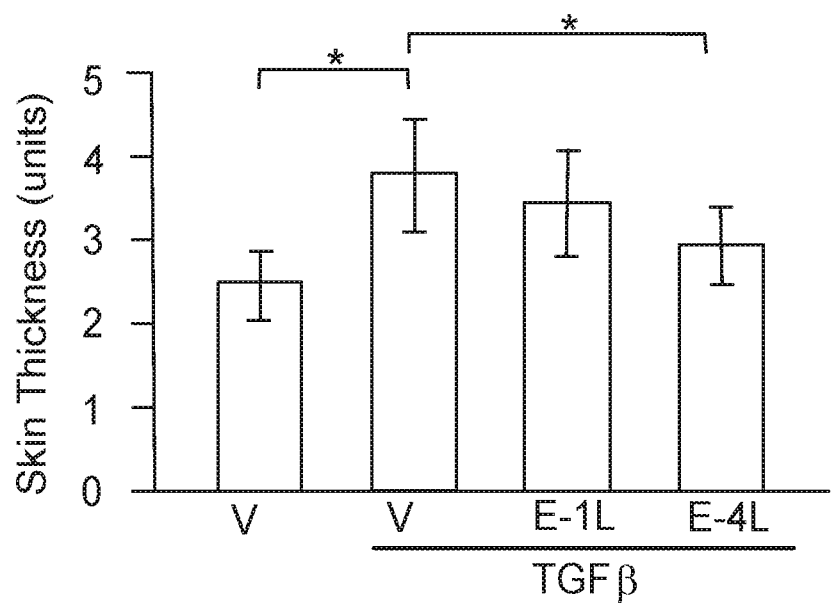

Endostatin Peptides Reduce TGF-β-Induced Fibrosis in Human Skin Ex Vivo and Reverse Existing Fibrosis To determine which part of endostatin is responsible for inhibiting TGF-β-induced fibrosis in human skin explants, endostatin peptides (10 μg/ml) were administrated in the presence of 10 ng/ml of TGF-β. Representative images are shown in FIG. 4A. E3 and E4 significantly abolished the development of fibrosis as measured by dermal thickness when compared to TGF-β alone (P=0.04, 0.01, respectively; FIG. 4). The dermal thickness of skin explants injected with different concentrations of E1 or E4 in combination with TGF-β was examined. As shown in FIG. 5, unlike E1, E4 at concentrations of 5-20 μg/ml clearly ameliorated TGF-β-induced skin fibrosis, indicating that the C-terminus of endostatin can suppress fibrosis (see FIG. 17).

Example 6

Endostatin Peptides Reduce TGF-β-Induced Fibrosis In Vivo in Mouse Skin

Figure 6A:
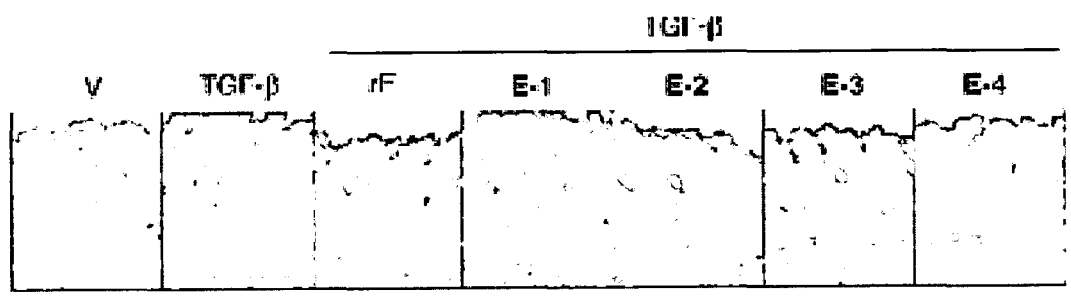
FIGS. 6A-6B. The effect of endostatin polypeptides in the development of fibrosis in vivo in mouse skin.
Figure 6B:
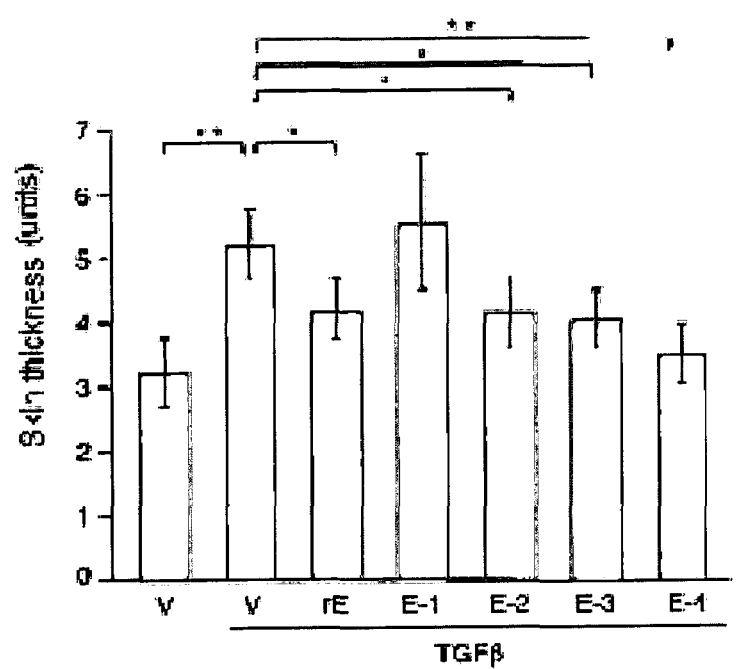

The anti-fibrotic effect of endostatin peptides was further assessed in vivo. rE and endostatin peptides in combination with TGF-β were injected in the skin of mice. One week post-injection, mice appeared healthy and showed no signs of distress. As shown in FIG. 6, human TGF-β strongly increased dermal thickness in mouse skin (P=0.004). Peptides E3 and E4 from the carboxy terminus of human endostatin peptide prevented dermal fibrosis induced by TGF-β (P=0.01, 0.007, respectively). In addition, E2 significantly reduced dermal thickness (P=0.03). E1, a peptide corresponding to the amino terminus of endostatin did not alter TGF-β-induced dermal fibrosis. These results confirmed those obtained in our human skin model and emphasize the importance of the C-terminal domain of endostatin in preventing TGF-β-induced fibrosis in vivo and ex vivo.

Example 7

The C-Terminal Peptide of Endostatin has Modest Anti-Angiogenic Activity

Figure 7A:
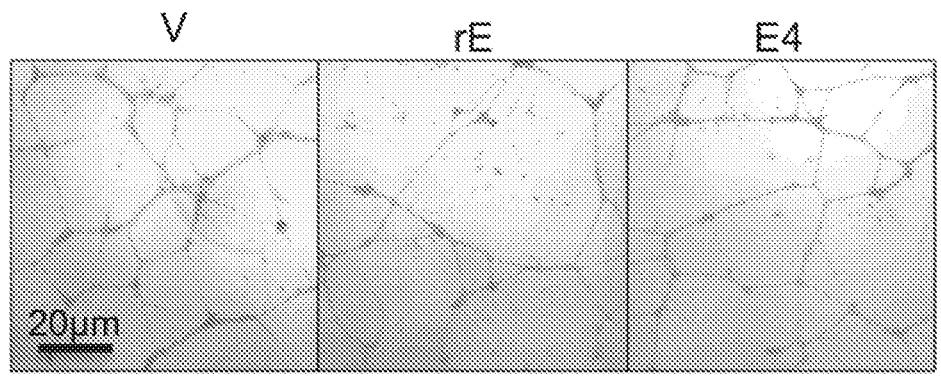
FIGS. 7A-7B. Capacity of endostatin polypeptide to inhibit tubular formation in MATRIGEL®.
Figure 7B:
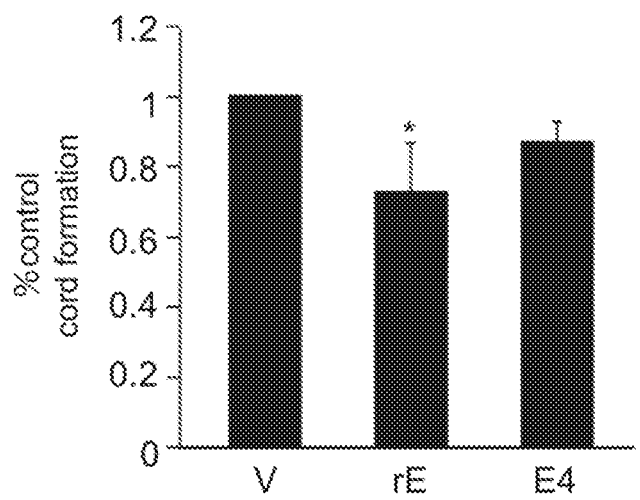

The anti-angiogenic effect of endostatin has been attributed to its amino terminal domain (Tjin Tham Sjin et al., Cancer Res 2005; 65:3656-63). To evaluate the anti-angiogenic capacity of the carboxy terminal regions of endostatin, the effect of E4 on in vitro tubular formation was examined using Matrigel. As shown in FIG. 7, the capacity of rE to inhibit tubular structure formation by HUVECs was significant, confirming previous reports. On the other hand, the ability of E4 to suppress angiogenesis was modest, suggesting that the region of endostatin corresponding to E4 does not significantly contribute to its anti-angiogenic activity.

Thus, E4, a peptide corresponding to the carboxy terminal region of endostatin, ameliorates TGF-β-induced fibrosis and even reverses it. E4 suppressed TGF-β-induced ECM production and downregulated α-SMA levels in primary lung and skin fibroblasts. In vivo and ex vivo analyses revealed that E4 impedes the increase of skin dermal thickness triggered by TGF-β. Furthermore, the anti-angiogenic capacity of E4 was low compared to that of rE. Taken together, the findings suggest that the domains of endostatin responsible for its anti-fibrotic and anti-angiogenic capacity are distinct. Other endostatin peptides (for example, E2 and E3) are shown to have anti-fibrotic activity.

The anti-angiogenic activity of endostatin has been the focus of numerous investigations directed at the development of anti-tumor therapy. Recently, elevated serum and BALF levels of endostatin in fibrotic disorders such as idiopathic pulmonary fibrosis (IPF) and systemic sclerosis (SSc) were reported. Endostatin levels were relatively increased in IPF patients with severe respiratory dysfunction and in SSc patients with pulmonary fibrosis, severe skin fibrosis, and with cutaneous scars, compared to patients without those clinical manifestations (Sumi *J Clin Lab Anal* 2005; 19:146-9; Richter et al., *Thorax* 2009; 64:156-61). In addition, collagen XVIII expression was increased in cultured dermal fibroblasts of SSc patients (Tan et al., *Arthritis Rheum* 2005; 52:865-76) and in whole lung extracts of patients with IPF (Yang et al., *Am J Respir Crit Care Med* 2007; 175:45-54). In this regard, since endostatin is a proteolytic product of collagen XVIII cleaved by several proteases including MMPs and cathepsin L (Wen et al., *Cancer Res* 1999; 59:6052-6; Felbor, *EMBO J* 2000; 19:1187-94), and since MMPs are also upregulated in SSc and IPF (Richter et. al., *Thorax* 2009; 64:156-61, Toubi et al., *Clin Exp Rheumatol* 2002; 20:221-4), the observations that cleaved endostatin levels are elevated in those patients is plausible. However, it is unclear how endostatin may be involved in the pathogenesis of fibrosis.

Without being bound by theory, increased endostatin in fibrotic tissues may constitute a negative feedback regulatory loop which, although unsuccessful, is directed at halting the progression of fibrosis. Since endostatin was originally identified in aberrant "angiogenic" endothelial cancer cells as a product that likely controls/inhibits its "angiogenic" capacity (O'Reilly et al., *Cell* 1997; 88:277-85), it is plausible that endostatin in fibrosis serves a similar regulatory function.

Reduced connective tissue but normal vessel density has been reported in recombinant endostatin-treated mouse skin using a wound healing model (Bloch et al., *FASEB J* 2000; 14:2373-6). Further, a peptide from the N-terminal region of endostatin prevented the progression of peritoneal sclerosis in a mouse model (Tanabe et al., *Kidney Int* 2007; 71:227-38); the peptide under investigation corresponded to the N-terminus of endostatin encompassing amino acids 1-27.

In contrast, the C-terminal region of endostatin, but not the N-terminus, is shown herein to be responsible for its anti-fibrotic effects. In fact, the peptide corresponding to the N-terminal domain of endostatin contributed to the fibrotic phenotype in some of the assays. Studies directed at defining the specific amino acid sequence responsible for endostatin's anti-angiogenic capacity (Richter et al., *Thorax* 2009; 64:156-61; Cattaneo et al., *Exp Cell Res* 2003; 283:230-6; Xu et al., *Curr Protein Pept Sci* 2008; 9:275-83) have shown that the entire angio-suppressive activity of endostatin was located in a 27-amino-acid peptide in the N-terminal domain (Richter et al., *Thorax* 2009; 64:156-61). Thus, the functional domain of endostatin that mediates its anti-fibrotic activity is different from that responsible for its anti-angiogenic capacity, implying different mechanisms for inhibiting angiogenesis and fibrosis. The anti-fibrotic C-terminal endostatin polypeptides disclosed herein are therefore capable of selectively inhibiting fibrosis without inhibiting angiogenesis. The C-terminal endostatin polypeptides can be used to more specifically and selectively target unwanted fibrosis without interfering with angiogenesis that may impact a desired therapeutic outcome.

The C-terminal endostatin polypeptide also reduces α-SMA expression in TGF-β-treated fibroblasts. In addition, the matrix reducing effects of E4 on normal fibroblasts was modest compared to that in fibrotic fibroblasts. This suggests that the therapeutic effect of endostatin C-terminal peptide in fibrosis could be due, in part, to hindrance of fibroblast activation by TGF-β and other fibrosis promoting growth factors.

In 2005, ENDSTAR®, a recombinant human endostatin purified from *E. coli* containing an additional nine-amino acid sequence produced as a His-tagged protein was approved for the treatment of non-small-cell lung cancer in China (Sun et al., *J Clin Oncol* 2005 (ASCO Annual meeting proceedings); 23:7138). Despite its effectiveness, the treatment had several disadvantages including a requirement for high doses, the protein's short half-life, poor stability and easy inactivation (see, for example, Crystal, *Nat Biotechnol* 1999; 17:336-7; Hu et al., *Acta Pharmacol Sin* 2008; 29:1357-69). The small synthetic peptides disclosed herein could overcome these obstacles. E4 significantly inhibited fibrosis compared to rE and even E3 in vitro, in vivo, and ex vivo. In addition, E4 had minimal anti-angiogenic activity compared to rE, confirming that the anti-angiogenic activity of endostatin resides in its N-terminal domain. The only difference between E3 and E4 was the presence of an amide-bond in the C-terminus of E4. Without being bound by theory, this amide renders the peptide more resistant to carboxy degradation by carboxypeptidases or other degrading molecules, thus stabilizing the peptide and likely maintaining its biological activity (Yang et. al. *Am J Respir Crit Care Med* 2007; 175:45-54).

Unfortunately, there are no effective therapies for organ fibrosis. The C-terminal domain of endostatin, corresponding to amino acid sequence 133-180 with amide-bond formation, suppressed ECM production by primary skin and lung fibroblasts and ameliorated dermal fibrosis induced by TGF-β in vivo and ex vivo in human skin. The findings presented herein demonstrate that E4 could be used for the treatment of fibrotic disorders, including IPF, SSc, morphea, as well as Graft-versus-host disease, keloid and hypertrophic scar, and other organ fibrosis such as subepithelial fibrosis in asthma.

Example 8

Confirmation of the Efficacy of E4

E4, a peptide representing the carboxy terminus of human endostatin, can attenuate fibrosis triggered by multiple fibrogenic factors. The anti-fibrotic effects of E4 can be detected whether administered concomitantly with or following the fibrogenic trigger. The efficacy of E4 was confirmed in four pre-clinical models of fibrosis: a) bleomycin-induced dermal fibrosis in vivo in mouse skin, b) TGF-β induced dermal fibrosis in mouse skin, and c) bleomycin-induced pulmonary fibrosis. E4 peptide or a control peptide (E1; representing the amino terminal region of endostatin) were administered at the same time as TGF-β or bleomycin or 3-4 days following TGF-β or bleomycin. Mice were sacrificed one and two weeks after TGF-β-initiation of dermal fibrosis, and two and three weeks after bleomycin-induced pulmonary fibrosis. Two different modes of administration of the E4 peptide were also tested. It was confirmed that intraperitoneal and intratracheal administration was effective. The amount of E4 that was administered was 10 µg/ml in a total volume of 100 µl for skin and IP injections and 50 µl for IT administration.

For these studies, fibrosis was assessed by measurement of dermal thickness on H&E skin sections (skin), assessment of collagen levels by Masson Trichrome staining (skin and lung), and measurement of collagen levels by Sircol assay (lung). Furthermore, to confirm the mechanism by which E4 exerts its anti-fibrotic effects, the production of extra-cellular matrix (ECM) components, the levels of enzymes that promote matrix stabilization and thus accumulation and levels of those that degrade ECM components, and levels of transcription factors downstream of the pro-fibrotic triggers were evaluated. Results were assessed using the unpaired t test and the 3-way ANOVA (for the ID1 data).

Results

Figure 8A:
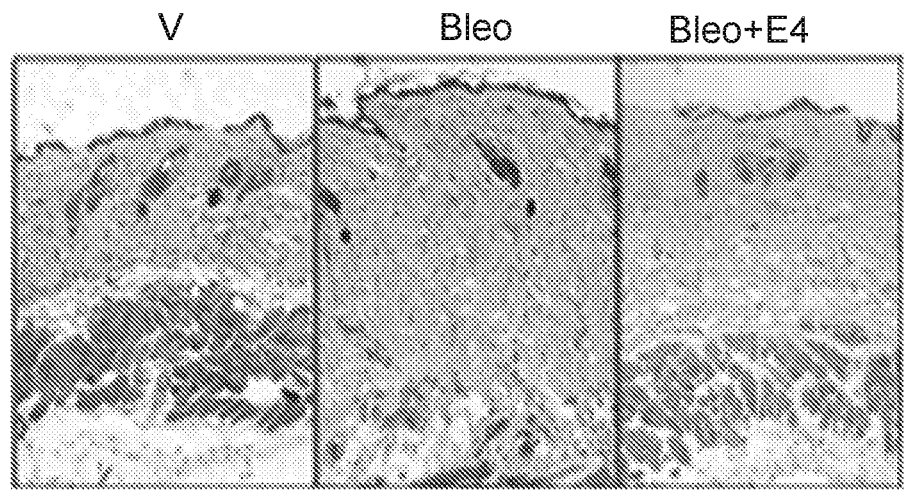
FIGS. 8A-8B. The effect of endostatin E-4 on bleomycin induced dermal fibrosis in vivo.
Figure 8B:
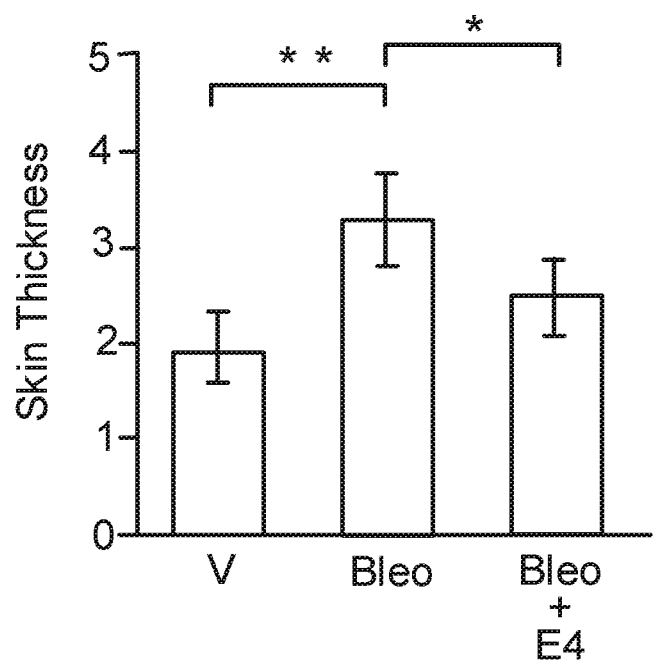

E4 caused a significant attenuation of bleomycin induced dermal fibrosis even with a single administration of E4 (FIG. 8). E4 caused a significant decrease of TGF-β induced dermal fibrosis on day 7. Thus E4 prevents (FIG. 8) and reverses (FIG. 9) dermal fibrosis triggered by TGF-β.

Figure 9:
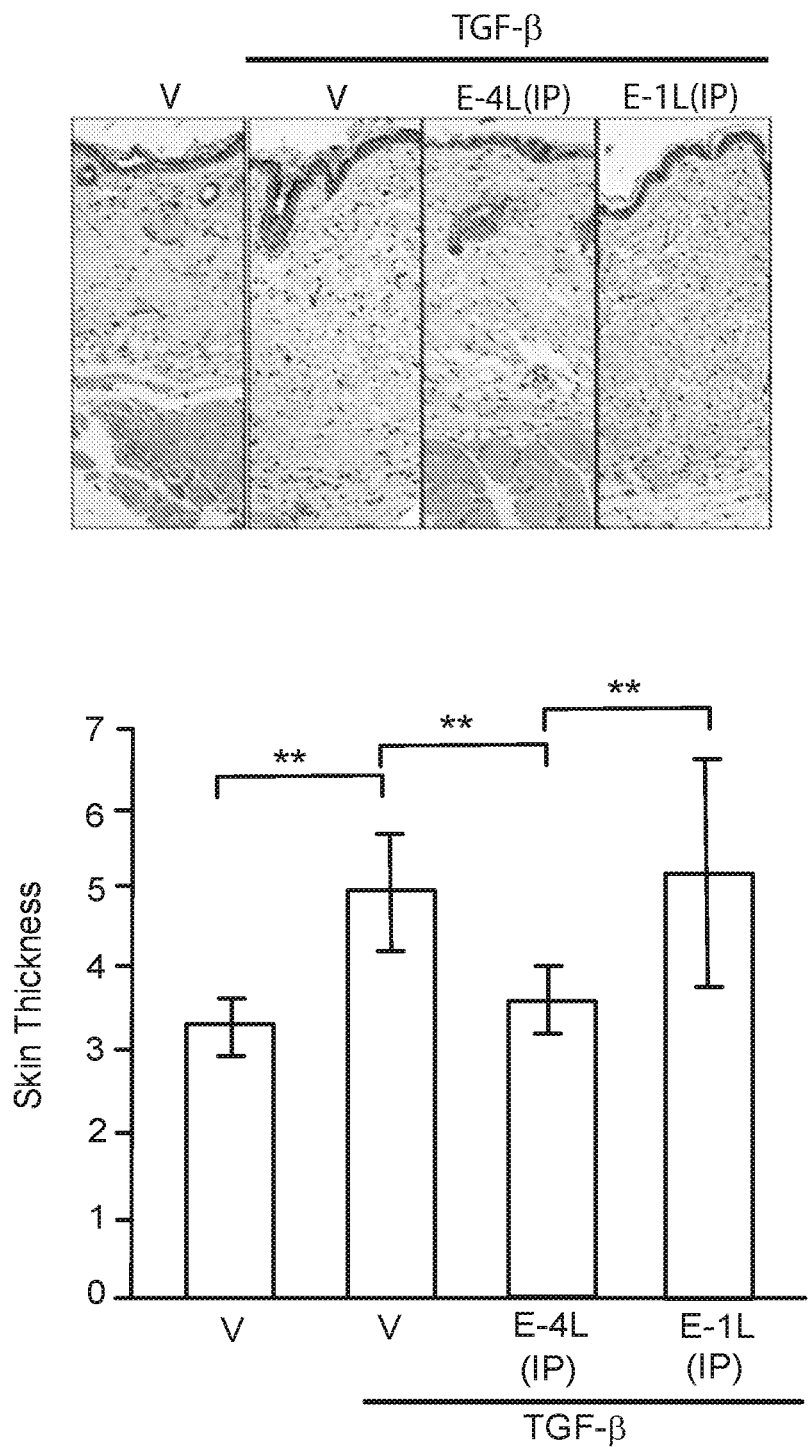
FIG. 9. E4 reverses TGF β-induced dermal fibrosis even if administered 3 days following TGF-β. Mouse skin was treated with TGF-β day 1 and E-4L or E-1L (this is E-4 and E-1 administered after a 3 day lag between administration of the fibrotic trigger and the administration of the peptide. E-1 or E-4 was administered intraperitoneally (IP) at day 3 and harvested at day 7. E4 caused a significant decrease of TGF-β induced dermal fibrosis on day 7. Thus E4 prevents (FIGS. 4-6) and reverses (FIG. 9) dermal fibrosis triggered by TGF-β.
Figure 10A:
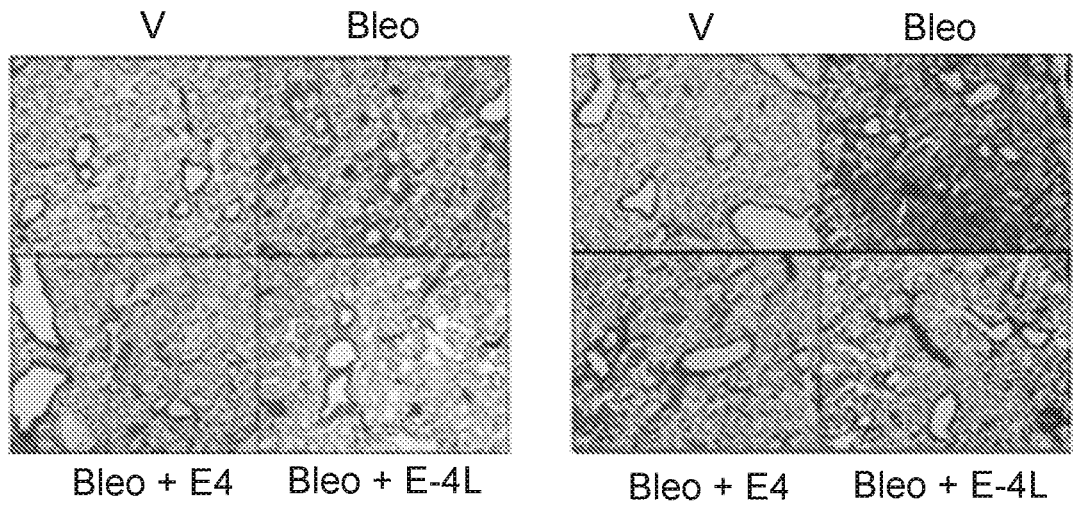
FIG. 10A-10C. E4 attenuates bleomycin induced lung fibrosis in vivo.
Figure 10B:
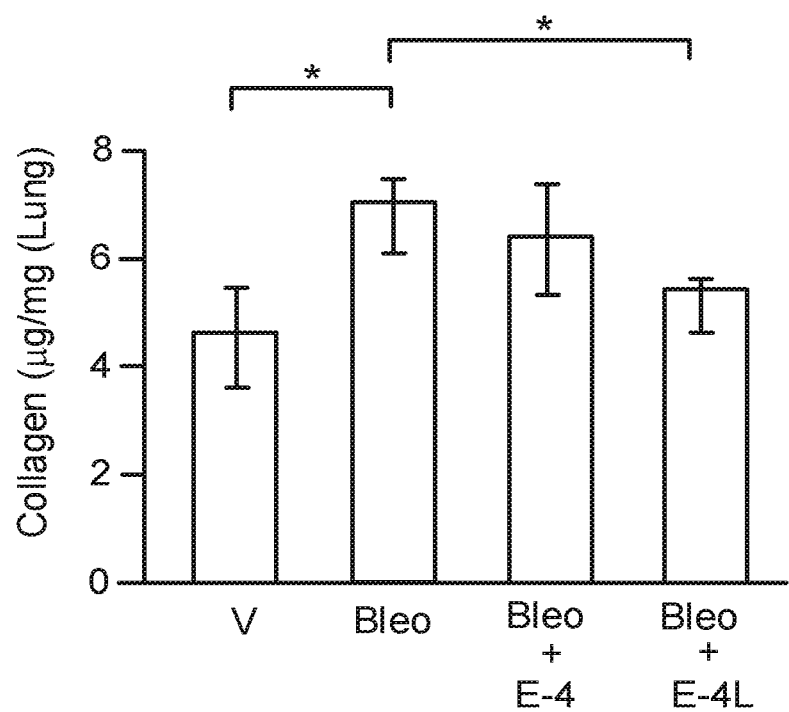
Figure 10C:
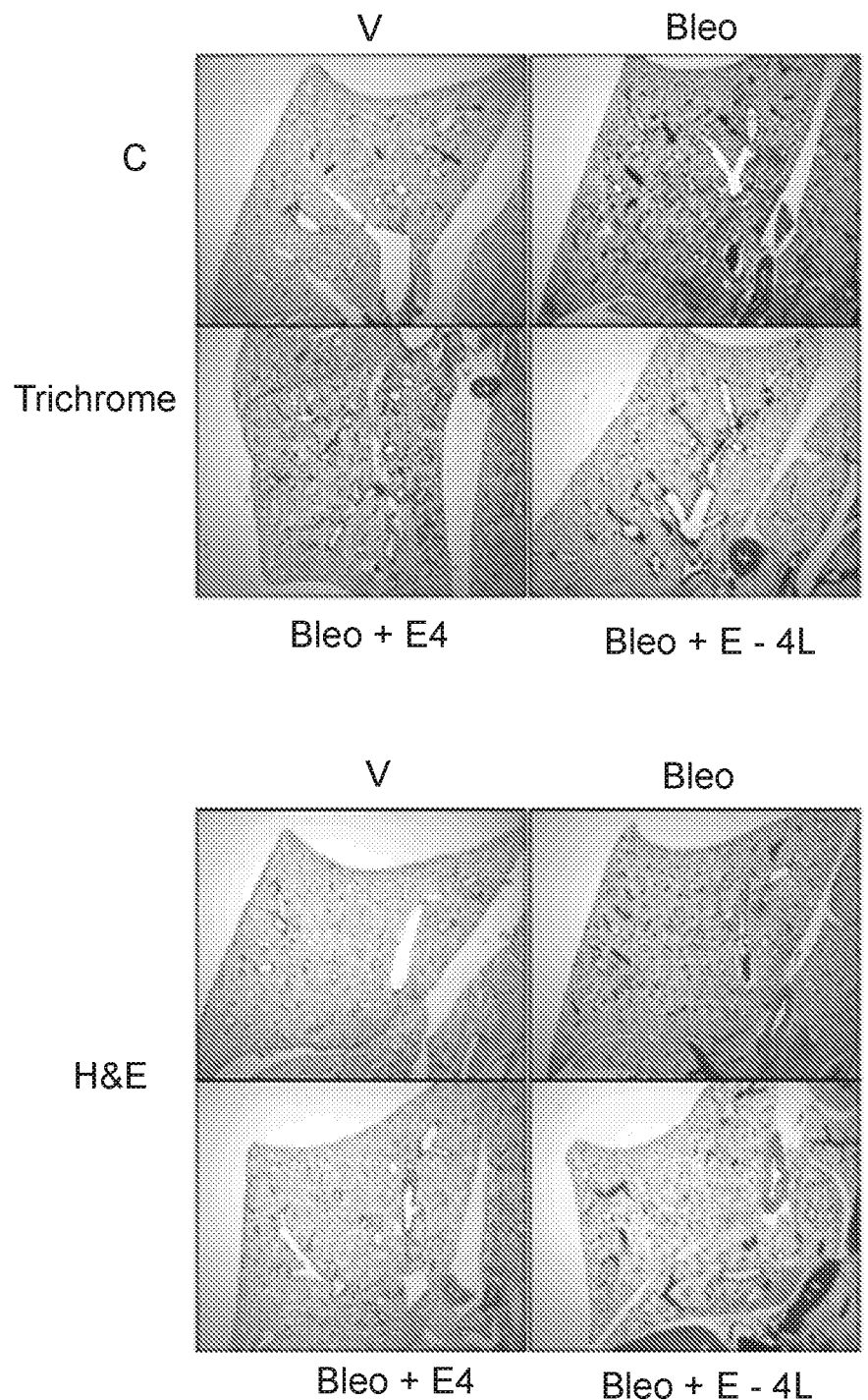

E4 administered concomitantly with bleomycin or three days following bleomycin caused a marked reduction in fibrosis and Masson Trichrome staining (see FIG. 9 and FIG. 10). E4 peptide given three days after bleomycin significantly reduced collagen levels in mouse lungs (FIG. 10B).

Figure 11:
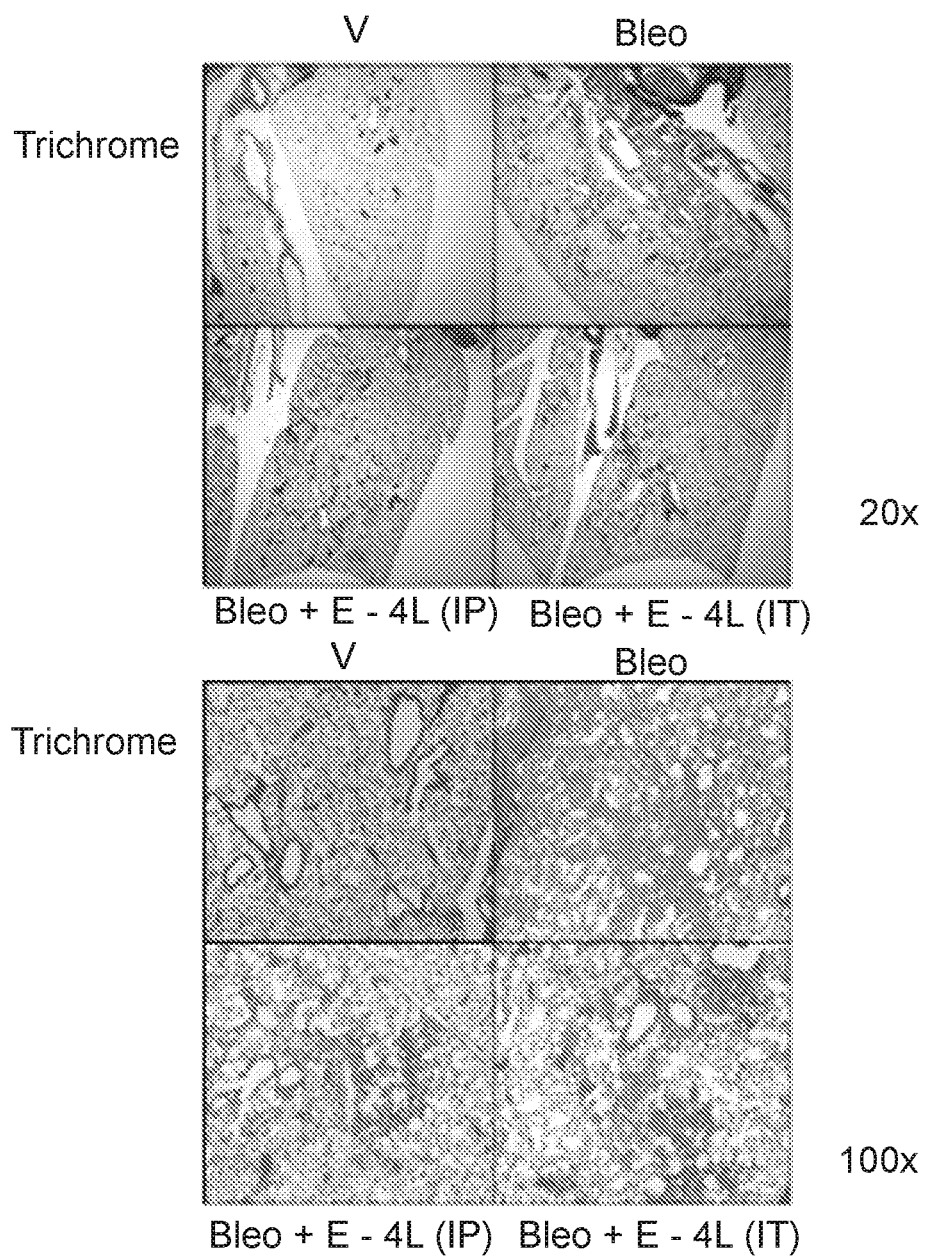
FIG. 11. E4 attenuates bleomycin induced lung fibrosis in vivo whether administered intraperitoneally (IP) or intratracheally (IT). Bleomycin was administered IT at day 1, and E4 was administered either IP or IT at day 3. Lungs were harvested at day 21. E4 caused a significant attenuation of bleomycin induced lung fibrosis on day 21 whether administered IP or IT. Thus E4 is effective at reducing fibrosis irrespective of the route of administration. Results are shown for vehicle alone (V), bleomycin alone (Bleo), bleomycin and E4 administered IP, and bleomycin and E4 administered IT.

E4 caused a statistically significant reduction in both TGF-β and bleomycin induced skin (FIG. 8) and lung fibrosis (FIG. 10) regardless of the mode of administration. Intraperitoneal and intratracheal administration of E4 were both effective in blocking dermal and pulmonary fibrosis. For example, E4 caused a significant attenuation of bleomycin induced lung fibrosis on day 21 whether administered intraperitoneally or intratracheally (FIG. 11). Thus E4 is effective at reducing fibrosis irrespective of the administration mode.

Figure 12:
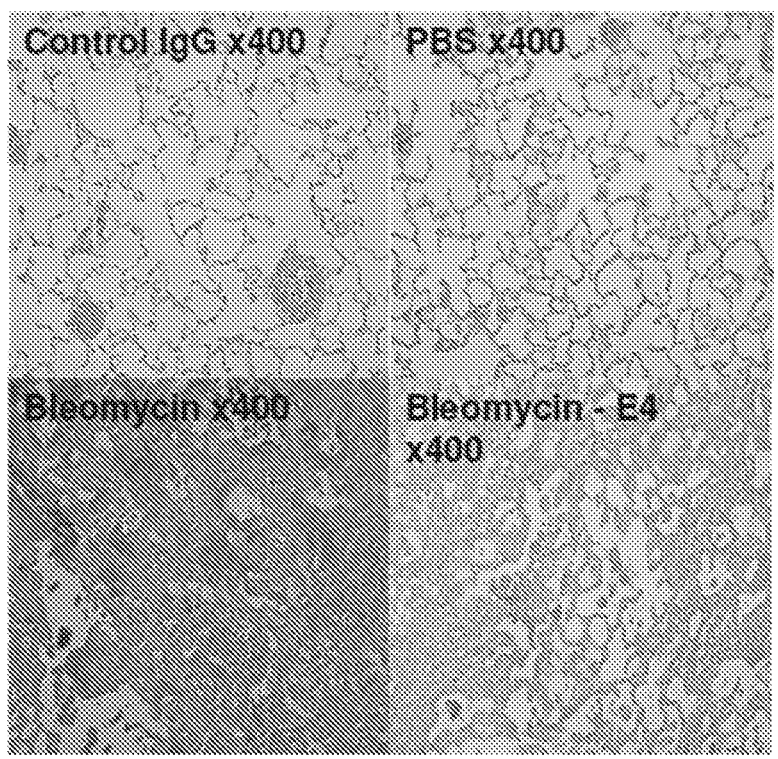
FIG. 12. E4 reduces fibrosis in vivo by reducing levels of lysyl oxidase (LOX), thus reducing crosslinking of collagen and rendering it less stable and more susceptible to proteolytic degradation. Lung sections of mice treated with BLM with or without E4 were used in immunohistochemistry to detect LOX. The sections shown are control IgG, phosphate buffered saline, bleomycin and bleomycin followed by treatment with E4.

The results also evidenced that E4 exerts its anti-fibrotic effects via multiple pathways. E4 reduces levels of lysyl oxidase (LOX), and enzyme responsible for the cross-linking of collagen, elastin, and other extracellular matrix (ECM) molecules and thus the stabilization of the ECM. E4 can make collagen less stable and more susceptible to proteolytic degradation. FIG. 12 shows lung sections of mice treated with bleomycin with or without E4.

Figure 13:
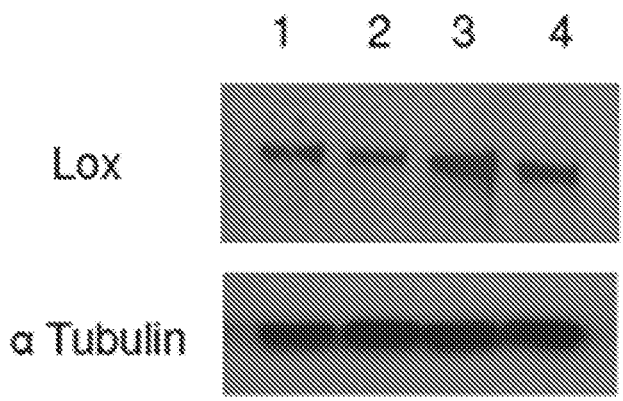
FIG. 13. E4 reduces fibrosis in vitro by blocking TGF-β-induced LOX production in primary human lung fibroblasts. Normal lung fibroblasts in passage 4 were treated with vehicle, E4, TGF-β, or TGF-β followed 30 min. later by E4. Media conditioned by the fibroblasts were analyzed using Western blot analysis after 48 hour. Lane 1: Vehicle (DMSO); Lane 2: E-4; Lane 3: TGF-β; Lane 4: TGF-β followed by E4. Similar results were obtained when LOX mRNA levels were examined by real-time PCR.

E4-mediated reduction of LOX was detected also was detected in vitro. Normal lung fibroblasts in passage 4 were treated with vehicle, E4, TGF-β, or TGF-β followed 30 minutes later by E4 (FIG. 13). Media conditioned by the fibroblasts were analyzed using Western blot analysis after 48 hrs. Treatment with E4 significantly reduced the level of LOX. Similar results were obtained when LOX mRNA levels were examined by real-time PCR.

Figure 14A:
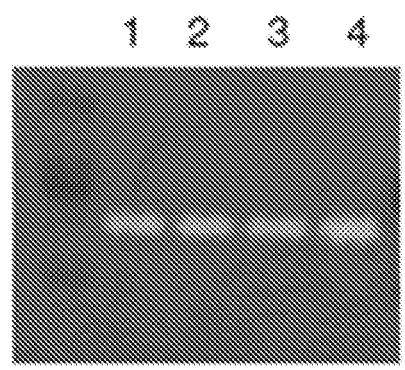
FIG. 14A-14B.
Figure 14B:
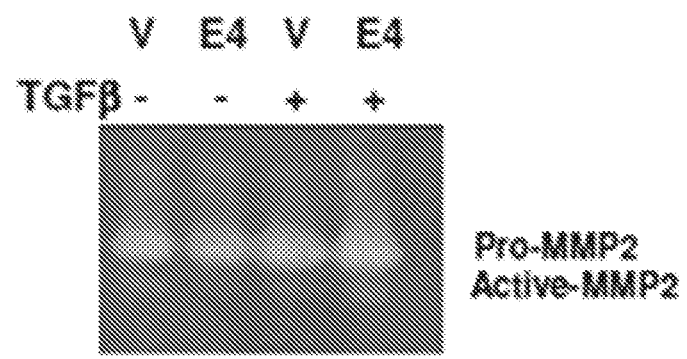
Figure 15:
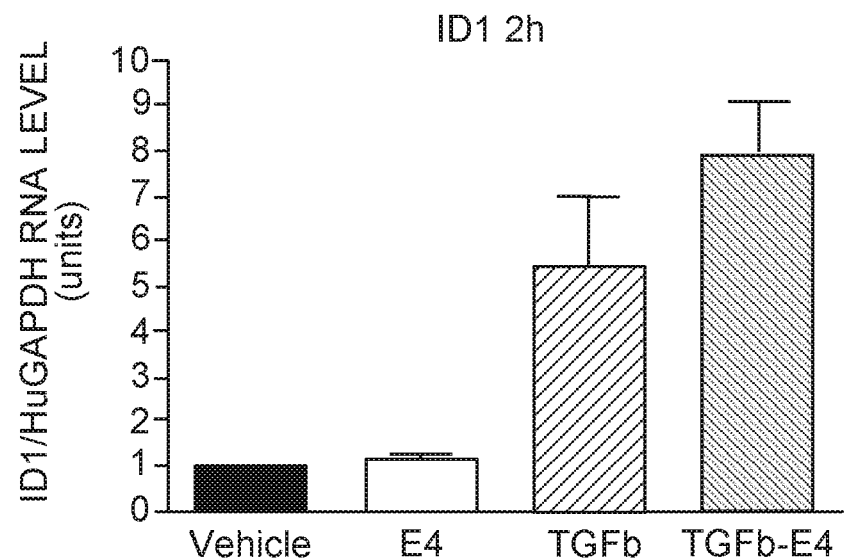
FIG. 15. E4 reduces fibrosis in vitro by inducing expression of ID1, an inhibitor of TGF-β, in primary human lung fibroblasts. Real-time PCR analysis was performed to determine the ID1 mRNA levels under the indicated conditions.
Figure 16:
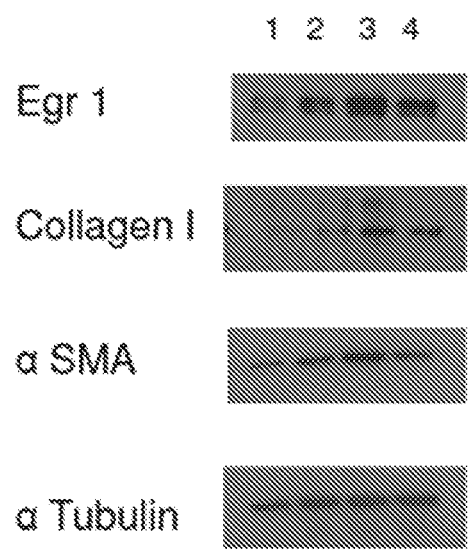
FIG. 16. E-4 reduces fibrosis in vitro by reducing levels of the master transcription factor Egr-1 in primary human lung fibroblasts. Reduction of Egr-1 levels parallels that of collagen, SMA, and fibronectin. Lane 1: vehicle (DMSO); Lane 2: E4; Lane 3: TGFβ, Lane 4 TGFβ followed by E4 after 60 minutes. The samples were harvested after 24 hours.

E4 also promotes the degradation of ECM components via induction and activation of matrix metalloprotease (MMP-2), an enzyme that degrades several ECM molecules including fibronectin and native and denatured collagens (FIG. 14). In addition, E4 increases levels of inhibitor of differentiation (ID)-1, a transcription factor that inhibits TGF-β effects (see FIG. 15). It was determined in a Western blot analysis that E4 reduces the levels of the master switch transcription factor, Egr-1 (see FIG. 16) in primary human lung fibroblasts, treated and harvested after 24 hours. The reduction of Egr-1 levels parallels a reduction in collagen, SMA and fibronectin. Egr-1 is known to mediate the effects of several fibrotic agents (including TGF-β and bleomycin).

Thus, E4 exerted significant anti-fibrotic effects. This peptide significantly attenuates the fibrogenic effects of TGF-β and bleomycin whether administered simultaneously with these fibrotic triggers or a few days following the initiation of fibrosis, suggesting that E4, and other C-terminal endostatin polypeptides is also effective at reversing established fibrosis. The anti-fibrotic effects of E4 were noted whether it was administered intratracheally or intraperitoneally to mice in which pulmonary fibrosis was induced by bleomycin and dermal fibrosis was induced by TGF-β. Furthermore, E4 exerted its anti-fibrotic effects via multiple pathways that included destabilization of ECM through reduction of LOX and thus decreased ECM cross-linking, induction of ECM degradation via activation of MMP-2, suppression of Egr-1 levels, and increased transcription factor ID-1.

Thus, several in vitro assays and four in vivo and ex vivo pre-clinical models of fibrosis suggest that C-terminal endostatin polypeptides, as exemplified by E4, are an effective anti-fibrotic peptide that can block and reverse fibrosis in two organs, lung and skin. These anti-fibrotic effects as well as the lack of anti-angiogenic effects characteristic of endostatin render E4 an attractive therapeutic peptide for organ fibrosis.

Example 9

Production of an Orally Active Anti-Fibrotic Protein in Plants

Studies were conducted to evaluate the expression, purification, and oral delivery of the E3-6His-KDEL, E3-Fc (C67A), and Expanded E3-6His-KDEL peptides shown in TABLE 2.

Methods

Peptides were expressed in plants using the IBIO-LAUNCH™ gene expression platform. C57BL/6 mice were given bleomycin intratracheally in conjunction with END-55 (also referred to herein as E3-Fc (C67A) and CFB03) intravenous (IV) administration, or followed by IV administration of END-55 eight days after bleomycin. The mice were sacrificed at day 12 and lung samples were taken for both hematoxylin and eosin (H&E) staining and hydroxyproline assay.

Results

Figure 18:
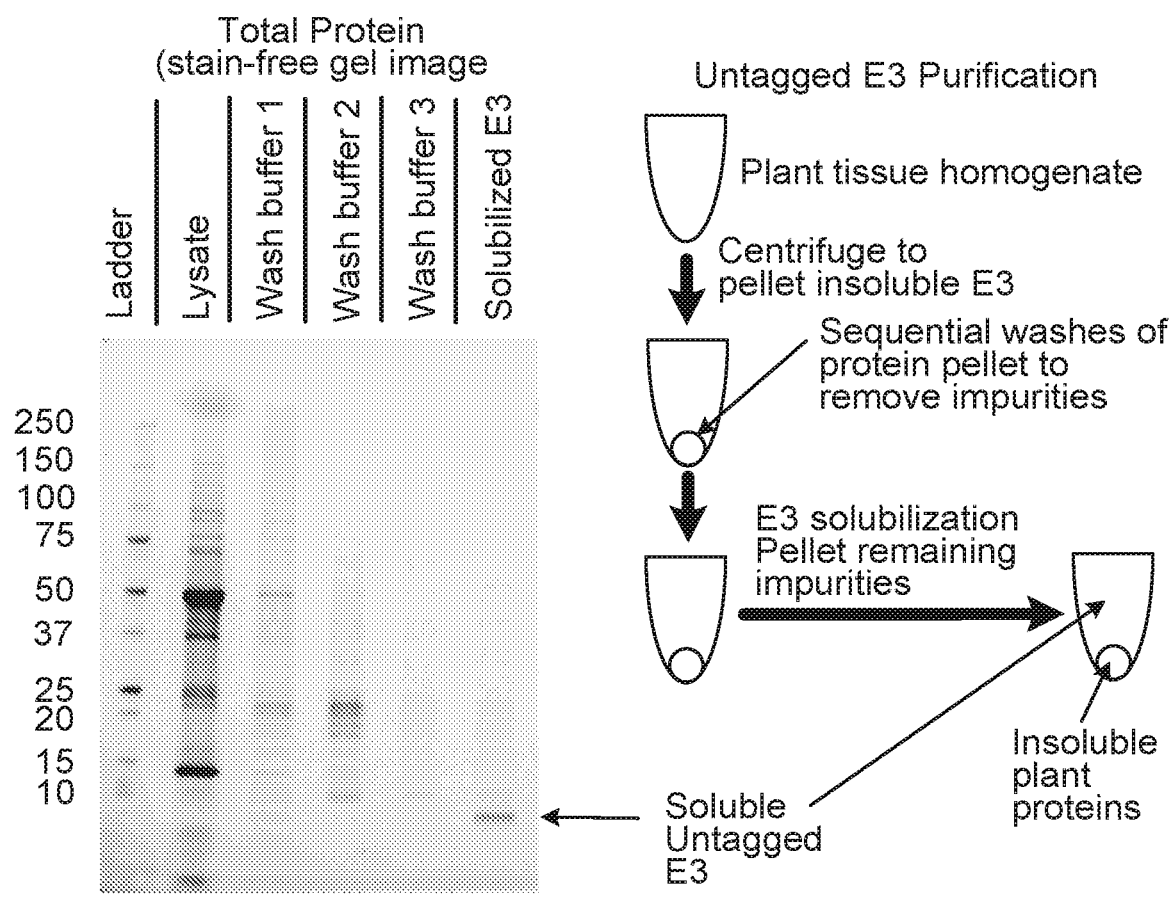
FIG. 18. Purification scheme for untagged E3 based on differential solubility.
Figure 19:
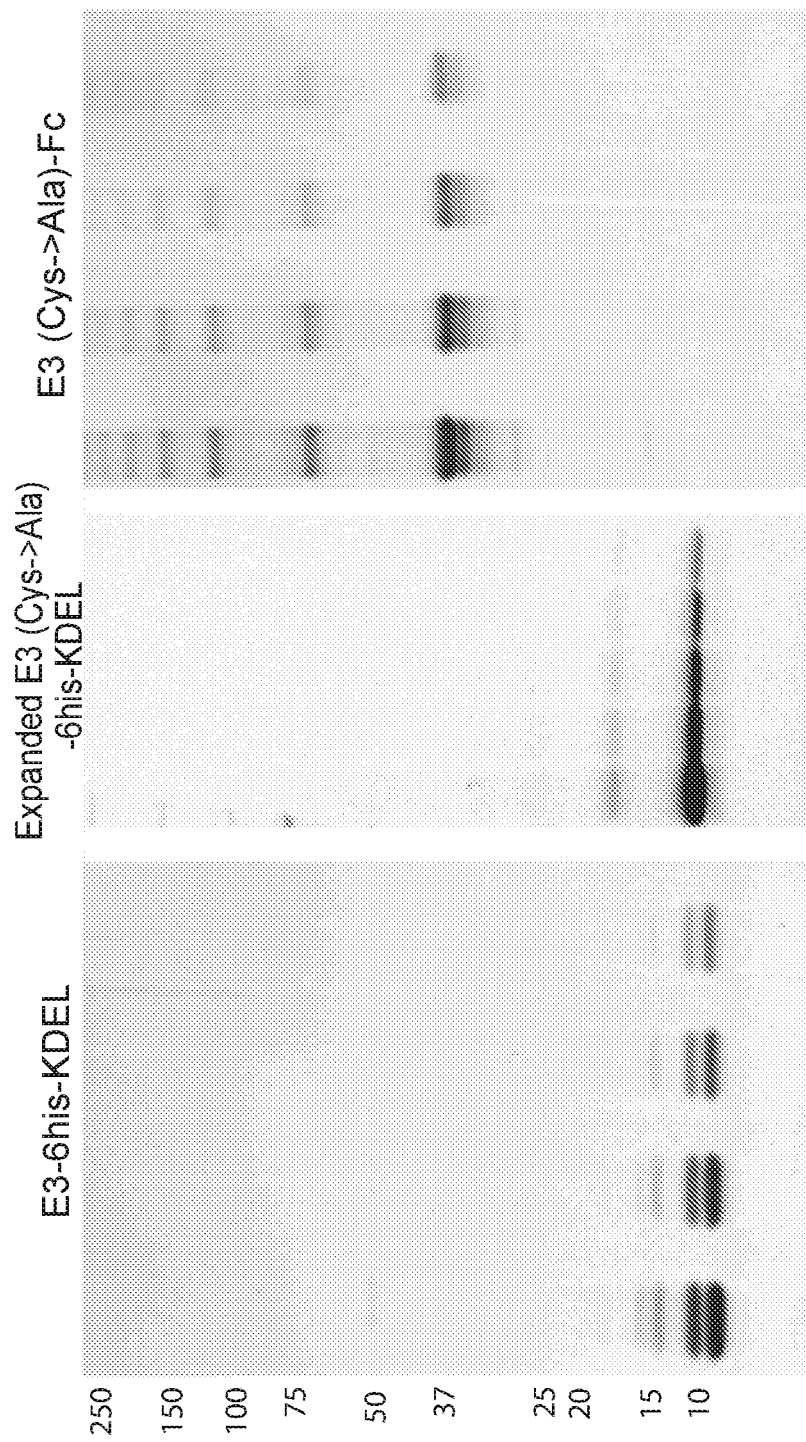
FIG. 19. E3 variants produced in plants.

E3 peptides were expressed in plants using the IBIO-LAUNCH™ platform. Untagged E3 peptides were purified based upon differential solubility. See FIG. 18. Each of E3 variant peptides (E3-6His-KDEL, Expanded E3-6His-KDEL (C67A), and E3-Fc (C67A)) was successfully produced and purified. See FIG. 19.

Figure 20:
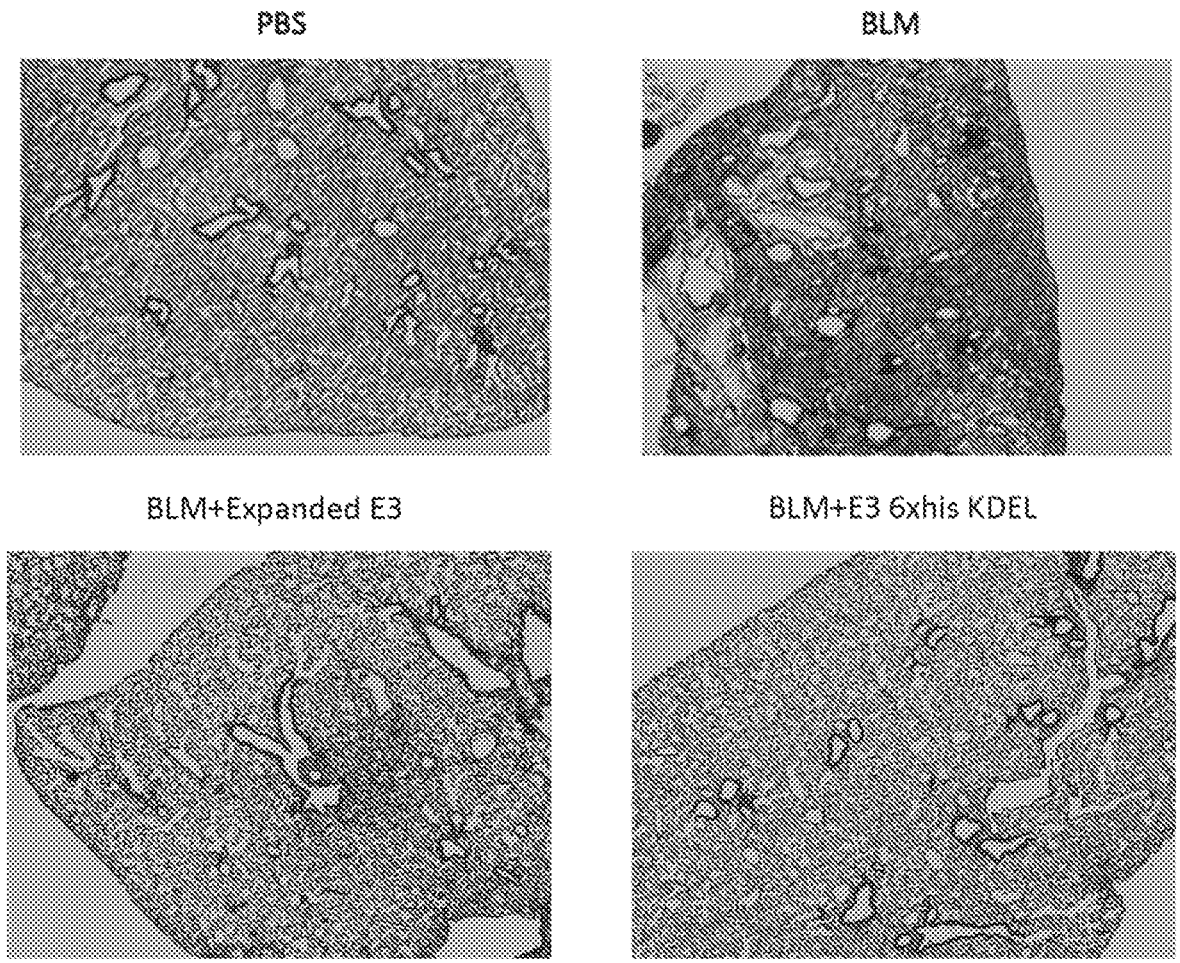
FIG. 20. Oral Plant-Made Pharmaceutical (PMP) E3 variants prevent bleomycin-induced pulmonary fibrosis.

Pulmonary fibrosis was induced in mice using bleomycin. Animals were treated orally with E3 variants or phosphate buffered saline (PBS). Lung histology was examined, showing that orally delivered E3 variants (E3-6His-KDEL and Expanded E3-6His-KDEL) prevented bleomycin-induced pulmonary fibrosis. See FIG. 20.

For the experiments shown in FIGS. 21 and 22, pulmonary fibrosis was again induced in mice using bleomycin. Controls were administered PBS, while experimental samples also had END55 (also referred to as E3-Fc (C67A)) administered orally or intravenously. Hydroxyproline content was measured in the lung.

Compared to mice treated with bleomycin only, mice treated with END-55 at 100 μg or 200 μg had reduced pulmonary fibrosis, as assessed using hydroxyproline assays (FIG. 21). Intravenously administered END-55 at either dose appeared to have similar efficacy to orally administered END-55 at 50 μg. END-55 administered eight days after bleomycin treatment (both orally and intravenously) also appeared to reduce fibrosis, although only three mice were treated in each of these groups. These studies thus indicated that oral and IV delivery of END55 prevented bleomycin-induced pulmonary fibrosis, and that IV dosing of the polypeptide was comparable to oral administration. See, FIGS. 21 and 22. In addition, END-55 ameliorated bleomycin-induced pulmonary fibrosis in vivo whether administered concomitantly or after a fibrotic trigger (represented as d8; FIG. 21). Therefore, IV administration of END55 has the potential to reverse lung fibrosis.

TABLE 2

| Construct | Sequence | SEQ ID NO: | Description |
|---|---|---|---|
| END16 | MGKMASLFATFLVVLVSLSLASESSASYC ETWRTEAPSATGQASSLLGGRLLGQSAASC HHAYIVLCIENSFMT*HHHHHHKDEL* | 15 | E3-6His-KDEL: secretory leader peptide (bold); tagged with 6X His and KDEL sequence (italics) |

TABLE 2-continued

| Construct | Sequence | SEQ ID NO: | Description |
|---|---|---|---|
| END55 | MGKMASLFATFLVVLVSLSLASESSASYC ETWRTEAPSATGQASSLLGGRLLGQSAASC HHAYIVLAIENSFMT*EPKSCDKTHTCPPCPA PELLGGPSVFLFPPKPKDTLMISRTPEVTCVV VDVSHEDPEVKFNWYVDGVEVHNAKTKPREE QYNSTYRVVSVLTVLHQDWLNGKEYKCKVSN KALPAPIEKTISKAKGQPREPQVYTLPPSRDEL TKNQVSLTCLVKGFYPSDIAVEWESNGQPENN YKTTPPVLDSDGSFFLYSKLTVDKSRWQQGN VFSCSVMHEALHNHYTQKSLSLSPGK* | 16 | E3-Fc (C67A): secretory leader peptide (bold); third cysteine changed to alanine (bold with dotted underline) and fused to human immunoglobulin IgG1 Fc domain (italics) |
| END56 | MGKMASLFATFLVVLVSLSLASESSAQKS VWHGSDPNGRRLTESYCETWRTEAPSATG QAYSLLGGRLLGQSAASCHHAYIVLAIENS FMT*ASK*HHHHHHKDEL | 17 | Expanded E3-6His-KDEL (C67A): secretory leader peptide (bold); an extra 17 amino acids from Collagen XVIII extending the N-terminus of the E3 peptide (highlighted); S→Y mutation from a natural endostatin variant (bold with underline); third cysteine changed to alanine (bold with dotted underline); three additional residues from the endostatin C-terminus (italics with underline); and tagged with 6X His KDEL (italics) |

Example 10

Ig Molecules Fused to E3

Various Fc domain fusions to E3 were expressed (in addition to E3-Fc(IgG1)). Sequences were as follows:

E3_C67A-Fc_IgG2:
(SEQ ID NO: 22)
MGKMASLFATFLVVLVSLSLASESSASYCETWRTEAPSATG
QASSLLGGRLLGQSAASCHHAYIVLAIENSFMTERKCCVECPPCPAPPVA
GPSVFLFPPKPKDTLMISRTPEVTCVVVDVSHEDPEVQFNWYVDGVEVHN
AKTKPREEQFNSTFRVVSVLTVVHQDWLNGKEYKCKVSNKGLPAPIEKTI
SKTKGQPREPQVYTLPPSREEMTKNQVSLTCLVKGFYPSDISVEWESNGQ
PENNYKTTPPMLDSDGSFFLYSKLTVDKSRWQQGNVFSCSVMHEALHNHY
TQKSLSLSPGK

E3_C67A-Fc_IgG3:
(SEQ ID NO: 23)
MGKMASLFATFLVVLVSLSLASESSASYCETWRTEAPSATG
QASSLLGGRLLGQSAASCHHAYIVLAIENSFMTELKTPLGDTTHTCPRCP
EPKSCDTPPPCPRCPEPKSCDTPPPCPRCPEPKSCDTPPPCPRCPAPELL
GGPSVFLFPPKPKDTLMISRTPEVTCVVVDVSHEDPEVQFKWYVDGVEVH
NAKTKPREEQYNSTFRVVSVLTVLHQDWLNGKEYKCKVSNKALPAPIEKT
ISKTKGQPREPQVYTLPPSREEMTKNQVSLTCLVKGFYPSDIAVEWESSG
QPENNYNTTPPMLDSDGSFFLYSKLTVDKSRWQQGNIFSCSVMHEALHNR
FTQKSLSLSPGK

E3_C67A-Fc_IgG4:
(SEQ ID NO: 24)
MGKMASLFATFLVVLVSLSLASESSASYCETWRTEAPSATG
QASSLLGGRLLGQSAASCHHAYIVLAIENSFMTESKYGPPCPSCPAPEFL

```
GGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKT

ISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNH

YTQKSLSLSLGK

E3_C67A-Fc_IgA1:
                                          (SEQ ID NO: 25)
MGKMASLFATFLVVLVSLSLASESSASYCETWRTEAPSATG

QASSLLGGRLLGQSAASCHHAYIVLAIENSFMTVPCPVPSTPPTPSPSTP

PTPSPSCCHPRLSLHRPALEDLLLGSEANLTCTLTGLRDASGVTFTWTPS

SGKSAVQGPPERDLCGCYSVSSVLPGCAEPWNHGKTFTCTAAYPESKTPL

TATLSKSGNTFRPEVHLLPPPSEELALNELVTLTCLARGFSPKDVLVRWL

QGSQELPREKYLTWASRQEPSQGTTTFAVTSILRVAAEDWKKGDTFSCMV

GHEALPLAFTQKTIDRLAGKPTHVNVSVVMAEVDGTCY

E3_C67A-Fc_IgA2:
                                          (SEQ ID NO: 26)
MGKMASLFATFLVVLVSLSLASESSASYCETWKTEAFSATG

QASSLLGGRLLGQSAASCHHAYIVLAIENSFMTVPCPVPPPPPCCHPRLS

LHRPALEDLLLGSEANLTCTLTGLRDASGATFTWTPSSGKSAVQGPPERD

LCGCYSVSSVLPGCAQPWNHGETFTCTAAHPELKTPLTANITKSGNTFRP

EVHLLPPPSEELALNELVTLTCLARGFSPKDVLVRWLQGSQELPREKYLT

WASRQEPSQGTTTFAVTSILRVAAEDWKKGDTFSCMVGHEALPLAFTQKT

IDRMAGKPTHVNVSVVMAEVDGTCY

E3_C67A-Fc_IgM:
                                          (SEQ ID NO: 27)
MGKMASLFATFLVVLVSLSLASESSASYCETWRTEAPSATG

QASSLLGGRLLGQSAASCHHAYIVLAIENSFMTVIAELPPKVSVFVPPRD

GFFGNPRKSKLICQATGFSPRQIQVSWLREGKQVGSGVTTDQVQAEAKES

GPTTYKVTSTLTIKESDWLGQSMFTCRVDHRGLTFQQNASSMCVPDQDTA

IRVFAIPPSFASIFLTKSTKLTCLVTDLTTYDSVTISWTRQNGEAVKTHT

NISESHPNATFSAVGEASICEDDWNSGERFTCTVTHTDLPSPLKQTISRP

KGVALHRPDVYLLPPAREQLNLRESATITCLVTGFSPADVFVQWMQRGQP

LSPEKYVTSAPMPEPQAPGRYFAHSILTVSEEEWNTGETYTCVAHEALPN

RVTERTVDKSTGKPTLYNVSLVMSDTAGTCY

J-Chain_PVX_sgp36:
                                          (SEQ ID NO: 28)
MGKMASLFATFLVVLVSLSLASESSAQEDERIVLVDNKCK

CARITSRIIRSSEDPNEDIVERNIRIIVPLNNRENISDPTSPLRTRFVYH

LSDLCKKCDPTEVELDNQIVTATQSNICDEDSATETCYTYDRNKCYTAVV

PLVYGGETKMVETALTPDACYPD

IgGI_Fc-E3_C67A (C-terminal fusion):
                                          (SEQ ID NO: 29)
MGKMASLFATFLVVLVSLSLASESSAEPKS

CDKTHTCPPCPAPELLGGPSVFLFPPKPKDTLMISRTPEVTCVVVDVSHE

DPEVICFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVMHEALHNHYTQKSLSLSPGKSYCETWRTEAPSATGQASSLL

GGRLLGQSAASCHHAYIVLAIENSFMT
```

Figure 23:
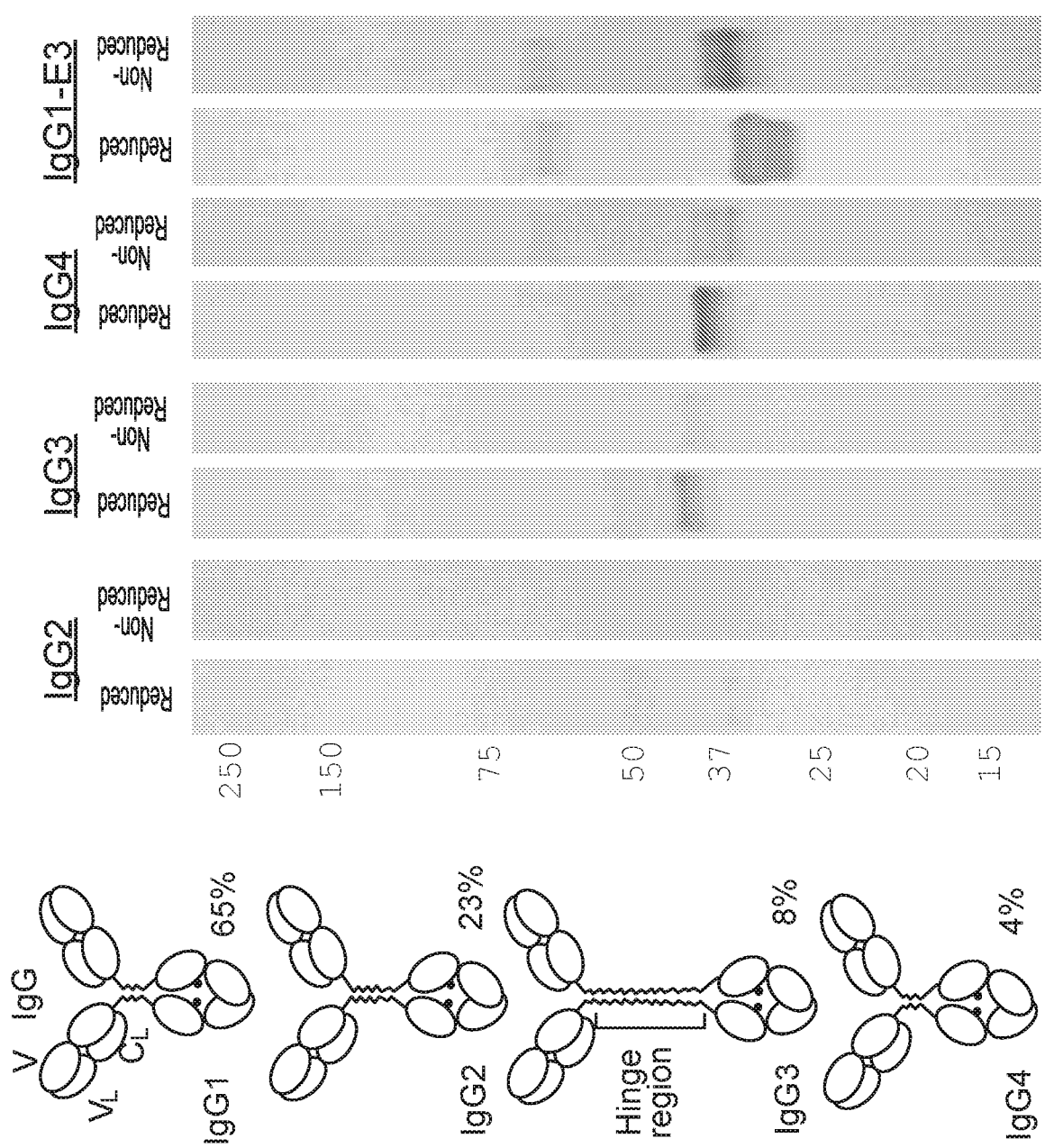
FIG. 23. Expression of human IgG Fc fusions to E3 in a schematic (left panel) and a Western blot (right panel).

As shown in FIG. 23, fusion of E3 to the Fc region of IgG2 demonstrated poor expression and was insufficient for purification, fusion to –IgG3 was soluble and purified, fusion to –IgG4 was soluble and purified, fusion to –IgA1 (±J-chain) was insoluble, fusion to –IgA2(±J-chain) was insoluble, and fusion to –IgM (±J-chain) demonstrated poor expression and was insufficient for purification, while Fc-E3 was soluble and purified.

Figure 24:
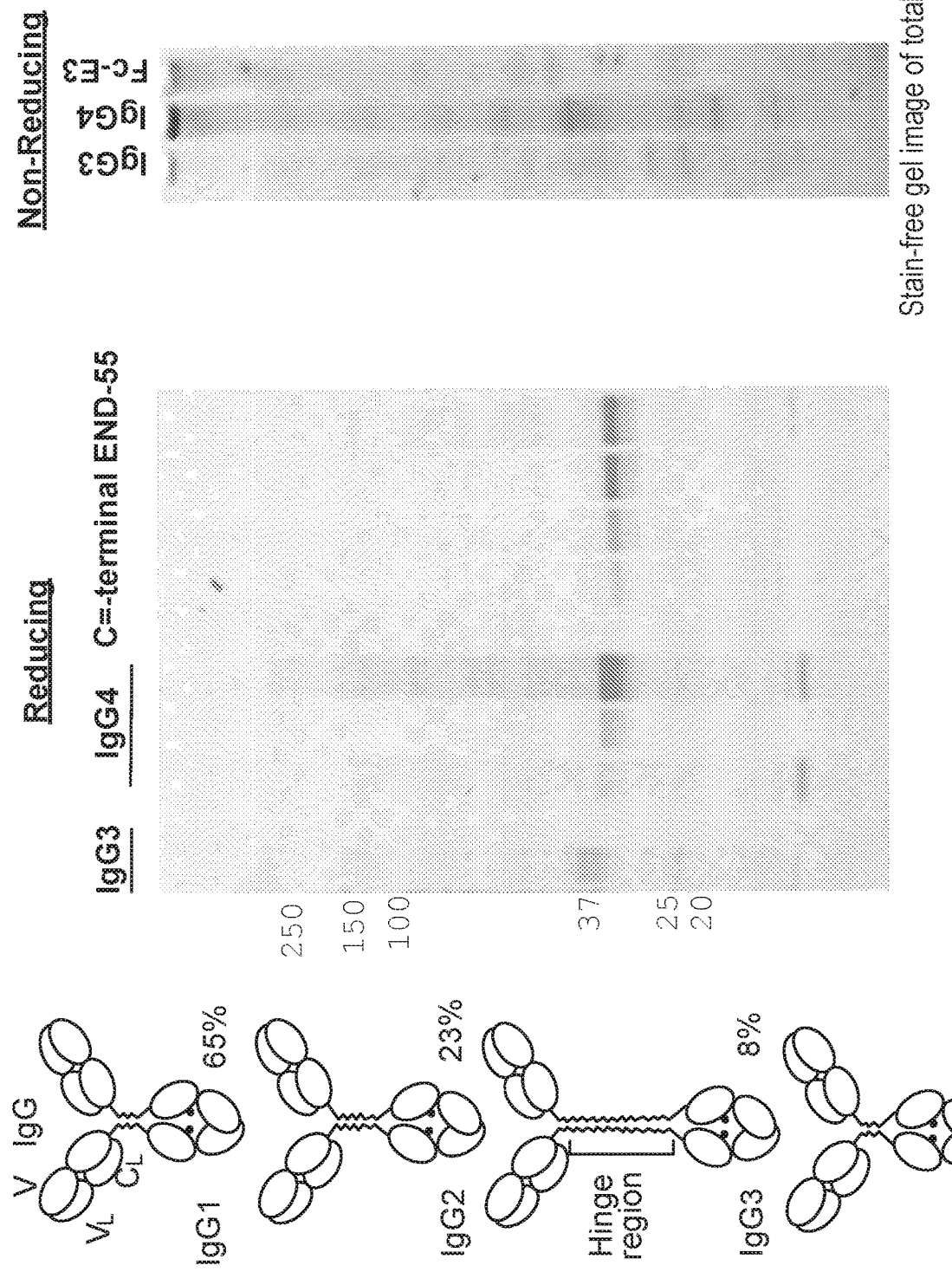
FIG. 24. Purification of human IgG Fc fusions to E3.

For IgG Fc expression, clarified plant lysates were run on a Western blot (Genway chicken E3 antibody). Fusions included E3 (C67A) linked to either the N-terminus of the hinge+Fc domains of IgG2, IgG3, or IgG4, or to the C-terminus of the hinge+Fc domain of IgG1. The IgG2 fusion demonstrated low expression, while the IgG3 and IgG4 fusions demonstrated moderate expression. The E3-IgG1 fusion expressed well. The non-reducing samples all appeared to form large structures, although perhaps not as large as the END-55 (iBioCFB03) HMW multimers (FIG. 24).

For IgA/M expression, clarified plant lysates were ground in either denaturing (total) or non-denaturing buffer (soluble) and run on a Western blot (Genway chicken E3 antibody). Fusions contained E3 (C67A) linked to the N-terminus of the hinge+Fc domains of IgA1, IgA2, or IgM. The IgA1 and IgA2 fusions were insoluble in normal grind buffer. The IgM fusion had very low expression. J-chain co-expression had no obvious effect. See FIG. 25

Example 11 iBio-CFB03: High Molecular Weight Multimer iBio-CFB03 (also referred to herein as END55 or E3-Fc (C67A)) is a high molecular weight multimer comprised of multiple subunits of a 306 amino acid-length fusion protein, with a 48 amino acid fragment derived from the C terminus of Collagen XVIII (sequence of E3), containing an added secretory leader peptide [bold; 26 amino acids; cleaved during secretion of the molecule into the endoplasmic reticulum (ER) by ER-localized signal peptidases] and fused to human immunoglobulin IgG1 Fc domain (italics; 232) as shown in FIG. 26. This fusion protein also contains a cysteine to alanine mutation at position 67 (underlined and bolded) and one glycosylation site (italics and underlined). The predicted molecular weight of the non-glycosylated E3-Fc is 31,153 Da.

Chemistry, Manufacturing and Controls iBio-CFB03 is a multimeric protein approximately 1.2 mega-Daltons (MDa) with a repeating monomer with two major glycoforms between 31 and 33 kDa. The multimer is soluble and stable when stored at 4° C. in phosphate buffered saline (PBS).

Figure 27:
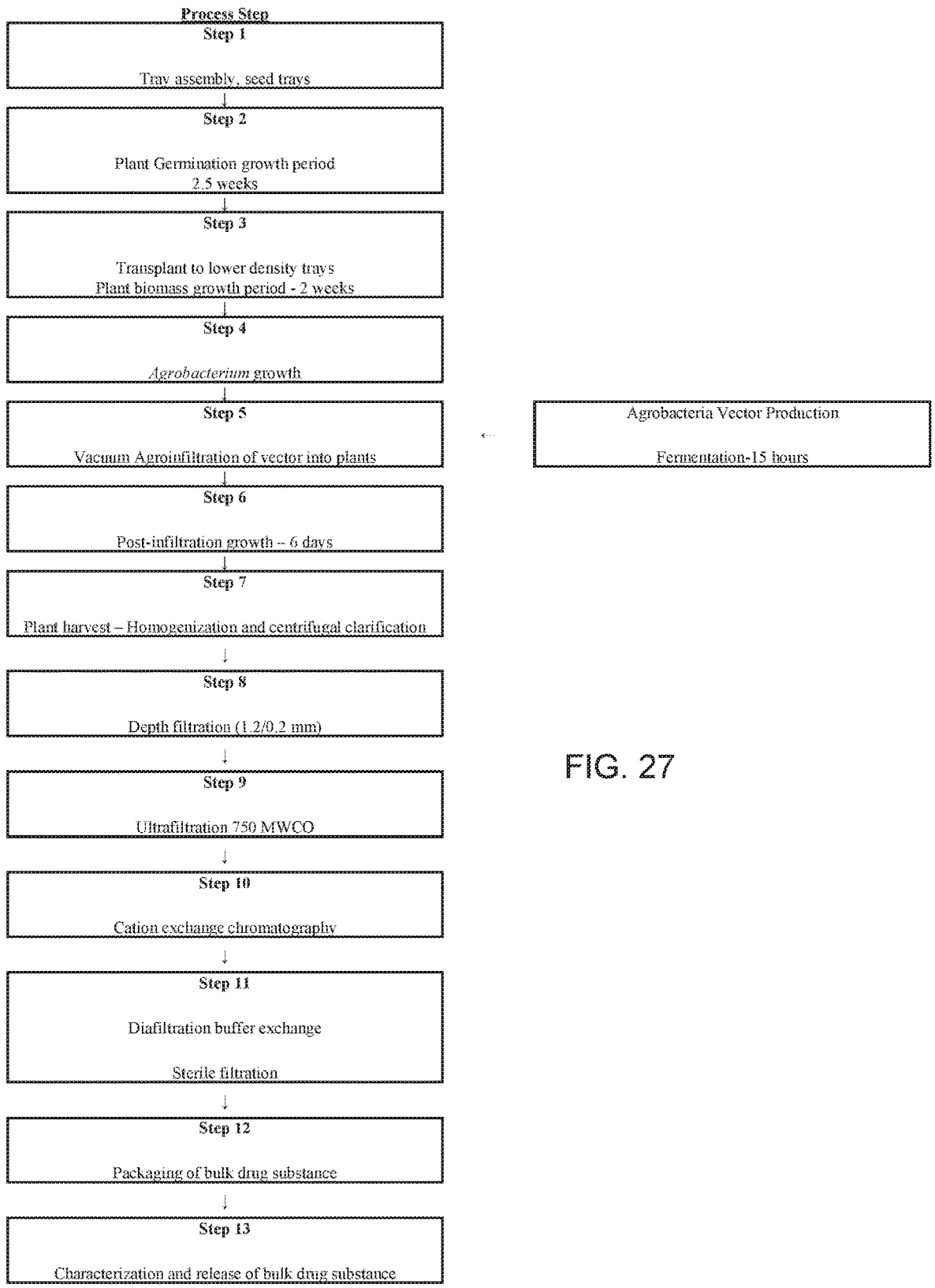
FIG. 27. iBio-CFB03 drug substance manufacturing process block diagram.

Method of Manufacture iBio-CFB03 Drug Substance was manufactured at Caliber Biotherapeutics, LLC (8800 HSC Pkwy, Bryan, Tex. 77807) using the IBIOLAUNCH™ platform that utilizes a transient plant-based expression system allowing agricultural scaling of the upstream production, followed by traditional downstream purification and formulation processes. An overview of the manufacturing processes is presented in FIG. 27.

Summary of Drug Substance Manufacturing Process
Generation of Master Cell Bank (MCB) and Working Cell Bank (WCB)

Codon Optimized Sequence

Figure 28:
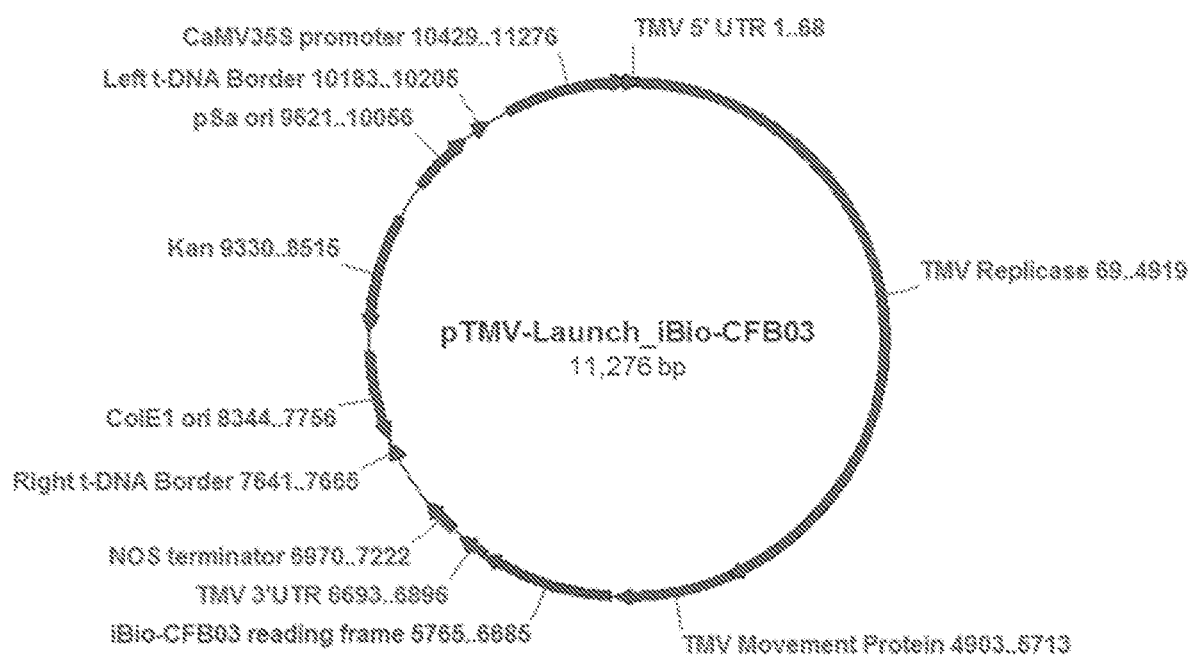
FIG. 28. Schematic of the pGR-D4 vector for expression of iBio-CFB03.

The genetic sequence of the endostatin E3 peptide (amino acid 1,466 to 1,513 of the human collagen alpha-1 (XVIII) chain preproprotein, GenBank NP_085059.02) was modified by mutating the last cysteine in the E3 peptide to alanine using Strand Overlap Extension (SOE) with mutant oligos. The resulting E3 peptide mutant C67A sequence was fused to the signal peptide of the *Nicotiana plumbaginifolia* extensin gene (GenBank AAA34073.1) and to the human immunoglobulin G1 Fc region (amino acid 216 to 447, GenBank: CAC20454) by SOE to form the candidate gene iBio-CFB03 (TABLE 3; FIG. 26). The iBio-CFB03 gene was codon optimized for plant expression using the *Nicotiana tabacum* codon usage table and cloned into the IBIO-LAUNCH™ tobacco mosaic virus-based vector pGR-D4 between restriction sites PacI and XhoI to generate vector pSM042 (FIG. 28).

TABLE 3 iBio-CFB03 Sequence Description

| Amino acid position | Sequence description |
|---|---|
| 1-26 | *Nicotiana plumbaginifolia* extensin signal peptide |
| 27-74 | Endostatin E3 peptide mutant C67A |
| 75-89 | Hinge region of the human IgG1 heavy chain |
| 90-306 | Fc region of the human IgG1 heavy chain |

Clone into *Agrobacterium* Vector Strain GV3101

Expression vector pSM042 was then mobilized into *Agrobacterium tumefaciens* strain GV3101 together with the helper plasmid, pSOUP, by electroporation (GenBank: EU048870.1) (Hellens et al., *Plant Mol Biol*. 2000; 42(6): 819-832). pSoup encodes RepA, which acts in trans upon the pSa Ori sequence contained in pGreen to permit its replication in *Agrobacterium*. *Agrobacterium* clones were selected on Luria-Bertani (LB) agar plate against 50 mg/L kanamycin, 25 mg/L rifampicin and 10 mg/L tetracycline. Kanamycin resistance was provided by the pGR-D4 expression vector, rifampicin resistance was provided by the GV3101 *Agrobacterium* strain and tetracycline resistance was provided by the helper vector pSOUP. After 3 days of incubation at 28° C., single colonies were picked to inoculate liquid LB media (supplemented with antibiotics as described above) to amplify each bacterial culture in a shaker incubator at 28° C., 225 rpm. Each clone was identified by the polymerase chain reaction (PCR) and specific inserts were confirmed by sequencing using specific primers binding upstream of the insert in the pGR-D4 expression vector. Once confirmed, initial Agrobacteria MCB and WCB were generated and stored at −70° C. in two separate freezers.

iBio-CFB03 Expression

Step 1—Tray Assembly, Seed Trays

Aluminum plant growing trays, nominally 4 feet by 3 feet in size, were used. Styrofoam plug trays containing 240 plugs of rockwool were seeded in an automated vacuum needle seeder. Four plug trays (960 plants) were placed in each of the aluminum germination trays and conveyed to the germination room.

Step 2—Plant Germination Growth

The plants were germinated for 3 weeks at 27° C. in vertical racks equipped with LED lighting with spectrally correct light of regulated intensity to optimize photosynthesis and optimum plant growth. Drip irrigation was employed to deliver a modified Hoagland's solution of required minerals for hydroponic growth. No soil or other materials were used to support plant growth.

Step 3—Transplant to Lower Density Trays

At 3 weeks of growth, the plugs containing the germinated plants were mechanically transplanted to 4 feet by 4 feet growing trays that only had 320 plant positions per tray to allow for the expansion of foliage. The plants were grown for another 2 weeks at 25° C. Each plant was approximately 8-10 grams of leaf biomass at this stage.

Step 4—*Agrobacterium* Growth

The selected *Agrobacterium* clone was grown from a working cell bank in culture flasks containing LB medium supplemented with 50 mg/L kanamycin, 25 mg/L rifampicin and 10 mg/L tetracycline at 28° C. with agitation at 225 rpm. Cultures reaching an $OD_{600\,nm}$ of ~1.5 were collected and diluted 50 fold in reverse osmosis-purified water containing 2 mM MES buffer, pH 5.6.

Step 5—Vacuum Agroinfiltration of Vector Into Plants

After induction of Agrobacteria for one hour, 5 week old plants were vacuum infiltrated at 23 inch Hg at the gauge. Prior to vacuum infiltration, *Nicotiana benthamiana* plants were grown hydroponically under proprietary red/blue LED light for five weeks at ~27° C. with relative humidity of ~50%. Agro-infiltrated plants were incubated under constant LED light at ~25° C. with relative humidity of ~50%.

Step 6—Post-Infiltration Growth

The post infiltration room hydroponic growth conditions maintained the plants at 25° C. under a regulated light regime. After six days post-infiltration, the plants were automatically conveyed to the harvest area for extraction.

iBio-CFB03—Purification Process

Step 7—Plant Harvest—Homogenization and Centrifugal Clarification

*Nicotiana benthamiana* biomass expressing iBio-CFB03 (E3-Fc) was mechanically homogenized with a Waring heavy duty laboratory grade stainless steel blender for one minute in aqueous acidified (pH 4.8-5.2) extraction buffer (50 mM sodium phosphate, 150 mM NaCl, 5 mM EDTA, 60 mM ascorbic acid, and 1 mM PMSF). Biomass was partially clarified by centrifugation followed by pH adjustment to 6.2 with 1 N NaOH.

Step 8—Depth Filtration

The extract was further clarified by depth filtration (nominal retention rating 1.2/0.2 μm).

Step 9—Ultrafiltration

Clarified extract was applied to a hollow fiber tangential flow filtration (TFF) module containing 1 mm fibers with 750 kDa molecular weight cutoff (MWCO) pore size. Extract was filtered through the 750 kDa MWCO with a shear rate of 6,000-8,000 see and a trans-membrane pressure of 5-7 psi.

Figure 29:
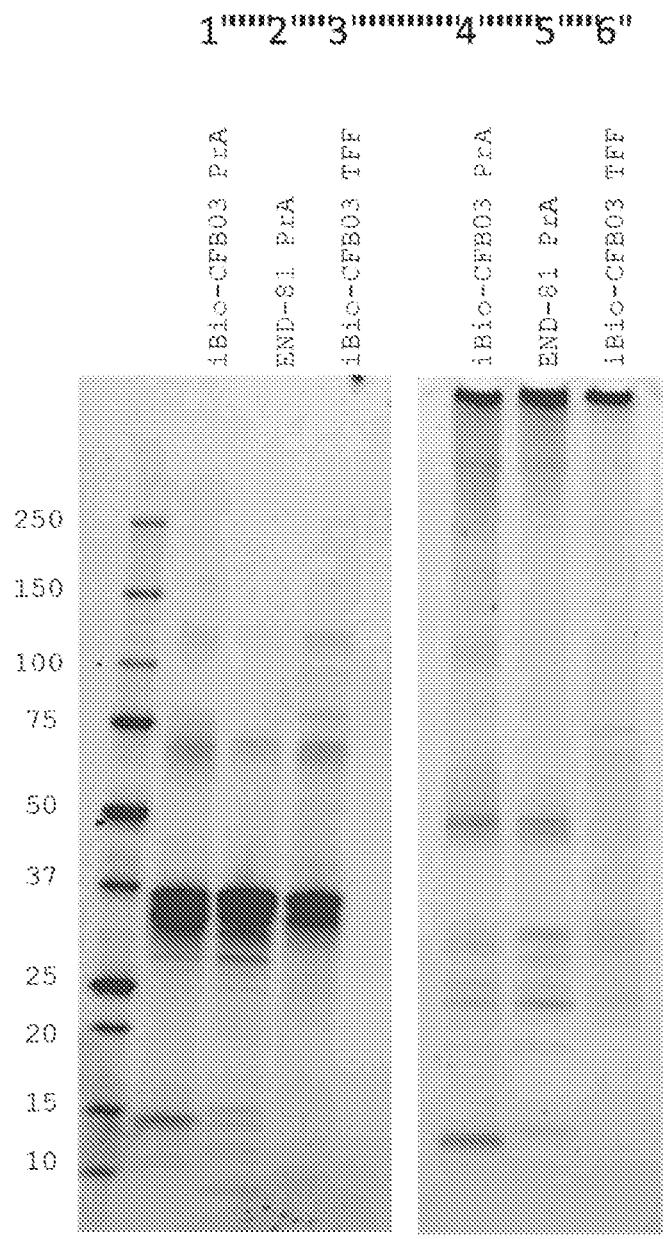
FIG. 29. Sodium dodecyl sulfate polyacrylamide gel electrophoresis (SDS-PAGE) of iBio-CFB03 Purified by Protein A and TFF.

Purification of iBio-CFB03 was initially assessed by sodium dodecyl sulfate polyacrylamide gel electrophoresis (SDS-PAGE). As can be seen in FIG. 29, iBio-CFB03 purified by the above procedure failed to enter the gel in an undenatured state (without heat treatment and β-mercaptoethanol; lane 6). A sample of iBio-CFB03 purified by Protein A affinity chromatography (lane 4) behaved similarly, as did a control reagent (END-81), a peptide of the same amino acid composition as E3 but with a scrambled primary sequence, fused to IgG1-Fc (lane 5), These results suggest that iBio-CFB03 naturally occurs as a high molecular weight array when produced in plants, that this behavior is not due to the purification method, and indeed may be intrinsic to Fc fusion proteins having a similar non-polar N terminal sequence. When electrophoresed under common SDS-PAGE denaturing condition (heat plus β-mercaptoethanol), the majority of purified iBio-CFB03 (lane 3) resolves into two bands of apparent molecular weight of ~35 kDa and ~32 kDa. Similar results are obtained for iBio-CFB03 purified by Protein A affinity chromatography (lane 1) and the END-81 control reagent (lane 2). These results indicate that the dual band pattern is not due to the purification method or primary sequence of the E3-related portion of the fusion protein, and may be due to differences in the glycosylation pattern of the Fc fusion partner. Additionally, bands with apparent molecular weights consistent with iBio-CFB03 dimers (~70 kDa), trimers (~110 kDa), and tetramers (>150 kDa) are also observed in denatured samples, and appear without regard to the purification method as well as in the control reagent. These additional bands indicate that the high molecular weight arrays are extraordinarily stable and resist common electrophoresis denaturing conditions, and may be an additional attribute of fusions of a hydrophobic peptide to human Fc. Due to these behaviors, SDS-PAGE is not a preferred method for characterizing iBio-CFB03.

Figure 30:
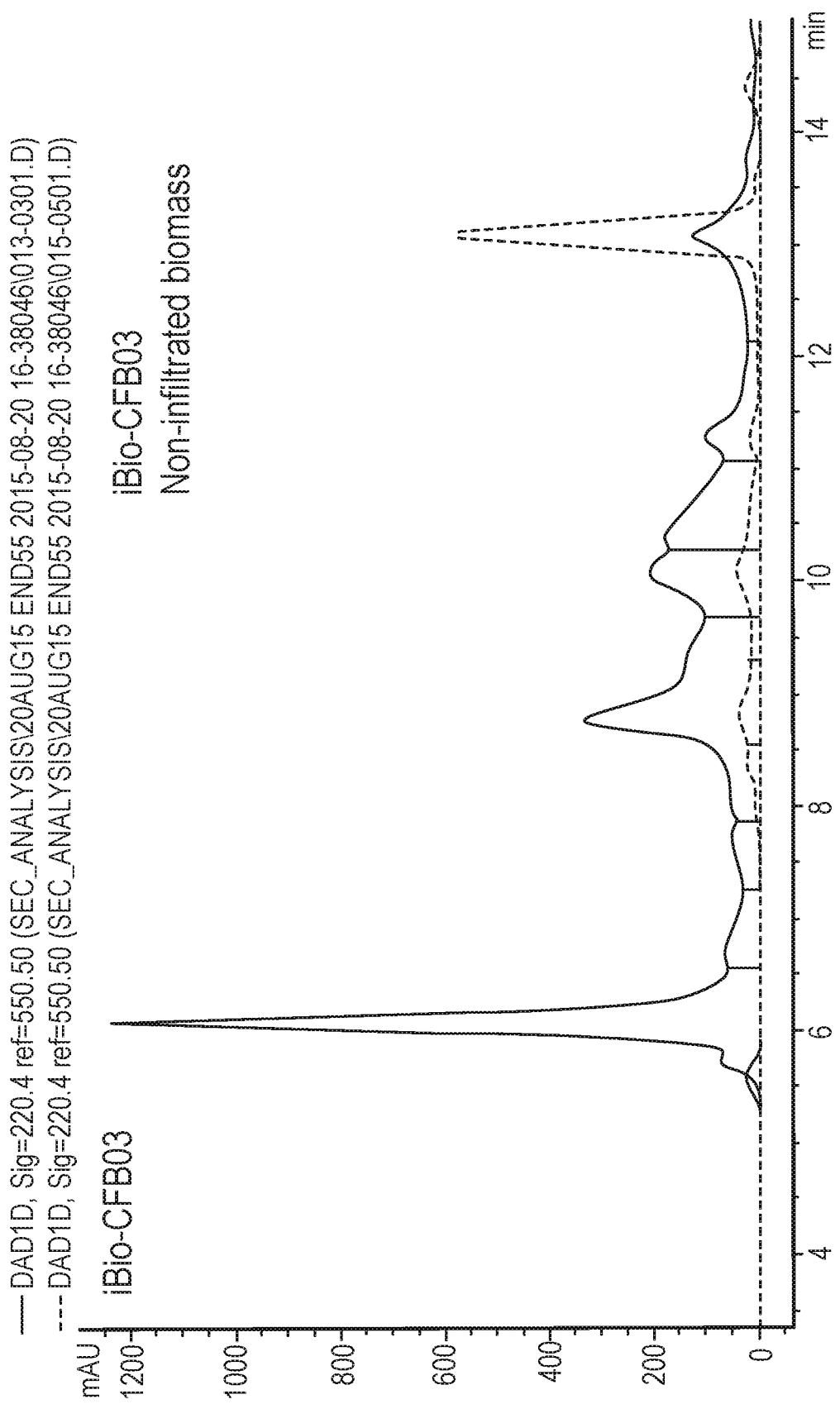
FIG. 30. Size exclusion chromatogram of TFF Purified iBio-CFB03.

Purity of the TFF retentate was evaluated with size exclusion chromatography (SEC) and compared to non-infiltrated retentate (FIG. 30). Under native non-reducing conditions, the SEC chromatogram reveals a single iBio-CFB03 peak at a retention time of 6 minutes (estimated to correspond to a molecular weight of 1.2 MDa) that is completely absent in non-infiltrated biomass. The retentate is largely comprised of iBio-CFB03 product, with plant host cell proteins contributing the remainder. The product is soluble in PBS and saline at a level of 50 mg/mL.

Step 10—Cation Exchange Chromatography

Figure 31:
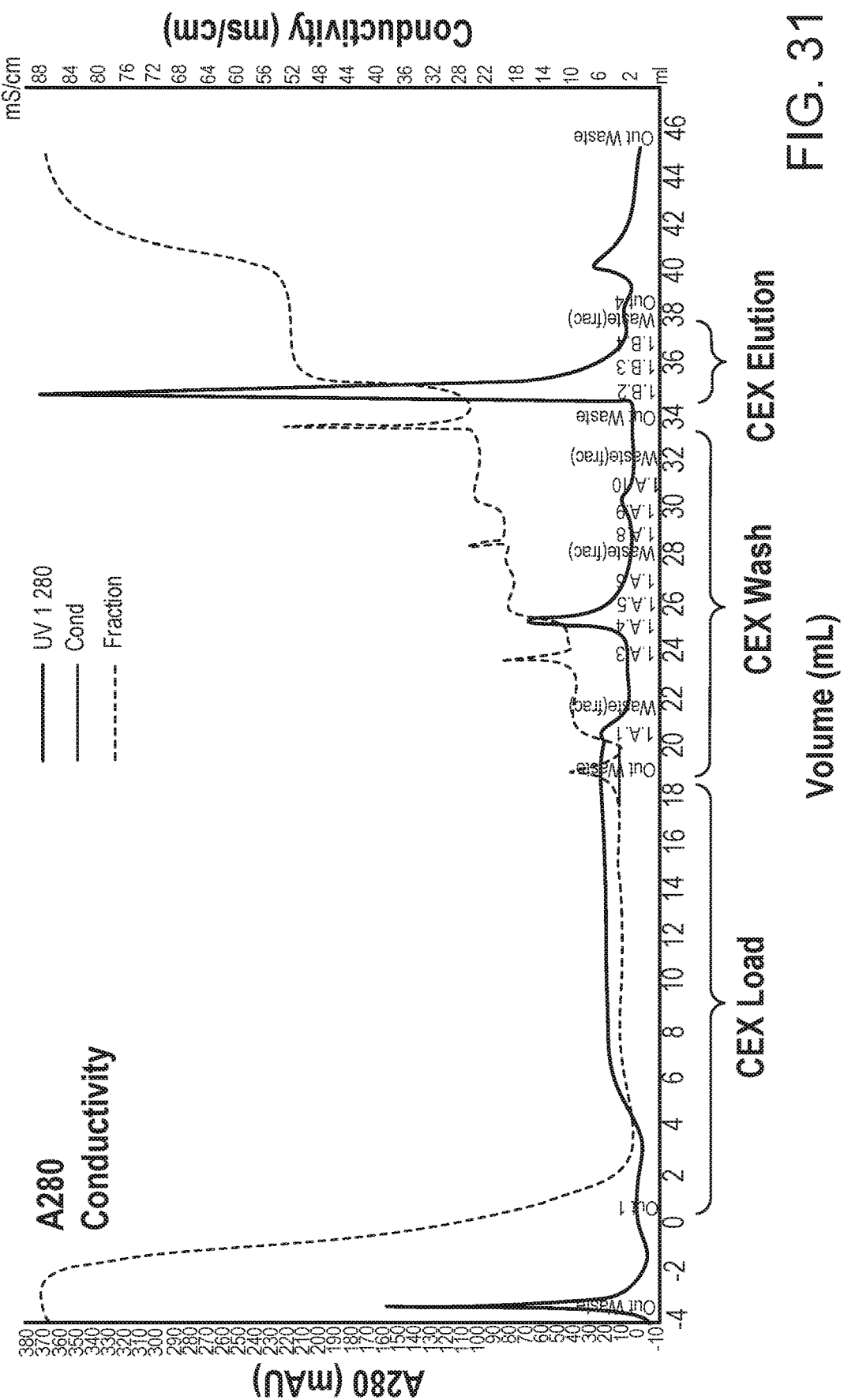
FIG. 31. Cation exchange (CEX) chromatogram of iBio-CFB03.
Figure 32:
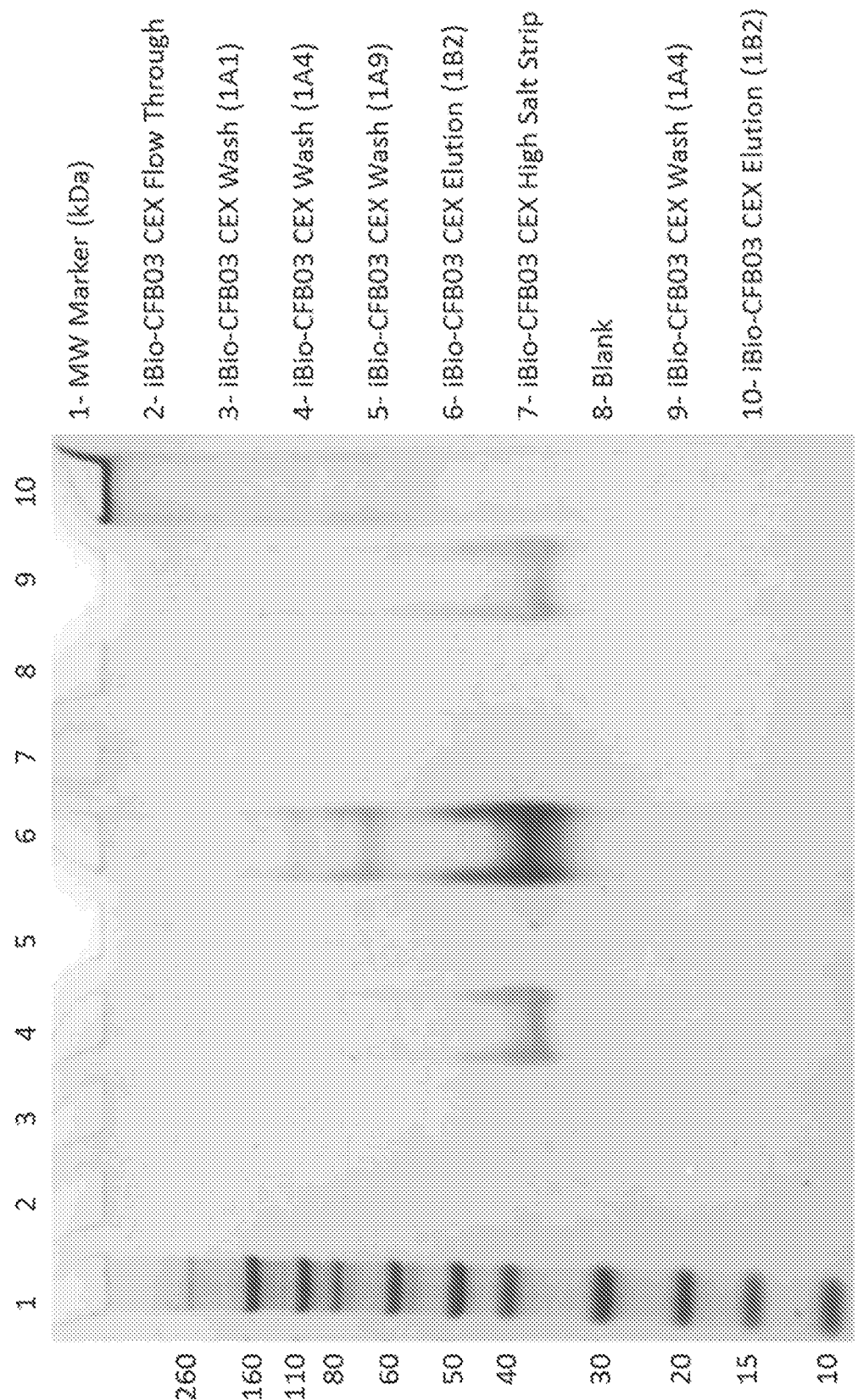
FIG. 32. SDS-PAGE gel image of iBio-CFB03 CEX fractions.
Figure 33:
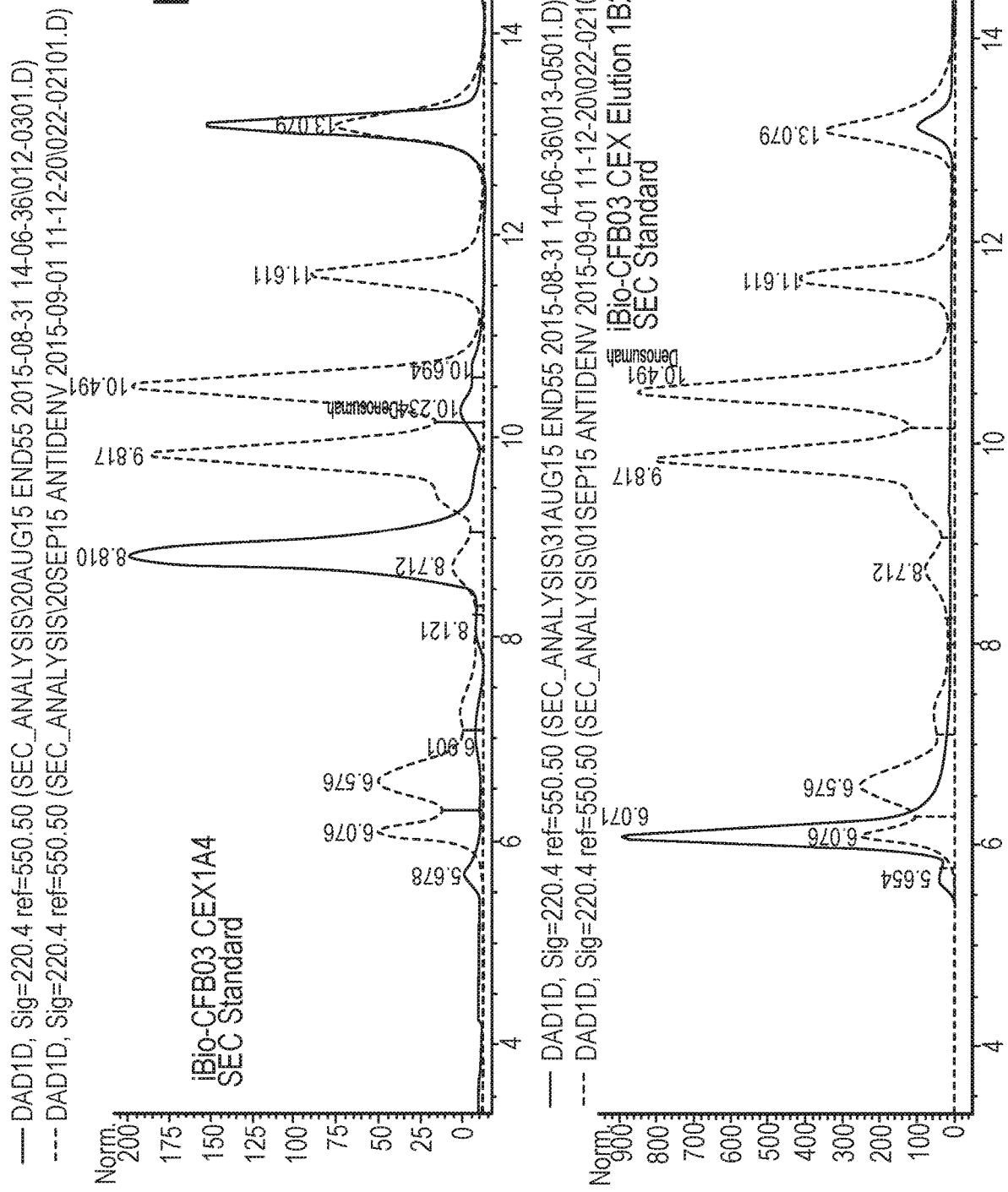
FIG. 33. Size exclusion chromatograms of CEX fractions 1A4 (top) and 1B2 (bottom).

TFF retentate was then prepared for cation exchange (CEX) chromatography by filtration (nominal retention rating 1.2/0.2 µm), pH adjustment to 5.3-5.7 with 1 M acetic acid and conductivity adjustment to 4-6 mS/cm by addition of ultrapure water. During CEX chromatography, remaining impurities were removed by washing with up to 250 mM sodium chloride (FIG. 31 CEX Wash; FIG. 32 lanes 3-5 and 9, FIG. 33 top) and iBio-CFB03 was eluted with 550 mM sodium chloride at ≥95% purity (FIG. 31 CEX Elution; FIG. 32 lanes 6 and 10; FIG. 33 bottom).

SDS-PAGE was used to assess contents of the CEX fractions (FIG. 32). Samples in lanes 2-7 were heated at 70° C. for 10 min in the presence of 266 mM β-mercaptoethanol prior to loading. Samples in lanes 9 and 10 did not contain β-mercaptoethanol and were not heated prior to electrophoresis. Lanes 3-5 correspond to wash fractions 1A1, 1A4 and 1A9 (FIG. 29) containing 100, 150 and 250 mM NaCl, respectively. Lane 6 displays elution fraction 1B2 (550 mM NaCl) and shows monomer (~35 kDa), dimer (~70 kDa), trimer (~110 kDa) and tetramer (~150 kDa) species, observable when the iBio-CFB03 product is exposed to reducing agents (e.g., heat and β-mercaptoethanol). When elution fraction 1B2 is loaded in the absence of β-mercaptoethanol and not heated prior to electrophoresis (lane 10) the HMW iBio-CFB-03 multimer can be visualized at the origin of the gel.

Step 11—Diafiltration Buffer Exchange and Sterile Filtration iBio-CFB03 CEX elution pool material was then concentrated up to 12.5 mg/mL and buffer was exchanged to phosphate buffered saline by TFF using a 100 kDa MWCO TFF (stabilized cellulose) at a transmembrane pressure of 2-4 psi.

Step 12—Packaging of Bulk Drug Substance

The bulk drug substance is sterile filtered and packaged in a sterile bag within a biosafety cabinet. The bulk product is transferred to a selected fill facility for final fill.

Characterization of iBio-CFB03

SE-HPLC Analysis of iBio-CFB03 iBio-CFB03 samples were analyzed by SE-HPLC to assess the purity of the HMW multimer. SE-HPLC analysis was performed on a TSKgel G3000SW xL, 7.8 mm×30 cm, 5 µm column using 1100 Series HPLC system with UV detection. Mobile phase for SE-HPLC consisted of 50 mM sodium phosphate (monobasic, monohydrate), sodium phosphate (dibasic, anhydrate) and 0.3 M sodium chloride, pH 7.0. Prior to sample analysis, protein mix standard was prepared and 20 µL was injected onto the column. SE-HPLC protein mix standard consisting of thyroglobulin (0.5 mg/mL), BSA (1 mg/mL), ovalbumin (1 mg/mL), α-lactalbumin (1 mg/mL) and aprotinin (0.4 mg/mL) was used to determine the molecular weight of the sample chromatographic peaks. Mobile phase buffer was used for blank injections. The column was equilibrated with the mobile phase before sample analysis. Samples were separated on the column at a flow rate of 1.0 mL/min for a total run time of 15 min.

Data analysis was performed with ChemStation Data Analysis software (Agilent Technologies, A.01.04 025). Absorbances were recorded at 220 nm and 280 nm. The UV signal of each sample was integrated and the relative percent abundance of each peak detected was determined. All peaks with a percent relative abundance >0.1% were considered for quantification.

Figure 34:
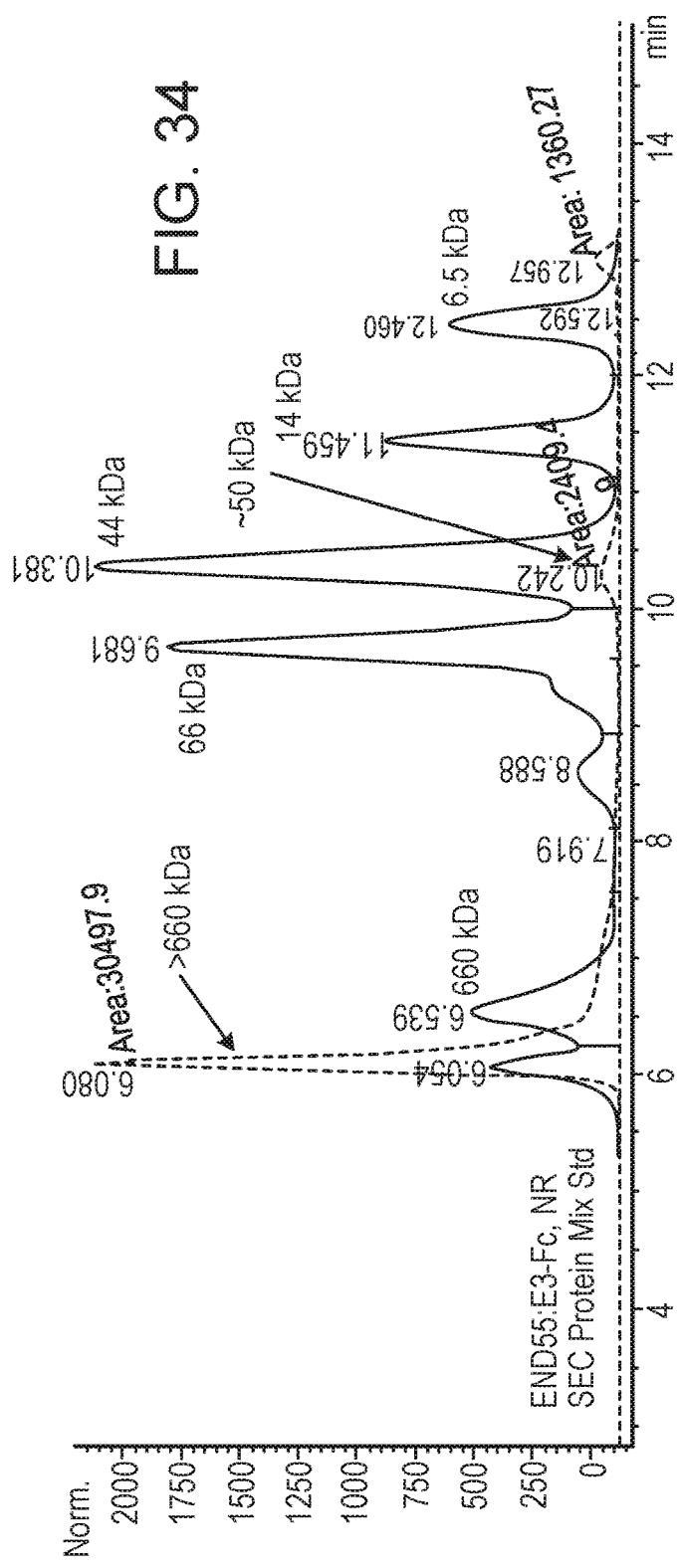
FIG. 34. Size Exclusion High Performance Liquid Chromatography (SE-HPLC) chromatograms of non-reduced iBio-CFB03 at 220 nm.

SE-HPLC analysis of iBio-CFB03 under non-reduced conditions displayed a major peak at 6 min which clearly overlays with the dimer of thyroglobulin peak (1.2 MDa) from the protein mix standard as shown in FIG. 34, indicating that iBio-CFB03 exists as a higher-order protein structure. Another small peak at 10.2 min was also observed which corresponds to approximately 50 kDa peak when overlaid with the protein mix standard. The two small peaks at 12.6 min and 12.9 min were not detected at 280 nm and were considered non-protein impurities. The peaks at 6 min and 10.2 min retention times were fraction collected separately and subject to tryptic digestion to determine their identity using MALDI-TOF MS.

MALDI-TOF MS Analysis of iBio-CFB03 iBio-CFB03 samples were analyzed by MALDI-TOF-MS under non-reduced and reduced conditions to obtain the molecular weight of the HMW multimer followed by tryptic digestion for sequence confirmation. For reduced analysis, the sample was treated with 0.5 M BME and heated at 70° C. for 10 min. Cyano-4-hydroxy cinnamic acid (α-CHCA) (Sigma) and sinapinic acid matrices were used for tryptic peptides and molecular weight determination respectively, using MALDI-TOF MS. The sinapinic acid matrix solution was prepared at 10 mg/mL in 30:70 acetonitrile (ACN):0.1% trifluoroacetic acid (TFA) and the α-CHCA matrix was prepared at 10 mg/mL in 1:1:1 Ethanol:ACN:0.1% TFA. The samples were then mixed at a 1:9 ratio in a 0.5 mL Eppendorf tube and 1.5 µL of mixture was spotted on a MALDI plate for analysis.

Samples were allowed to air dry completely prior to analysis as they co-crystallize with the matrix for approximately 2-3 min. The plate was then loaded into the MALDI-TOF mass spectrometer. Acquisitions were manual for peptide analysis, and the instrument mode was set to "Reflector", "Delayed", and "Positive" and the accelerating voltage and grid were set to 20 kV and between 66-74%, respectively with a delay time of ~125 nsec. Shots/Spectrum was set to 150 with a mass range of 500-4,000 Da and a low mass gate of 400 Da. α-CHCA matrix was selected to acquire the calibration and data file spectra. The ion source and mirror pressures were always less than $5.0 \times 10^{-7}$ and $1.2 \times 10^{-7}$ torr, respectively before acquisition was initiated. The initial laser power was set to 1250 for calibration and adjusted as necessary during spectrum acquisition. A two-point mass calibration curve was generated using the ACTH (1-17 fragment at 2,093.0867 Da) resolved mass peak and the Bradykinin (2-9 fragment at 904.4681 Da) mass peak in the standard test mix and applied to the protein sample analysis as detailed in the standard operating procedures (SOP). The calibration file was tested by re-acquiring the test mixture spectrum and the file was rejected and re-acquired if the monoisotopic mass for either peptide was >±0.2 Da. The monoisotopic mass for each peptide was used in the calibration.

Similarly, for molecular weight analysis, the instrument mode was set to "Linear", "Delayed" and "Positive" mode with accelerating voltage 25 kV, grid set to 66-74% and delay time of 200 nsec. Shots/Spectrum was set to 200 with a mass range of 4,500-200,000 Da and a low mass gate of 4,000 Da. Sinapinic acid matrix was selected to acquire the calibration and data file spectra. The initial laser power was set to 1800 for calibration and adjusted as necessary during spectrum acquisition. A one point calibration curve was generated using Myoglobin (11,652.52 Da) average mass peak.

Figure 35:
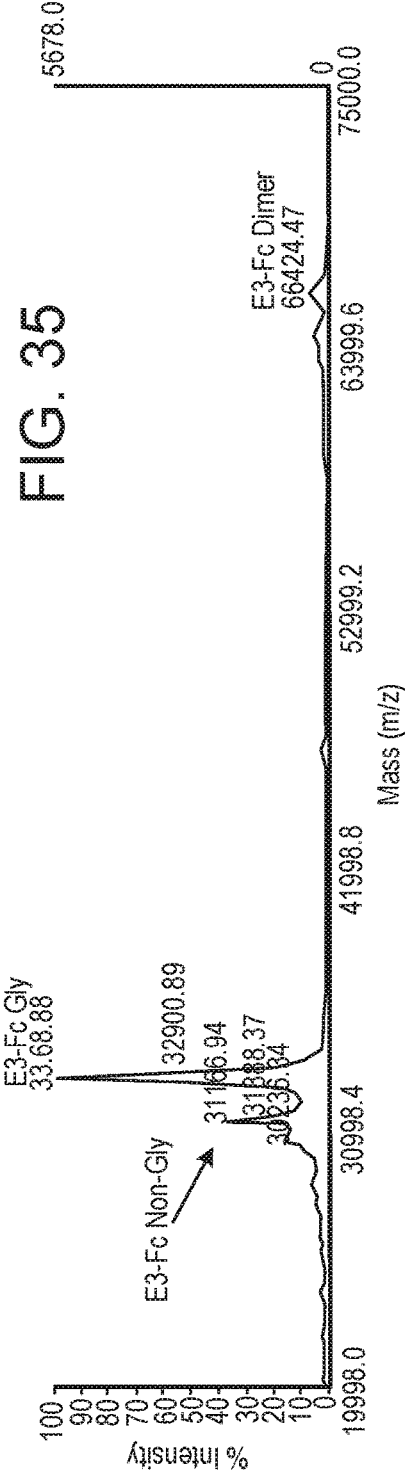
FIG. 35. Matrix Assisted Laser Desorption/Ionization Time-of-Flight Mass Spectrometry (MALDI-TOF MS) spectrum of reduced iBio-CFB03.

The MALDI spectrum of iBio-CFB03 under reduced conditions displayed m/z 31,166.94 $[M+H]^+$ and m/z 33,068.88 $[M+H]^+$ representing non-glycosylated (E3-Fc Non-gly) and glycosylated (E3-Fc Gly) iBio-CFB03, respectively (FIG. 35). The spectrum shows the monomeric subunit of the stable multimer.

Figure 36:
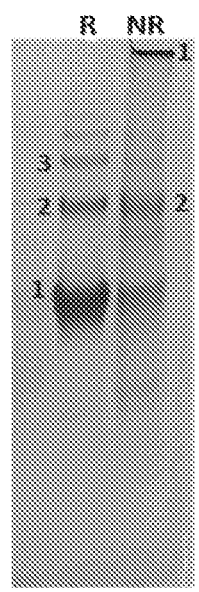
FIG. 36. SDS-PAGE gel image of iBio-CFB03 under reduced (R) and non-reduced (NR) conditions.

In-gel trypsin digestion of reduced and non-reduced bands of iBio-CFB03 was performed to confirm the identity of the bands (FIG. 36). For reduced conditions, band 1 corresponds to ~35 kDa, band 2 corresponds to ~70 kDa, and band 3 corresponds to ~100 kDa in accordance to the molecular weight marker. The tryptic peptides from each band were then used to obtain the sequence coverage of iBio-CFB03. For non-reduced conditions, band 1 is the HMW multimer which never leaves the well.

Figures 37, 38:
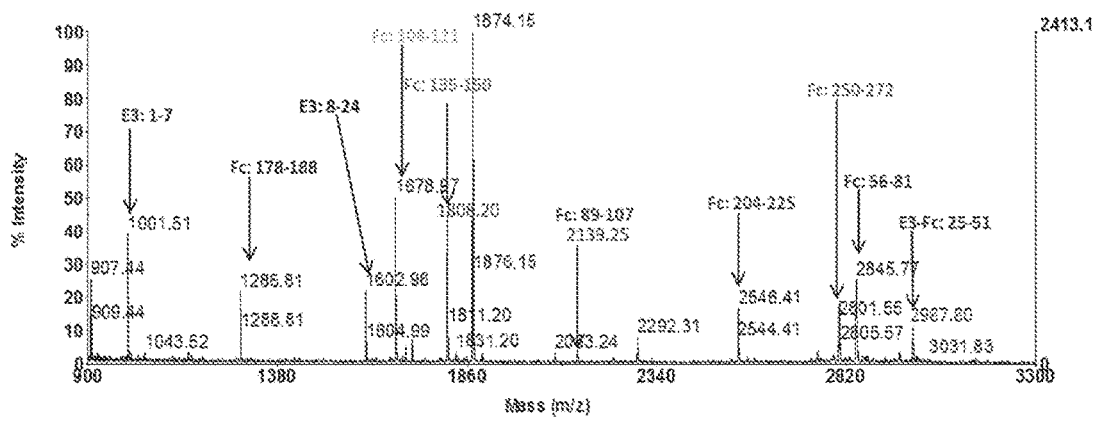
FIG. 37. iBio-CFB03 sequence (residues 27-306 of SEQ ID NO:16; e.g., E3-Fc amino acid sequence lacking the secretory sequence) with tryptic peptide fragments highlighted for correlation with FIG. 38.
FIG. 38. MALDI-TOF MS spectrum of in-gel tryptic digested iBio-CFB03 band 1 (reduced).

In-gel tryptic digestion of iBio-CFB03 reduced band 1 resulted in several peptides from the E3 and Fc regions of the HMW multimer (FIG. 37). In the iBio-CFB03 sequence given below, E3 peptide is highlighted in yellow. All the identified peptides are color coded in the sequence with their respective masses highlighted in the MALDI spectrum (FIG. 38).

Further Characterization of iBio-CFB03

Additional analyses are used to characterize iBio-CFB03. Negative-stain electron microscopy is used to assess the uniformity of iBio-CFB03 and determine a molecular diameter from which an estimate of molecular weight can be derived. Characterization of the glycosylation pattern of iBio-CFB03 also is performed.

Further mass spectrometric analyses will be performed using quadrupole-time of flight (Q-TOF) interfaced to a HPLC to determine a precise molecular weight of iBio-CFB03 prepared via separation on a RP HPLC column.

Potency Assay

The proposed assessment of potency for iBio-CFB03 takes a bimodal approach to assess the activity of urokinase plasminogen activator (uPA) and the protein content of matrix metalloprotease-1 (MMP-1), two mediators involved in fibrosis. The uPA and MMP-1 assays are used to estimate the potency of iBio-CFB03 batches, based on their robustness in earlier mechanistic studies.

A number of experiments were performed to determine the proof of concept and specific mechanism of action of iBio-CFB03. These studies and results are described in detail herein. The majority of the proof of concept assays and the mechanism of action experiments were performed with E4, an amidated form of the E3 peptide. The potency assays proposed below will be performed and qualified using recombinant iBio-CFB03.

uPA Activity Assay

Urokinase plasminogen activator, along with its receptor uPAR, initiates a proteolytic cascade that results in the conversion of plasminogen to plasmin (Choong et al., *Clin Orthop Relat Res.* 2003; 415:S46-58). uPA has an important function in extracellular proteolysis via its role in the plasminogen system, which activates downstream enzymes and interacts with the extracellular matrix (ECM). Further, in select organs, uPA is important in stoichiometrically activating latent HGF, an anti-fibrotic factor (Naldini et al., *J. Biol. Chemistry* 1995; 270:603-611). uPA is produced as an inactive protein that is proteolytically activated in the extracellular milieu or while bound to uPAR. Levels of uPA are significantly decreased in IPF patients (Gunther et al., *Thrombosis and Haemostasis* 2000; 83:853-860) and impaired plasminogen activation has been reported in bronchoalveolar lavage fluid of patients with pulmonary fibrosis. Multiple groups have demonstrated that uPA has anti-fibrotic effects in different organs and animal models. For example, inhaled uPA reduces airway remodeling in a murine model of asthma (Kuramoto et al., *Am. J Physiol.—Lung Cell. Mol. Physiol.* 2009; 296:L337-346) and transgenic expression of uPA in mouse lungs protects from fibrosis (Sisson et al., *Human Gene Therapy* 1999; 10:2315-2323; Sisson et al., *Am. J Physiol.—Lung Cell. Mol. Physiol.* 2002; 283:L1023-1032; Idell, *Am J Respir Crit Care Med* 2003; 168:1268-1269). Hsu et al have shown decreased levels of uPA in fibrotic lung tissues of patients with SSc and IPF (*Arthritis Rheum* 2011; 63:783-794). Studies also have demonstrated that E4 increases uPA levels and activity.

The assay is performed by incubating primary human fibroblasts with human recombinant TGF-β (10 ng/ml) or PBS as vehicle control with iBio-CFB03 (10 µg/ml) or DMSO (negative control). The uPA activity assay from Molecular Innovations (Human uPA Activity ELISA Kit Catalog # HUPAKT) is used to measure the activity of uPA in primary human fibroblasts. The assay is an ELISA that detects uPA that is able to bind covalently with human PA-1. The principle of the assay is that functionally active uPA in samples forms a covalent complex with the biotinylated human PA-1, which is bound to an avidin coated plate. Bound uPA is then detected with an anti-uPA primary antibody (Ab), reacted with horseradish peroxidase secondary Ab, followed by detection with tetramethylbenzidine (TMB) substrate at 450 nm. Inactive or complexed uPA does not bind and is not detected. The amount of color development is directly proportional to the concentration of active uPA in the sample. The concentration of active uPA in samples is determined from a uPA standard curve.

MMP-1 Protein and Activity Assay

MMPs are zinc-dependent proteases that cleave ECM and other proteins (Amalinei et al., 2007) (Parks et al., *Nature Reviews Immunology* 2004; 4:617-629). MMP-1 is the prototype interstitial collagenase 1 and is a key enzyme for degradation of fibrillar collagens in human tissues (Amalinei et al., *Rom J Morphol Embryol* 2007; 48:323-334). Evidence that increased activity of MMPs may resolve fibrosis comes from reports of clinical trials using broad-acting metalloprotease inhibitors for the treatment of various cancers where patients developed skin thickening and joint contractures with MMP inhibitors (reviewed in Parks et al., *Nature Reviews Immunology* 2004; 4:617-629), both of which occur in SSc. There is scientific evidence supportive of the therapeutic potential of MMP-1, e.g. transient expression of MMP-1 is sufficient to attenuate liver fibrosis (Iimuro et al., *Gastroenterology* 2003; 124:445-458; transgenic mice expressing MMP-1 in mouse macrophages have decreased collagen deposition George, *Clin Sci* (Lond) 2012; 122:83-92; Foronjy, *Hypertension Res.* 2008; 31:725-735); expression of human MMP-1 prevents myocardial fibrosis (Foronjy et al., *Hypertension Res.* 2008; 31:725-735); and recombinant MMP-1 resolves muscle fibrosis (Kaar et al., *Acta Biomaterialia* 2008; 4:1411-1420). Yamaguchi et al. have previously reported that E4 reduces levels of lysyl oxidase (LOX), an enzyme responsible for cross-linking and stabilizing collagen (*Sci Transl Med.* 2012; 4:136ra171). These findings suggest that E4 weakens the ECM by reducing LOX, thus facilitating its degradation by increased MMP-1 and -3 levels. This also explains the ability of E4 to reduce ongoing fibrosis via MMP-mediated matrix degradation. Activation of MMP-1 and -3 via the plasminogen system is well documented (reviewed in Gharaee-Kermani et al., *Exp. Op. Invest. Drugs* 2008; 17:905-916). MMP-1 and -3 can also be induced by HGF (Jinnin et al., *Nucleic Acids Research* 2005; 33:3540-3549; Kanemura et al., *Hepatology Res.* 2008; 38:930-939; Monvoisin et al., *Int. J. Cancer* 2002; 97:157-162; Dunsmore et al., *J. Biol. Chem.* 1996; 271:24576-24582; Huet et al., *Biochem. Pharmacol.* 2004; 67:643-654).

Other studies revealed that E4 induces MMP-1 expression in human primary fibroblast cells. Data also show that MMP-1 activity is increased in supernatants of fibroblasts treated with E4. MMP-1 levels are assayed using a commercially available ELISA kit (Sigma-Aldrich Catalog # RAB0362-1KT) for the quantitative measurement of a MMP-1 protein levels in primary fibroblasts as part of the potency testing for iBio-CFB03. Briefly, samples are pipetted into a 96-well plate coated with immobilized MMP-1 antibody and after subsequent washing, form a covalent complex with the biotinylated human MMP-1 antibody. Bound MMP-1 is reacted with horseradish peroxidase followed by detection with TMB substrate solution. Inactive or complexed MMP-1 will not bind and will not be detected. The amount of color development is directly proportional to the concentration of MMP-1 in the sample, with the overall intensity of the color being determined by absorbance at 450 nm.

MMP-1 activity levels in primary fibroblasts also is assayed using a commercially available antibody array kit (RayBiotech Catalog # AAH-MMP-1). Briefly, samples are pipetted and incubated in an 8-well incubation tray containing antibody coated membranes. After subsequent washing, the samples are incubated with biotinylated antibody. Bound MMP-1 is reacted with streptavidin conjugated with horseradish peroxidase followed by detection with detection buffers. The signal intensity is directly proportional to the concentration of active MMP-1 in the sample as measured with a FluorChemR imaging system (ProteinSimple).

Stability Assessment iBio-CFB03 is evaluated for real-time, real-condition stability under the labeled conditions of storage, frozen conditions, and accelerated conditions for at least three batches of plant-produced polypeptide (DS) and for each lot of the polypeptide as formulated for administration (DP). The duration of the stability studies for DS are 12 months for real-time, real-condition and frozen conditions and 6 months for accelerated conditions. The duration of the stability studies for DP are 36 months for real-time, real-condition and frozen conditions and 6 months for accelerated conditions. Testing frequency for all conditions is done at release and every 3 months for DS. Testing frequency for DP in real-time, real-condition and frozen conditions is done at release and 3, 6, 9, 12, 18, 24 and 36 months, and at release and every 3 months for accelerated conditions. Stability is assessed for the storage orientation of DP in upright, inverted and horizontal positions.

Nonclinical

Summary of Nonclinical Efficacy Studies

Studies performed with endostatin and chemically synthesized peptides E3 and E4 provided further evidence of an anti-fibrotic effect. These chemically synthesized peptides do not form high molecular weight multimers as seen with iBio-CFB03. Efficacy was observed in models of SSc, with fibrosis induced in human skin ex vivo models by intradermal injection of TGF-β, or in C57BL/6 mice by subcutaneous (s.c.) administration of either TGF-β or bleomycin. The E3 and E4 peptides produced through chemical synthesis attenuated fibrosis in these models upon intradermal or s.c. administration, demonstrated by decreases in dermal thickness, collagen content, and hydroxyproline content. In the bleomycin-induced SSc mouse model, fibrosis reduction was achieved with both prophylactic and interventional dosing regimens. These peptides were also effective in IPF models induced by TGF-β treatment in primary cultures of human lung fibroblasts or instillation of bleomycin into the lungs of C57BL/6 mice. Peptides were administered to fibroblast cultures, or given orally, intravenously or intratracheally to mice.

Endostatin may be useful as an anti-fibrotic. Endostatin reversed injury parameters in a rabbit ear scar model induced by mechanical wounding (Zhiyong et al., *Int J Low Extrem Wounds* 2012; 11(4):271-276; Ren et al., *J. Zhejiang Univ. Sci. B.* 2013; 14(3):224-230), in an IPF model induced by intra-tracheal (i.t.) bleomycin administration to rats (Wan et al., *Respir Res.* 2013; 14(1):56), in a liver fibrosis model induced by administration of carbon tetrachloride to mice (Chen et al., *Exp Biol Med.* 2014; 239(8):998-1006), and in a diabetes/renal fibrosis model induced by streptozotocin administration to rats (Bai et al., *Plos One.* 2014; 9(4):1-12).

In vivo studies are conducted with iBio-CFB03 at various doses and dosing schedules based on models previously established with the peptides E3 and E4. Recombinant iBio-CFB03 also is used in the potency assays.

TABLE 4

Summary of efficacy of endostatin and endostatin peptides in fibrosis models

| Model | Product under test | Route of test product administration | Outcome | Reference |
|---|---|---|---|---|
| Normal human lung fibroblasts | Endostatin | In vitro | Adenovirally-expressed endostatin markedly reduced fibronectin (FN) and type I collagen αI chain (Col1α1) protein levels in fibroblasts pretreated with TGF-β. | Yamaguchi et al., *Sci Transl Med.* 2012; 4: 136ra171 |

TABLE 4-continued

Summary of efficacy of endostatin and endostatin peptides in fibrosis models

| Model | Product under test | Route of test product administration | Outcome | Reference |
|---|---|---|---|---|
| Human skin explants, TGF-β induced model of SSc | E4 peptide | Ex vivo | Single dose of E4, administered concurrently with TGF-β, significantly decreased skin thickness and attenuated collagen increase. E4 also ameliorated fibrosis when administered two days after TGF-β administration. | Yamaguchi et al., Sci Transl Med. 2012; 4: 136ra171 |
| Mouse TGF-β dermal model of SSc | E3 & E4 peptides | In vivo | Single dose of E3 or E4 peptide, administered concurrently with TGF-β, significantly decreased skin thickness. | Yamaguchi et al, Sci Transl Med. 2012; 4: 136ra171 |
| Mouse bleomycin s.c. dermal model of SSc | E4 peptide | In vivo s.c. | E4 significantly decreased skin thickness when administered as a single dose prophylactically and when given in a multiple dose treatment regimen starting 3 days after initial exposure to bleomycin. | Yamaguchi et al, Sci Transl Med. 2012; 4: 136ra171 |
| Mouse bleomycin i.t. model of pulmonary fibrosis | E4 peptide | In vivo i.t. | E4 significantly decreased pulmonary fibrosis assessed microscopically and by hydroxyproline/collagen quantification in lung samples when administered concomitantly or 3 days after bleomycin. | Yamaguchi et al., Sci Transl Med. 2012; 4: 136ra171 |
| Mouse bleomycin i.t. model of pulmonary fibrosis | Biotinylated E4 peptide | In vivo oral | E4 significantly reduced pulmonary fibrosis measured by hydroxyproline/collagen quantification in lung samples when administered concomitantly with bleomycin. | Yamaguchi et al, Sci Transl Med. 2012; 4: 136ra171 |
| Mouse bleomycin i.t. model of pulmonary fibrosis | iBio-CFB03 | In vivo IV oral | iBio-CFB03 significantly reduced pulmonary fibrosis compared to vehicle-treated mice when administered by either route concomitantly with or 8 days following bleomycin. | |
| Mouse bleomycin s.c. dermal model of SSc | iBio-CFB03 | In vivo s.c. | iBio-CFB03 significantly reduced dermal thickness as assessed using the hydroxyproline/collagen quantification assay when administered continuously for 7 days following bleomycin delivery. | |
| Human skin explants, TGF-β induced model of SSc | iBio-CFB03 | Ex vivo | Single dose of iBio-CFB03, administered concurrently with TGF-β, significantly attenuated collagen increase as assessed using the hydroxyproline/collagen quantification assay. | |

In Vivo Mouse Model of SSc

Figure 39:
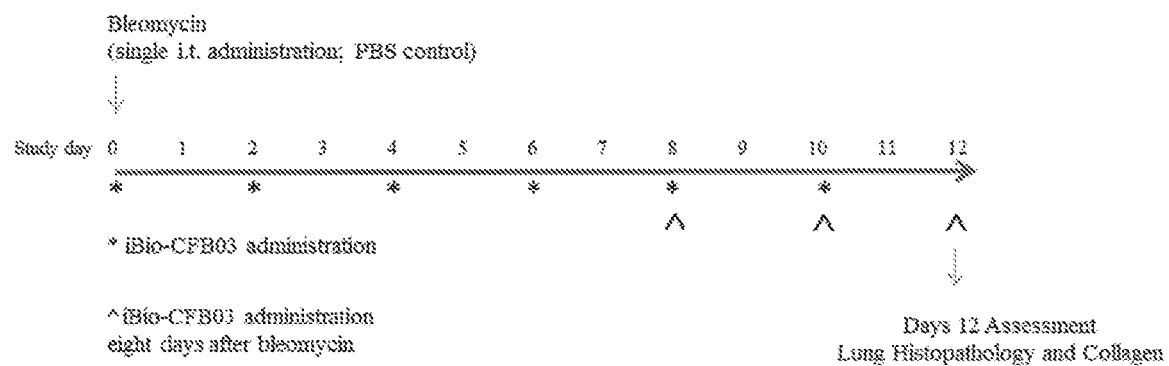
FIG. 39. Schematic for oral and IV administration in a bleomycin model.

A mouse model of SSc has been established in which bleomycin administered intratracheally can induce pulmonary fibrosis within a 12 day timeframe (see FIG. 39). This model has been used to demonstrate the efficacy of iBio-CFB03, building on the experience using endostatin peptides E3 and E4 to attenuate the development of fibrosis (Yamaguchi et al., Sci Transl Med. 2012; 4:136ra171). In this model, lung histology and collagen content were measured with a Sircol assay 10 and 21 days after treatment with bleomycin (Yamaguchi et al., Sci Transl Med. 2012; 4:136ra171).

Hydroxyproline is an amino acid unique to collagen, and is traditionally employed to quantify this protein. The method provides a quantitative determination of the total amount of hydroxyproline per mg wet tissue. The technique provides a high-throughput and accurate method to measure hydroxyproline, enabling the quantification of collagen in a variety of formats. In some instances, a hydroxyproline content assay should be complemented by independent histological determinations of fibrosis using a trichrome staining technique (or suitable alternative) to assess the proportion and distribution of fibrotic tissue.

To evaluate tissue fibrosis/collagen deposition, a hydroxyproline quantification assay was performed. Lung samples were removed and digested overnight at 110° C. in 1 mL 6 N HCl. After neutralization with 6 N NaOH, the pH was adjusted within the range of 6.0-9.0 and samples were mixed with 1 mL chloramine T solution (1.4% chloramine T, 10% isopropanol, 0.5 M sodium acetate, pH 6.0) for 20 minutes at room temperature. Following treatment with chloramine T solution, samples were mixed with 1 mL Erlich's solution (14.9% p dimethylaminobenzaldehyde, 70% isopropanol, 20% perchloric acid; Sigma-Aldrich) and incubated for 15 minutes at 65° C. Aliquots were transferred to 96-well plates, and absorbance was measured at 570 nm. Collagen content was calculated by comparison with a standard curve generated with cis-4 hydroxy-L-proline (Sigma-Aldrich), using the conversion factor of 1 µg hydroxyproline corresponding to 6.94 µg. This assay has been used in the studies described below using iBio-CFB03 and is used in non-clinical studies in this mouse model.

Intravenous and Oral Administration of iBio-CFB03 in Bleomycin Mouse Model

Figure 40:
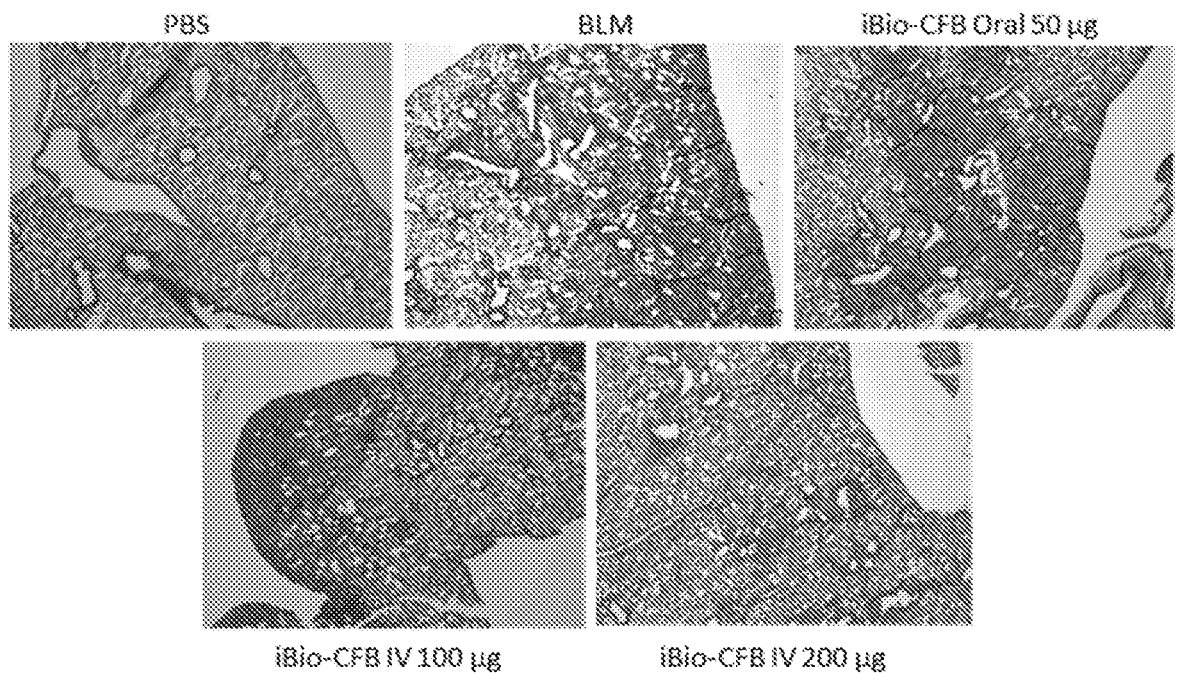
FIG. 40. Hematoxylin and eosin stain of mouse lung treated with oral and IV administration of iBio-CFB03.
Figure 41:
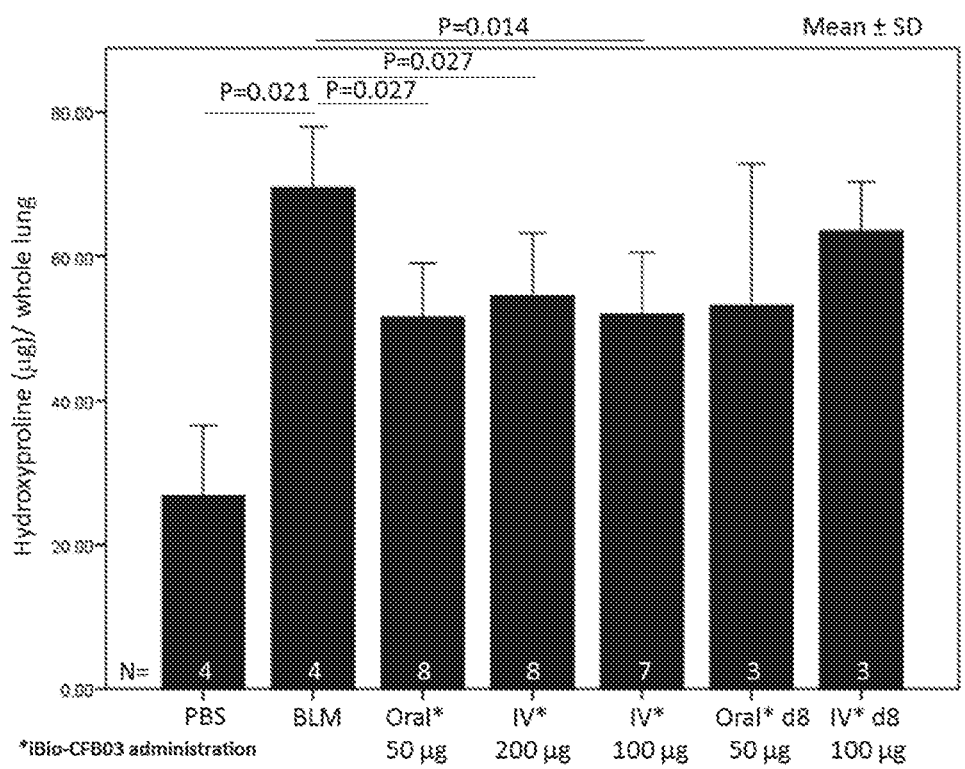
FIG. 41. Hydroxyproline assay of mouse lung in bleomycin model treated with oral and IV iBio-CFB03.
Figure 42:
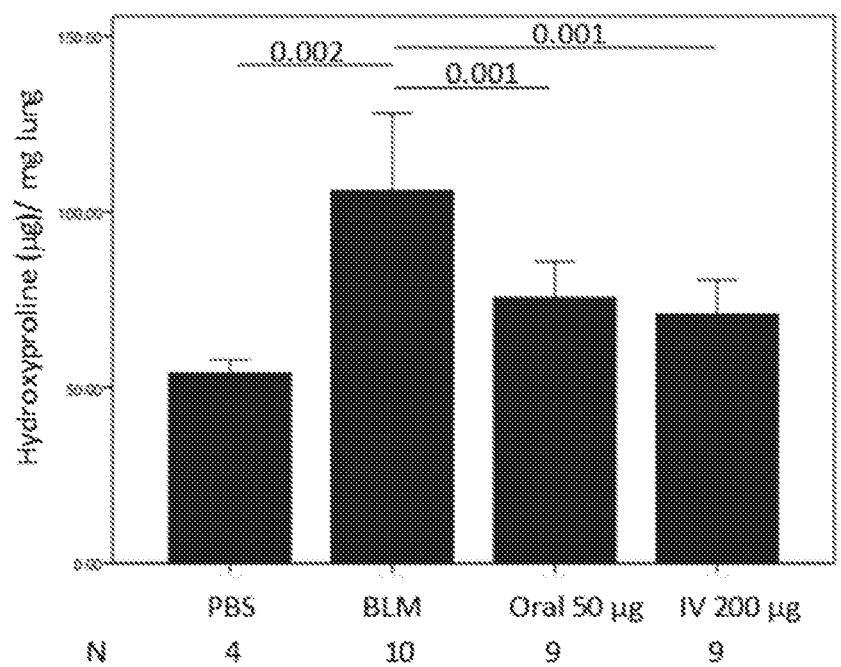
FIG. 42. Hydroxyproline assay of mouse lung in repeat experiment of bleomycin model treated with oral and IV iBio-CFB03.

C57BL/6 mice were given bleomycin i.t. in conjunction with iBio-CFB03 intravenous (IV) administration or followed by IV administration of iBio-CFB03 eight days after bleomycin. The mice were sacrificed at day 12 and lung samples were taken for both H&E staining (FIG. 40) and hydroxyproline assay (FIG. 41). A diagram of the experimental design can be found in FIG. 39. Compared to mice treated with bleomycin only, mice treated repeatedly with iBio-CFB03 IV at 100 µg or 200 µg/mouse had reduced pulmonary fibrosis as assessed using hydroxyproline assays. Intravenously administered iBio-CFB03 at either dose appeared to have similar efficacy to orally administered iBio-CFB03 at 50 µg. iBio-CFB03 administered eight days after bleomycin treatment (both orally and intravenously) also appeared to reduce fibrosis. However only 3 mice were treated in each of these groups. These experiments were therefore repeated with iBio-CFB03 administered IV at 200 µg/mouse (n=9) or orally at 50 µg/mouse (n=9) (FIG. 42). Mice treated IV with 100 µg/mouse iBio-CFB03 had reduced pulmonary fibrosis compared to mice treated with bleomycin only. Administration either by IV or oral route appeared to have similar efficacy.

iBio-CFB03 ameliorated bleomycin-induced pulmonary fibrosis in vivo, whether administered concomitantly or after a fibrotic trigger (represented as d8). 1×PBS was used as vehicle. Mean collagen values are presented as micrograms per lung. iBio-CFB03 was administered either orally (oral) or intravenously (IV). Error bars in FIG. 41 represent standard deviation of the mean. P-values were calculated using Kruskal-Wallis test, followed by Mann-Whitney U test.

Osmotic Pump Administration of iBio-CFB03 in Mouse Dermal Model of SSc

Figure 43:
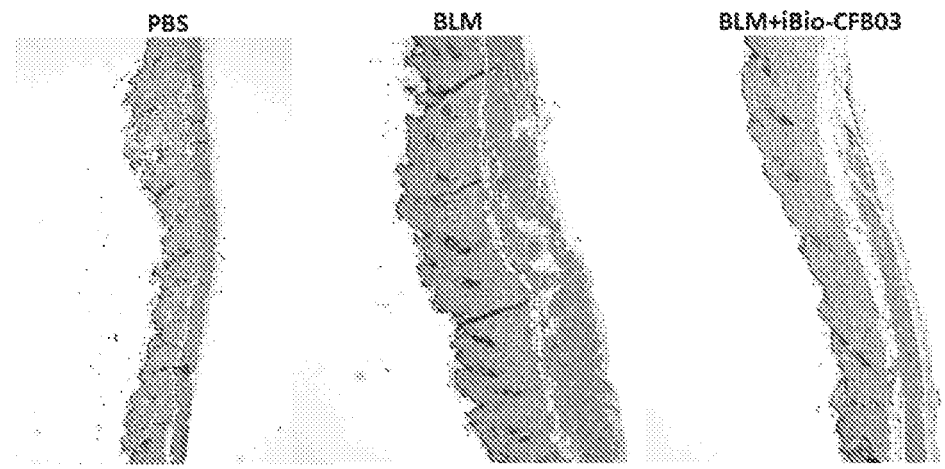
FIG. 43. Hematoxylin and eosin stain of mouse skin treated with osmotic pump subcutaneous (s.c.) administration of iBio-CFB03.
Figure 44:
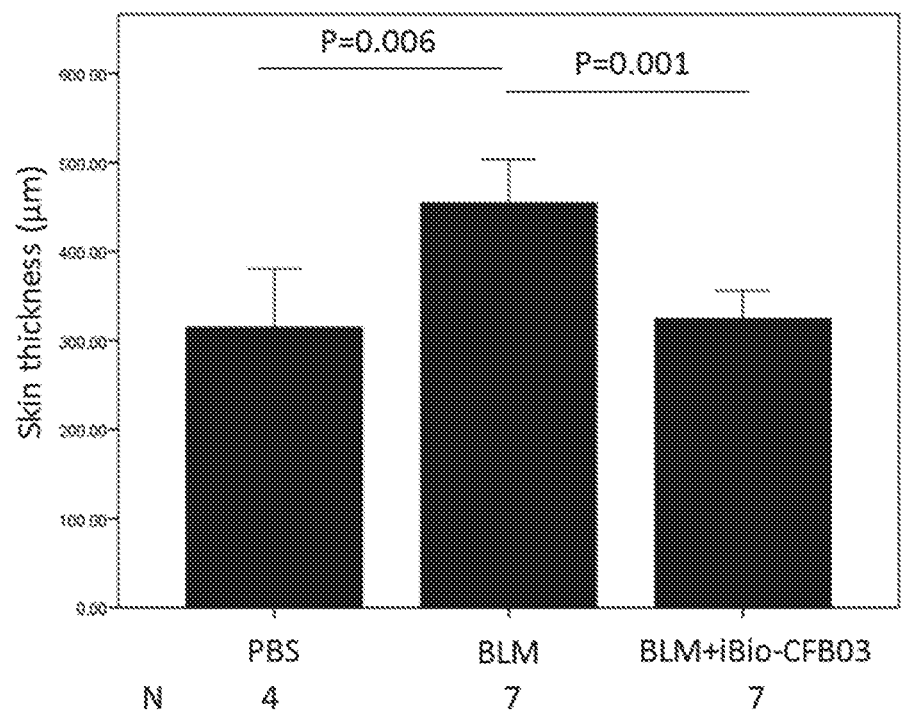
FIG. 44. Skin thickness of mice treated with osmotic pump s.c. administration of iBio-CFB03.

C57BL/6 mice were given 33 mU of bleomycin for seven days using mini-osmotic pumps surgically implanted on the backs of the mice to deliver bleomycin subcutaneously. On day 7, the pumps were removed and replaced with pumps containing 460 µg of iBio-CFB03 administered s.c. for an additional seven days. Mice were sacrificed at day 35 and skin from the back on the opposite side of the pump site was excised, formalin-fixed and embedded in paraffin. Skin sections were stained with H&E (FIG. 43) and dermal thickness (FIG. 44) was measured. Mice treated with iBio-CFB03 had reduced dermal thickness as assessed using hydroxyproline assays.

Ex Vivo Human Skin Model of SSc

Figure 45:
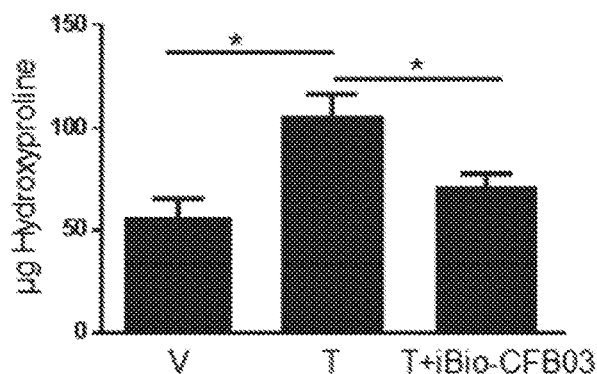
FIG. 45. Hydroxyproline assay of human skin in TGF-β model treated with iBio-CFB03.

Efficacy of iBio-CFB03 was assessed in human skin models of SSc induced by injection of TGF-β. TGF-β induces pathological changes in skin characteristic of SSc. iBio-CFB03 attenuated TGF-β induced fibrosis in human skin when administered concurrently with TGF-β. When administered concurrently with 10 ng TGF-β, a single intradermal dose of 100 µg iBio-CFB03 prevented the increased collagen when evaluated one week post dosing via hydroxyproline assay (FIG. 45).

Human skin was obtained from abdominal surgery, trimmed, fat cleaned, and cut into ~1×1 inch pieces. Pieces were maintained in organ culture in an air-liquid interface. Pieces were injected with vehicle (V), TGF-β (T) or TGF-β+iBio-CFB03 (T+iBio-CFB03) in a volume of 100 µl. Doses: Vehicle=100 µl of 1×PBS; T=10 ng of TGF-β; T+iBio-CFB03=10 ng TGF-β+100 µg iBio-CFB03. After one week (7 days), 3 mm punches of skin were obtained and hydroxyproline measured in the skin punches. The data represent n=3/group. * denotes p<0.05.

Justification of E4 Data Supportive of iBIO-CFB03

Evaluation of the efficacy and mechanism of action of C-terminal endostatin peptides in preclinical fibrosis models has been performed using chemically-synthesized E3, and the closely related peptide, E4. E4 differs from E3 by an addition of a C-terminal amide to stabilize the E3 peptide. Efficacy and mechanistic studies using recombinant iBio-CFB03 are done to confirm the anti-fibrotic activity previously demonstrated with chemically-synthesized E3 and E4. iBio-CFB03 improves the solubility, stability and purification of E3/E4, and has shown promising results in further pre-clinical testing.

Mechanism of Action Studies with E4 Peptide

Several experiments have been performed to identify the mechanisms by which E4 exerts its anti-fibrotic activity. Real-time quantitative PCR (qPCR)-based arrays were performed on RNA extracted from primary human lung fibroblasts or mouse lung tissue stimulated with various fibrotic triggers in the absence and presence of E4 treatment in order to identify genes influenced by the endostatin peptide.

The arrays identified several genes that have been previously implicated in fibrosis to be influenced by E4 treatment. These genes included connective tissue growth factor (CTGF), insulin-like growth factor binding protein (IGFBP)-3, matrix metalloproteases (MMP)-1 and MMP-3, urokinase plasminogen activator (uPA), plasminogen activator inhibitor (PAI)-1, and hepatocyte growth factor (HGF) with levels either decreased or increased in the presence of E4 as shown in TABLE 5.

TABLE 5

| Genes regulated by E4 | | | |
| --- | --- | --- | --- |
| Gene | Model | Method | Effect of E4 peptide |
| CTGF | Primary human fibroblasts treated with bleomycin (HuF-bleo) or TGF-β (HuF-T) as fibrogenic trigger | RT-qPCR | Decrease |
| IGFBP-3 | HuF-T | RT-qPCR Protein expression levels | Decrease |
| uPA | HuF-T | RT-qPCR Protein expression levels Enzyme activity | Increase |

TABLE 5-continued

Genes regulated by E4

| Gene | Model | Method | Effect of E4 peptide |
|---|---|---|---|
| PAI-1 | HuF-T Mouse bleomycin model of pulmonary fibrosis | RT-qPCR Protein expression | Decrease |
| HGF | HuF-T Mouse bleomycin model of pulmonary fibrosis | RT-qPCR Protein expression | Increase |
| MMP-1 | HuF-T | RT-qPCR Protein expression levels Zymography MMP-1 activity assay | Increase |
| MMP-3 | HuF-T | RT-qPCR Protein expression levels Zymography | Increase |

Summary and Model for Mechanism of Action

Figure 46:
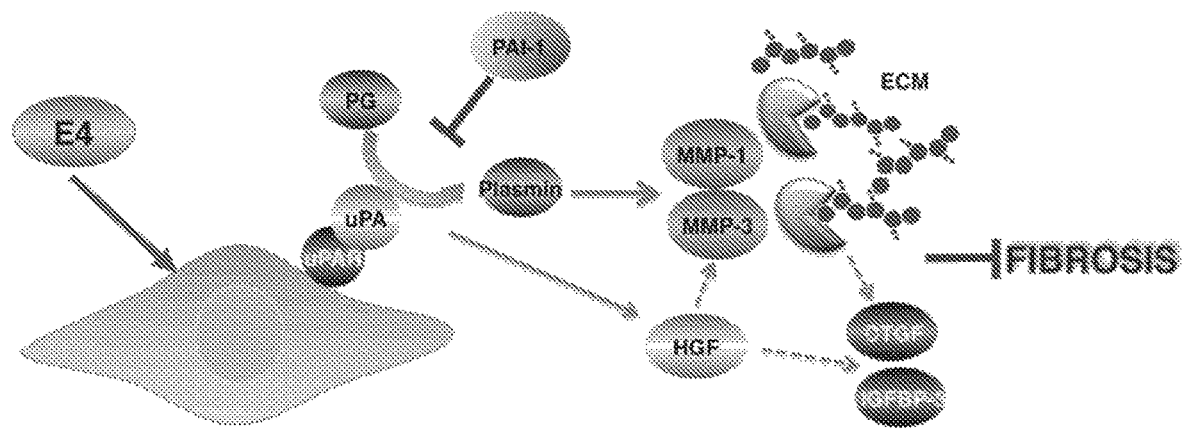
FIG. 46. Schematic of mechanism of action for E4 endostatin peptide.

In summary, E4, a peptide derived from endostatin, exerts anti-fibrotic effects in vitro, in vivo and ex vivo after application of two different fibrotic triggers, bleomycin and TGF-β (Yamaguchi et al., *Sci Transl Med.* 2012; 4:136ra171). E4 reduces levels of the pro-fibrotic factors CTGF and IGFBP-3 and induces increased levels and activity of MMP-1 and MMP-3. Further, E4 activates the plasminogen system, increases uPA levels and activity, reduces levels of the uPA inhibitor PAI-1, and induces conversion of pro-HGF to its active chains. E4 exerts anti-fibrotic effects via down-modulation of PM-1 and an increase of uPA activity, leading to HGF activation, decreased fibrotic intermediaries CTGF and IGFBP-3, and increased ECM degradation through induction of active MMP-1 and MMP-3 production. Target specificity is summarized in the schematic shown in FIG. 46.

PK and Toxicology Studies
Pharmacokinetic Studies

Method(s) of detection for iBio-CFB03 in biological specimens, including serum and skin, are established. Pharmacokinetics and metabolism of iBio-CFB03 are evaluated in animals. Initial, exploratory studies are conducted in mice to determine serum concentration of iBio-CFB03, and begin to establish a relationship between an efficacious IV dose and circulating drug levels. Exploratory PK studies in rats and rabbits are also done to examine potential species differences in iBio-CFB03 absorption, and to determine serum concentration of iBio-CFB03 in the two species proposed for acute and chronic toxicology studies. More comprehensive PK/ADME assessments of iBio-CFB03 in rats and rabbits are conducted to characterize PK profiles and dose linearity. Some of the PK/ADME assessments are conducted in the toxicokinetic portion of the proposed toxicology studies.

The commercially available polyclonal enzyme immunoassay (EIA) 96-well plate assay (Accucyte, Cytimmune Sciences Inc., College Park, Md.) used for assessing endostatin PK (Thomas et al., *J Clin Oncol.* 2003; 21(2): 223-231) is tested for its ability to detect iBio-CFB03. In addition to the published method in Thomas et al., the feasibility of using an immunoglobulin Y (IgY) antibody for immunological studies is investigated. IgY antibodies produce less cross-reactivity and background against a mammalian antigen than systems in which the antibody/antigen complex are both from mammalian sources. Additionally, murine monoclonal antibodies are developed against iBio-CFB03 for the purpose of constructing a sandwich ELISA for PK analysis and other quantification needs in tissue or biofluids. As an additional technology to generate iBio-CFB03-specific immune reagents, chicken spleen cells are used for generating polyclonal IgY anti-iBio-CFB03 antibodies as starting material to generate single-chain variable binding fragments (scFv) or recombinant monoclonal IgY antibodies that could be engineered to generate binding and detection reagents.

If a sensitive and specific sandwich ELISA for detection of iBio-CFB03 in tissue and biofluids is not possible, a MS/MS-based assay is developed for selective detection of endostatin-related peptide using multiple reaction monitoring, which provides a high level of sensitivity for specific peptide fragments. Ideally, such an assay focuses on peptide fragments unique to the iBio-CFB03 to distinguish it from the natural level of endostatin or its precursor collagen molecule. The success of this approach also depends on being able to detect such fragments in complex biological samples, and involves specific tissue/biological fluid preparation and separation protocols to "decomplex" the sample to maximize detection and reproducibility.

In some cases, the methods for characterization of iBio-CFB03 are adopted for bioanalytical assessments. These methods include matrix-assisted laser desorption/ionization (MALDI), immunoassays, and LC/MS-MS.

Following establishment of an adequate bioanalytical method for iBio-CFB03, initial pilot studies are conducted in mice to assess IV administration of iBio-CFB03, and to begin to establish a possible relationship between efficacious dose levels identified from the proof of concept mouse studies and levels of drug in serum and target tissue. Pilot PK studies in rats and rabbits also are used to establish that iBio-CFB03 is efficacious in the two species used for acute and chronic toxicology studies. Additionally, potential species differences in iBio-CFB03 absorption and PK profiles are identified.

After exploratory studies, more comprehensive PK/ADME assessments of iBio-CFB03 in rats and rabbits are carried out characterize PK profiles and dose linearity, and to support dose selection in the Phase 1 study. Designs for these studies include blood collection pre-dose, immediately post-dose, and up to 120 h post-dose. Groups of animals are staggered or slated for terminal collection (rats only) during sampling depending on species and frequency of sampling. Skin also is collected from rats slated for terminal collection. Serum and skin levels of iBio-CFB03 are assessed.

Additional PK/ADME assessments are conducted in the toxicokinetic portion of the toxicology studies, and the PK of iBio-CFB03 is evaluated following single and multiple (daily/weekly) dose administration.

Single Dose Toxicology

Non-GLP single dose toxicology studies in Sprague-Dawley rats and New Zealand White rabbits are done to facilitate dose selection for GLP animal toxicology studies, and to support initiation of testing in healthy volunteers in the Phase 1 study.

Non-GLP Acute Rat Toxicology Study

Toxicity of iBio-CFB03 is assessed in male and female adult Sprague-Dawley rats following a single IV administration. Three dose levels of IV administered iBio-CFB03 are evaluated, and compared to one group of rats given a single IV administration of vehicle as control. Three rats per group and per gender are used based on standard practice for this type of study in order to provide adequate determination of potential toxicity and statistical differences among study groups.

Evaluations include assessments of mortality, morbidity, clinical observations, and body weight changes. Blood samples are collected for hematology, clinical chemistries, and coagulation parameters assessments. Organs are weighed and examined for any gross pathological changes. Histopathology is performed on organs pending gross necropsy findings.

Determination of iBio-CFB03 in skin specimens and serum are used to evaluate systemic and target organ exposure. MMP-1 and uPA levels in skin specimens and serum are determined for baseline assessments of these SSc biomarkers.

Rats are used for these tests since they are one of the model species for the assessment of toxicity, and one of the species recommended for this purpose by toxicity testing guidelines of all regulatory agencies.

Non-GLP Acute Rabbit Toxicology Study

Toxicity of iBio-CFB03 also is assessed in New Zealand White male and female adult rabbits following a single IV administration. Three dose levels of intravenously administered iBio-CFB03 are evaluated, and compared to one group of rabbits given a single IV administration of vehicle as control. Two rabbits per group and per gender are used, based on standard practice for this type of study in order to provide adequate determination of potential toxicity and statistical differences among study groups.

Evaluations include assessments of mortality, morbidity, clinical observations, and body weight changes. Blood samples are collected for hematology, clinical chemistries, and coagulation parameters assessments. Organs are weighed and examined for any gross pathological changes. Histopathology is performed on organs pending gross necropsy findings.

Determination of iBio-CFB03 in skin specimens and serum are used to evaluate systemic and target organ exposure. MMP-1 and uPA levels in skin specimens and serum are determined for baseline assessments of these SSc biomarkers.

Rabbits are used for these tests as they are another of the model species for the assessment of toxicity and one of the species recommended for this purpose by toxicity testing guidelines of all regulatory agencies.

Repeat Dose Toxicology

Twenty-eight (28) day repeat dose GLP toxicology studies are conducted in Sprague-Dawley rats and New Zealand White rabbits to support initiation of testing in healthy volunteers in the Phase 1 study.

Twenty-Eight Day Repeat Dose GLP Rat Toxicology Study

Toxicity of iBio-CFB03 is assessed in male and female adult Sprague-Dawley rats following 28 consecutive days of every other day (3×/week) IV administration. Three dose levels of IV administered iBio-CFB03 are evaluated, and compared to one group of rats given a single IV administration of vehicle as control. Dose selection are based on findings from the PK rat studies, as well as maximum tolerated/feasible and NOAEL doses identified in pilot and single dose rat toxicology studies.

In addition to a main study portion, satellite groups of animals are included for 28 day recovery period and toxicokinetic analyses.

The study design is summarized in TABLE 6.

TABLE 6

Design for the 28 Day Repeat Dose GLP Rat Toxicology Study

| | | Dose Level (mg/kg) | Number of Animals | | | | | |
|---|---|---|---|---|---|---|---|---|
| | | | Main Study | | Recovery | | Satellite TK | |
| Group | Treatment | | Males | Females | Males | Females | Males | Females |
| 1 | Control | 0 | 10 | 10 | 5 | 5 | | |
| 2 | iBio-CFB03 | 2.5 mg/kg | 10 | 10 | | | 6 | 6 |
| 3 | iBio-CFB03 | 5 mg/kg | 10 | 10 | | | 6 | 6 |
| 4 | iBio-CFB03 | 10 mg/kg | 10 | 10 | 5 | 5 | 6 | 6 |

The number of rats per group and per gender are based on standard practice for this type of study in order to provide adequate determination of potential toxicity and statistical differences among study groups.

Evaluations include assessments of mortality, morbidity, clinical observations, and body weight changes. Blood samples are collected for hematology, clinical chemistries, and coagulation parameters assessments. Organs are weighed and examined for any gross pathological changes. Histopathology is performed on organs pending gross necropsy findings.

Determination of iBio-CFB03 levels in skin specimens and serum are used to evaluate systemic and target organ exposure. MMP-1 and uPA levels in skin specimens and serum are determined for baseline assessments of these SSc biomarkers.

Rats are used for these tests as they are one of the model species for the assessment of toxicity and one of the species recommended for this purpose by toxicity testing guidelines of all regulatory agencies.

Twenty-Eight Day Repeat Dose GLP Rabbit Toxicology Study

Toxicity of iBio-CFB03 is assessed in New Zealand White male and female adult rabbits following 28 consecutive days of once daily IV administration. Three dose levels of IV administered iBio-CFB03 are evaluated and compared to one group of rabbits given a single IV administration of vehicle as control. Dose selection is based on findings from the PK rabbit studies, as well as maximal tolerated/feasible and NOAEL doses identified in pilot and single dose rabbit toxicology studies.

In addition to a main study portion, satellite groups of animals are included for 28 day recovery period and toxicokinetic analyses.

The study design is summarized in TABLE 7.

TABLE 7

Design for the 28 Day Repeat Dose GLP Rabbit Toxicology Study

| Group | Treatment | Dose Level (mg/kg) | Number of Animals | | | | | |
|---|---|---|---|---|---|---|---|---|
| | | | Main Study | | Recovery (optional) | | Satellite TK (optional) | |
| | | | Males | Females | Males | Females | Males | Females |
| 1 | Control | 0 | 4 | 4 | 2 | 2 | | |
| 2 | iBio-CFB03 | 2.5 mg/kg | 4 | 4 | | | 2 | 2 |
| 3 | iBio-CFB03 | 5 mg/kg | 4 | 4 | | | 2 | 2 |
| 4 | iBio-CFB03 | 10 mg/kg | 4 | 4 | 2 | 2 | 2 | 2 |

The number of rabbits per group and per gender are based on standard practice for this type of study in order to provide adequate determination of potential toxicity and statistical differences among study groups.

Evaluations include assessments of mortality, morbidity, clinical observations, and body weight changes. Blood samples are collected for hematology, clinical chemistries, and coagulation parameters assessments. Organs are weighed and examined for any gross pathological changes. Histopathology is performed on organs pending gross necropsy findings.

Determination of iBio-CFB03 in skin specimens and serum are used to evaluate systemic and target organ exposure. MMP-1 and uPA levels in skin specimens and serum are determined for baseline assessments of these SSc biomarkers.

Rabbits are used for these tests as they are a model species for the assessment of toxicity and one of the species recommended for this purpose by toxicity testing guidelines of all regulatory agencies.

Nonclinical Development Plan

Nonclinical development of iBio-CFB03 includes evaluating efficacy in fibrosis models to confirm the previously demonstrated anti-fibrotic activity demonstrated with structurally related endostatin peptides. Studies exploring the mechanism of action of iBio-CFB03 also are used to further characterize its anti-fibrotic activity. In addition, pharmacokinetics of iBio-CFB03 are evaluated.

Immunogenicity of iBio-CFB03 is evaluated in rats and rabbits for anti-drug antibodies. Initial screening assays are conducted and samples testing positive in the screening assay are re-tested using a confirmatory assay. A neutralization assay also is performed to measure any neutralizing antibody activity.

Potential toxicity of iBio-CFB03 is evaluated in rats and rabbits. Initial pilot studies are used to explore the ability to achieve a maximal tolerated dose, or otherwise, establish a maximal feasible dose, based on animal tolerability and compound availability following an acute, single dose administration of iBio-CFB03. Repeat dose studies in rats and rabbits are also conducted to explore potential toxicity of iBio-CFB03 following 28 days of repeat dose administration (every other day; 3x/week) under GLP compliance. Pending outcome of single dose and 28 day GLP repeat dose studies, chronic toxicology studies are conducted in both rodent and non-rodent species in 6 month repeat dose GLP studies to support chronic use.

Clinical

In a Phase 1 PK and PD study of recombinant human endostatin in patients with advanced solid tumors, it was demonstrated that endostatin is essentially free of significant drug-related toxicity and was well tolerated when given daily as a 1-hour intravenous infusion at doses up to 300 mg/m2 (Thomas et al., *J Clin Oncol.* 2003; 21(2):223-231).

An open label, two segment Phase 1 trial is conducted in normal healthy volunteers (NHV) and SSc patients to assess the safety, immunogenicity, and pharmacokinetics of intravenously administered iBio-CFB03. Segment A is a single-dose, dose escalating design. After the completion of this segment, a Data Safety Monitoring Board (DSMB) reviews the PK and safety data to determine the Maximum Tolerated Dose (MTD). SSc patients are enrolled in Segment B of the study for repeat dose exposure at the MTD from the first segment. The waiting period between first and second doses (1 week) and/or dosing schedule (other day after dose 2) are adjusted as needed in Segment B.

The maximum dose for evaluation in Segment A of the study, 5 mg, was selected as a possible therapeutic dose based on results from the proof of concept studies in the mouse-bleomycin model. In those studies, the minimum dose at which significant effects of iBio-CFB-3 were observed was 20 μg per animal. Scaling this to a human equivalent dose (HED) using the conversion factor provided in FDA Guidance to Industry: Estimating the Maximum Safe Starting Dose in Initial Clinical Trials for Therapeutics in Adult Healthy Volunteers (July 2005), gives:

[20 μg/20 g mouse]*0.081*60 kg human=4.8 mg per dose

The toxicology studies are designed to provide a safety factor of 10 fold excess above this maximum human dose for the Phase 1 clinical trial.

Immunogenicity Sampling

Because iBio-CFB03 is a therapeutic protein, volunteers enrolled in the clinical study are monitored for the incidence of anti-drug antibodies (ADA). Serum samples for ADA screening are collected prior to administration of the first dose, prior to the administration of the final dose (Segment B participants only), 14 days, and 28 days after the administration of the final dose.

Pharmacokinetics Sampling

In Segment A of the study, serum samples for assessment of iBio-CFB03 pharmacokinetics (Cmax, AUC0 ∞, serum concentration, elimination constant, clearance) are collected at the following time points:

0 min (pre-dose baseline)
5 min
15 min
30 min
1 h
2 h
6 h
12 h

In Segment B of the study, Dose 1 PK serum samples are collected from participating SSc patients according to the same sampling plan described above. For subsequent study doses, a single serum PK sample is collected at the timepoint closest to Tmax⁻ observed in Segment A.

Pharmacologic Activity

SSc patients enrolled in Segment B are assessed for possible pharmacological activity of iBio-CFB03 by serial skin biopsy. Skin biopsies are performed at baseline, four weeks and twelve weeks. Two biopsies are taken at baseline, one from each arm. The four week biopsy is taken on one arm and the twelve week biopsy on the other. Two skin biopsies are taken on each individual arm in a FIG. 8 pattern. One is used for histology with appropriate staining to assess any changes in skin thickness or collagen organization (e.g., H&E, Mason's trichrome, Verhoeff-Van Gieson) and the other for a hydroxyproline assay.

Clinical Development Plan

An open label Phase 2a study is conducted to assess the safety, PK and preliminary efficacy of the iBio-CFB03 in diffuse SSc patients via intravenous administration. This study is a repeat-dose open-label trial designed to evaluate the dose effect and dose tolerance relationships as well as to determine the appropriate dosing regimen. The dose levels chosen for this Phase 2a study are chosen based on data from the Phase 1 study and non-clinical toxicology studies performed with the same route of administration. Subsequent to the Phase 2a study, a conduct 3-6 month Phase 2b study is conducted using an intravenous administration of iBio-CFB03 to assess safety and efficacy, followed by a placebo-controlled Phase 3 study of iBio-CFB03 in diffuse SSc patients. A summary of the clinical development plan (CDP) is shown in TABLE 8.

TABLE 8

Clinical Development Plan

| Phase | Description | Population | Sample size | Primary Objectives | Secondary and Exploratory Objectives |
|---|---|---|---|---|---|
| Phase 1 | PK, immunogenicity and safety study (1 month) Segment A: Single dose, dose escalating design Segment B: Repeat dose, fixed dose level | Segment A: Normal healthy adult (>18 years) volunteers Segment B: Diffuse SSc patients | Segment A: 20 subjects Segment B: 20 subjects | Safety and tolerability of intravenously administered iBio-CFB03 Evaluate immunogenicity of iBio-CFB03 | Evaluate the pharmacokinetic profile of iBio-CFB03 Determine dose needed to reach potentially therapeutic serum levels Assessment of potential on pharmacodynamic biomarkers in serum/plasma and skin |
| Phase 2a | Multiple doses, dose escalating, PK/PD and safety study (~3 months) | Patients (diffuse SSc; early stage <18 months) | TBD | Safety and tolerability of intravenously administered iBio-CFB03 Pharmacokinetic profile Preliminary efficacy based on Rodnan skin scores | Define dose effect and dose tolerance relationships Determine appropriate dose and dosing regimen Preliminary efficacy data based on Rodnan skin scores |
| Phase 2b | High vs. low dose, efficacy study (3-6 months) | Patients (diffuse SSc; early lung or early kidney involvement) | TBD | Efficacy (high vs. low dose) | Skin biopsies to determine potential markers (uPA; MMP-1) Exploratory serum biomarkers Risk/benefit analysis Exploratory: lung improvement |
| Phase 3 | Randomized controlled trial(s) | Patients (diffuse SSc; early stage, 18 months) | TBD | Efficacy against comparator (placebo) | Efficacy Skin biopsies; look at various markers Exploratory: lung improvement |

Development of an Oral Route of Administration

Preliminary data suggests that oral dosing with iBio-CFB03 is at least as efficacious as an IV route of administration. Based on these data and the benefits of an oral route of administration for what will likely be chronic use, an oral formulation of iBio-CFB03 is developed. If it is determined that an oral formulation is beneficial to the program, the studies outlined in TABLE 9 are performed prior to introducing the oral formulation into clinical studies.

TABLE 9

Non-Clinical Studies to Support Oral Administration

| Study | Model | Dosing Route | Objective |
| --- | --- | --- | --- |
| Oral bioavailability | Mouse and rats | Oral and IV | Determine serum levels of orally administered iBio-CFB03 compared to IV administration |
| Food effect | Rats | Oral | Determine the effect of food on the pharmacokinetics of iBio-CFB03 |
| 90 Day Repeat Dose Toxicology | Rats | Oral | Assessment of potential toxicity of iBio-CFB03; recovery, and TK parameters |

Example 12

Oral Delivery Fc Fusion Proteins

Figure 47:
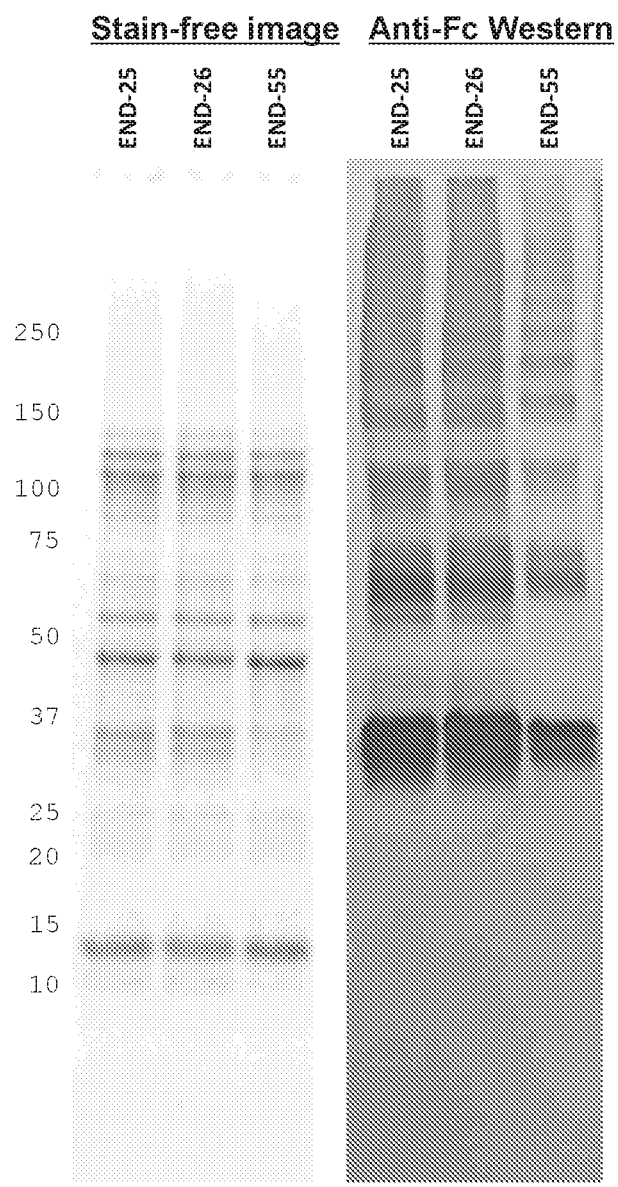
FIG. 47. SDS-PAGE gel of E3 Fc fusions E3-Fc (END-25), E3-linker-Fc (END-26), and C67A E3-Fc (END-55) lysates imaged for total protein (left panel), and Western blotted with an anti-Fc antibody by Western blot (right panel).

E3-Fc (END-25), E3-linker-Fc (END-26), and C67A E3-Fc (END-55) lysates were run on an SDS-PAGE gel, imaged for total protein (FIG. 47, left panel), and probed with an anti-Fc antibody by Western blot (FIG. 47, right panel).

Figure 48:
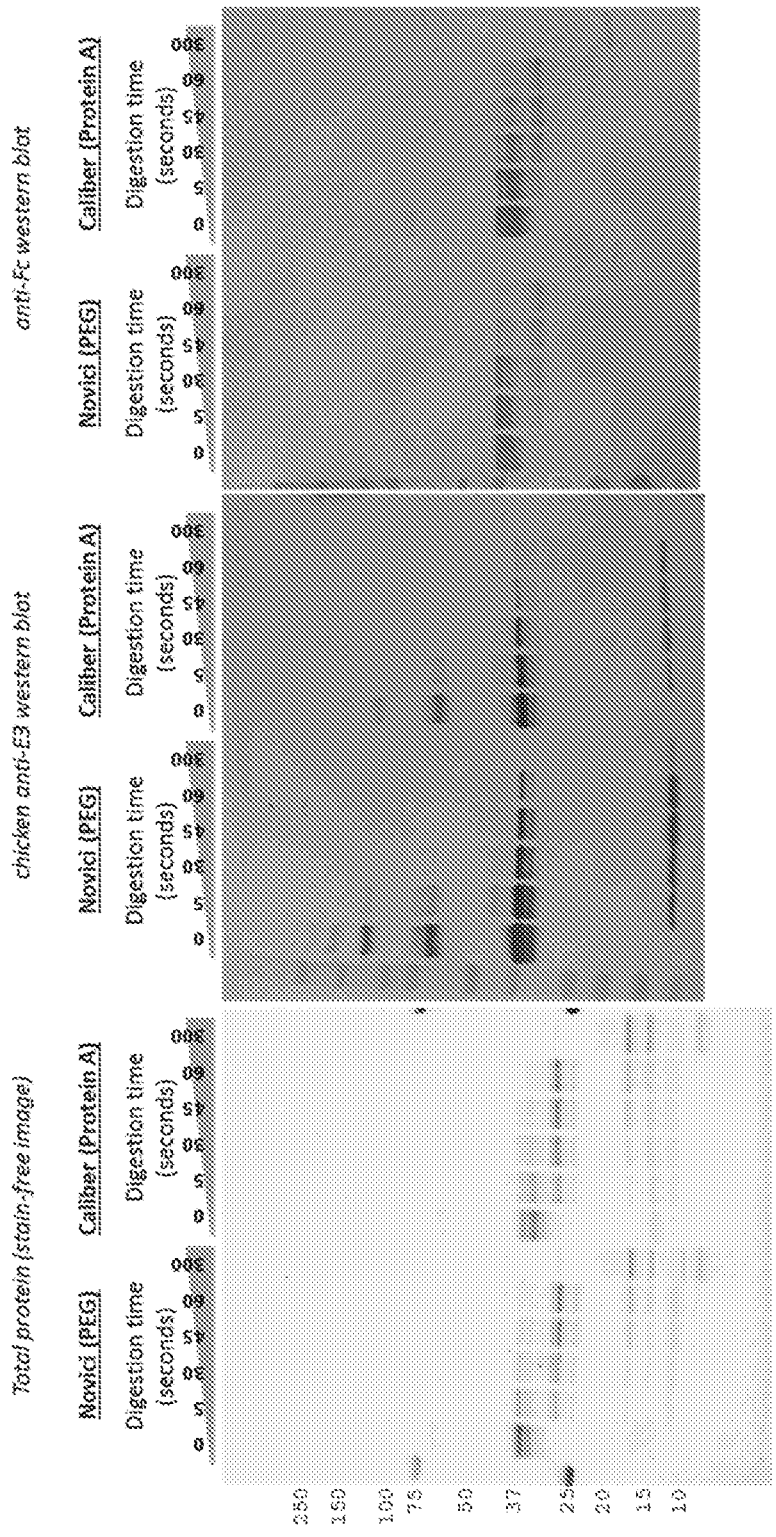
FIG. 48. END-55 Simulated Gastric Fluid (pepsin) digestion. SDS-PAGE gel of total protein (left panel), and Western blotted with either a chicken anti-E3 antibody (middle panel) or anti-human Fc antibody (right panel).

Equal amounts of purified END-55 from Novici (PEG purified) or Caliber (Protein A purified) were digested in Simulated Gastric Fluid (SGF) for 0, 5, 30, 45, 60, or 300 seconds. The reaction was stopped with 160 mM sodium carbonate. Samples were then run on a 4-20% SDS-PAGE gel and imaged on a stain-free gel imager for total protein (FIG. 48, left panel). Gel was then transferred to nitrocellulose and probed with either a chicken anti-E3 antibody (FIG. 48, middle panel) or anti-human Fc antibody (FIG. 48, right panel) for Western blot. E3 plus probably the hinge region of Fc does appear to be liberated from the Fc molecule, but is largely degraded by the 300 second time point. Differences between the Caliber and Novici samples appear to be a ~14 kD band which is more prominent in the early time points for Caliber material and less glycosylated E3-Fc in the Caliber samples. The ~10 kD E3-positive band is slightly weaker in the Caliber samples. All images are scaled and aligned with each other.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for producing a soluble fusion polypeptide having anti-fibrotic activity, wherein the fusion polypeptide comprises the sequence set forth in SEQ ID NO: 16, the method comprising:
   introducing into a plant a plant viral vector that includes a polynucleotide encoding the fusion polypeptide having anti-fibrotic activity of SEQ ID NO:16.

2. The method of claim 1, wherein the introducing comprises vacuum infiltration.

3. The method of claim 1, further comprising harvesting the plant, wherein the plant comprises the fusion polypeptide having anti-fibrotic activity.

4. The method of claim 1, further comprising extracting the fusion polypeptide of SEQ ID NO:16 from the plant.

5. The method of claim 4, further comprising purifying the fusion polypeptide of SEQ ID NO:16 having antifibrotic activity extracted from the plant.

6. A method for producing high molecular weight multimer of a soluble fusion polypeptide comprising the amino acid sequence set forth in SEQ ID NO: 16, wherein the fusion polypeptide has anti-fibrotic activity, the method comprising:
   (a) introducing into a plant a plant viral vector that includes a polynucleotide encoding the fusion polypeptide of SEQ ID NO:16;
   (b) maintaining the plant under conditions and for a time sufficient that the polynucleotide is expressed in at least some plant cells; and
   (c) obtaining an extract from a plurality of plant cells.

7. The method of claim 1, wherein the plant is a transgenic plant.

8. The method of claim 1, wherein the plant is a Leguminosae, Gramineae, Solanaceae, Lycopersicon, Solanum, Capsium, Nicotiana, Umbelliferae, Compositae, or Brassicaceae plant.

9. The method of claim 1, wherein the polynucleotide is operably linked to a heterologous promoter.

10. The method of claim 1, wherein the polynucleotide is operably linked to a promoter that expresses in a mature plants, seedlings, sprouts, or seeds.

11. The method of claim 6, wherein the plant is a transgenic plant.

12. The method of claim 6, wherein the introducing comprises vacuum infiltration.

13. The method of claim 6, further comprising extracting the fusion polypeptide of SEQ ID NO:16 from the plant cells.

14. The method of claim 6, further comprising purifying the fusion polypeptide of SEQ ID NO:16 from the extract.

15. The method of claim 6, wherein the polynucleotide is operably linked to a heterologous promoter.

16. The method of claim 6, wherein the polynucleotide is operably linked to a promoter that expresses in a mature plants, seedlings, sprouts, or seeds.

17. The method of claim 6, wherein the plant is a Leguminosae, Gramineae, Solanaceae, Lycopersicon, Solanum, Capsium, Nicotiana, Umbelliferae, Compositae, or Brassicaceae plant.

18. A transgenic plant comprising a nucleic acid expression vector that comprises a polynucleotide that encodes a fusion polypeptide comprising SEQ ID NO:16.

19. The transgenic of claim 18, wherein the plant is a Leguminosae, Gramineae, Solanaceae, Lycopersicon, Solanum, Capsium, Nicotiana, Umbelliferae, Compositae, or Brassicaceae plant.

* * * * *